US012760268B2

(12) United States Patent
Pun et al.

(10) Patent No.: US 12,760,268 B2
(45) Date of Patent: Oct. 13, 2026

(54) COMPOSITIONS AND METHODS RELATED TO TRANSFERRIN RECEPTOR-BINDING APTAMERS

(71) Applicants: University of Washington, Seattle, WA (US); Seattle Children's Hospital, Seattle, WA (US)

(72) Inventors: Suzie Hwang Pun, Seattle, WA (US); Nataly Kacherovsky, Seattle, WA (US); Emmeline Cheng, Seattle, WA (US); Ian Cardle, Seattle, WA (US); Michael Jensen, Seattle, WA (US)

(73) Assignees: University of Washington, Seattle, WA (US); Seattle Children's Hospital, Seattle, WA (US)

( * ) Notice: Subject to any disclaimer, the term of this patent is extended or adjusted under 35 U.S.C. 154(b) by 1015 days.

(21) Appl. No.: 17/813,021

(22) Filed: Jul. 15, 2022

(65) Prior Publication Data

US 2023/0050022 A1 Feb. 16, 2023

Related U.S. Application Data

(60) Provisional application No. 63/222,086, filed on Jul. 15, 2021.

(51) Int. Cl.

| | |
|---|---|
| ***C12N 5/00*** | (2006.01) |
| ***A61K 40/11*** | (2025.01) |
| ***A61K 40/15*** | (2025.01) |
| ***A61K 40/31*** | (2025.01) |
| ***A61K 40/42*** | (2025.01) |
| ***A61K 40/50*** | (2025.01) |
| ***A61K 47/54*** | (2017.01) |
| ***C12N 15/115*** | (2010.01) |

(52) U.S. Cl.

CPC ............ *C12N 5/0093* (2013.01); *A61K 40/11* (2025.01); *A61K 40/15* (2025.01); *A61K 40/31* (2025.01); *A61K 40/4211* (2025.01); *A61K 47/549* (2017.08); *C12N 15/115* (2013.01); *A61K 40/50* (2025.01); *C12N 2310/16* (2013.01)

(58) Field of Classification Search

None

See application file for complete search history.

(56) References Cited

U.S. PATENT DOCUMENTS

| | | | | |
|---|---|---|---|---|
| 8,409,573 | B2 | 4/2013 | Boumsell | |
| 2015/0301058 | A1* | 10/2015 | Schettini ............ | G01N 33/5076 424/193.1 |
| 2025/0020645 | A1* | 1/2025 | Pun .................... | C12N 15/1138 |

OTHER PUBLICATIONS

Robertson, Debra L., and Gerald F. Joyce. "Selection in vitro of an RNA enzyme that specifically cleaves single-stranded DNA." Nature 344.6265 (1990): 467-468.
Roxo, Carolina, Weronika Kotkowiak, and Anna Pasternak. "G-quadruplex-forming aptamers—characteristics, applications, and perspectives." Molecules 24.20 (2019): 3781.
Ruella, Marco, et al. "Induction of resistance to chimeric antigen receptor T cell therapy by transduction of a single leukemic B cell." Nature medicine 24.10 (2018): 1499-1503.
Ruigrok, Vincent JB, et al. "Characterization of aptamer-protein complexes by X-ray crystallography and alternative approaches." International journal of molecular sciences 13.8 (2012): 10537-10552.
Rusconi, Christopher P., et al. "Antidote-mediated control of an anticoagulant aptamer in vivo." Nature biotechnology 22.11 (2004): 1423-1428.
Rusconi, Christopher P., et al. "RNA aptamers as reversible antagonists of coagulation factor IXa." Nature 419.6902 (2002): 90-94.
Salmikangas, Paula, Niamh Kinsella, and Paul Chamberlain. "Chimeric antigen receptor T-cells (CAR T-cells) for cancer immunotherapy-moving target for industry?." Pharmaceutical research 35.152 (2018): 1-8.
Schindelin, Johannes, et al. "Fiji: an open-source platform for biological-image analysis." Nature methods 9.7 (2012): 676-682.
Schmidt, Thomas GM, et al. "Molecular interaction between the Strep-tag affinity peptide and its cognate target, streptavidin." Journal of molecular biology 255.5 (1996): 753-766.
Schmidt, Thomas GM, and Arne Skerra. "The random peptide library-assisted engineering of a C-terminal affinity peptide, useful for the detection and purification of a functional Ig Fv fragment." Protein Engineering, Design and Selection 6.1 (1993): 109-122.
Schmidt, Thomas GM, and Arne Skerra. "The Strep-tag system for one-step purification and high-affinity detection or capturing of proteins." Nature protocols 2.6 (2007): 1528-1535.
Schmidt, Paul J., et al. "The transferrin receptor modulates Hfe-dependent regulation of hepcidin expression." Cell metabolism 7.3 (2008): 1-20.
Schuster, Stephen J., et al. "Tisagenlecleucel in adult relapsed or refractory diffuse large B-cell lymphoma." New England Journal of Medicine 380.1 (2019): 45-56.
Scott, C. S., et al. "Membrane transferrin receptor (TfR) and nuclear proliferation-associated Ki-67 expression in hemopoietic malignancies." Leukemia 2.7 (1988): 438-442.
Sefah, Kwame, et al. "Development of DNA aptamers using Cell-SELEX." Nature protocols 5.6 (2010): 1169-1185.
Shangguan, Dihua, et al. "Aptamers evolved from live cells as effective molecular probes for cancer study." Proceedings of the National Academy of Sciences 103.32 (2006): 11838-11843.

(Continued)

*Primary Examiner* — Brian Whiteman

(74) *Attorney, Agent, or Firm* — Christensen O'Connor Johnson Kindness PLLC

(57) ABSTRACT

Described herein are aptamers that bind to the transferrin receptor (e.g., CD71) and can be used, in part, for depleting transferrin receptor-expressing cells from a population of therapeutic cells. These aptamer compositions can be used in methods for isolating and/or enriching cells expressing CD71 or depleting cell populations of cells expressing CD71, including for example, tumor cells. Further provided are methods of using the aptamers or cell populations generated using them in the methods disclosed herein for therapies and/or drug delivery.

20 Claims, 78 Drawing Sheets
(69 of 78 Drawing Sheet(s) Filed in Color)

Specification includes a Sequence Listing.

(56) References Cited

OTHER PUBLICATIONS

Shangguan, Dihua, et al. "Cell-specific aptamer probes for membrane protein elucidation in cancer cells." Journal of proteome research 7.5 (2008): 2133-2139.
Shangguan, Dihua, et al. "Identification of liver cancer-specific aptamers using whole live cells." Analytical chemistry 80.3 (2008): 721-728.
Shangguan, Dihua, et al. "Optimization and modifications of aptamers selected from live cancer cell lines." ChemBioChem 8.6 (2007): 603-606.
Sievers, Fabian, et al. "Fast, scalable generation of high-quality protein multiple sequence alignments using Clustal Omega." Molecular systems biology 7.539 (2011): 1-6.
Sommermeyer, Daniel, et al. "Chimeric antigen receptor-modified T cells derived from defined CD8+ and CD4+ subsets confer superior antitumor reactivity in vivo." Leukemia 30.2 (2016): 492-500.
Stemberger, Christian, et al. "Novel serial positive enrichment technology enables clinical multiparameter cell sorting." PloS one 7.4 (2012): e35798.
Stroncek, David F., et al. "Elutriated lymphocytes for manufacturing chimeric antigen receptor T cells." Journal of translational medicine 15.59 (2017): 1-8.
Stroncek, David F., et al. "Myeloid cells in peripheral blood mononuclear cell concentrates inhibit the expansion of chimeric antigen receptor T cells." Cytotherapy 18.7 (2016): 1-17.
Sylvestre, Meilyn, et al. "Identification of a DNA aptamer that binds to human monocytes and macrophages." Bioconjugate Chemistry 31.8 (2020): 1899-1907.
Teoh, Jeffrey, et al. "Lisocabtagene maraleucel (liso-cel) manufacturing process control and robustness across CD19+ hematological malignancies." Blood 134 (2019): 593.
Thiel, Andreas, Alexander Scheffold, and Andreas Radbruch. "Immunomagnetic cell sorting—pushing the limits." Immunotechnology 4.2 (1998): 89-96.
Timonen, T., and E1 Saksela. "Isolation of human NK cells by density gradient centrifugation." Journal of Immunological methods 36.3-4 (1980): 285-291.
Tondreau, T., et al. "Isolation of BM mesenchymal stem cells by plastic adhesion or negative selection: phenotype, proliferation kinetics and differentiation potential." Cytotherapy 6.4 (2004): 372-379.
Tortorella, Stephanie, and Tom C. Karagiannis. "Transferrin receptor-mediated endocytosis: a useful target for cancer therapy." The Journal of membrane biology 247.4 (2014): 291-307.
Tuerk, Craig, and Larry Gold. "Systematic evolution of ligands by exponential enrichment: RNA ligands to bacteriophage T4 DNA polymerase." science 249.4968 (1990): 505-510.
Van Agthoven, André, et al. "Structural characteristics of the mouse transferrin receptor." European journal of biochemistry 140.2 (1984): 433-440.
Vormittag, Philipp, et al. "A guide to manufacturing CAR T cell therapies." Current opinion in biotechnology 53 (2018): 164-181.
Vujić, Maja. "Molecular basis of HFE-hemochromatosis." Frontiers in pharmacology 5 (2014): 42.
Waheed, Abdul, et al. "Regulation of transferrin-mediated iron uptake by HFE, the protein defective in hereditary hemochromatosis." Proceedings of the National Academy of Sciences 99.5 (2002): 3117-3122.
Walter, Johanna-Gabriela, Frank Stahl, and Thomas Scheper. "Aptamers as affinity ligands for downstream processing." Engineering in Life Sciences 12.5 (2012): 496-506.
Wang, Michael, et al. "KTE-X19 CAR T-cell therapy in relapsed or refractory mantle-cell lymphoma." New England Journal of medicine 382.14 (2020): 1-17.
Wang, Guodong, et al. "Selection and characterization of DNA aptamer against glucagon receptor by cell-SELEX." Scientific reports 7.7179 (2017): 1-10.
Weiss, Ronald, et al. "A comparative study of two separation methods to isolate monocytes." Cytometry Part A 95.2 (2019): 234-241.
Weiss, A., and J. D. Stobo. "Requirement for the coexpression of T3 and the T cell antigen receptor on a malignant human T cell line." The Journal of experimental medicine 160.5 (1984): 1284-1299.
Wilner, Samantha E., et al. "An RNA alternative to human transferrin: a new tool for targeting human cells." Molecular Therapy-Nucleic Acids 1 (2012): e21.
Worthen, Christal A., and Caroline A. Enns. "The role of hepatic transferrin receptor 2 in the regulation of iron homeostasis in the body." Frontiers in pharmacology 5 (2014): 34.
Wu, Xiaoqiu, et al. "DNA aptamer selected against pancreatic ductal adenocarcinoma for in vivo imaging and clinical tissue recognition." Theranostics 5.9 (2015): 985-994.
Wu, Xiaoqiu, et al. "Elucidation and structural modeling of CD71 as a molecular target for cell-specific aptamer binding." Journal of the American Chemical Society 141.27 (2019): 10760-10769.
Xu, Yingxi, et al. "2B4 costimulatory domain enhancing cytotoxic ability of anti-CD5 chimeric antigen receptor engineered natural killer cells against T cell malignancies." Journal of hematology & oncology 12.49 (2019): 1-13.
Xu, Jie, et al. "Exploratory trial of a biepitopic CAR T-targeting B cell maturation antigen in relapsed/refractory multiple myeloma." Proceedings of the National Academy of Sciences 116.19 (2019): 9543-9551.
Yang, Xiaolong, et al. "Regulation of DNA strand displacement using an allosteric DNA toehold." Journal of the American Chemical Society 138.42 (2016): 14076-14082.
Yeh, Chang-Jing G., Colin G. Taylor, and W. Page Faulka. "Transferrin binding by peripheral blood mononuclear cells in human lymphomas, myelomas and leukemias." Vox sanguinis 46.4 (1984): 217-223.
Ying, Zhitao, et al. "A safe and potent anti-CD19 CAR T cell therapy." Nature medicine 25.6 (2019): 947-953.
Yoon, Jung Won, et al. "Isolation of foreign material-free endothelial progenitor cells using CD31 aptamer and therapeutic application for ischemic injury." PloS one 10.7 (2015): e0131785.
Abramson, Jeremy S., et al. "Lisocabtagene maraleucel for patients with relapsed or refractory large B-cell lymphomas (Transcend NHL 001): a multicentre seamless design study." The Lancet 396.10254 (2020): 839-852.
Alam, Khalid K., Jonathan L. Chang, and Donald H. Burke. "FASTAptamer: a bioinformatic toolkit for high-throughput sequence analysis of combinatorial selections." Molecular Therapy-Nucleic Acids 4 (2015): e230.
Alcantara, Marion, et al. "CAR T-cells for T-cell malignancies: challenges in distinguishing between therapeutic, normal, and neoplastic T-cells." Leukemia 32.11 (2018): 2307-2315.
Allen, Elizabeth S., et al. "Autologous lymphapheresis for the production of chimeric antigen receptor T cells." Transfusion 57.5 (2017): 1-21.
Armas, Pablo, Sofía Nasif, and Nora B. Calcaterra. "Cellular nucleic acid binding protein binds G-rich single-stranded nucleic acids and may function as a nucleic acid chaperone." Journal of cellular biochemistry 103.3 (2008): 1013-1036.
Asnafi, Vahid, et al. "Analysis of TCR, pTα, and RAG-1 in T-acute lymphoblastic leukemias improves understanding of early human T-lymphoid lineage commitment." Blood, The Journal of the American Society of Hematology 101.7 (2003): 2693-2703.
Bailey, Timothy L., et al. "Meme Suite: tools for motif discovery and searching." Nucleic acids research 37.suppl_2 (2009): W202-W208.
Bates, Paula J., et al. "Antiproliferative activity of G-rich oligonucleotides correlates with protein binding." Journal of Biological Chemistry 274.37 (1999): 26369-26377.
Benhalevy, Daniel, et al. "The human CCHC-type zinc finger nucleic acid-binding protein binds G-rich elements in target mRNA coding sequences and promotes translation." Cell reports 18.12 (2017): 1-25.

(56) References Cited

OTHER PUBLICATIONS

Bennett, Melanie J., José A. Lebrón, and Pamela J. Bjorkman. "Crystal structure of the hereditary haemochromatosis protein HFE complexed with transferrin receptor." Nature 403.6765 (2000): 46-53.
Berdeja, Jesus G., et al. "Ciltacabtagene autoleucel, a B-cell maturation antigen-directed chimeric antigen receptor T-cell therapy in patients with relapsed or refractory multiple myeloma (Cartitude-1): a phase 1b/2 open-label study." The Lancet 398.10297 (2021): 314-324.
Bersenev, Alexey. "CAR-T cell manufacturing: time to put it in gear." Transfusion 57.5 (2017): 1104-1106.
Biglione, Catalina, et al. "Optimizing circulating tumor cells' capture efficiency of magnetic nanogels by transferrin decoration." Polymers 10.2 (2018): 174.
Bonner, W. A., et al. "Fluorescence activated cell sorting." Review of Scientific Instruments 43.3 (1972): 404-409.
Brada, M., et al. "Circulating lymphoma cells in patients with B & T non-Hodgkin's lymphoma detected by immunoglobulin and T-cell receptor gene rearrangement." British journal of cancer 56.2 (1987): 147-152.
Cardle, Ian I., et al. "Biomaterials in chimeric antigen receptor T-cell process development." Accounts of Chemical Research 53.9 (2020): 1724-1738.
Caroli, Jimmy, et al. "Aptani: a computational tool to select aptamers through sequence-structure motif analysis of HT-SELEX data." 2015.
Caruso, Arnoldo, et al. "Flow cytometric analysis of activation markers on stimulated T cells and their correlation with cell proliferation." Cytometry: The Journal of the International Society for Analytical Cytology 27.1 (1997): 71-76.
Chen, Yvonne Y. "Cell fishing with DNA aptamers." Nature Biomedical Engineering 3.10 (2019): 757-758.
Chen, Lina, Casey Yan, and Zijian Zheng. "Functional polymer surfaces for controlling cell behaviors." Materials Today 21.1 (2018): 38-59.
Chen, Kangfu, et al. "Incorporation of lateral microfiltration with immunoaffinity for enhancing the capture efficiency of rare cells." Scientific reports 10.1 (2020): 1-12.
Chen, Yongli, et al. "Regenerative nanooctopus based on multivalent-aptamer-functionalized magnetic microparticles for effective cell capture in whole blood." Analytical chemistry 91.6 (2019): 4017-4022.
Cheng, Emmeline L., et al. "Discovery of a Transferrin Receptor 1-Binding Aptamer and Its Application in Cancer Cell Depletion for Adoptive T-Cell Therapy Manufacturing." Journal of the American Chemical Society 144.30 (2022): 13851-13864.
Cheng, Yifan, et al. "Structure of the human transferrin receptor-transferrin complex." Cell 116.4 (2004): 565-576.
Cooper, Matthew L., et al. "An "off-the-shelf" fratricide-resistant CAR-T for the treatment of T cell hematologic malignancies." Leukemia 32.9 (2018): 1970-1983.
Dahotre, Shreyas N., et al. "Individually addressable and dynamic DNA gates for multiplexed cell sorting." Proceedings of the National Academy of Sciences 115.17 (2018): 4357-4362.
Das Gupta, A., et al. "Correlation of transferrin receptor expression with histologic grade and immunophenotype in chronic lymphocytic leukemia and non-Hodgkin's lymphoma." Hematologic pathology 4.1 (1990): 37-41.
David, Aldana P., et al. "CNBP controls transcription by unfolding DNA G-quadruplex structures." Nucleic Acids Research 47.15 (2019): 7901-7913.
Ding, Pi, et al. "Aptamer-based nanostructured interfaces for the detection and release of circulating tumor cells." Journal of materials chemistry B 8.16 (2020): 3408-3422.
Dong, Zhao Ming, Lydgia Jackson, and Juneann W. Murphy. "Mechanisms for induction of L-selectin loss from T lymphocytes by a cryptococcal polysaccharide, glucuronoxylomannan." Infection and immunity 67.1 (1999): 220-229.
Elkord, Eyad, et al. "Human monocyte isolation methods influence cytokine production from in vitro generated dendritic cells." Immunology 114.2 (2005): 204-212.
Ellington, Andrew D., and Jack W. Szostak. "In vitro selection of RNA molecules that bind specific ligands." nature 346.6287 (1990): 818-822.
Feder, J. N., et al. "A novel MHC class I-like gene is mutated in patients with hereditary haemochromatosis." Nature genetics 13.4 (1996): 399-408.
Feder, John N., et al. "The hemochromatosis gene product complexes with the transferrin receptor and lowers its affinity for ligand binding." Proceedings of the National Academy of Sciences 95.4 (1998): 1472-1477.
Rambaut, Andrew, 2007, "FigTree," Molecular evolution, phylogenetics and epidemiology, <tree.bio.ed.ac.uk/software/figtree/> [Retrieved Nov. 3, 2022], 6 pages.
Finney, Olivia C., et al. "CD19 CAR T cell product and disease attributes predict leukemia remission durability." The Journal of clinical investigation 129.5 (2019): 2123-2132.
Fleischer, Lauren C., H. Trent Spencer, and Sunil S. Raikar. "Targeting T cell malignancies using CAR-based immunotherapy: challenges and potential solutions." Journal of hematology & oncology 12.141 (2019): 1-21.
Gatter, Kevin C., et al. "Transferrin receptors in human tissues: their distribution and possible clinical relevance." Journal of clinical pathology 36.5 (1983): 539-545.
Gelinas, Amy D., Douglas R. Davies, and Nebojsa Janjic. "Embracing proteins: structural themes in aptamer-protein complexes." Current opinion in structural biology 36 (2016): 122-132.
Gold, Larry, et al. "Aptamer-based multiplexed proteomic technology for biomarker discovery." Nature Precedings 5.12 (2010): e15004.
Goujon, Mickael, et al. "A new bioinformatics analysis tools framework at EMBL-EBI." Nucleic acids research 38. suppl_2 (2010): W695-W699.
Gray, Bethany Powell, et al. "Aptamers as reversible sorting ligands for preparation of cells in their native state." Cell chemical biology 27.2 (2020): 232-244.e1-e7.
Habeshaw, J. A., et al. "Correlation of transferrin receptor expression with histological class and outcome in non-Hodgkin lymphoma." The Lancet 321.8323 (1983): 498-501.
Hagag, Adel A., et al. "Prognostic value of transferrin receptor-1 (CD71) expression in acute lymphoblastic leukemia." Endocrine, Metabolic & Immune Disorders—Drug Targets. 2018. vol. 18. No. 00.
Hao, Yaya, et al. "Programmable Live-Cell CRISPR Imaging with Toehold-Switch-Mediated Strand Displacement." Angew. Chem. Int. Ed. 2020, 59, 20612-20618.
Harding, Fiona A., et al. "The immunogenicity of humanized and fully human antibodies: residual immunogenicity resides in the CDR regions." MAbs. vol. 2. No. 3. 2010, pp. 256-265.
Hoffmann, Jean-Marc, et al. "Differences in expansion potential of naive chimeric antigen receptor T cells from healthy donors and untreated chronic lymphocytic leukemia patients." Frontiers in immunology 8 (2018): 1956.
Hovanessian, Ara G., et al. "The cell-surface-expressed nucleolin is associated with the actin cytoskeleton." Experimental cell research 261.2 (2000): 312-328.
Iyer, Rohin K., et al. "Industrializing autologous adoptive immunotherapies: manufacturing advances and challenges." Frontiers in medicine 5 (2018): 150.
Jackson, C. J., et al. "Binding of human endothelium to Ulex europaeus I-coated Dynabeads: application to the solation of microvascular endothelium." Journal of cell science 96.2 (1990): 257-262.
Janssen, William Earl, and Angelyn M. Rios. "Non-specific cell binding characteristics of para-magnetic polystyrene microspheres used for antibody-mediated cell selection." Journal of immunological methods 121.2 (1989): 289-294.
Kacherovsky, Nataly, et al. "Discovery and characterization of spike N-terminal domain-binding Aptamers for rapid SARS-CoV-2 detection." Angew. Chem. Int. Ed. 2021, 60, 21211-21215.

(56) References Cited

OTHER PUBLICATIONS

Kacherovsky, Nataly, et al. "Multiplexed gene transfer to a human T-cell line by combining Sleeping Beauty transposon system with methotrexate selection." Biotechnology and Bioengineering 112.7 (2015): 1429-1436.
Kacherovsky, Nataly, et al. "Traceless aptamer-mediated isolation of CD8+ T cells for chimeric antigen receptor T-cell therapy." Nature biomedical engineering 3.10 (2019): 783-795.
Kikin, Oleg, Lawrence D'Antonio, and Paramjeet S. Bagga. "QGRS Mapper: a web-based server for predicting G-quadruplexes in nucleotide sequences." Nucleic acids research 34.suppl_2 (2006): W676-W682.
Korndörfer, Ingo P., and Arne Skerra. "Improved affinity of engineered streptavidin for the Strep-tag II peptide is due to a fixed open conformation of the lid-like loop at the binding site." Protein science 11.4 (2002): 883-893.
Kosuri, Sriram, and George M. Church. "Large-scale de novo DNA synthesis: technologies and applications." Nature methods 11.5 (2014): 499-507.
Kozlowski, R., et al. "Transferrin receptor expression on AML blasts is related to their proliferative potential." British Journal of haematology 69.2 (1988): 275-280.
Kumar, Ashok, and Akshay Srivastava. "Cell separation using cryogel-based affinity chromatography." Nature protocols 5.11 (2010): 1737-1747.
Laghmouchi, Aicha, et al. "Long-term in vitro persistence of magnetic properties after magnetic bead-based cell separation of T cells." Scandinavian journal of immunology 92.3 (2020): e12924.
Lebrón, José A., et al. "Crystal structure of the hemochromatosis protein HFE and characterization of its interaction with transferrin receptor." Cell 93.1 (1998): 111-123.
Lee, Eunhye, et al. "CNBP controls tumor cell biology by regulating tumor-promoting gene expression." Molecular Carcinogenesis 58.8 (2019): 1492-1501.
Levine, Bruce L., et al. "Global manufacturing of CAR T cell therapy." Molecular Therapy—Methods & Clinical Development 4 (2017): 92-101.
Li, Long, et al. "Aptamer displacement reaction from live-cell surfaces and its applications." J. Am. Chem. Soc. 2019, 141, 17174-17179.
Li, Xiaowei, et al. "Enhanced in vivo blood-brain barrier penetration by circular Tau-transferrin receptor bifunctional aptamer for tauopathy therapy." Journal of the American Chemical Society 142.8 (2020): 3862-3872.
Li, Wan-Ming, et al. "Selection of metastatic breast cancer cell-specific aptamers for the capture of CTCs with a metastatic phenotype by cell-SELEX." Molecular Therapy-Nucleic Acids 12 (2018): 707-717.
Lin, Paul, et al. "Efficient lentiviral transduction of human mesenchymal stem cells that preserves proliferation and differentiation capabilities." Stem cells translational medicine 1.12 (2012): 886-897.
Liu, Hongfei, et al. "Alternative splicing analysis in human monocytes and macrophages reveals MBNL1 as major regulator." Nucleic acids research 46.12 (2018): 6069-6086.
Liu, Zhian, et al. "Negative enrichment by immunomagnetic nanobeads for unbiased characterization of circulating tumor cells from peripheral blood of cancer patients." Journal of translational medicine 9.1 (2011): 1-8.
Liu, Qian, et al. "Significance of CD71 expression by flow cytometry in diagnosis of acute leukemia." Leukemia & lymphoma 55.4 (2014): 892-898.
Locke, Frederick L., et al. "Long-term safety and activity of axicabtagene ciloleucel in refractory large B-cell lymphoma (ZUMA-1): a single-arm, multicentre, phase 1-2 trial." The lancet oncology 20.1 (2019): 1-24.
Lyons, Paul A., et al. "Microarray analysis of human leucocyte subsets: the advantages of positive selection and rapid purification." BMC genomics 8.64 (2007): 1-12.
Lyu, Yifan, et al. "Generating cell targeting aptamers for nanotheranostics using cell-SELEX." Theranostics 6.9 (2016): 1440-1452.
Mallikaratchy, Prabodhika, et al. "Aptamer directly evolved from live cells recognizes membrane bound immunoglobin heavy mu chain in Burkitt's lymphoma cells." Molecular & Cellular Proteomics 6.12 (2007): 2230-2238.
Marek, Ryan, et al. "Magnetic cell sorting: a fast and effective method of concurrent isolation of high purity viable astrocytes and microglia from neonatal mouse brain tissue." Journal of Neuroscience Methods 175.1 (2008): 108-118.
Marks, David I., et al. "T-cell acute lymphoblastic leukemia in adults: clinical features, immunophenotype, cytogenetics, and outcome from the large randomized prospective trial (UKALL XII/ ECOG 2993)." Blood, The Journal of the American Society of Hematology 114.25 (2009): 5136-5145.
Maude, Shannon L., et al. "Chimeric antigen receptor T cells for sustained remissions in leukemia." New England Journal of Medicine 371.16 (2014): 1-17.
Maude, Shannon L., et al. "Tisagenlecleucel in children and young adults with B-cell lymphoblastic leukemia." New England Journal of Medicine 378.5 (2018): 1-18.
Mayle, Kristine M., Alexander M. Le, and Daniel T. Kamei. "The intracellular trafficking pathway of transferrin." Biochimica et Biophysica Acta (BBA)—General Subjects 1820.3 (2012): 264-281.
Jeffrey Medeiros, L., et al. "Transferrin receptor expression by non-hodgkin's lymphomas. Correlation with morphologic grade and survival." Cancer 61.9 (1988): 1844-1851.
Miltenyi, Stefan, et al. "High gradient magnetic cell separation with MACS." Cytometry 11:231-238 (1990).
Mohr, Fabian, et al. "Efficient immunoaffinity chromatography of lymphocytes directly from whole blood." Scientific reports 8.16731 (2018): 1-6.
Mohr, Fabian, et al. "Minimally manipulated murine regulatory T cells purified by reversible Fab Multimers are potent suppressors for adoptive T-cell therapy." European Journal of Immunology 47.12 (2017): 2153-2162.
Montemiglio, Linda Celeste, et al. "Cryo-EM structure of the human ferritin-transferrin receptor 1 complex." Nature communications 10.1 (2019): 1-8.
Motamedi, Melika, Lai Xu, and Shokrollah Elahi. "Correlation of transferrin receptor (CD71) with Ki67 expression on stimulated human and mouse T cells: The kinetics of expression of T cell activation markers." Journal of immunological methods 437 (2016): 43-52.
Munshi, Nikhil C., et al. "Idecabtagene vicleucel in relapsed and refractory multiple myeloma." New England Journal of Medicine 384.8 (2021): 705-716.
Neelapu, Sattva S., et al. "Axicabtagene ciloleucel CAR T-cell therapy in refractory large B-cell lymphoma." New England Journal of Medicine 377.26 (2017): 1-21.
Neudorfer, Julia, et al. "Reversible HLA multimers (Streptamers) for the isolation of human cytotoxic T lymphocytes functionally active against tumor-and virus-derived antigens." Journal of immunological methods 320.1-2 (2007): 119-131.
Odendahl, Marcus, et al. "Clinical-scale isolation of 'minimally manipulated' cytomegalovirus-specific donor lymphocytes for the treatment of refractory cytomegalovirus disease." Cytotherapy 16.9 (2014): 1245-1256.
Ohashi, Pamela S., et al. "Reconstitution of an active surface T3/T-cell antigen receptor by DNA transfer." Nature 316.6029 (1985): 606-609.
Olden, Brynn R., et al. "Cationic polymers for non-viral gene delivery to human T cells." Journal of Controlled Release 282 (2018): 140-147.
Olden, Brynn R., et al. "Identifying key barriers in cationic polymer gene delivery to human T cells." Biomaterials science 7.3 (2019): 789-797.
Øren, Anita, et al. "A comparative study of immunomagnetic methods used for separation of human natural killer cells from peripheral blood." Journal of immunological methods 303.1-2 (2005): 1-10.
Padmanabhan, K. A. I. L. L. A. T. H. E., et al. "The structure of alpha-thrombin inhibited by a 15-mer single-stranded DNA aptamer." Journal of Biological Chemistry 268.24 (1993): 17651-17654.

(56) References Cited

OTHER PUBLICATIONS

Płoszyńska, Anna, et al. "Cytometric evaluation of transferrin receptor 1 (CD71) in childhood acute lymphoblastic leukemia." Folia Histochemica et Cytobiologica 50.2 (2012): 304-311.
Powell Jr, Daniel J., et al. "Efficient clinical-scale enrichment of lymphocytes for use in adoptive immunotherapy using a modified counterflow centrifugal elutriation program." Cytotherapy 11.7 (2009): 923-935.
Probst, Christine E., Pavel Zrazhevskiy, and Xiaohu Gao. "Rapid multitarget immunomagnetic separation through programmable DNA linker displacement." Journal of the American Chemical Society 133.43 (2011): 17126-17129.
Raje, Noopur, et al. "Anti-BCMA CAR T-cell therapy bb2121 in relapsed or refractory multiple myeloma." New England Journal of Medicine 380.18 (2019): 1-21.
Ren, Simei, et al. "The RNA/DNA-binding protein PSF relocates to cell membrane and contributes cells' sensitivity to antitumor drug, doxorubicin." Cytometry Part A 85.3 (2014): 231-241.
Reyes-Reyes, E., Yun Teng, and Paula J. Bates. "A New Paradigm for Aptamer Therapeutic AS1411 Action: Uptake by Macropinocytosis and Its Stimulation by a Nucleolin-Dependent MechanismRole of Macropinocytosis in AS1411 Uptake and Mechanism." Cancer research 70.21 (2010): 1-21.
Zadeh, Joseph N., et al. "Nupack: Analysis and design of nucleic acid systems." Journal of computational chemistry 32.1 (2011): 170-173.
Zhang, Nan, et al. "A DNA aptameric ligand of human transferrin receptor generated by cell-SELEX." International Journal of Molecular Sciences 22.16 (2021): 8923.
Zhang, David Yu, and Erik Winfree. "Control of DNA strand displacement kinetics using toehold exchange." Journal of the American Chemical Society 131.47 (2009): 17303-17314.
Zhang, Kaiming, et al. "Cryo-EM structure of a 40 kDa SAM-IV riboswitch RNA at 3.7 Å resolution." Nature communications 10.5511 (2019): 1-6.
Zhang, David Yu, and Georg Seelig. "Dynamic DNA nanotechnology using strand-displacement reactions." Nature chemistry 3.2 (2011): 103-113.
Zhang, Zhaoyang, et al. "Programmable hydrogels for controlled cell catch and release using hybridized aptamers and complementary sequences." Journal of the American Chemical Society 134.38 (2012): 15716-15719.
Zhang, Nan, et al. "Transferrin receptor-mediated internalization and intracellular fate of conjugates of a DNA aptamer." Molecular Therapy—Nucleic Acids 27 (2022): 1249-1259.
Zhou, Jiehua, and John Rossi. "Aptamers as targeted therapeutics: current potential and challenges." Nature reviews Drug discovery 16.3 (2017): 181-202.
Zhu, Beili, and Shashi K. Murthy. "Stem cell separation technologies." Current opinion in chemical engineering 2.1 (2013): 3-7.

* cited by examiner

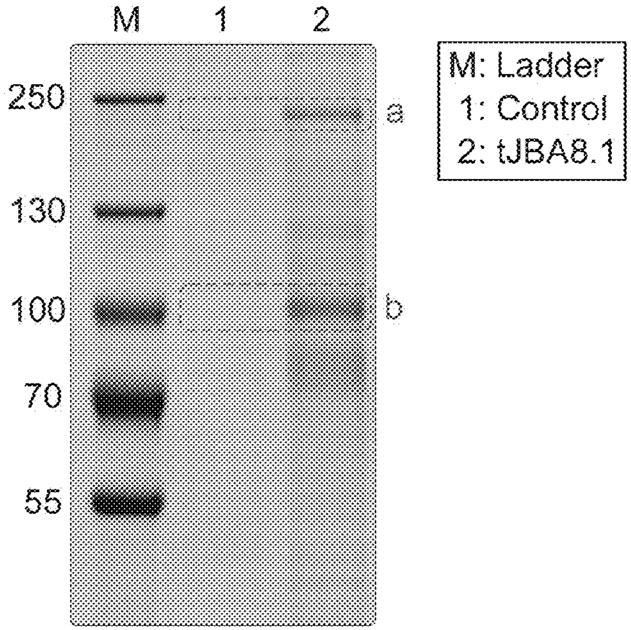
FIG. 3A
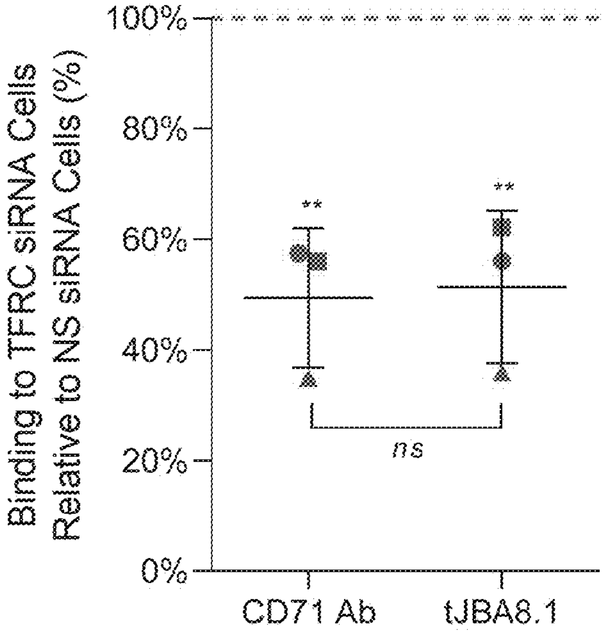
FIG. 3C
| Band | Description | Lane 1: Peptide Coverage (Control) | Lane 2: Peptide Coverage (tJBA8.1) | Lane 1: # of Peptides (Control) | Lane 2: # of Peptides (tJBA8.1) |
|---|---|---|---|---|---|
| a | Transferrin receptor protein 1 | 9% | 62% | 4 | 52 |
| b | Transferrin receptor protein 1 | 13% | 58% | 5 | 50 |
FIG. 3B

JBA8.1 ATCCAGAGTGACGCAGCAGCGTAAAGGGGGTGTTTGTGCGGTGTGGAGTGCGCGTGCTGCTGCTGGACACGGTGGCTTAGT rvCD71apt GGAGTCACACGCATTAGCGTAAAGGGGGTGTTTGTGCGGTGTGGAGTGCGCGTGCTAATGCTGGAGTGTTTCC*CAGGACCC*

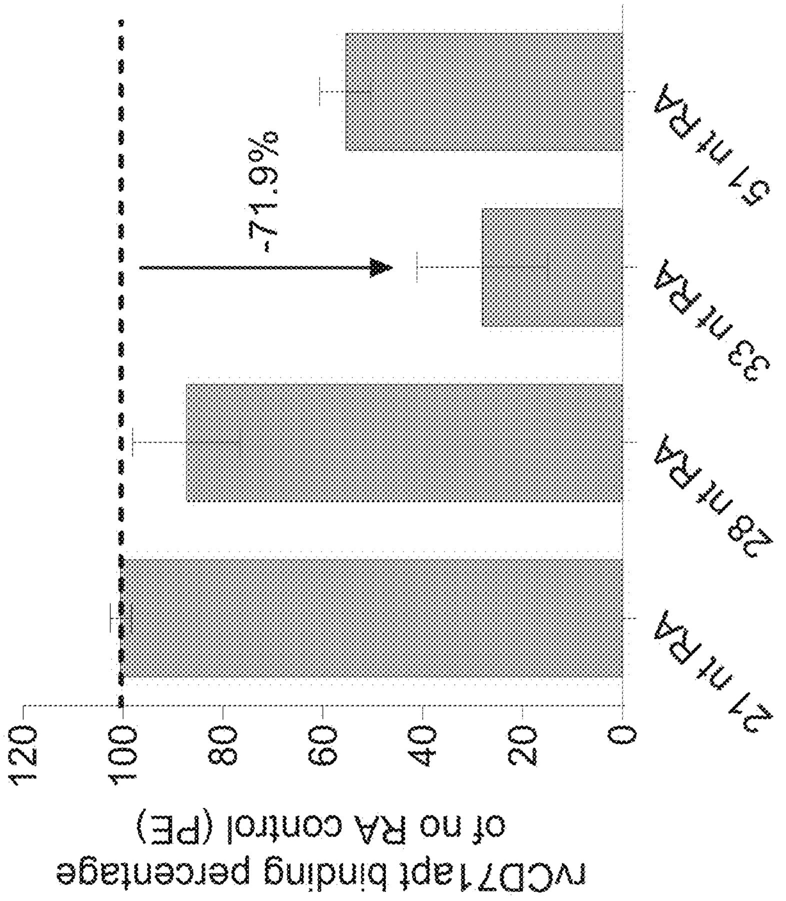
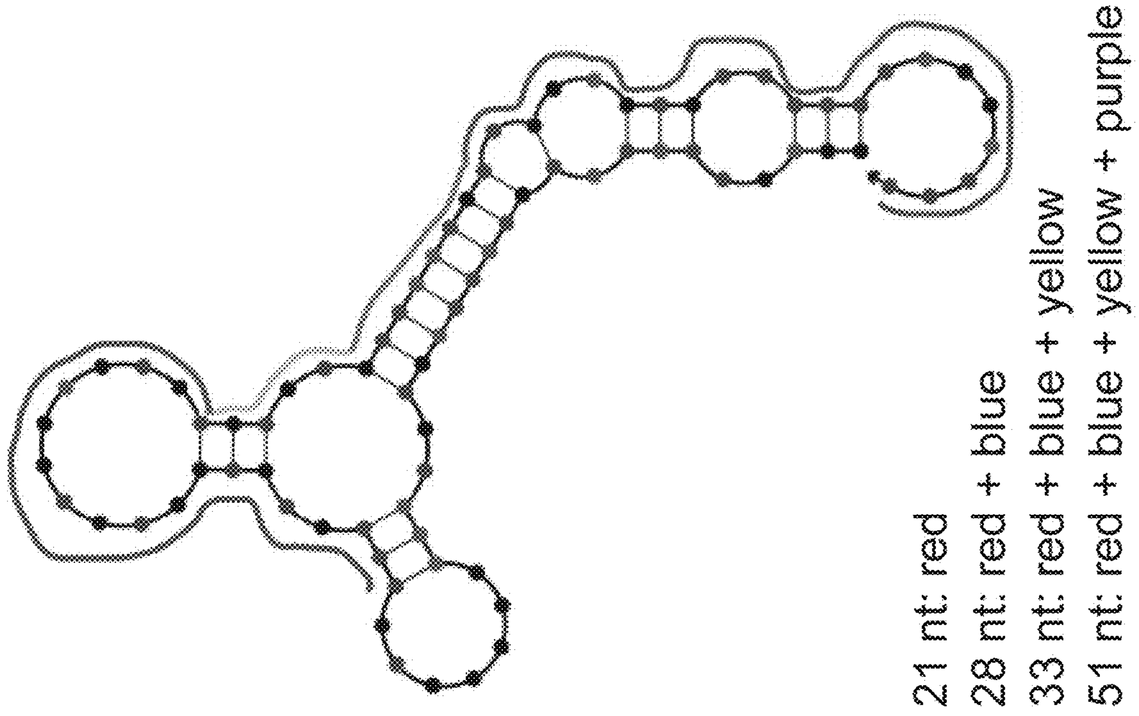
*FIG. 8A*

| Toehold sequences |
|---|
| 1 GC: ATTCAATA |
| 3 GC: ATACCCTA |
| 6 GC: CAGGACCC |

```
JBA8.1       TCCAGAGTGACGCAGCAGCGTAAAGGGG------GTGTTTGTGC----GGTGTGGAGTGCGCGTGCTGCTGCTGGACACGGTGGCTTAGT
rvCD8apt      CCAGAGTGACGCAGCAAC--AGAGGTGTAGAAGTACACGTGAACAAGCTTGAAATTGTCTCTGACAGAGGTGGACACGGTGGCTTTTAGT
(A3t)
```

Round 8
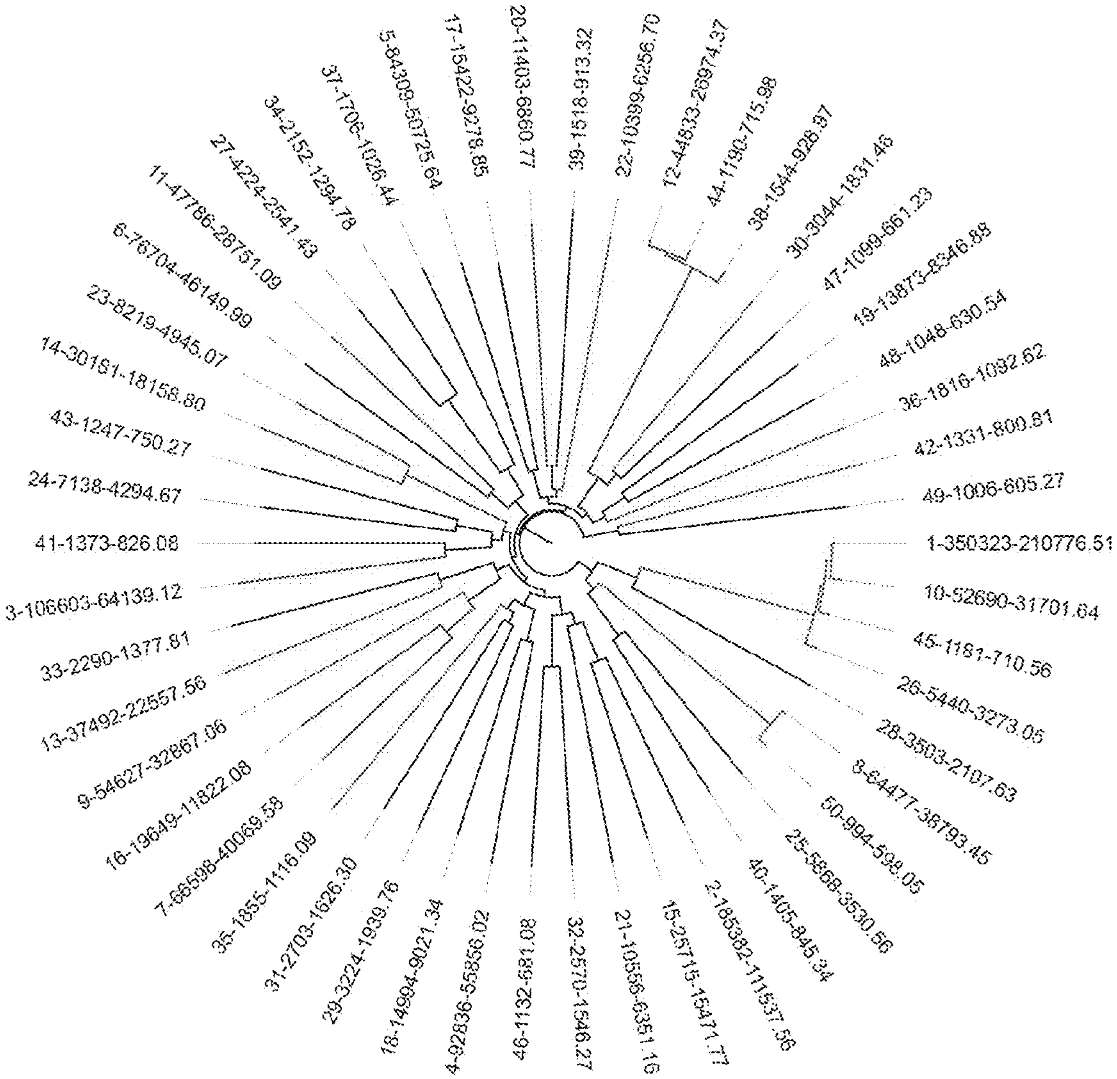
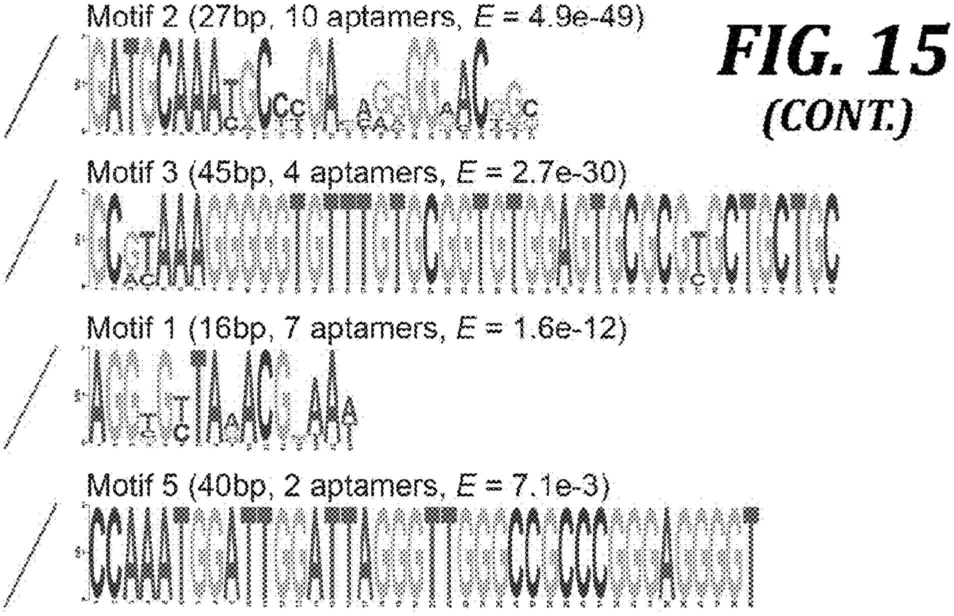
*FIG. 15 (CONT.)* tJBA8.1: GCAGCA-GCGTAAAGGGGGTGTTTGTGCGGTGTGGAG-TGCGCGTGCTGCTGC
XQ-2d: ACTCATAGGGTT-AGGGGCTGCTGGCCAGATACTCAGATGGTAGGGTTACTATGAGC

N45 Random Region

JBA8.1: GCGTAAAGGGGGTGTTTGTGCGGTGTGGAGTGCGCGTGCTGCTGC
JBA8.2: ATCCGGGAGAGTCGTTGTGTTGAGGTCCGCCCCTGCTCGCCCGCG
JBA8.3: GGGGCCGCGGATGCAAACGCCCGATA GGGGGACGGCACTGGAGCT
JBA8.4: ACCCAAACCACCAGCCGGGGATGCAAACACCGCACAGGGAACGGC
JBA8.7: ACCACAGATGCAAATGCGCGAGAGCGGGACGGTTTGCTAGGCTCA
JBA8.8: GTGGGCCAAATGGATTGGATTAGGGTTGGGCCGCCCGGGAGGGGT
JBA8.11: GCCGGTCGCAGATGCAAATGCCCGACAGGGGGACGCGGGCTGCCA
JBA8.15: CTCTCGGGGGGTAGGTGGGAAGGGGGCCGCCCCCTGGGTTAGGCT
JBA8.17: AGGTGGCTGTGGGCGGATGGTGGGCTCGCGTGGGCGGCCACCTGA

*FIG. 28C*

| Band | Description | Control Lane: Peptide Coverage | tUBA8.1 Lane: Peptide Coverage | Control Lane: # of Peptides | tUBA8.1 Lane: # of Peptides |
|---|---|---|---|---|---|
| f | Cellular nucleic-acid binding protein | 5% | 20% | 1 | 3 |

```
SP|P02786|TFR1_HUMAN MMDQARSAFSNLFGGEPLSYTRFSLARQVDGDN-SHVEMKLAVDEEENAD---------- 49
SP|Q9UP52|TFR2_HUMAN -MERLWGLFQRAQQLSPRSS--QTVYQRVEGPRKGHLEEEE-EDGEEGAETLAHFCPMEL 56
                      *::  . *..    .* *    :: ::*:* . .*:* :   * **.*:

SP|P02786|TFR1_HUMAN -------NNTKANVTKPKRCS--GSICYGTIAVIVFFLIGFMIGYLGYCKGVEPKTECER 100
SP|Q9UP52|TFR2_HUMAN RGPEPLGSRPRQPNLIPWAAAGRRAAPYLVLTALLIFTGAFLLGYVAFRGSCQACGDS-- 114
                            .. :     *  .:   :  * .::.:::*  .*::**:.:  . :   :.

SP|P02786|TFR1_HUMAN LAGTESPVREEPGEDFPAARRLYWDDLKRKLSEKLDSTDFTGTIKLLNENSYVPREAGSQ 160
SP|Q9UP52|TFR2_HUMAN VLVVSEDVNYEPDLDFH-QGRLYWSDLQAMFLQFLGEGRLEDTIRQ---TSLRERVAGSA 170
                     :  ... *. **. **    ****.**:  : : *..  : .**:     .*   * ***

SP|P02786|TFR1_HUMAN KDENLALYVENQFREFKLSKVWRDQHFVKIQVKDSAQNSV-IIVDKNGRL--VYLVENPG 217
SP|Q9UP52|TFR2_HUMAN GMAALTQDIRAALSRQKLDHVWTDTHYVGLQFPDPAHPNTLHWVDEAGKVGEQLPLEDPD 230
                         *:  :.  : . **.:** * *:* :*. * *: ..   **: *::     :*:*.

SP|P02786|TFR1_HUMAN GYVAYSKAATVTGKLVHANFGTKKDFEDLYTP---VNGSIVIVRAGKITFAEKVANAESL 274
SP|Q9UP52|TFR2_HUMAN VYCPYSAIGNVTGELVYAHYGRPEDLQDLRARGVDPVGRLLLVRVGVISFAQKVTNAQDF 290
                      *  **  ..***:**:*::*  :*::** :       * :::**.* *:**:**:**:.:

SP|P02786|TFR1_HUMAN NAIGVLIYMDQTKF------PIVNAELSFFGHAHLGTGDPYTPGFPSFNHTQFPPSRSSG 328
SP|Q9UP52|TFR2_HUMAN GAQGVLIYPEPADFSQDPPKPSLSSQQAVYGHVHLGTGDPYTPGFPSFNQTQFPPVASSG 350
                     .* ***** : :.*      * :.:: :.:**.***************:*****  ***

SP|P02786|TFR1_HUMAN LPNIPVQTISRAAAEKLFGNMEGDC-PSDWKTDSTCR-MVTSESKNVKLTVSNVLKEIKI 386
SP|Q9UP52|TFR2_HUMAN LPSIPAQPISADIASRLLRKLKGPVAPQEWQGSLLGSPYHLGPGPRLRLVVNNHRTSTPI 410
                     **.**.* **   *.:*: :::*   *.:*: .         . . .::*.*.*  ..  *
```

FIG. 31

```
SP|P02786|TFR1_HUMAN LNIFGVIKGFVEPDHYVVVGAQRDAWGPGAAKSGVGTALLLKLAQMFSDMVLKDGFQPSR 446
SP|Q9UP52|TFR2_HUMAN NNIFGCIEGRSEPDHYVVIGAQRDAWGPGAAKSAVGTAILLELVRTFSSMV-SNGFRPRR 469
                      **** *:*  *******:*************.****:**:*.: **.** .:**:* *

SP|P02786|TFR1_HUMAN SIIFASWSAGDFGSVGATEWLEGYLSSLHLKAFTYINLDKAVLGTSNFKVSASPLLYTLI 506
SP|Q9UP52|TFR2_HUMAN SLLFISWDGGDFGSVGSTEWLEGYLSVLHLKAVVYVSLDNAVLGDDKFHAKTSPLLTSLI 529
                     *::* **..******:********* *****..*:.**:****  .:*:..:**** :**

SP|P02786|TFR1_HUMAN EKTMQNVKHPVT-------GQFLYQDSNWASK-VEKLTLDNAAFPFLAYSGIPAVSFCFCE 559
SP|Q9UP52|TFR2_HUMAN ESVLKQVDSPNHSGQTLYEQVVFTNPSWDAEVIRPLPMDSSAYSFTAFVGVPAVEFSFME 589
                     *..:::*. *        *.:: : .* :: :. * :*.:*: * *: *:***.*.* *

SP|P02786|TFR1_HUMAN D-TDYPYLGTTMDTYKELIERIP-ELNKVARAAAEVAGQFVIKLTHDVELNLDYERYNSQ 617
SP|Q9UP52|TFR2_HUMAN DDQAYPFLHTKEDTYENLHKVLQGRLPAVAQAVAQLAGQLLIRLSHDRLLPLDFGRYGDV 649
                     *   **:* *. ***::* : :  .*  **:*.*::***::*:*:**  * **: **..

SP|P02786|TFR1_HUMAN LLSFVRDLNQYRADIKEMGLSLQWLYSARGDFFRATSRLTTDFGNAEKTDRFVMKKLNDR 677
SP|Q9UP52|TFR2_HUMAN VLRHIGNLNEFSGDLKARGLTLQWVYSARGDYIRAAEKLRQEIYSSEERDERLTRMYNVR 709
                     :* .: :**:: .*:*  **:***:******::**:.:*  :: .:*: *. : :  * *

SP|P02786|TFR1_HUMAN VMRVEYHFLSPYVSPKESPFRHVFWGSGSHTLPALLENLKLRKQNN---------GAFNE 728
SP|Q9UP52|TFR2_HUMAN IMRVEFYFLSQYVSPADSPFRHIFMGRGDHTLGALLDHLRLLRSNSSGTPGATSSTGFQE 769
                     :****::*** **** :*****:* * *.*** ***::*:* :.*.          .*:*

SP|P02786|TFR1_HUMAN TLFRNQLALATWTIQGAANALSGDVWDIDNEF 760
SP|Q9UP52|TFR2_HUMAN SRFRRQLALLTWTLQGAANALSGDVWNIDNNF 801
                     : **.**** ***:************:***:*
```

*FIG. 31*
*(CONT.)*

```
SP|P02786|TFR1_HUMAN MMDQARSAFSNLFGGEPLSYTRFSLARQVDGDNSHVEMKLAVDEEENADNNTKANVTKPK 60
SP|Q62351|TFR1_MOUSE MMDQARSAFSNLFGGEPLSYTRFSLARQVDGDNSHVEMKLAADEEENADNNMKASVRKPK 60
                     *****************************************.********* **.* ***

SP|P02786|TFR1_HUMAN RCSGSICYGTIAVIVFFLIGFMIGYLGYCKGVEPKTECERLAGTESPVREE--PGEDFPA 118
SP|Q62351|TFR1_MOUSE RFNGRLCFAAIALVIFFLIGFMSGYLGYCKRVEQKEECVKLAETEETDKSETMETEDVPT 120
                     * .* :*:.:**:::******* ******* ** * ** :** **.   :.*    **.*:

SP|P02786|TFR1_HUMAN ARRLYWDDLKRKLSEKLDSTDFTGTIKLLNENSYVPREAGSQKDENLALYVENQFREFKL 178
SP|Q62351|TFR1_MOUSE SSRLYWADLKTLLSEKLNSIEFADTIKQLSQNTYTPREAGSQKDESLAYYIENQFHEFKF 180
                     : **** ***  *****:* :*:.*** *.:*:*.**********.** *:****:***:

SP|P02786|TFR1_HUMAN SKVWRDQHFVKIQVKDSAQNSVIIVDKNGRLVYLVENPGGYVAYSKAATVTGKLVHANFG 238
SP|Q62351|TFR1_MOUSE SKVWRDEHYVKIQVKSSIGQNMVTIVQSNGNLDPVESPEGYVAFSKPTEVSGKLVHANFG 240
                     ******:*:******.*  :.:: : :..  :  **.* ****:** : *:*********

SP|P02786|TFR1_HUMAN TKKDFEDLYTPVNGSIVIVRAGKITFAEKVANAESLNAIGVLIYMDQTKFPIVNAELSFF 298
SP|Q62351|TFR1_MOUSE TKKDFEELSYSVNGSLVIVRAGEITFAEKVANAQSFNAIGVLIYMDKNKFPVVEADLALF 300
                     ******:*   ****:******:**********:*:**********:.***:*:*:*::*

SP|P02786|TFR1_HUMAN GHAHLGTGDPYTPGFPSFNHTQFPPSRSSGLPNIPVQTISRAAAEKLFGNMEGDCPSDWK 358
SP|Q62351|TFR1_MOUSE GHAHLGTGDPYTPGFPSFNHTQFPPSQSSGLPNIPVQTISRAAAEKLFGKMEGSCPARWN 360
                     **************************:*********************:***.**: *:
```

FIG. 32

```
SP|P02786|TFR1_HUMAN TDSTCRMVTSESKNVKLTVSNVLKEIKILNIFGVIKGFVEPDHYVVVGAQRDAWGPGA-A 417
SP|Q62351|TFR1_MOUSE IDSSCKLELSQNQNVKLIVKNVLKERRILNIFGVIKGYEEPDRYVVVGAQRDALGAGVAA 420
                      **:*::  *:.:**** *.***** :*********: ***:********* * *. *

SP|P02786|TFR1_HUMAN KSGVGTALLLKLAQMFSDMVLKDGFQPSRSIIFASWSAGDFGSVGATEWLEGYLSSLHLK 477
SP|Q62351|TFR1_MOUSE KSSVGTGLLLKLAQVFSDMISKDGFRPSRSIIFASWTAGDFGAVGATEWLEGYLSSLHLK 480
                     **.***.*******:****: ****:**********:*****:*****************

SP|P02786|TFR1_HUMAN AFTYINLDKAVLGTSNFKVSASPLLYTLIEKTMQNVKHPVTGQFLYQDSNWASKVEKLTL 537
SP|Q62351|TFR1_MOUSE AFTYINLDKVVLGTSNFKVSASPLLYTLMGKIMQDVKHPVDGKSLYRDSNWISKVEKLSF 540
                     *********.******************: * **:***** *: **:**** ******::

SP|P02786|TFR1_HUMAN DNAAFPFLAYSGIPAVSFCFCEDTDYPYLGTTMDTYKELIERIPELNKVARAAAEVAGQF 597
SP|Q62351|TFR1_MOUSE DNAAYPFLAYSGIPAVSFCFCEDADYPYLGTRLDTYEALTQKVPQLNQMVRTAAEVAGQL 600
                     ****:******************:*******  :***: *  :::*:**::.*:*******:

SP|P02786|TFR1_HUMAN VIKLTHDVELNLDYERYNSQLLSFVRDLNQYRADIKEMGLSLQWLYSARGDFFRATSRLT 657
SP|Q62351|TFR1_MOUSE IIKLTHDVELNLDYEMYNSKLLSFMKDLNQFKTDIRDMGLSLQWLYSARGDYFRATSRLT 660
                     :************* ***:****::****:::**::*************:*******

SP|P02786|TFR1_HUMAN TDFGNAEKTDRFVMKKLNDRVMRVEYHFLSPYVSPKESPFRHVFWGSGSHTLPALLENLK 717
SP|Q62351|TFR1_MOUSE TDFHNAEKTNRFVMREINDRIMKVEYHFLSPYVSPRESPFRHIFWGSGSHTLSALVENLK 720
                     *** *****:****::***:*:***********:******:********* **:****

SP|P02786|TFR1_HUMAN LRKQNNGAFNETLFRNQLALATWTIQGAANALSGDVWDIDNEF 760
SP|Q62351|TFR1_MOUSE LRQKNITAFNETLFRNQLALATWTIQGVANALSGDIWNIDNEF 763
                     **::*  *******************.*******:*:*****
```

FIG. 32
(CONT.)

N=3-40 any nucleotides
75% similarity to remaining sequence

COMPOSITIONS AND METHODS RELATED TO TRANSFERRIN RECEPTOR-BINDING APTAMERS

CROSS-REFERENCE TO RELATED APPLICATION

This application claims the benefit of U.S. Patent Application No. 63/222,086, filed Jul. 15, 2021, expressly incorporated herein by reference in its entirety.

STATEMENT OF GOVERNMENT LICENSE RIGHTS

This invention was made with government support under Grant Nos. R01 CA177272 and U54 CA199090, awarded by the National Institutes of Health. The government has certain rights in the invention.

STATEMENT REGARDING SEQUENCE LISTING

The Sequence Listing XML associated with this application is provided in XML format and is hereby incorporated by reference into the specification. The name of the XML file containing the sequence listing is 3915-P1270US_SEQ_final_2022-7-15. The XML file is 135 kb; was created on Jul. 15, 2022; and is being submitted via Patent Center with the filing of the specification.

STATEMENT OF GOVERNMENT LICENSE RIGHTS

This invention was made with government support under Grant Nos. R01 CA177272 and U54 CA199090, awarded by the National Institutes of Health. The government has certain rights in the invention.

FIELD

The present disclosure relates to DNA aptamers that specifically bind the transferrin receptor and can be used, for example, in methods of cell selection or cell depletion.

BACKGROUND

The manufacturing process of chimeric antigen receptor T cells includes cell selection, activation, gene transduction, and expansion. The T cell selection process from each manufacturing company varies. Some groups collect Ficoll®-enriched peripheral blood mononuclear cells (PBMCs) to obtain increased percentage of T cell content, while other groups use antibodies to isolate helper T cells and cytotoxic T cells separately. However, neither of these methods actively eliminate the cancer cells in the patient's blood collected along with the healthy white blood cells. Alarmingly, it has been found that transduction of these tumor-containing white blood cell specimens could lead to treatment failure. A 2018 case study reported a B-ALL patient who underwent anti-CD19 chimeric antigen receptor (CAR) T cell treatment relapsed due to anti-CD19 CAR expressing leukemic cells. These CAR leukemic cells were generated during the T cell transduction process and were unknowingly grafted back to the patient. As a result, the anti-CD19 CAR in cis masked the CD19 on the same cancer cell, protecting it from being detected by the therapeutic CAR T cells.

SUMMARY

Provided herein are aptamers that specifically bind the transferrin receptor on the surface of proliferating or cancerous cells. Such aptamers can be used to deplete such proliferating or cancerous cells from a therapeutic population of cells prior to manipulation and administration (e.g., CAR T cells) to a subject for treatment of a disease. Alternatively, the aptamers can be used herein in methods of enriching transferrin receptor-expressing cells, for example, for the purpose of genomic analysis, diagnosis or prognosis of cancer, or monitoring efficacy of a given treatment of e.g., cancer. Another alternative use relates to the targeted delivery of drugs via binding of aptamer-drug conjugates to the transferrin receptor, which is upregulated in rapidly dividing cells as well as, for example, the brain endothelium.

Accordingly, one aspect provided herein relates to a composition comprising an aptamer that selectively binds to the transferrin receptor (also referred to herein as CD71), wherein the aptamer comprises a sequence having at least 75% sequence identity to a composition comprising an aptamer that selectively binds to CD71, wherein the aptamer comprises a sequence having at least 75% sequence identity to residues 22-54 of SEQ ID NO: 2; and wherein the aptamer can further comprise a number (N) of nucleotides at each end wherein each nucleotide is selected independently, and wherein each N comprises from 3 nt to 40 nt, from 3 nt to 30 nt, from 3 nt to 20 nt, or from 3 nt to 10 nt. In another embodiment of this aspect and all other aspects provided herein, the aptamer comprises a sequence having at least 75% identity to SEQ ID NO: 1 (tJBA8.1), SEQ ID NO: 2 (JBA8.1), SEQ ID NO: 26 (tJBA8.26), or SEQ ID NO: 27 (JBA8.26). In another embodiment of this aspect and all other aspects provided herein, the aptamer comprises a central loop region, wherein a stem formed by base pairing of nucleotides from the 5' and 3' ends of the aptamer projects from the central loop region, and wherein first and second stem loops project from the central loop region.

In another embodiment of this aspect and all other aspects provided herein, the central loop comprises nucleotides 8-11, 23-26 and 41-44 of SEQ ID NO: 1.

In another embodiment of this aspect and all other aspects provided herein, the central loop comprises nucleotides 9-11, 23-26, and 41-43 of SEQ ID NO: 26.

In another embodiment of this aspect and all other aspects provided herein, nucleotides 8 and 44, 11 and 23, and 26 and 41 or nucleotides 9 and 43, 11 and 23, and 26 and 41 are base paired to each other, respectively.

In one embodiment of this aspect and all other aspects provided herein, the aptamer is attached to a solid support or phase-changing agent.

In another embodiment of this aspect and all other aspects provided herein, the solid support comprises a particle, bead, platform, column, filter or sheet, dish, a microfluidic capture device, capillary tube, electrochemical responsive platform, scaffold, cartridge, resin, fiber, or matrix.

In another embodiment of this aspect and all other aspects provided herein, the aptamer further comprises a detectable moiety, a label, a tag, or a probe.

In another embodiment of this aspect and all other aspects provided herein, the aptamer is formulated for use as a sensor.

Another aspect provided herein relates to an aptamer composition comprising an effective amount of an aptamer as described herein and further comprising a pharmaceutically acceptable carrier. In one embodiment of this aspect, the aptamer is attached to polymeric carrier to facilitate drug, nucleic acid, or nucleoprotein delivery. In another embodiment of this aspect, the aptamer is attached to a lipid formulation to facilitate drug, nucleic acid, and/or nucleoprotein delivery. In another embodiment the aptamer is attached directly to the pharmaceutically active agent, such as an antibody or small molecule drug.

Another aspect provided herein relates to a method for preparing cell a composition depleted of cells expressing CD71, the method comprising: contacting a biological sample comprising a desired cell population with an aptamer of claim 1, under conditions and for a time permitting binding of the aptamer to CD71 expressed on the cells in said sample; and separating cells bound to the aptamer from the cells not bound to the aptamer, thereby providing a preparation of cells depleted in CD71 expressing cells for use in generating a therapeutic cell composition.

Another aspect provided herein relates to a method for preparing T cells to be used in generating a therapeutic cell composition, the method comprising: contacting a biological sample comprising T cells with an aptamer as described herein or a composition thereof under conditions and for a time permitting binding of the aptamer to CD71 expressed on cells in said sample; and separating cells bound to the aptamer from cells not bound to the aptamer, thereby providing a preparation of T cells depleted in CD71 expressing cells, for use in generating a therapeutic cell composition.

In one embodiment of this aspect and all other aspects provided herein, the aptamer is bound to a solid support.

In another embodiment of this aspect and all other aspects provided herein, the method further comprises genetically modifying T cells either before or after separation.

In another embodiment of this aspect and all other aspects provided herein, the genetic modification optionally comprises introducing a nucleic acid construct encoding a chimeric antigen receptor.

Also provided herein, in another aspect, is a method for depleting CD71-expressing cells from a biological sample comprising a plurality of cell types, the method comprising: (i) contacting a biological sample comprising a plurality of cell types with an aptamer of claim 1 under conditions and for a time permitting binding of the aptamer to CD71 expressed on cells in said sample; and (ii) separating cells bound to the aptamer from cells not bound to the aptamer, thereby providing a preparation depleted in CD71 expressing cells from the biological sample.

In one embodiment of this aspect and all other aspects provided herein, the active removal of CD71-expressing cells comprises (i) contacting the biological sample with an aptamer composition as described herein under conditions and for a time to permit cells expressing CD71 to bind to the aptamer, and separating cells bound to the aptamer from cells not bound to the aptamer; and (ii) isolating cells expressing CD71 from the cells not bound to the aptamer.

In one embodiment of this aspect of the method the cell preparation depleted of CD71 expression cells comprises NK cells, monocytes, or macrophage.

In another embodiment of this aspect and all other aspects provided herein, the biological sample is isolated from a subject having circulating tumor cells.

Also, provided herein in another aspect is a method for isolating cells expressing CD71, the method comprising: contacting a biological sample comprising CD71-expressing cells with a composition of claim 1 under conditions and for a time permitting binding of the aptamer to CD71 expressed on cells in said sample; and separating cells bound to the aptamer from cells not bound to the aptamer, thereby isolating cells expressing CD71 from the biological sample.

In one embodiment of this aspect of the method, the isolated cells are tumor cells or fetal nucleated red blood cells.

Also provided herein in another aspect is a method of treating a disease, the method comprising: administering the T cells depleted of the cells expressing CD71 by a method set forth above or an engineered or differentiated cell thereof to a subject in need thereof, thereby treating the disease.

Also provided herein in another aspect is a method of delivering a therapeutic agent, the method comprising administering an aptamer described herein, wherein the aptamer is attached to a therapeutic drug, a formulation comprising a therapeutic drug, or a therapeutic cell.

In one embodiment of this aspect and all other aspects provided herein, the therapeutic drug is a nucleic acid or a ribonucleoprotein.

In another embodiment of this aspect and all other aspects provided herein the delivery comprises receptor-mediated transcytosis.

Also provided herein are aptamer dimers comprising one or more of the sequences provided herein. In one embodiment, the dimer is formed by digestion, followed by ligation (see e.g., FIGS. 34A-34B).

In other embodiments, the aptamer monomers self-assemble into dimers (see e.g., FIG. 35).

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A. Schematic of cell-SELEX using $CD3^+CD28^+$ Jurkat cells for positive selection and $CD3^-CD28^-$ J.RT3-T3.5 cells for negative selection. FIG. 1B. Binding median fluorescence intensity (MFI) of 250 nM aptamer pools from consecutive rounds of cell-SELEX to Jurkat cells and J.RT3-T3.5 cells by flow cytometry. Graph bars and error bars represent mean±standard deviation; n=1-3 technical replicates. Replicates vary due to some rounds having limited aptamer pool. FIG. 1C. Binding MFI of 100 nM RANL and individual aptamers identified from round 8 of cell-SELEX to Jurkat cells and J.RT3-T3.5 cells by flow cytometry. Aptamers belonging to predicted motifs are indicated. Graph bars and error bars represent mean±standard deviation; n=3 independent experiments. ns>0.05, *P<0.05, ****P<0.0001 (ordinary two-way ANOVA with Šidík correction). FAM, 6-carboxyfluorescein.

FIG. 2A. MFE secondary structures of JBA8.1 and its truncation (tJBA8.1), predicted using NUPACK™ (temperature=4° C.; $Na^+$=137 mM; $Mg^{2+}$=5.5 mM). The dashed line indicates the site of truncation, whereas the orange highlighting denotes the 18-bp flanking constant regions. FIG. 2B. Flow cytometry binding curves of RANL, JBA8.1, and tJBA8.1 to Jurkat cells, normalized to 400 nM tJBA8.1 binding. The curves represent a nonlinear regression assuming one-site total binding. $K_D$ values were calculated by averaging the individual regression values of the independent experiments. Data points and error bars, and $K_D$ values, represent mean±standard deviation; n=3 independent experiments with technical duplicates. *P<0.05 (two-sided unpaired t-test). Cy5, cyanine 5.

FIGS. 3A-3C. TfR1 is identified as the target of tJBA8.1. FIG. 3A. Colloidal blue-stained 8% SDS-PAGE gel of Jurkat cell membrane proteins pulled down by tJBA8.1. The control lane represents proteins captured by biotin-saturated magnetic beads only. Bands a and b (dashed red boxes) from both lanes were excised for mass spectrometry analysis. FIG. 3B. Summary of the protein with the highest peptide coverage and number of peptides identified in each excised band by mass spectrometry. FIG. 3C. Flow cytometry analysis of FITC-labeled CD71 Ab and 25 nM Cy5-labeled tJBA8.1 binding to Jurkat cells 24 h after nucleofection with TFRC siRNA duplexes. Red, dashed horizontal line represents binding to non-specific (NS) siRNA-treated controls to which the TFRC siRNA data points were normalized. Horizontal lines and error bars represent mean±standard deviation; n=3 independent experiments. **P<0.01 (significance between ligand staining on TFRC siRNA- and NS siRNA-treated cells; one-way ANOVA with Bonferroni correction). ns>0.05 (significance between the relative CD71 Ab and tJBA8.1 staining in pairwise experiments; two-sided paired t-test). Cy5, cyanine 5; FITC, fluorescein isothiocyanate.

FIG. 4A. Overlaid flow cytometry plots of unstained (grey), FITC-labeled CD71 Ab single-stained (black), 25 nM Cy5-labeled tJBA8.1 single-stained (red), and antibody and aptamer co-stained (dark red) Jurkat cells. Plots are representative of n=2 independent experiments. FIG. 4B. Association and dissociation kinetics of serially diluted FAM-labeled tJBA8.1 binding to biotinylated TfR1 immobilized on streptavidin biosensors by BLI. The association phase is illustrated from 0-450 s, whereas dissociation is shown from 450-1350 s (separated by the vertical dotted line). $K_D$ values were calculated by performing a global fit of the multi-concentration kinetic data to a 1:1 binding model. $K_D$ values represent mean±standard deviation; n=4 individual concentrations of aptamers. FIGS. 4C and 4D.) Competitive binding of 25 nM Cy5-labeled tJBA8.1 with varying fold-excess of holo-Tf (FIG. 4C) and CD3 or CD71 Ab (FIG. 4D) to Jurkat cells by flow cytometry. Binding was normalized to aptamer-stained controls without holo-Tf or antibody. Data points and error bars represent mean±standard deviation; n=3 independent experiments. ns>0.05, *P<0.05 (ordinary two-way ANOVA with Šídík correction). FITC, fluorescein isothiocyanate; Cy5, cyanine 5; FAM, 6-carboxyfluorescein.

FIG. 5A Schematic of malignant cell depletion from PBMCs using tJBA8.1-mediated MACS. FIG. 5B. Flow cytometry plots of CM-Dil$^+$ Raji cell depletion from high (10%) Raji spiked PBMCs. The different cell fractions from the depletion process are shown. Plots for low (0.1%) and medium (1%) Raji spiked PBMCs can be found in FIGS. 26B, 26C. Plots are representative of n=3 independent experiments with different PBMC donors. FIG. 5C. Flow cytometry analysis of the percentage of CM-Dil$^+$ Raji cells in each cell fraction of the depletion process using low (0.1%), medium (1%), and high (10%) Raji spiked PBMCs. Un-spiked PBMCs were included as a benchmark of complete depletion. Graph bars and error bars represent mean±standard deviation; n=3 independent experiments with different PBMC donors. ns>0.05 (ordinary one-way ANOVA with Dunnett's correction). FIG. 5D. Flow cytometry analysis of the healthy immune cell composition within CM-Dil$^-$ PBMCs before (pre-sort) and after (flow through) Raji depletion from high (10%) Raji spiked PBMCs. Analysis for low (0.1%) and medium (1%) Raji spiked PBMCs can be found in FIGS. 27A, 27B. The circles, squares and triangles represent different PBMC donors from separate depletion studies. Graph bars and error bars represent mean±standard deviation; n=3 independent experiments with different PBMC donors. ns>0.05 (paired two-way ANOVA with Šídík correction). CM-Dil, chloromethylbenzamido-1,1'-dioctadecyl-3,3,3',3'-tetramethylindocarbocyanine perchlorate.

FIG. 7A. JBA8.1 (SEQ ID NO:2) sequence modification as compared with rvCD71apt (SEQ ID NO: 130). Red font color on the sequence and red shading on the 2-dimensional structure indicate the changed sequences. Blue font color and blue shading indicate the added toehold. FIG. 7B. Flow cytometry binding study using Jurkat cells. Aptamers were modified with biotin and labeled with secondary Streptavidin FITC staining. Data are shown as mean±s.d., n=3. FIG. 7C. Flow cytometry binding study of rvCD71apt with or without the presence of rvCD8apt reversal agent. Jurkat cells were stained with 20 nM rvCD71apt, followed by Streptavidin PE labeling, and 2 μM (100×) rvCD8apt reversal agent incubation at room temperature. Data are shown as mean±s.d., n=3, ns (two-tailed unpaired t-test, P=0.9659). Each point represents one independent biological repeat. MFI: median fluorescence intensity; FITC: fluorescein isothiocyanate; PE: phycoerythrin; RA: reversal agent.

FIGS. 8A-8D. rvCD71apt toehold and reversal agent optimization evaluated by flow cytometry. FIG. 8A Jurkat cells were stained with 20 nM of rvCD71apt and displaced with 2 μM (100×) reversal agents with lengths of 21, 28, 33, 51 nt. Dotted line indicates 100% aptamer binding without reversal agent incubation. Data are shown as mean±s.d., n=3. FIG. 8B. Toehold sequences with various G-C contents were designed and placed at the 3' end of rvCD71apt. FIG. 8C. 2 μM of the corresponding 33 nt reversal agents were applied to Jurkat cells labeled with 20 nM rvCD71apt carrying various G-C content toeholds. Dotted line indicates 100% aptamer binding without reversal agent incubation. Data are shown as mean±s.d., n=3, ns (one-way ANOVA with Tukey's test, P>0.05). FIG. 8D. Normalized MFI value of rvCD71apt containing different toeholds binding to Jurkat cells. Data are shown as mean±s.d., n=3, ns (one-way ANOVA with Tukey's test, P>0.05). RA: reversal agent; MFI: median fluorescence intensity; PE: phycoerythrin; nt: nucleotides.

FIG. 9C. Evaluation of reversal agent-specific removal of bound aptamer. CD4$^+$ T cells and resting CD8$^+$ T cells were mixed together and stained with both 20 nM PE-labeled rvCD71apt and 5 nM FAM-labeled rvCD8apt (left-most panel). Application of rvCD71apt reversal agent (second panel from left) or rvCD8apt reversal agent (third panel from left) selectively reduces aptamer labeling in the target cells. Application of both reversal agents reduces binding in both populations (right-most panel). Streptavidin-PE was used as secondary staining. 100-fold excess reversal agent were incubated with stained cells. MFI: median fluorescence intensity; FAM: 6-carboxyfluorescein; PE: phycoerythrin; RA: reversal agent.

FIG. 10A. Simplified schematic of aptamer labeling and 2-step reversal agent elution. FIG.

10B. Representative flow cytometry plots of isolated cells in different fractions stained with CD4, CD8, and CD71 antibodies. rvCD71apt target cells were gated as $CD4^+CD71^+$ cells. rvCD8apt target cells were gated as $CD8^+$ cells. FIG. 10C. Purity of target cells in the pre-sort and eluted fractions. Data are shown as mean±s.d., n=3 (two-tailed unpaired t test). FIG. 10D. Yield of target cells in the eluted fractions. Data are shown as mean±s.d., n=3 (two-tailed unpaired t test). RA: reversal agent; FITC: fluorescein isothiocyanate; APC: allophycocyanin; APC-Cy7: allophycocyanin-Cy7.

FIG. 11A. Sequence alignment of JBA8.1 (SEQ ID NO: 2) and rvCD8apt (SEQ ID NO: 131). Overlapping sequences are marked in red. FIG. 11B. NUPACK™ 2-dimensional structure prediction of JBA8.1 aptamer and rvCD8apt aptamer at 4° C. (left), and the predicted structures when aptamers are incubated with rvCD8apt reversal agent at 25° C. NUPACK™ settings: $Na^+$=137 mM; $Mg^{2+}$=5.5 mM. Strand displacement of (FIG. 11C) rvCD8apt and (FIG. 11D) JBA8.1 evaluated with flow cytometry by staining apheresis cells with individual or combined aptamers at 4° C. for 30 min. Strand displacement took place at 25° C. for 10 min. RA: reversal agent; MFI: median fluorescence intensity; Cy5: Cyanine 5; FAM: 6-carboxyfluorescein.

FIG. 12A. Percentage of PBMC compositions in the inactivated, pre-sort, and sorted cell fractions measured by flow cytometry. NK cells were gated on $CD3^-$ $CD56^+$ population. B cells were gated on $CD3^{mid}CD19^+$ population. Monocytes were gated on $CD14^+$ population. CD4 T cells were gated on $CD3^+$CD8-population. CD8 T cells were gated on $CD3^+CD8^+$ population. FIG. 12B. Flow cytometry evaluation of CD71 expression on PBMCs bulk stimulated with rhIL-7, rhIL-15, rhIL-2 cytokines and human CD3/CD28 activation beads. FIG. 12C. CD71 expression on the sorted cells in flow through, reversal agent elution, and flush fractions measured by flow cytometry. FIG. 12D. Percentages of total cell count found in flow through, reversal agent elution, and flush fractions. Figures were generated with results from 1 biological repeat. RA: reversal agent; FITC: fluorescein isothiocyanate.

FIG. 16A. Flow cytometry histograms of 100 nM Cy5-labeled tJBA8.1 binding to Jurkat cells with and without trypsin treatment. Histograms are representative of n=1 independent experiment with technical triplicates. FIG. 16B. Subcellular localization of 200 nM Cy5-labeled RANL (left) and tJBA8.1 (right) binding to Jurkat cells at 4° C. by confocal microscopy imaging. Phalloidin recognizes F-actin, which primarily localizes to the cell membrane in Jurkat cells. Scale bars=10 Wm. Cy5, cyanine 5; DAPI, 4',6-diamidino-2-phenylindole; FITC, fluorescein isothiocyanate.

FIG. 17A. Flow cytometry histograms of FITC-labeled anti-CD71 antibody (CD71 Ab) binding to Jurkat and J.RT3-T3.5 cells. A FITC-labeled anti-CD14 antibody was used as an isotype control (Isotype Ab). Histograms are representative of n=1 independent experiment. FIG. 17B. Corresponding median fluorescence intensity (MFI) of CD71 Ab binding to Jurkat and J.RT3-T3.5 cells minus Isotype Ab binding. Data are representative of n=1 independent experiment. FITC, fluorescein isothiocyanate.

FIG. 18A. Flow cytometry histograms of 100 nM biotinylated RANL and tJBA8.1 binding to unactivated, and day 3 CD3/CD28 Dynabead™-activated $CD4^+$ and $CD8^+$ T cells. Histograms are representative of n=2 independent experiment. FIG. 18B. MFI of 25 nM Cy5-labeled JBA8.1 (red, left y-axis) and FITC-labeled CD71 Ab (green, right y-axis) binding to $CD4^+$ and $CD8^+$ T cells over 7 days of CD3/CD28 Dynabead™ activation by flow cytometry. Data are representative of n=1 independent experiment carried out on each day of activation. SA-AF647, streptavidin Alexa Fluor™ 647; Cy5, cyanine 5; FITC, fluorescein isothiocyanate.

FIG. 20A. Association and dissociation kinetics of 200 nM His-tagged mouse TfR1 (mTfR1) protein binding to biotinylated tJBA8.1 immobilized on streptavidin biosensors by BLI. The association phase is illustrated from 0-600 s, whereas dissociation is shown from 600-1200 s (separated by the vertical dotted line). Data are representative of n=1 independent experiment with one individual concentration of mTFR1.

FIG. 20B. Positive control binding of 100 nM FITC-labeled anti-mCD71 antibody (mCD71 Ab) to his-tagged mTfR1 immobilized on nickel-charged tris-nitriloacetic acid biosensors by BLI. A FITC-labeled anti-mCD3e antibody was used as an isotype control (Isotype Ab). The association phase is illustrated from 0-100 s, whereas dissociation is shown from 100-1000 s (separated by the vertical dotted line). Data are representative of n=1 independent experiment with one individual concentration of antibody.

FIG. 21A. Sequence alignment and MFE structure comparison of tJBA8.1 and XQ-2d. MFE structures were predicted using NUPACK™ (temperature=4° C.; $Na^+$=137 mM; $Mg^{2+}$=5.5 mM). Red font and highlighting indicate overlapping nucleotides between the two aptamers. Dashes in sequence alignment represent single gap introductions and underlined nucleotides denote constant regions. FIG. 21B. Overlaid flow cytometry plots of unstained (grey), FITC-labeled CD71 Ab single-stained (black), 25 nM Cy5-labeled XQ-2d single-stained (blue), and antibody and aptamer co-stained (dark blue) Jurkat cells. Plots are representative of n=2 independent experiments. FIG. 21C. Flow cytometry binding curves of Cy5-labeled tJBA8.1 and XQ-2d to Jurkat cells, normalized to 400 nM tJBA8.1 binding. The binding curve for tJBA8.1 is the same as the one in FIG. 2B. The curves represent a nonlinear regression assuming one-site total binding. $K_D$ values were calculated by averaging the individual regression values of the independent experiments. Data points and error bars, and $K_D$ values, represent mean±standard deviation; n=3 independent experiments with technical duplicates. P<0.01 (two-sided unpaired t-test). FIG. 21D. Association and dissociation kinetics of serially diluted FAM-labeled XQ-2d binding to biotinylated TfR1 immobilized on streptavidin biosensors by BLI. The association phase is illustrated from 0-450 s, whereas dissociation is shown from 450-1350 s (separated by the vertical dotted line). $K_D$ values were calculated by performing a global fit of the multi-concentration kinetic data to a 1:1 binding model. $K_D$ values represent mean±standard deviation; n=4 individual concentrations of aptamers. FIGS. 21E and 21F. Competitive binding of 25 nM Cy5-labeled XQ-2d with varying fold-excess of holo-Tf (FIG. 21E) and CD3 or CD71 Ab (FIG. 21**F) to Jurkat cells by flow cytometry. Binding was normalized to aptamer-stained controls without holo-Tf or antibody. Data points and error bars represent mean±standard deviation; n=3 independent experiments. ns>0.05, *P<0.05, P<0.01, *P<0.001 (ordinary two-way ANOVA with Šídík correction). FITC, fluorescein isothiocyanate; Cy5, cyanine 5; FAM, 6-carboxyfluorescein.

FIG. 22A. Flow cytometry MFI of FITC-labeled CD71 Ab binding to H9 and Jurkat cells relative to unstained controls. Graph bars and error bars represent mean±standard deviation; n=3 independent experiments. **P<0.0001 (two-sided unpaired t-test). FIG. 22B. Flow cytometry histograms of 160 nM FAM-labeled RANL, tJBA8.1, and XQ-2d binding to H9 cells. Histograms are representative of n=1 independent experiment. FIG. 22**C. Competitive binding of 25 nM Cy5-labeled tJBA8.1 and XQ-2d with varying fold-excess of holo-transferrin (holo-Tf) to H9 cells by flow cytometry. Binding was normalized to aptamer-stained controls without holo-Tf. Data points and error bars represent mean±standard deviation; n=3 independent experiments. ns>0.05 (ordinary two-way ANOVA with Šídík correction). FITC, fluorescein isothiocyanate; FAM, 6-carboxyfluorescein; Cy5, cyanine 5.

FIG. 26A. Flow cytometry plots demonstrating gating strategy for tracking CM-Dil-labeled Raji cells in depletion studies. CM-Dil$^-$ un-spiked PBMCs and CM-Dil$^+$ Raji cells are shown. Plots are representative of n=3 independent experiments with different PBMC donors. FIGS. 26B and 26C. Flow cytometry plots of CM-Dil$^+$ Raji cell depletion from low (0.1%) (FIG. 26B) and medium (1%) (FIG. 26C) Raji spiked PBMCs. The different cell fractions from the depletion process are shown. Plots are representative of n=3 independent experiments with different PBMC donors. CM-Dil, chloromethylbenzamido-1,1'-dioctadecyl-3,3,3',3'-tetramethylindocarbocyanine perchlorate.

FIGS. 28A-28D. TfR1-independent binding of tJBA8.1 to PBMCs is likely caused by a G-quintet motif. FIG. 28A. Binding MFI multiplied by percent positivity of 100 nM RANL and individual aptamers identified from round 8 of cell-SELEX to CD3$^+$ and CD3$^-$ PBMCs by flow cytometry. Aptamers belonging to predicted motifs are indicated. Graph bars and error bars represent mean±standard deviation; n=3 independent experiments with the same PBMC donor. ns>0.05, *P<0.001, P<0.0001 (ordinary two-way ANOVA with Šídík correction). FIG. 28B Flow cytometry plots of PBMCs co-stained with APC-Cy7-labeled CD3, FITC-labeled CD14, and APC-labeled CD19 antibodies and 100 nM biotinylated RANL and JBA8.1 aptamers. Plots are representative of n=1 independent experiment. FIG. 28**C. Random region sequences of individual aptamers identified from round 8 of cell-SELEX. JBA8.1: residues 19-63 of SEQ ID NO: 2; JBA8.2: residues 19-63 of SEQ ID NO: 118; JBA8.3: residues 19-63 of SEQ ID NO: 119; JBA8.4:

residues 19-63 of SEQ ID NO: 120; JBA8.7: residues 19-63 of SEQ ID NO: 121; JBA8.8: residues 19-63 of SEQ ID NO: 122; JBA8.11: residues 19-63 of SEQ ID NO: 123; JBA8.15: residues 19-63 of SEQ ID NO: 124; JBA8.17: residues 19-63 of SEQ ID NO: 125. Yellow highlighting indicates G-quintet motifs. FIG. 28D. MFE structures of JBA8.1, JBA8.3, JBA8.11, and JBA8.15, predicted using NUPACK™ (temperature=4° C.; $Na^+$=137 mM; $Mg^{2+}$=5.5 mM). Yellow highlighting indicates G-quintet motifs. FAM, 6-carboxyfluorescein; APC-Cy7, allophycocyanin-cyanine 7; FITC, fluorescein isothiocyanate; APC, allophycocyanin; SA-PE, streptavidin-phycoerythrin.

FIG. 29A. Summary of the top relevant protein hit identified by mass spectrometry in band f uniquely enriched by tJBA8.1 in FIG. 24A. FIG. 29B. Flow cytometry histograms of anti-CNBP antibody (clone 38F10, CNBP Ab) binding to Jurkat cells, H9 cells, and $CD3^-$ PBMCs. A FITC-labeled goat anti-mouse antibody was used for secondary staining and alone as a negative control. Histograms are representative of n=1 independent experiment. FIG. 29C. Flow cytometry plots of PBMCs co-stained with CNBP Ab and 25 nM Cy5-labeled tJBA8.1. A FITC-labeled goat anti-mouse antibody was used for secondary staining of the CNBP Ab. Plots are representative of n=1 independent experiment. FIG. 29D. Association and dissociation kinetics of serially diluted FAM-labeled tJBA8.1 binding to His-tagged CNBP immobilized on Ni-NTA biosensors by BLI. The association phase is illustrated from 0-600 s, whereas dissociation is shown from 600-1400 s (separated by the vertical dotted line). $K_D$ values were calculated by performing a global fit of the multi-concentration kinetic data to a 2:1 heterogeneous ligand model. $K_D$ values represent mean±standard deviation; n=5 individual concentrations of aptamers. FIG. 29E. MFE structures of tJBA8.1 GGAGG, tJBA8.1 GGGAG, and tJBA8.1 GGGGC, predicted using NUPACK™ (temperature=4° C.; $Na^+$=137 mM; $Mg^{2+}$=5.5 mM). Circles indicate G+A or G+C point mutations from original tJBA8.1 sequence. FIG. 29F. Flow cytometry binding of 100 nM FAM-labeled tJBA8.1 and GGGGG-mutated variants to Jurkat cells, H9 cells, and $CD3^-$ PBMC, normalized to respective tJBA8.1 binding. Graph bars and error bars represent mean±standard deviation; n=3 independent experiments. FIG. 29G. Association and dissociation kinetics of 100 nM FAM-labeled RANL, tJBA8.1, XQ-2d, and GGGGG-mutated tJBA8.1 aptamer binding to His-tagged CNBP immobilized on Ni-NTA biosensors by BLI. The association phase is illustrated from 0-600 s, whereas dissociation is shown from 600-1400 s (separated by the vertical dotted line). Data are representative of n=1 independent experiment with one individual concentration of aptamer. FITC, fluorescein isothiocyanate; Cy5, cyanine 5; FAM, 6-carboxyfluorescein.

FIG. 30A. MFE structure of JBA8.1 and JBA8.26, predicted using NUPACK™ (temperature=4° C.; $Na^+$=137 mM; $Mg^{2+}$=5.5 mM). Circles indicate T→C point mutation from original JBA8.1 sequence and subsequent base pairing. The bidirectional arrows call attention to the increased distance between the outbranching hairpins in the JBA8.26 structure. FIG. 30B. Flow cytometry binding curves of FAM-labeled tJBA8.1, XQ-2d, and JBA8.26 to H9 cells, normalized to 400 nM aptamer binding. The curves represent a nonlinear regression assuming one-site specific binding with Hill slope. $K_D$ values were calculated by averaging the individual regression values of the independent experiments. Data points and error bars, and $K_D$ values, represent mean±standard deviation; n=3 independent experiments. ns>0.05, *P<0.05 (ordinary one-way ANOVA with Tukey correction). FIG. 30C. Association and dissociation kinetics of serially diluted FAM-labeled JBA8.26 binding to biotinylated TfR1 immobilized on streptavidin biosensors by BLI. The association phase is illustrated from 0-450 s, whereas dissociation is shown from 450-1350 s (separated by the vertical dotted line). $K_D$ values were calculated by performing a global fit of the multi-concentration kinetic data to a 1:1 binding model. $K_D$ values represent mean±standard deviation; n=5 individual concentrations of aptamers. FAM, 6-carboxyfluorescein.

FIG. 31. Mouse TfR1 (SEQ ID NO: 147) has mutations at multiple residues of a helices 1, 2, and 3 of the human TfR1 (SEQ ID NO: 145) helical domain bound by holo-transferrin. Protein sequence alignment of human TfR1 and mouse TfR1 using the Clustal Omega program. Underlined groups of amino acids in the human sequence indicate the a helices 1, 2, and 3 of the TfR1 helical domain. Red font and highlighting represent the TfR1 residues in the helical domain that do not overlap between the mouse and human sequences (i.e., the human TfR1 residues mutated in mouse TfR1).

FIG. 32. TfR2 has low conservation of residues in a helices 1, 2, and 3 of the Tfr1 helical domain bound by holo-transferrin. Protein sequence alignment of human TfR1 (SEQ ID NO: 145) and TfR2 (SEQ ID NO: 146) using the Clustal Omega program. Underlined groups of amino acids in the TfR1 sequence indicate the helices 1, 2, and 3 of the helical domain. Red font and highlighting represent the TfR1 residues in the helical domain that do not overlap with TfR2 (i.e., the TfR1 residues mutated in TfR2).

FIG. 34A. MFE structure of JBA dimer, predicted using NUPACK™ (temperature=4° C.; $Na^+$=137 mM; $Mg^{2+}$=5.5 mM). The dimer is comprised of a JBA monomer that has an EcoRI cut site at the end of an extended stem. After EcoRI digestion, a palindromic, complementary 5' overhang consisting of AATT is formed on the monomer that can self-dimerize and be ligated together using a DNA ligase, forming a circular dimer. FIG. 34B. Flow cytometry binding curves of Cy5-labeled JBA dimer to Jurkat cells, normalized to 400 nM aptamer binding. The curves represent a nonlinear regression assuming one-site specific binding. $K_D$ values were calculated by averaging the individual regression values of the independent experiments. Data points and error bars, and $K_D$ values, represent mean±standard deviation; n=3 independent experiments. (JBA EcoR1 monomer that folds into dimer after digestion:

```
                                    (SEQ ID NO: 147)
GTAGAATTCGAGTGA/iCy5/CGCAGCAGCGTAAAGGGGGTGTTTGTGCG

GTGTGGAGTGCGCGTGCTGCTGCGTCACTCGAATTCTAC)
```

Figure 35:
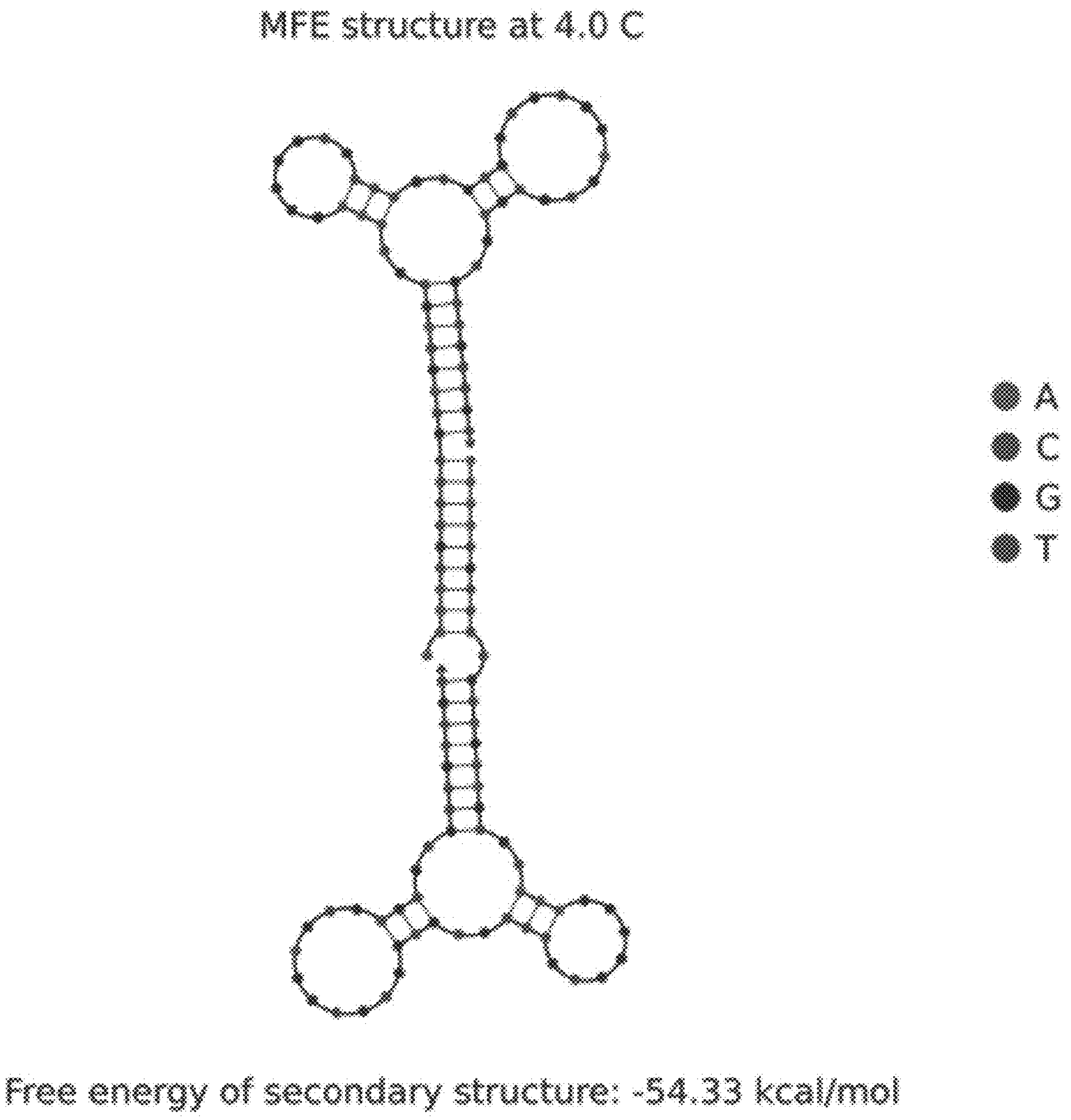

FIG. 35. MFE structure of JBA dimer, predicted using NUPACK™ (temperature=4° C.; $Na^+$=137 mM; $Mg^{2+}$=5.5 mM). This particular dimer is comprised of a self-dimerizing JBA monomer with a 5' phosphorylation modification and 10-bp overhang. After dimerization, a DNA ligase is used to ligate the open ends, forming a circular dimer. (JBA Overhang monomer that self-folds into a dimer:

(SEQ ID NO: 148)
/5Phos/AAAAC/iCy5/GTTTTGCAGCAGCGTAAAGGGGGTGTTTGTGC

GGTGTGGAGTGCGCGTGCTGCTGC).

Figure 36:
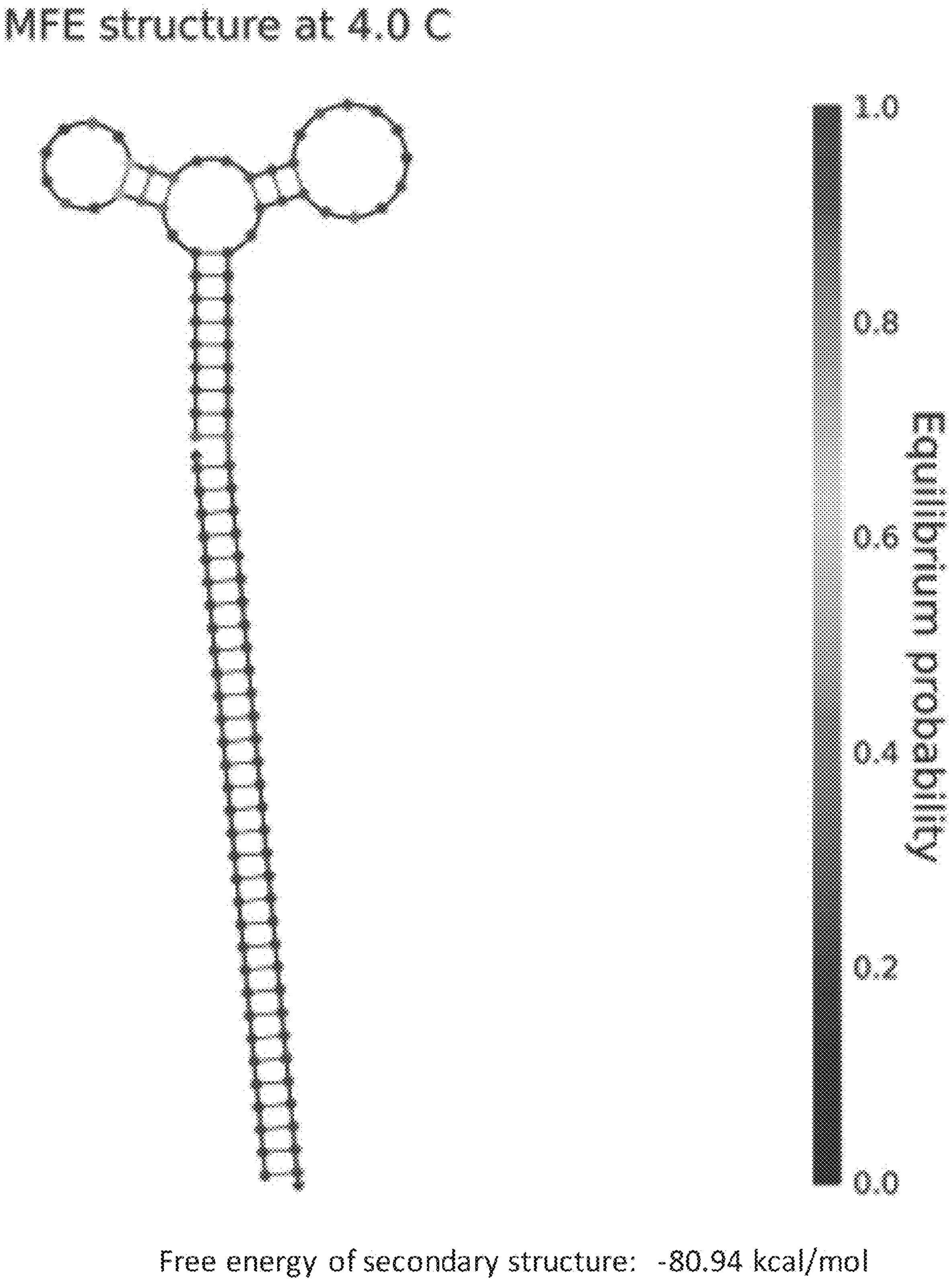

FIG. 36. Aptamer tJBA8.26 was fused to a drug loading overhang and annealed with the label complementary strand in a one step method and snap cooled on ice. The MFE predicted secondary structure of aptamer and DLO at 10 μM is presented.

Figure 37A:
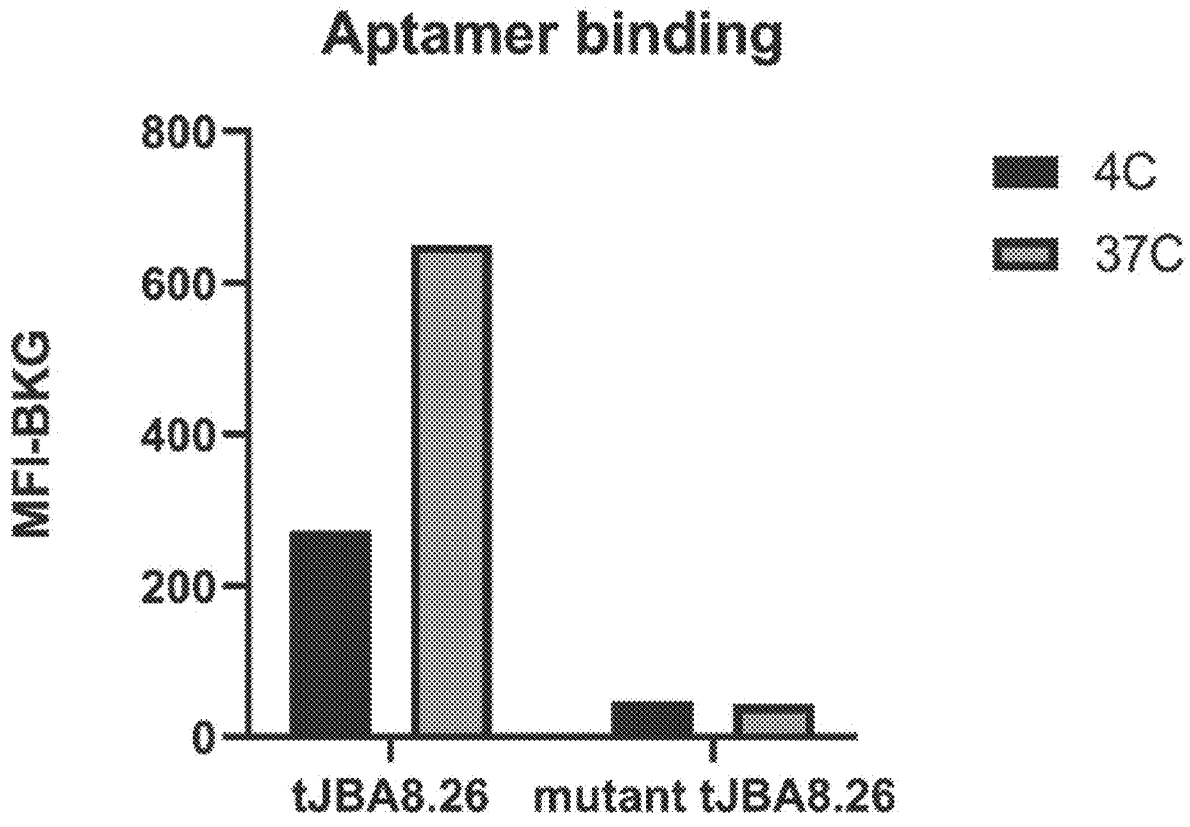
Figure 37B:
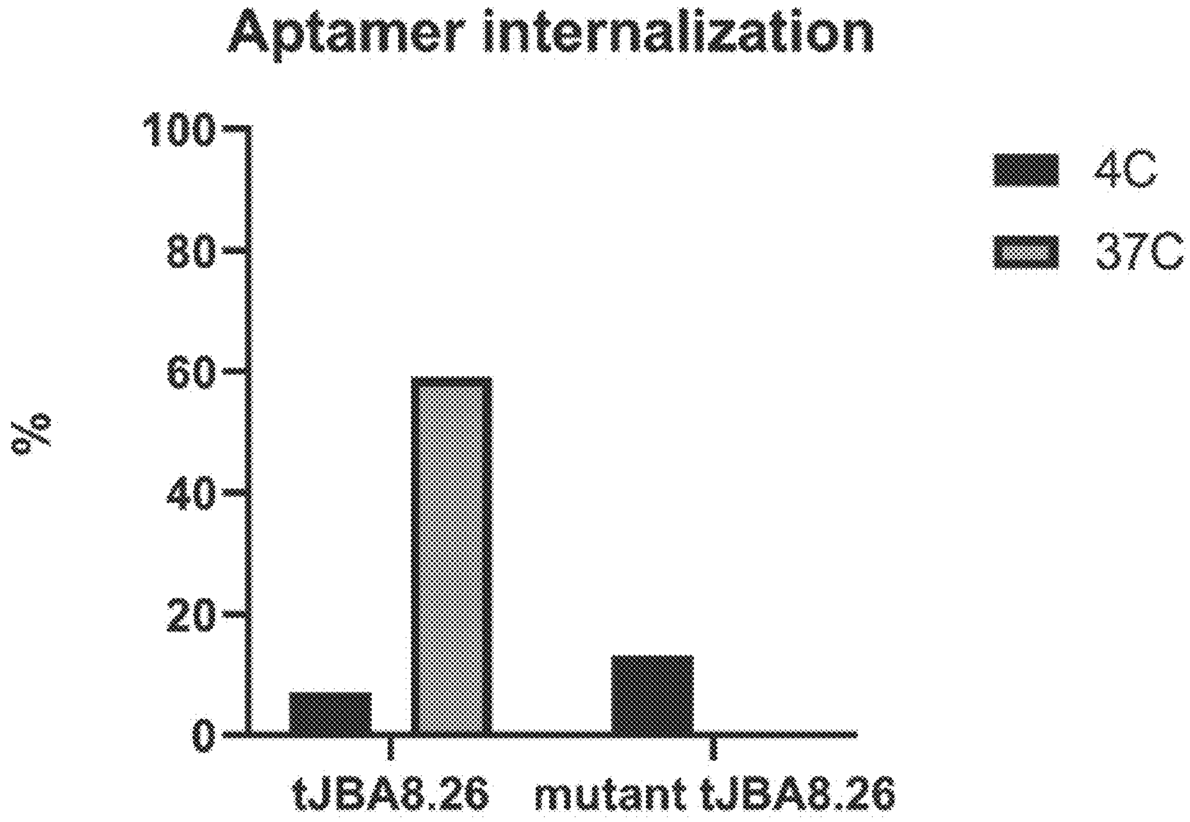

FIGS. 37A-37B. Aptamer mediated cell delivery into cells. FIG. 37A. Aptamer associate with cells was analyzed by flow cytometry. tJBA8.26 showed high binding at 4° C. with increased cell association at 37° C., a temperature permissible for cell internalization. FIG. 37B. Internalization of the aptamer was assessed by treating aptamer bound cells with 0.25% trypsin, that cleaves TfR1 from the cell surface. Observed fluorescence seen is due to internalized aptamer complex. Percent internalization was calculated as a ration of MFI of trypsin treated cells/MFI of untreated cells.

Figure 38A:
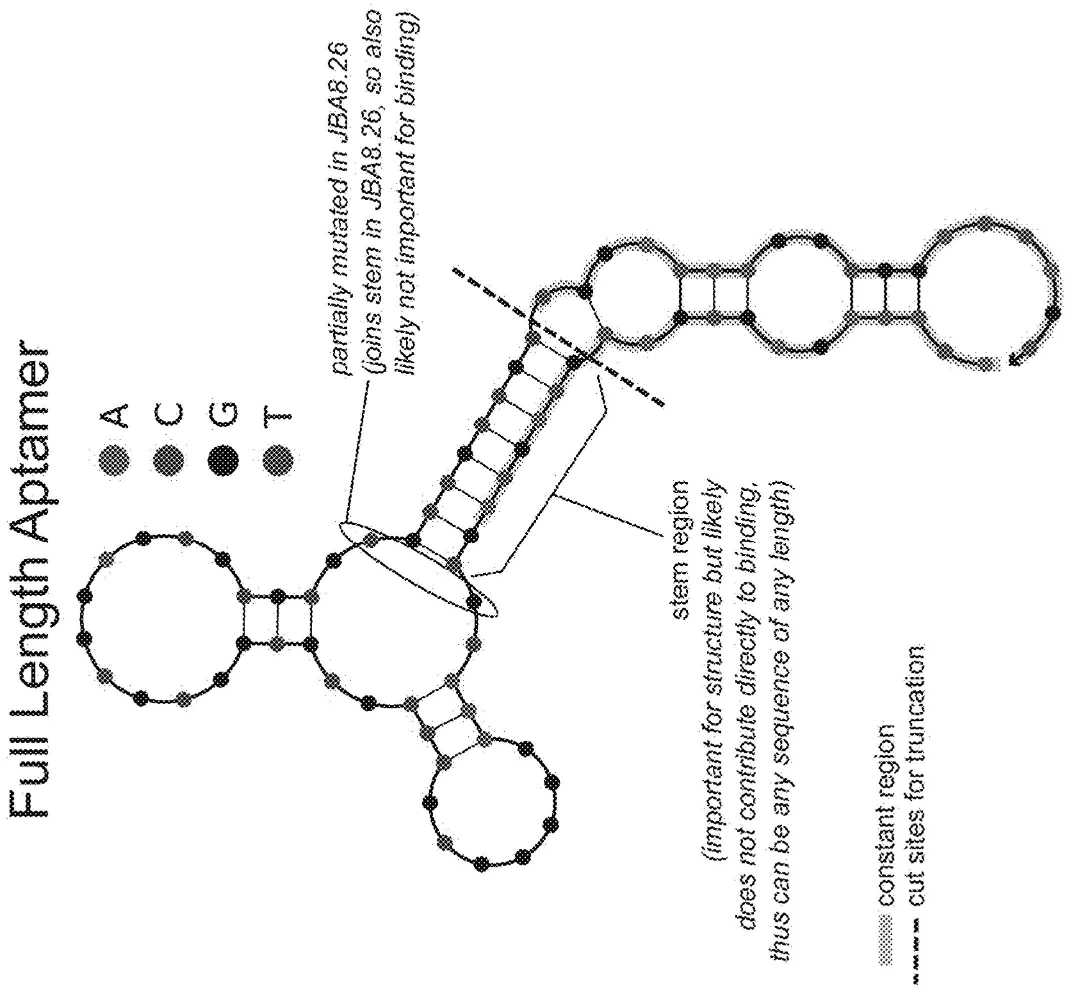
Figure 38B:
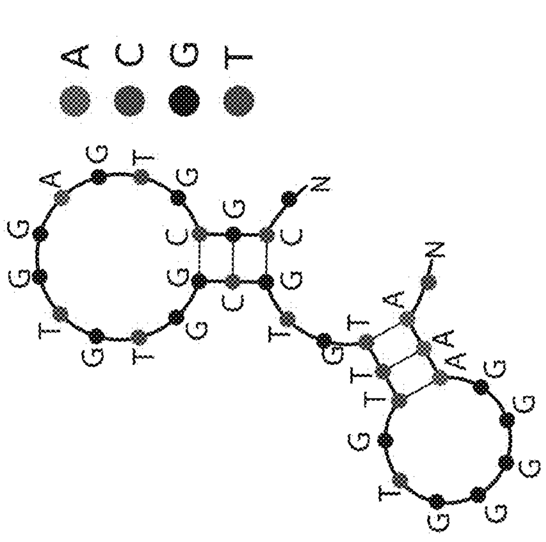

FIG. 38A-38B. Depicts a predicted secondary structure of the full-length aptamer JBA8.1. The dotted line shows a truncation site and the stem region that appears to be important for secondary structure but not directly to binding is indicated. The constant region shared by the aptamers described herein is highlighted. FIG. 38B. depicts the minimal aptamer with specific binding activity to CD71. Residues 22-54 of aptamer JBA8.1 (SEQ ID NO: 2). N=3-40 nucleotide positions wherein each position can be any nucleotide.

DETAILED DESCRIPTION

The compositions and methods described herein are related, in part, on the discovery of DNA based aptamers that can bind to the transferrin receptor (also referred to herein as CD71), which is highly expressed on proliferating cells, including cancer cells. As such, the DNA based aptamers described herein can be used to deplete cancerous cells from a biological sample, for use in cell-based therapeutics. Alternatively, the aptamers described herein can be used to isolate proliferating cells, for example, for use in the analysis of such cells or diagnosis of cancer.

Definitions

As used herein, the term "isolating a cell of interest" refers to the selective separation or enrichment of a target cell, cell type or class of cells from a sample comprising other cells, cell types of cell classes such that the cell population resulting from such separation has a high degree of cell purity as determined by specific cell markers (e.g., CD71 for a CD71 positive T cell or B cell). Such isolated cells can be used in the analysis of proliferating cells in a subject or diagnosis of cancer.

While higher degrees of cell purity are preferred over lower, cell "isolation" as the term is used herein does not require 100% purity of the resulting cell population. Target cells (e.g., transferrin positive cells) or a population thereof will generally be considered "isolated" as the term is used herein if they comprise at least 60% of a target cell population, such as a CD71 positive cell population, resulting from an isolation method as described herein, and preferably at least 70%, at least 80%, at least 90% or more.

A "plurality" contains at least two members. In certain cases, a plurality may have at least 10, at least 100, at least 1000, at least 10,000, at least 100,000, or at least 1,000,000 or more members. As used herein, a "plurality of cell types" refers to a biological sample comprising cells with distinct cell surface markers or compositions thereof and/or physiological functions.

As used herein, surface markers "specific for" a target cell or cell fraction or population of interest are polypeptides or other molecules expressed on the surface of a target cell or cell fraction that are distinct to that target cell or cell fraction and thereby permit the identification and isolation of that cell or cell fraction using a method as described herein. In some embodiments, a single surface marker is sufficient to identify a target cell, e.g., CD8a identifies a $CD8^+$ T cell while CD71/transferrin receptor identifies proliferating cells such as cancer cells. In other embodiments, two or more markers can together identify a target cell or cell population or fraction. In other embodiments, a single marker can identify a class of target cells, e.g., CD71 identifies proliferating cells or cancer cells as a class. In other embodiments the cell surface marker is a membrane lipid, peptide, polypeptide, or protein.

As used herein, the term "contacting a biological sample," when used in the context of an aptamer or nucleic acid as described herein, refers to addition of an aptamer to a biological sample under conditions that permit specific or selective binding of the aptamer to a target moiety or marker on the cell surface or extracellular matrix of the cell.

As used herein, the term "conditions that permit forming aptamer-bound cells" refers to incubation of cells at 4° C. for 30 minutes in a binding buffer comprising 0.1 mg/mL tRNA, 0.1 g/L $CaCl_2$, 0.2 g/L KCl, 0.2 g/L $KH_2PO_4$, 0.1 g/L $MgCl_2$ hexahydrate, 8.0 g/L NaCl, 2.1716 $Na_2HPO_4$ septahydrate, supplemented with 25 mM glucose, 5 mM $MgCl_2$, varying amounts of bovine serum albumin (BSA), with a pH of 7.5, or to conditions that provide binding substantially equivalent to binding permitted under these conditions. In this context, substantially equivalent means±10% of the binding permitted under these conditions.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

As described herein, a "compensatory change" refers to a change in a nucleoside or nucleobase pair that maintains predicted secondary structure and/or target binding of an aptamer. Non-limiting examples of compensatory changes include changing a G:C base pair to a C:G base pair or changing an A:T base pair to a T:A base pair, e.g., in a stem-loop structure of a nucleic acid. Because of differences in the hydrogen-bonding characteristics between A:T and C:G base pairs, replacing an A:T base pair with a C:G base pair would be expected to alter the stability of the secondary structure, i.e., to increase its stability. Thus, a compensatory change described herein can further include such change. It is contemplated that a change from a C:G or G:C base pair to an A:T or T:A base pair can sometimes be tolerated without significantly affecting the secondary structure or target binding characteristics. However, this type of compensatory change should be considered in the context of the overall stem stability of the aptamer. As described herein, a compensatory change in the nucleotide sequence of an aptamer can involve, where appropriate, a modified nucleoside selected from but not limited to the nucleobases or nucleosides described in Table 1.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

As described herein, a "solid support" is a structure upon which one or more aptamers can be displayed for contact with a target cell. A solid support provides a ready means for isolating or removing bound target cells from a mixture or suspension. A solid support can be in the form, for example, of a particle, bead, filter or sheet, resin, scaffold, matrix, or column. Non-limiting classes of materials that the solid support can comprise include polymer, metal, ceramic, gels, paper, or glass. The materials can include, but are not limited to polystyrene, agarose, gelatin, iron oxide, stainless steel, polycarbonate, polydimethylsiloxane, polyethylene, acrylonitrile butadiene styrene, cyclo-olefin polymers and cyclo-olefin copolymers.

As described herein, a "phase changing agent" is an agent that is soluble in aqueous solution under one set of conditions, but can be induced to an insoluble, precipitating form under another set of conditions. The conditions for both soluble and insoluble forms should be compatible with maintaining the viability of target cells. Non-limiting examples of conditions that change phase include temperature, pH and salt or solute concentration. An example of a phase-changing agent includes poly(N-isopropylacrylamide) phase-changing polymers that are soluble at one temperature and then at a different temperature precipitate out from solution.

As used herein, the term "affinity pair" refers to a pair of moieties that specifically bind each other with high affinity, generally in the low micromolar to picomolar range. When one member of an affinity pair is conjugated to a first element and the other member of the pair is conjugated to a second element, the first and second elements will be brought together by the interaction of the members of the affinity pair. Non-limiting examples of affinity pairs that can be conjugated to an aptamer or solid support include ligand-receptor pairs, antibody-antigen pairs, as well as smaller pairs such as biotin-avidin, or biotin-avidin variant, such as biotin streptavidin or biotin-neutravidin, among others. As but one example, the biotin-streptavidin interaction has a $K_d$ of $10^{-14}$ to $10^{-15}$ molar.

As used herein, the term "conjugated to" encompasses association of an aptamer with a solid support, a phase-changing agent or a member of an affinity pair by covalent bonding, including but not limited to cross-linking via a cross-linking agent, or by a strong non-covalent interaction that is maintained under conditions in which the conjugate is to be used.

As used herein, the term "hybridize" refers to the phenomenon of a single-stranded nucleic acid or region thereof forming hydrogen-bonded base pair interactions with either another single stranded nucleic acid or region thereof (intermolecular hybridization) or with another single-stranded region of the same nucleic acid (intramolecular hybridization). Hybridization between a "reversal agent" or "antidote" and an aptamer permits the disruption of binding of the aptamer to a target by destabilization of the aptamer's secondary structure, allowing for reversible cell selection to occur. Hybridization is governed by the base sequences involved, with complementary nucleobases forming hydrogen bonds, and the stability of any hybrid being determined by the identity of the base pairs (e.g., G:C base pairs being stronger than A:T base pairs) and the number of contiguous base pairs, with longer stretches of complementary bases forming more stable hybrids.

As used herein, a "magnetoresponsive bead" refers to a solid support particle that can be attracted to a magnetic device or magnetic field. A magnetoresponsive bead coated with or otherwise conjugated to an aptamer can be used to separate aptamer-bound cells from a biological sample. While the term "bead" infers a spherical form, this is not a limitation of the shape of magnetoresponsive solid support that can be used to separate the aptamer-bound cells from non-aptamer bound cells. The shape can be irregular, or some variation of spherical, oval, cuboid, and the like. In various embodiments, a magnetoresponsive bead can be conjugated to an aptamer covalently, e.g., via a cross-linking reaction, or can be conjugated non-covalently, e.g., via the interaction of members of an affinity pair.

As used herein, a "cell fraction" refers to a subset of cells in a sample population that shares a given characteristic, e.g., expression of a certain marker or set of markers. A targeted cell fraction can include more than one cell type; as but one example, where T cells are a cell fraction, that fraction can include, for example, $CD4^+$ T cells and $CD8^+$ T cells, among others. In some embodiments, a targeted cell fraction includes a single cell type. T cells, like other cells, can be identified by cluster of differentiation (CD) markers, or chemokine receptors (CCR). Non-limiting examples of T cell markers include CD8, CD19, CD4, CD3, CD28, CD45, CD62, CD31, CD27, or CCR-7.

As used herein the term "selectively binds transferrin receptor 1 (TfR1)/CD71" refers to the capacity of an aptamer as described herein to bind to TfR1/CD71, under conditions that maintain the viability of mammalian cells, with at least 1,000× greater affinity than it binds to CD8 or to CD4, e.g., at least 1,000× greater, at least 5,000× greater, at least 7,500× greater, at least 10,000× greater, at least 15,000× greater, at least 20,000× greater or more. Affinity can be determined, e.g., as described in the Examples herein.

As used herein, the term "specifically binds the transferrin receptor/CD71" refers to the capacity of an aptamer as described herein to bind to the transferrin receptor (also known as CD71) or a given target cell expressing the receptor thereupon, under conditions that maintain the viability of mammalian cells, such that the aptamer binds the transferrin receptor to a significantly greater degree than it binds to other markers or other cells that do not express the transferrin receptor. At a minimum, an aptamer that specifically binds the transferrin receptor binds with a Kd of 1 micromolar or less, e.g., 1 micromolar or less, 900 nanomolar or less, 800 nanomolar or less, 700 nanomolar or less, 600 nanomolar or less, 500 nanomolar or less, 400 nanomolar or less, 300 nanomolar or less, 200 nanomolar or less, 100 nanomolar or less, 90 nanomolar or less, 80 nanomolar or less, 70 nanomolar or less, 60 nanomolar or less, 50 nanomolar or less, 40 nanomolar or less, 30 nanomolar or less, 20 nanomolar or less, or 10 nanomolar or less.

The terms "decrease," "reduce," "reduction," or "inhibit" are all used herein to mean a decrease or lessening of a property, level, or other parameter (such as a disease symptom) by a statistically significant amount. In some embodiments, "reduce," "reduction" or "decrease" or "inhibit" typically means a decrease or reduction in the number of target cells expressing the transferrin receptor (e.g., in a depletion method) by at least 10% as compared to number of transferrin receptor-expressing cells in the starting population prior to depletion and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. In other embodiments, "reduce," "reduction" or "decrease" or "inhibit" typically means a decrease in at least one symptom of a given disease (e.g., cancer) by at least 10% as compared to the symptom prior to onset of treatment and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. Rather, the term "complete inhibition" is used to refer to a 100% inhibition as compared to an appropriate reference level. A decrease in a symptom of a given disease can be preferably down to a level accepted as within the range of normal for an individual without the disease.

The terms "increased," "increase" or "enhance" or "activate" are all used herein to generally mean an increase of a property, level, or other parameter (e.g., number of cells bound to aptamer) by a statistically significant amount; for the avoidance of any doubt, the terms "increased," "increase" or "enhance" or "activate" means an increase in the number of target cells in a given population, for example, following a cell enrichment method by at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, or an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other forms of such compounds that are compatible with cell viability. In one embodiment, the small molecule comprises a reversal agent and is present at a concentration effective to release an aptamer from a cell surface marker on a cell without undue cell toxicity.

As defined herein, "flow cytometry" refers to a technique for counting and examining microscopic particles, such as cells and chromosomes, by suspending them in a stream of fluid and passing them through an electronic detection apparatus. Flow cytometry allows simultaneous multiparametric analysis of the physical and/or chemical parameters of up to thousands of particles per second, such as fluorescent parameters. Modern flow cytometric instruments usually have multiple lasers and fluorescence detectors. Increasing the number of lasers and detectors allows for labeling by multiple antibodies and can more precisely identify a target population by their phenotypic markers. Certain flow cytometric instruments can take digital images of individual cells, allowing for the analysis of fluorescent signal location within or on the surface of cells.

As used herein, the term "immunotherapy" refers to the treatment of disease via the stimulation, induction, subversion, mimicry, enhancement, augmentation or any other modulation of a subject's immune system to elicit or amplify adaptive or innate immunity (actively or passively) against cancerous or otherwise harmful proteins, cells or tissues. Immunotherapies (i.e., immunotherapeutic agents) include cancer vaccines, immunomodulators, "antibody-based immunotherapies" or monoclonal antibodies (e.g., humanized monoclonal antibodies), immunostimulants, cell-based therapies such as adoptive T-cell therapies or dendritic cell immunotherapies or dendritic cell vaccines, and viral therapies, whether designed to treat existing cancers or prevent the development of cancers or for use in the adjuvant setting to reduce likelihood of recurrence of cancer.

As used herein, the term "toehold" describes a 5-15 nucleotide overhang region of an aptamer that is designed to be single-stranded and complementary to a region of a reversal agent or antidote. The complementary nature of the toehold permits the reversal agent/antidote to readily hybridize to the single stranded region and facilitates the remainder of the reversal agent, which is complementary to an adjacent double-stranded region of the aptamer, to initiate strand displacement at the adjacent double-stranded region. Thus, a toehold will generally be designed or chosen to be adjacent to a region of double stranded sequence one wishes to disrupt or displace, which will generally be a stem structure in an aptamer. The toehold provides a kinetic advantage for a reversal agent to initiate hybridization and strand displacement to thereby efficiently disrupt aptamer binding to its cell surface marker target. A toehold is generally, but not necessarily, added to an aptamer once the aptamer is found to bind a desired target. As an alternative, every member of an aptamer library can, for example, have the same sequence at one end or the other that will serve as a toehold. Accordingly, internal regions of the aptamer that are not base paired under structure prediction can act as toehold sequences. A toehold can include, for example, a relatively high GC content to provide an improvement in strand displacement rate constant for hybridization to its complement relative to a sequence with lower GC content. In one embodiment, the toehold comprises a 5, 6, 7, 8, 9, 10, 11, 12, 13, 14 or 15 nucleotide overhang.

As used herein, the term "treating" includes reducing or alleviating at least one adverse effect or symptom of a condition, disease, or disorder, for example, cancer. For example, the term "treating" and "treatment" refers to administering to a subject an effective amount of a composition, e.g., a therapeutic cell composition that is depleted of transferrin receptor-expressing cells by the aptamers described herein so that the subject has a reduction in at least one symptom of the disease (e.g., fatigue, pain, tumor size, tumor growth, reduction in need for chemotherapeutics, improved prognosis, improvement in predicted mortality, and the like) or an improvement in the disease, for example, beneficial or desired clinical results. For purposes of this disclosure, beneficial or desired clinical results include, but are not limited to, alleviation of one or more symptoms, diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition but may not be a complete cure for the disease. Successful treatment can also be assessed by a reduction in the need for medical interventions, reduction in hospital or emergency room visits, reduction in fatigue, or other markers of an improved quality of life. In some embodiments, treatment can include prophylaxis. However, in alternative embodiments, treatment does not include prophylaxis.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the terms "pharmaceutically acceptable", "physiologically tolerable" and grammatical variations thereof, as they refer to compositions, carriers, diluents, and reagents, are used interchangeably and represent that the materials are capable of administration to or upon a mammal without the production of undesirable physiological effects such as nausea, dizziness, gastric upset, and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. Therapeutic compositions as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used with the methods described herein that will be effective in the treatment of a particular disorder or condition will depend on the nature of the disorder or condition and can be determined by standard clinical techniques.

As used herein, the term "subject" includes humans and mammals. The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a mammal is a human. A subject can be of any age including a neonate, toddler, child, teen, adult, or a geriatric subject.

As used herein the term "comprising" or "comprises" is used in reference to compositions, methods, and respective component(s) thereof, that are essential to the claimed technology, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Nucleic Acid Aptamer Compositions

Nucleic acid aptamers, single-strands of nucleic acid oligonucleotides capable of binding target molecules, are an attractive alternative to antibodies for cell selection. Aptamers can possess binding affinities comparable to or even higher than antibodies. Importantly, aptamers are produced synthetically as well-defined, low variability products with long storage stability. Aptamers can be discovered through a library selection method known as systematic evolution of ligands by exponential enrichment (SELEX), and further optimized for chemical stability. With their favorable attributes, the application field for aptamers has escalated in the last quarter century to encompass areas including sensing, purification, diagnostics, drug delivery, for example, transcytosis and aptamer-mediated delivery of, for example, a nucleic acid or a ribonucleoprotein, and the like, and other therapeutically effective agents.

Nucleic acid aptamers include RNA, DNA, and/or synthetic nucleic acid analogs (e.g., PNA) capable of specifically binding target molecules. Aptamers are an attractive alternative to antibodies for cell selection because of their high level of specificity and affinity for cell surface markers. Synthetic aptamers were first developed in the 1990s by the Szostak and Gold groups, and it was discovered that aptamers can possess binding affinities comparable to or even higher than antibodies.

Provided herein are methods and compositions for generating functional nucleic acid aptamers for cell selection. The composition of the nucleic acid aptamer can include but is not limited to the nucleobases described in Table 1 (below) and can comprise one or more combinations of backbone or nucleobase structure characteristic of DNA, RNA, or synthetic nucleic acid analogs such as PNAs or BNAs.

TABLE 1

| Nucleosides and Nucleobases |
|---|
| Adenosine (A) |
| Thymine (T) |
| Guanosine (G) |
| 5-Methyluridine (U) |
| Uridine (U) |
| Cytidine (C) |
| Deoxyadenosine (dA) |
| Deoxy guanosine (dG) |
| Thymidine (dT) |
| Deoxyuridine (dU) |
| Deoxycytidine (dC) |
| Hypoxanthine-adenine (I-A) |
| Hypoxanthine-cytosine (I-C) |
| Hypoxanthine-uracil (I-U) |

TABLE 1-continued

| Nucleosides and Nucleobases |
|---|
| Guanine-uracil (G-U) |
| N-(2-aminoethyl)-glycine-purine |
| N-(2-aminoethyl)-glycine-adenosine (PNA-A) |
| N-(2-aminoethyl)-glycine-guanosine (PNA-G) |
| N-(2-aminoethyl)-glycine-thymine (PNA-T) |
| N-(2-aminoethyl)-glycine-uridine (PNA-U) |
| N-(2-aminoethyl)-glycine-cytidine (PNA-C) |
| Xanthine |
| Theobromine |
| Isoguanine |
| 5-hydroxymethyl cytosine |
| hypoxanthine, |
| 2-aminoadenine |
| 6-methyl-adenine |
| 6-methyl-guanine |
| 2-propyl-adenine |
| 2-propyl-guanine |
| 2-thiouracil |
| 2-thiothymine |
| 2-thiocytosine |
| 5-halouracil |
| 5-halocytosine |
| 5-propynyl uracil |
| 5-propynyl cytosine |
| 6-azo uracil |
| 6-azo cytosine |
| 6-azo thymine |
| 5-uracil (pseudouracil) |
| 4-thiouracil |
| 8-halo adenine |
| 8-halo guanosine |
| 8-amino adenine |
| 8-amino guanosine |
| 8-thiol adenine |
| 8-thiol guanosine |
| 8-thioalkyl adenine |
| 8-thioalkyl guanosine |
| 8-hydroxyl adenine |
| 8-hydroxyl guanosine |
| 2',4'-BNANC[NBn] |
| 2',4'-BNANC[NMe] |
| 2',4'-BNANC[NH] |
| 2',4'-BNA-1-isoquinolone |
| 2',4'-ENA |
| 2',4'-BNA-2-pridone |
| 3'-amino-2',4'-BNA |

Aptamers generally consist of relatively short oligonucleotides that typically range from 20 to 80 nucleotides in length, for example, at least 20 nucleotides, at least 30 nucleotides, at least 40 nucleotides, at least 50 nucleotides, at least 60 nucleotides, at least 70 nucleotides, at least 80 nucleotides or more. An aptamer can be attached to a longer sequence, e.g., at one end or the other of the aptamer, although appended sequences that affect the secondary structure of the aptamer can affect aptamer function. In certain embodiments, the aptamer, for example, an aptamer that selectively binds to CD71 and comprises a sequence having 75% sequence identity to residues 22-54 of the aptamer JBA8.1 (SEQ ID NO:2) and wherein the aptamer can further comprise a number (N) of nucleotides (nt) at either the 5' and/or 3' end, wherein each nucleotide is independently selected from adenine, thymine/uracil, guanine, and/or cytosine. N can be present independently at either end, and can be from 3 to 40 nucleotides, and optionally from 3 to 30 nucleotides, from 3 to 20, and preferably 3 to 10 nucleotides. Preferably, the number (N) nucleotides at each end form a stem structure.

The functional activity of an aptamer, i.e., binding to a given target molecule such as the transferrin receptor, involves interactions between moieties or elements in the aptamer with moieties or elements on the target molecule.

The interactions can include, for example, hydrophobic/hydrophilic interactions, charge or electrostatic interactions, hydrogen bonding, and the like, and the specific interactions of a given aptamer with a given target are determined by the sequence of the aptamer and the secondary and tertiary structure assumed by that sequence under binding conditions. Thus, the occurrence of intramolecular base pairing in the aptamer is a primary factor in aptamer structure and therefore aptamer function. Intramolecular base pairing can result, for example, in double stranded stem structures, stem-loop structures, and exposure of various elements of the aptamer that can participate in binding interactions with a target molecule. Where the secondary structure of an aptamer is defined by its sequence, including the presence of intramolecular base pairs between regions of complementary sequence that fold the molecule into a functional shape, it should be understood that changes in aptamer sequence occurring in a stem structure or that introduce new options for intramolecular base pairing can disrupt the conformation of the molecule and thereby its function. That said, when a change of one nucleotide in a base-paired stem structure is accompanied by a compensatory change in the complementary nucleotide that maintains the ability to base pair, the structure, and thereby the function of the aptamer can be maintained. That is, some aptamers can tolerate some degree of sequence change and still retain binding activity. Furthermore, a truncated or partial sequence of an aptamer as described herein can also retain binding activity provided that the truncation does not alter intramolecular base-pairing necessary for the secondary structure of the aptamer. In particular, it is contemplated that removal of some sequence from the 5' or 3' end of an aptamer described herein can result in an aptamer molecule that retains binding activity. Indeed, some changes can improve binding activity. This, of course, is one basis for an iterative selection approach used to identify aptamers that bind a given target and do so with high affinity.

As described herein, an aptamer can additionally or alternatively comprise nucleobase (often referred to in the art simply as "base") modifications or substitutions. Such substitutions can modify stability of the aptamer or reversal agent, e.g., by reducing susceptibility to enzymatic or chemical degradation, or can modify (increase or decrease) intra- or inter-molecular interactions, including but not limited to base-pairing interactions. Aptamer and reversal agent nucleobases include the purine bases adenine (A) and guanine (G), and the pyrimidine bases thymine (T), cytosine (C), and uracil (U) or modified or related forms thereof. Modified nucleobases include, as non-limiting examples, other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine, among others. The base pairing behavior and preferences of these nucleobases are known in the art.

Synthetic oligonucleotides comprising an aptamer can include but are not limited to peptide nucleic acid (PNA), bridged nucleic acid (BNA), morpholinos, locked nucleic acids (LNA), glycol nucleic acids (GNA), threose nucleic acids (TNA), or any other xeno nucleic acid (XNA) described in the art.

One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone.

In some embodiments, a transferrin receptor-binding aptamer as described herein comprises one of the sequences in Table 2. In another embodiment, a transferrin receptor-binding aptamer as described herein comprises at least 75% sequence identity to one of the sequences in Table 2. In other embodiments, the transferrin receptor-binding aptamer comprises at least 80%, at least 85%, at least 90%, at least 91%, at least 92%, at least 93%, at least 94%, at least 95%, at least 96%, at least 97%, at least 98%, or at least 99% sequence identity to one of the sequences in Table 2. In certain embodiments, the transferrin receptor-binding aptamer consists essentially of one of the sequences in Table 2. In other embodiments, the transferrin receptor-binding aptamer consists of one of the sequences in Table 2.

TABLE 2

Exemplary motif 3 aptamer sequences predicted to bind the transferrin receptor

| Aptamer Name | Sequence (5' to 3' order) | SEQ ID NO: |
|---|---|---|
| tJBA8.1 | GCAGCAGCGTAAAGGGGGTGTTTGTGCGGTGTGGAGTGCGCGTGCTGCTGC | 1 |
| tJBA8.1 | ATCCAGAGTGACGCAGCAGCGTAAAGGGGGTGTTTGTGCGGTGTGGAGTGC GCGTGCTGCTGCTGGACACGGTGGCTTAGT | 2 |
| tJBA8.193c | GCAGCAACGTAAAGGGGGTGTTTGTGCGGTGTGGAGTGCGCGTGCTGCTGC | 3 |
| tJBA8.193a | GCAGCAGCGTAAAGGGAGTGTTTGTGCGGTGTGGAGTGCGCGTGCTGCTGC | 4 |
| tJBA8.189a | GCAGCAGCGTAAAGGGGGTGTTTGTGCGGTGTGGAGTGCGCGTGCTGCTAC | 5 |
| tJBA8.185b | GCAGCAGCGTAAAGGGGGTGTTTGTGCAGTGTGGAGTGCGCGTGCTGCTGC | 6 |
| tJBA8.177b | GCAGCAGCGTAAAGGAGGTGTTTGTGCGGTGTGGAGTGCGCGTGCTGCTGC | 7 |

TABLE 2-continued

Exemplary motif 3 aptamer sequences predicted to bind the transferrin receptor

| Aptamer Name | Sequence (5' to 3' order) | SEQ ID NO: |
|---|---|---|
| tJBA8.173c | GCAGCAGCGTAAAGGGGGTGTTTGTGCGGTGTGAAGTGCGCGTGCTGCTGC | 8 |
| tJBA8.170c | GCAGCAGCGTAAAGGGGGTGTTTGTGCGGTGTGGAGTGCGCGTGCTACTGC | 9 |
| tJBA8.166b | GCAGCAGCGTAAAGGGGGTGTTTATGCGGTGTGGAGTGCGCGTGCTGCTGC | 10 |
| tJBA8.164a | GCAGCAGCGTAAAGGGGGTGTTTGTGCGGTGTGGAGTGCACGTGCTGCTGC | 11 |
| tJBA8.135a | GCAGCAGCGTAAAGGGGGTGTTTGTGCGGTATGGAGTGCGCGTGCTGCTGC | 12 |
| tJBA8.61 | GCAGCAGCGTAAAGGGGGTGTTTGTGCGGTGTGGAGTGCGCATGCTGCTGC | 13 |
| tJBA8.10 | GCAGCAGCATAAAGGGGGTGTTTGTGCGGTGTGGAGTGCGCGTGCTGCTGC | 14 |
| tJBA8.201d | GCAGCAGCGTAAAGGGGGTGTTTGTGCGGTTTGGAGTGCGCGTGCTGCTGC | 15 |
| tJBA8.185a | GCAGCAGCGTAAAGGGGGTGTTTGTGCTGTGTGGAGTGCGCGTGCTGCTGC | 16 |
| tJBA8.153b | GCAGCATCGTAAAGGGGGTGTTTGTGCGGTGTGGAGTGCGCGTGCTGCTGC | 17 |
| tJBA8.116 | GCAGCAGCTTAAAGGGGGTGTTTGTGCGGTGTGGAGTGCGCGTGCTGCTGC | 18 |
| tJBA8.108 | GCAGCAGCGTAAAGGGGGTGTTTGTGCGGTGTGTAGTGCGCGTGCTGCTGC | 19 |
| tJBA8.159b | GCAGCAGCGTAAAGGGGGTGTTTGTGCGGTGTGGAGTGCGCGTGCTGCTGA | 20 |
| tJBA8.197c | GCAGCAGCGTAAAGGGGGTGTTTGTGCGGTGTGGAGTGCGTGTGCTGCTGC | 21 |
| tJBA8.143 | GCAGCAGCGTAAAGGGGGTGTTTGTGCGGTGTGGAGTGTGCGTGCTGCTGC | 22 |
| tJBA8.139 | GCAGCAGCGTAAAGGGGGTGTTTGTGTGGTGTGGAGTGCGCGTGCTGCTGC | 23 |
| tJBA8.107 | GCAGCAGCGTAAAGGGGGTGTTTGTGCGGTGTGGAGTGCGCGTGCTGCTGT | 24 |
| tJBA8.45 | GCAGCAGCGCAAAGGGGGTGTTTGTGCGGTGTGGAGTGCGCGTGCTGCTGC | 25 |
| tJBA8.26 | GCAGCAGCGTAAAGGGGGTGTTTGTGCGGTGTGGAGTGCGCGCGCTGCTGC | 26 |
| tJBA8.26 | ATCCAGAGTGACGCAGCAGCGTAAAGGGGGTGTTTGTGCGGTGTGGAGTGC GCGCGCTGCTGCTGGACACGGTGGCTTAGT | 27 |
| tJBA8.193b | GCAGCAGCGTAAAGGGGGTGTTTGTGCGGTGTGGAGTGCGCGTGCGGCTGC | 28 |
| tJBA8.170b | GCAGCAGCGTAAAGGGGGTGTTTGGGCGGTGTGGAGTGCGCGTGCTGCTGC | 29 |
| tJBA8.166d | GCAGCAGCGTAAAGGGGGTGTGTGTGCGGTGTGGAGTGCGCGTGCTGCTGC | 30 |
| tJBA8.189c | GCAGCAGCGTAGAGGGGGTGTTTGTGCGGTGTGGAGTGCGCGTGCTGCTGC | 31 |

In some embodiments, the transferrin receptor-binding aptamer comprises the sequence: GCAGCANCN-NANAGGNNGTGTNTNNGNNGTNTG-NAGTGNNNNNGCNNCTNN (SEQ ID NO: 32), wherein N is A, T, C, or G. In other embodiments, the transferrin receptor-binding aptamer comprises a sequence selected from the group consisting of:

(SEQ ID NO: 33)
GCAGCANCGTAAAGGGGGTGTTTGTGCGGTGTGGAGTGCGCGTGCTGCTG
C;

(SEQ ID NO: 34)
GCAGCAGCNTAAAGGGGGTGTTTGTGCGGTGTGGAGTGCGCGTGCTGCTG
C;

-continued (SEQ ID NO: 35)
GCAGCAGCAGCAGCGNAAAGGGGGTGTTTGTGCGGTGTGGAGTGCGCGTG
CTGCTGC;

(SEQ ID NO: 36)
GCAGCAGCGTANAGGGGGTGTTTGTGCGGTGTGGAGTGCGCGTGCTGCTG
C;

(SEQ ID NO: 37)
GCAGCAGCGTAAAGGNGGTGTTTGTGCGGTGTGGAGTGCGCGTGCTGCTG
C;

(SEQ ID NO: 38)
GCAGCAGCGTAAAGGGNGTGTTTGTGCGGTGTGGAGTGCGCGTGCTGCTG
C;

-continued (SEQ ID NO: 39)
GCAGCAGCGTAAAGGGGGTGTNTGTGCGGTGTGGAGTGCGCGTGCTGCTG
C;

(SEQ ID NO: 40)
GCAGCAGCGTAAAGGGGGTGTTTNTGCGGTGTGGAGTGCGCGTGCTGCTG
C;

(SEQ ID NO: 41)
GCAGCAGCGTAAAGGGGGTGTTTGNGCGGTGTGGAGTGCGCGTGCTGCTG
C;

(SEQ ID NO: 42)
GCAGCAGCGTAAAGGGGGTGTTTGTGNGGTGTGGAGTGCGCGTGCTGCTG
C;

(SEQ ID NO: 43)
GCAGCAGCGTAAAGGGGGTGTTTGTGCNGTGTGGAGTGCGCGTGCTGCTG
C;

(SEQ ID NO: 44)
GCAGCAGCGTAAAGGGGGTGTTTGTGCGGTNTGGAGTGCGCGTGCTGCTG
C;

(SEQ ID NO: 45)
GCAGCAGCGTAAAGGGGGTGTTTGTGCGGTGTGNAGTGCGCGTGCTGCTG
C;

(SEQ ID NO: 46)
GCAGCAGCGTAAAGGGGGTGTTTGTGCGGTGTGGAGTGNGCGTGCTGCTG
C;

(SEQ ID NO: 47)
GCAGCAGCGTAAAGGGGGTGTTTGTGCGGTGTGGAGTGCNCGTGCTGCTG
C;

(SEQ ID NO: 48)
GCAGCAGCGTAAAGGGGGTGTTTGTGCGGTGTGGAGTGCGNGTGCTGCTG
C;

(SEQ ID NO: 49)
GCAGCAGCGTAAAGGGGGTGTTTGTGCGGTGTGGAGTGCGCNTGCTGCTG
C;

(SEQ ID NO: 50)
GCAGCAGCGTAAAGGGGGTGTTTGTGCGGTGTGGAGTGCGCGNGCTGCTG
C;

(SEQ ID NO: 51)
GCAGCAGCGTAAAGGGGGTGTTTGTGCGGTGTGGAGTGCGCGTGCNGCTG
C;

(SEQ ID NO: 52)
GCAGCAGCGTAAAGGGGGTGTTTGTGCGGTGTGGAGTGCGCGTGCTNCTG
C;

(SEQ ID NO: 53)
GCAGCAGCGTAAAGGGGGTGTTTGTGCGGTGTGGAGTGCGCGTGCTGCTN
C;
and (SEQ ID NO: 54)
GCAGCAGCGTAAAGGGGGTGTTTGTGCGGTGTGGAGTGCGCGTGCTGCTG
N, wherein N is A, T, C, or G.

In some embodiments, the transferrin receptor-binding aptamer described herein comprises at least one mutation in the sequence of SEQ ID NO: 1 (JBA8.1) at the following nucleic acids (in 5' to 3' order): G at position 7, G at position 9, A at position 12, G at position 16, G at position 17, T at position 22, G at position 24, T at position 25, C at position 27, G at position 28, G at position 31, G at position 34, C at position 39, G at position 40, C at position 41, G at position 42, T at position 43, T at position 46, G at position 47, G at position 50, or C at position 51. In some embodiments, the aptamer comprises at least two, at least 3, at least 4, at least 5, at least 6, at least 7, at least 8, at least 9, or at least 10 nucleic acid mutations selected from the afore-cited nucleic acid positions in SEQ ID NO: 1 and/or SEQ ID NO: 2, provided that the aptamer retains at least 75% sequence identity to residues 10-42 of SEQ ID NO: 1 or 22-55 of SEQ ID NO:2. The nucleic acid at a given position described above can be mutated to any of the other naturally occurring nucleic acids (e.g., a G, can be mutated to a T, C, or A) or a synthetic nucleic acid as desired. If necessary, the aptamer binding characteristics can be determined using the methods outlined in the Example section for binding to transferrin receptor-expressing cells.

In one embodiment, the transferrin receptor-binding aptamer described herein comprises (or consists essentially or consists of) tJBA8.1 (SEQ ID NO: 1). SEQ ID NO: 1 comprises secondary structure including a first, second and third stem region as follows:

Stem 1 includes nucleotides 1-8 of SEQ ID NO: 1 (5'-GCAGCAGC-3') and the complement thereof at nucleotides 44-51 of SEQ ID NO: 1 (5'-GCTGCTGC-3');

Stem 2 includes nucleotides 11-13 of SEQ ID NO: 1 (5'-AAA-3') and the complementary sequence at nucleotides 21-23 of SEQ ID NO: 1 (5'-TTT-3'); and Stem 3 includes nucleotides 26-28 of SEQ ID NO: 1 (5'-GCG-3') and the complementary sequence at nucleotides 39-41 of SEQ ID NO: 1 (5'-CGC-3').

SEQ ID NO: 1 Also Comprises a First, Second and Third Loop Region as Follows:

Loop 1 includes non-base paired nucleotides 9 and 10, 24 and 25, and 43 and 44 of SEQ ID NO: 1; non-contiguous nucleotides 8 and 41, 11 and 23, and 26 and 41 of SEQ ID NO: 1 are base paired to each other, respectively in the formation of Loop 1;

Loop 2 includes non-base-paired nucleotides 14-20 of SEQ ID NO: 1 (5'-GGGGGTG-3'); non-contiguous nucleotides 13 and 21 of SEQ ID NO: 1 are base paired to each other in the formation of Loop 2;

Loop 3 includes non-base paired nucleotides 29-38 of SEQ ID NO:1 (5'-GTGTGGAGTG-3'); nucleotides 28 and 39 of SEQ ID NO: 1 are base paired to each other.

Nucleic Acid Aptamer Secondary Structure and Cell Targeting

As noted above, the aptamers described herein have the ability to fold into 2-dimensional (2D) and 3-dimensional (3D) structures that interact with specific targets. Aptamers generally bind to specific targets through non-covalent interactions with a target, e.g., a cell surface marker, via interactions including but not limited to electrostatic interactions, hydrophobic interactions, and/or their complementary shapes.

It will be understood by one of skill in the art that the aptamer 2-D and 3-D structures can be predicted by any of several methods to define properties such as equilibrium probability and stability. The NUPACK™ web application can be used to generate predicted secondary structures of aptamer sequences (see, e.g., Zadeh, J. N., Steenberg, C. D., Bois, J. S., Wolfe, B. R., Pierce, M. B., Khan, A. R., Dirks, R. M. & Pierce, N. A. NUPACK: Analysis and design of nucleic acid systems. *J. Comput. Chem.* (2011) doi:10.1002/jcc.21596, which is incorporated herein by reference in its entirety). Additional non-limiting examples of aptamer structure prediction methods include in silico models such as UNPACK™, APTANI™, 3D-DART™, ModeRNA™, or Unified Nucleic Acid Folding and hybridization package (UNAFold™), or any other oligonucleotide structure prediction in silico model known in the art.

Different structure prediction models can produce different predicted structures, and even the same model can produce different predicted structures if different baseline parameter are used, e.g., temperature, ionic strength, etc.

It is contemplated that the reverse, complement, reverse complement, or truncated sequences of the aptamers described in the Examples can be used for isolation of cells, as it is contemplated that these sequences would maintain the secondary structure of the aptamer.

For any given secondary structure prediction model, the maintenance or improvement in aptamer binding to its target when a modification, e.g., a compensatory or non-compensatory change is made on the basis of predicted structure should be tested experimentally.

A cell can be designated "positive" or "high," "dim" or "low," or "negative" for the transferrin receptor (i.e., CD71), and such designations can be useful for the practice of the assays and cell isolation/depletion methods described herein. A cell is considered "positive" for a cell-surface marker if it expresses the marker on its cell-surface in amounts sufficient to be detected using methods known to those of skill in the art, such as contacting a cell with an antibody or aptamer that binds selectively or specifically to that marker, and subsequently performing flow cytometric analysis of such a contacted cell to determine whether the antibody or aptamer is bound the cell. It is to be understood that while a cell may express messenger RNA for a cell-surface marker, in order to be considered positive for the assays and methods described herein, the cell must express it on its surface. A cell is considered "dim" or "low" for the transferrin receptor if it expresses the receptor on its cell-surface in amounts sufficient to be detected using methods known to those of skill in the art, such as contacting a cell with an antibody or aptamer that binds selectively or specifically to the transferrin receptor, and subsequently performing flow cytometric analysis of such a contacted cell to determine whether the antibody or aptamer is bound to the cell, but there exists another distinct population of cells that expresses CD71 at a higher level, giving rise to at least two populations that are distinguishable when analyzed using, for example, flow cytometry. Similarly, a cell is considered "negative" for the transferrin receptor/CD71 if it does not express the marker on its cell-surface in amounts sufficient to be detected using methods known to those of skill in the art, such as contacting a cell with an antibody or aptamer that binds selectively or specifically to the transferrin receptor and subsequently performing flow cytometric analysis of such a contacted cell to determine whether the antibody or aptamer is bound the cell.

In some embodiments, the aptamers (e.g., aptamer monomers) described herein can self-associate or be induced to self-associate to form higher secondary structures including, but not limited, to dimers, trimers, tetramers, pentamers and the like. In one embodiment, the aptamers described herein are provided in the form of a dimer. It is specifically contemplated herein that such higher order structures can improve affinity or avidity; or lower the $K_D$ of a given aptamer as compared to its monomer, for example, as shown in FIG. 32B in the working Examples.

Nucleic Acid Aptamer Synthesis and Modifications

Aptamers as described herein can be chemically synthesized using, as a non-limiting example, a nucleoside phosphoramidite approach. Furthermore, aptamers can be isolated from a biological sample by DNA or RNA extraction methods. These methods include but are not limited to column purification, ethanol precipitation, phenol-chloroform extraction, or acid guanidinium thiocyanate-phenol chloroform extraction (AGPC).

Following extraction or synthesis, the aptamers described herein can be characterized by liquid chromatography, mass spectrometry, next generation sequencing, polymerase chain reaction (PCR), gel electrophoresis, or any other method of identifying nucleoside sequences, secondary structures, chemical composition, expression, thermodynamics, binding, or function. Aptamers identified by cell-SELEX can further be characterized by aptamer cell binding assays, flow cytometry, or in vivo function as described in the EXAMPLES.

The aptamers described herein can also be modified or conjugated to a solid support or phase-changing agent for cell selection and cell processing. Non-limiting examples of conjugation methods include chemical, thermodynamic, or structural modifications to the aptamer that allows for separation of the aptamer-bound cells from the aptamer unbound cells or biological sample.

In certain embodiments, the aptamers as described herein can be labeled. Non limiting examples of labels can include, for example, fluorophores, and or members of an affinity pair.

Non-limiting examples of affinity pairs that can be conjugated to the aptamer include, for example, biotin:avidin, biotin:streptavidin. biotin:neutravidin (or other variants of avidin that bind biotin).

Solid Supports

In certain embodiments, aptamers are bound directly or indirectly to a solid support. Aptamer-bound solid supports described herein can exist in the form of a platform, column, filter or sheet, dish, a microfluidic capture device, capillary tube, electrochemical responsive platform, scaffold, cartridge, resin, matrix, bead, or another solid support known in the art.

In some embodiments, the solid support comprises materials that include, but are not limited to, a polymer, metal, ceramic, gels, paper, or glass. The materials of the solid support can further comprise, as non-limiting examples, polystyrene, agarose, gelatin, alginate, iron oxide, stainless steel, gold nanobeads or particles, copper, silver chloride, polycarbonate, polydimethylsiloxane, polyethylene, acrylonitrile butadiene styrene, cyclo-olefin polymers or cyclo-olefin copolymers, or Sepharose™ resin.

The aptamer-bound solid support can further comprise a magnetoresponsive element such as a magnetoresponsive bead. In some embodiments, the magnetoresponsive element or bead is in the form of a sphere, cube, rectangle, cylinder, cone, or any other shape described in the art. Aptamer bound to magnetoresponsive beads provides a simple method of separating aptamer-bound cells from non-bound cells by permitting a suspension of the cells to interact with the aptamer-conjugated beads, and then subjecting the sample to a magnetic field. The beads, with aptamer-bound cells, are attracted to the magnetic source, permitting the removal of non-bound cells, e.g., via pipette.

Beads with bound cells can be washed and subjected to the magnetic field again to increase the relative purity of the isolated cell fraction.

In some embodiments, the magnetoresponsive element comprises magnetite, iron (III) oxide, samarium-cobalt, terfenol-D, or any other element attracted to a magnet as described in the art.

In some embodiments the solid support is in contact with an extracellular matrix protein or composition. Non-limiting examples include fibronectin, collagen, laminin, poly-L-lysine, Matrigel™ vitronectin, tenascin, fibrillin, brevican, elastin, or other extracellular matrix protein or composition known in the art.

A solid support bound to the aptamer can also contain a label. In some embodiments, the label is conjugated to the aptamer. In some embodiments, the label is a heterologous protein. In some embodiments, the heterologous protein is a tag, such as a fluorescent protein. Such proteins can facilitate tracking and/or visualization of the aptamers. Examples of fluorescent proteins include, but are not limited to, green fluorescent protein (GFP) from the jellyfish *Aequorea victoria*; mutant versions of GFP that fluoresce different colors (such as BFP, blue fluorescent protein; YFP, yellow fluorescent protein; and CFP, cyan fluorescent protein); dsRed fluorescent protein (dsRed2FP); eqFP611, a red fluorescent protein isolated from Entacmaea quadricolor; AmCyan1, a cyan fluorescent protein isolated from *Anemonia majano*, and originally named amFP486; Azami Green, a bright fluorescent protein isolated from Galaxeidae; ZSGREEN™, a fluorescent protein isolated from Zoanthus; or any other fluorescent protein or element described in the art.

In some embodiments the aptamers are labeled with a fluorophore. Non-limiting examples of fluorophores include fluorescein, rhodamine, Oregon green, eosin, Texas red, cyanins, e.g., Cy5.5, among others.

In one embodiment, the aptamer can further comprise a "tag," which refers to a component that provides a means for attaching or immobilizing an aptamer (and any target molecule that is bound to it) to a solid support, such as a bead, e.g., an agarose bead. A "tag" is a set of copies of one type or species of component that is capable of associating with a probe. "Tags" refers to more than one such set of components. The tag can be attached to or included in the aptamer by any method known in the art. Generally, the tag allows the aptamer to associate, either directly or indirectly, with a probe that is attached to the solid support, e.g., a bead. A tag can enable the localization of an aptamer covalent complex to a spatially defined address on a solid support.

Different tags, therefore, can permit the localization of different aptamer covalent complexes to different spatially defined addresses on a solid support. A tag can be a polynucleotide, a polypeptide, a peptide nucleic acid, a locked nucleic acid, an oligosaccharide, a polysaccharide, an antibody, an affibody, an antibody mimic, a cell receptor, a ligand, a lipid, any fragment or derivative of these structures, any combination of the foregoing, or any other structure with which a probe (or linker molecule, as described below) can be designed or configured to bind or otherwise associate with specificity. Generally, a tag is configured such that it does not interact intramolecularly with either itself or the aptamer to which it is attached or of which it is a part. In one embodiment, the tag is included on the 5'-end of the aptamer. In another embodiment, the tag is included on the 3'-end of the aptamer. In one embodiment, the tag is a biotin molecule. In another embodiment, the tag is a streptavidin molecule.

In another embodiment, an aptamer is attached to a solid support through interactions between the tag and a probe on the beads or solid support. A "probe" is a set of copies of one type or species of component that is capable of associating with a tag. "Probes" refers to more than one such set of components. The probe can be attached to or included in the beads or solid support by any method known in the art. Generally, the probe allows the bead or solid support to associate, either directly or indirectly, with a tag that is attached to the aptamer. A probe can be a polynucleotide, a polypeptide, a peptide nucleic acid, a locked nucleic acid, an oligosaccharide, a polysaccharide, an antibody, an affibody, an antibody mimic, a cell receptor, a ligand, a lipid, any fragment or derivative of these structures, any combination of the foregoing, or any other structure with which a probe can be designed or configured to bind or otherwise associate with specificity with a tag. In one embodiment, the probe is a streptavidin molecule, for example, the streptavidin moiety binds to the biotin groups on the aptamer, thereby localizing the aptamers on the solid support to which the streptavidin-coupled beads are bound. In another embodiment, the probe is a biotin molecule.

In one embodiment, the aptamers and solid supports as described herein can be used in a device for enriching a cell population of CD71-expressing cells or alternatively, depleting a cell population of such CD71-expressing cells. The device can optionally comprise a column containing the beads and the filter. In some embodiments, the column is fitted with a syringe. In some embodiments, the column can be sized to fit in a centrifuge tube. In some embodiments the device further comprises a centrifuge tube housing the column.

In some embodiments, the beads with attached aptamer are packed in a column. In other embodiments, the beads with attached aptamer are present in a suspension and collected by centrifugation. The column containing the beads can be of a size and character to allow release of cells without removal of beads. In some embodiments, the column can be of a volume of about 1 mL, 2 mL, 3 mL, 4 mL, 5 mL, 6 mL, 7 mL, 8 mL, 9 mL, 10 mL, 15 mL, 20 mL, 30 mL, 40 mL, 50 mL, 60 mL, 70 mL, 80 mL, 90 mL, 100 mL, 500 mL, 1000 mL, and the like. To facilitate removal of cells from beads, the column can be sized to fit in a centrifuge tube, for example, a small Eppendorf™ tube or a large falcon tube, such that cells can be collected by centrifugation using either a tabletop centrifuge or a large centrifuge. When beads are packed in a column, the column can contain a filter with pores sized to allow cells to pass through while retaining beads in the column. In one embodiment, the filter has a pore size smaller than the diameter of the beads. In another embodiment, the filter has a pore size larger than the diameter of the cells to be enriched. In some embodiments, the filter has a pore size of, for example, about 10-100 μm, e.g., about 10 μm, 20 μm, 30 μm, 40 μm, 50 μm, 60 μm, 70 μm, 80 μm, 90 μm, or 100 μm. In other embodiments, the filter has a pore size of about 10-50 μm, about 10-30 μm, about 10-25 μm, about 10-20 μm, or about 10-15 μm. In some embodiments, the filter has a pore size of less than 10 μm.

The size of beads to which the aptamer is attached can vary. In some embodiments, the beads have a diameter of about 30-200 μm.

In some embodiments, the beads are separated from the captured transferrin receptor-expressing cells by applying mechanical forces, without the addition of any other reagents. As a result, the isolated cell population is free or substantially free of beads, aptamer, antibody, or any other undesired reagents to maintain cell phenotype for additional analysis. In some embodiments, mechanical forces can be applied to the beads without removing them from the column. Release of captured transferrin receptor-expressing cells can be accomplished by, for example, resuspension in a buffer, shaking, pipetting, or vortexing the aptamer-coupled beads. In other embodiments, the column is fitted with a syringe. The syringe can be used to mechanically agitate the beads/cells, thereby disrupting the interaction between beads and cells. The use of mechanical force to separate cells from the aptamer coated beads allows the bound cells to be released without adding any extraneous reagents that could subsequently contaminate the cell population and limit the use of the cell population in clinical applications.

In other embodiments, captured cells can be released from the device using a change in temperature. For example, the beads can be exposed to elevated temperatures for a minimal amount of time sufficient to denature the nucleic acid aptamer and release the cells, without significantly impacting cell viability. In other embodiments, captured cells can be released from the device using a nucleic acid molecule complementary to all or a part of the nucleic acid aptamer (also referred to herein as a "release agent"). Such release agents can compete for binding to the aptamer with cells containing the target, causing release of cells when the aptamer binds to the complementary nucleic acid. Temperature and/or complementary nucleic acid can be used to release cells from the aptamer independently or in conjunction with mechanical disruption, as described herein.

In alternative embodiments, a phase-changing agent can be used in place of a solid support. Phase change agents can change phase or precipitate under a given set of conditions and can thereby facilitate the separation of aptamer-bound from aptamer-unbound cells. In some embodiments, a phase-changing agent can be bound to the aptamer. For example, the phase-changing agent can be soluble in aqueous solution under one set of conditions, but induced to an insoluble, precipitating form under another set of conditions. Further exemplary conditions that can induce a phase change include temperature, pH, salt or solute concentration, light (e.g., ultraviolet or fluorescent), or mechanical forces. For example, poly(N-isopropylacrylamide) is a phase-changing polymer that is soluble, for example, at one temperature and then at a different temperature precipitates out from solution. Upon induction of precipitation, cells bound to the aptamer will be pulled into the precipitated phase. It is also contemplated that a phase changing agent can act in a similar manner to riboflavin that is activated by ultraviolet light.

Reversal Agents for Reversible Cell Selection

Reversal agents or "antidotes" include molecules that disrupt the structure of an aptamer and thereby cause release of cells or molecules bound by the aptamer, or molecules that bind with the aptamer thereby reducing cell-binding affinity. In some embodiments, a reversal agent (also referred to herein as an 'antidote') is specific for one or a limited number of aptamers that share a given sequence motif or structure, while in other embodiments, a reversal agent disrupts aptamer structure non-specifically, such that one reversal agent can be used for any of a number of different aptamers. Such non-specific reversal agents include, but are not limited to, for example, polyanions such as dextran sulfate, heparin sulfate, phytic acid, or polyphosphates. In other embodiments, the aptamer of interest can be fused with a small-molecule binding aptamer so that the reversal agent can comprise a small molecule that binds to and affects the folded structure of an aptamer, thereby causing release of bound target molecules or cells. In another example, reversal agents can be chelators that bind essential ions that promote the secondary structure of the aptamer. A small molecule reversal agent can be non-specific or specific, depending upon how it interacts with the aptamer. For example, small molecules that can be used include but are not limited to ATP, ampicillin, tetracycline, dopamine and sulforhodamine B. Further examples of small molecules that bind to aptamers are described in McKeague and DeRosa, *J. Nucleic Acids*. Vol. 2012, Article ID No. 748913 (2102), which is incorporated herein by reference in its entirety.

In other embodiments, a reversal agent can comprise an oligonucleotide or oligonucleotide mimic (PNA, LNA, BNA, and the like) that includes sequence complementary to a portion of an aptamer that forms a double-stranded stem structure. The hybridization of the oligonucleotide reversal agent to its complement in the aptamer disrupts the structure of the aptamer and causes release of the aptamer's target molecule. An oligonucleotide reversal agent can also include sequence complementary to a non-double stranded region of an aptamer. One such oligonucleotide reversal agent configuration includes a sequence element complementary to a single-stranded portion of a target aptamer and a sequence element complementary to an adjacent double-stranded portion of the target aptamer. In this configuration, the oligonucleotide reversal agent can efficiently initiate hybridization to the single-stranded portion of the aptamer, and then strand-displace the adjacent double-stranded portion of the aptamer to promote release of the aptamer from its target.

Small molecule reversal agents can be selected from, for example, a library of small molecules, which can include, for example, amino acids, oligopeptides, polypeptides, proteins, or fragments of peptides or proteins; nucleic acids (e.g., antisense; DNA; RNA; or peptide nucleic acids, PNA); carbohydrates or polysaccharides, or an organic or inorganic compound (e.g., including heterorganic and organometallic compounds). Each member of the library can be singular or can be a part of a mixture (e.g., a compressed library). The library can contain purified compounds or can be "dirty" (i.e., containing a significant quantity of impurities). Commercially available libraries can be obtained, for example, from Affymetrix, ArQule, Neose Technologies, Sarco, Ciddco, Oxford Asymmetry, Maybridge, Aldrich, Panlabs, Pharmacopoeia, Sigma, or Tripose, among others.

The use of reversal agents permits a reversible, tag-less cell selection. An advantage of the release of aptamer-bound cells in this manner is that the isolated cells will have relatively little aptamer bound to them. This contrasts with the use of antibodies to isolate cells, in which it is difficult to get the antibodies to dissociate from the cells after the cells are isolated. Depending upon how cells are incubated with aptamer, e.g., whether the aptamers are initially bound to a solid support or are first incubated in solution then pulled down via an affinity pair, and how cells are incubated with reversal agent (e.g., reversal agent concentration, timing, and the like) the amounts of aptamer remaining bound to isolated cells after reversal can be, for example, 50% or less, 40% or less, 30% or less, 20% or less, 10% or less, or even 5% or less of the aptamer used for binding.

As described herein, an oligonucleotide reversal agent can additionally or alternatively comprise nucleobase (often referred to in the art simply as "base") modifications or substitutions. As used herein, aptamer and reversal agent nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Synthetic oligonucleotides of a reversal agent can include but are not limited to peptide nucleic acid (PNA), bridged nucleic acids (BNA), morpholinos, locked nucleic acids (LNA), glycol nucleic acids (GNA), threose nucleic acids (TNA), or any other xeno nucleic acid (XNA) described in the art.

Oligonucleotide reversal agents can be synthesized by the same methods used for the synthesis of nucleic acid aptamers as described herein.

Oligonucleotide reversal agents generally consist of short oligonucleotide strands that typically range from 8 to 50 nucleobases in length but can be as long as the target aptamer or longer. In some embodiments, oligonucleotide reversal agents can comprise polynucleotide lengths of 8 or more, 10 or more, 20 or more, 30 or more, 40 or more, 50 or more, 60 or more, 70 or more, 80 or more, 90 or more, 100 or more and beyond.

Reversal agent selection can include designing complementary oligonucleotide sequences to the 3' end of an aptamer, or to any region of the aptamer known or predicted to participate in intramolecular base pairing.

In some embodiments dissociation of the aptamer from cells can be carried out by using shear force, changing the temperature, changing the buffer composition, ionic strength of the buffer solution, and the like.

In some embodiments, binding of the cells of interest with 5 nM aptamer can be carried out with secondary fluorescent streptavidin labeling. Labeled cells can be incubated with varying fold-excess (over the amount of aptamer used) in, e.g., 200 microliters (μL) of reversal agent in wash buffer with 1% (weight/volume) BSA for different times and temperatures. Cells can be washed twice with wash buffer and 1% (weight/volume) BSA to remove eluted aptamers, followed by fixation, and/or flow cytometry analysis.

In some embodiments, the concentration of reversal agent added to the mixture of cells is 1 nanomolar or more, 10 nanomolar or more, 100 nanomolar or more, 1 micromolar or more, 10 micromolar or more, 100 micromolar or more, 1 millimolar or more and beyond. The reversal agent can be from 0.1-fold to 100-fold excess of the aptamer concentration.

In some embodiments, a toehold region of an aptamer can facilitate reversal agent hybridization that disrupts the secondary structure of the chosen aptamer. The toehold region can be at the end of the aptamer or internally within the aptamer at a single stranded region, depending on the predicted secondary structure.

In some embodiments, reversal of aptamer binding can be accomplished by degrading the aptamer, e.g., by introducing a nuclease to the aptamer-bound cell composition. Nucleases can be non-specific, such as DNAse I, or specific or cleavage at one or more particular sequences. Other approaches for reversal include, for example, contacting with a single strand binding protein (SSBP); binding of such factors to a single-stranded loop of the aptamer can promote unwinding of hybridized stem regions and promote loss of aptamer binding. Further approaches for reversal can include, for example, changing ionic strength, buffer or temperature conditions, changing the pH, or the presence of divalent cations, such that aptamer tertiary or secondary structure is altered to promote loss of aptamer binding.

Characterization of Aptamer Cell Binding

Nucleic acid aptamers identified by the cell-SELEX method described herein, or by another method as known in the art can be characterized by a number of approaches including, but not limited to, aptamer binding assays, next generation sequencing, gene profiling, functional assays such as cytotoxicity assays, cytokine release assays, and in vivo delivery of, for example, native or modified cells isolated through use of the aptamers to an animal or human model. The above methods can serve as quality control of the compositions and method of cell selection described herein.

To characterize aptamer binding to target cells or cells of interest, an in vitro binding assay can be performed, for example, as follows. A population comprising, e.g., $2\times10^5$ or more cells of interest (e.g., Jurkat T cells expressing CD71) is incubated with folded FAM-labeled ssDNA pools or FAM/biotin-labeled individual aptamers for 30 minutes at 4° C. in binding buffer as described herein, and at various concentrations of aptamer. In some embodiments, the aptamers are labeled with biotin, avidin, streptavidin, agarose, or neutravidin. In some embodiments the aptamers are labeled with a fluorophore. Non-limiting examples of fluorophores include fluorescein, rhodamine, Oregon green, eosin, Texas red, cyanins, e.g., Cy5.5, among others.

Following incubation, e.g., in a total volume of 100 μL, cells are washed twice in, e.g., 200 μL of wash buffer supplemented with 1% (weight/volume) BSA to remove excess aptamer. If the aptamers used were biotinylated, cells can undergo a second incubation with 100 μL fluorescently-labeled streptavidin or neutravidin secondary label for 20 min at 4° C. in wash buffer with 1% BSA before again washing twice. Stained cells can be fixed, e.g., in 200 μL wash buffer with 1% BSA (weight/volume) and 0.1% (weight/volume) paraformaldehyde (PFA) before analyzing via flow cytometry.

At a minimum, an aptamer that specifically binds a given target cell or a cell expressing the transferrin receptor with at least 100× greater affinity than the binding of the aptamer to a cell that does not express the transferrin receptor, and preferably with at least 200× greater affinity, at least 300× greater affinity, at least 500× greater affinity, at least 600× greater affinity, at least 700× greater affinity, at least 800× greater affinity, at least 900× greater affinity, at least 1,000× greater affinity or more.

Affinity can be expressed in terms of dissociation constant, or $K_D$. An aptamer that selectively binds the transferrin receptor/CD71 will generally bind with a $K_D$ below 1 micromolar (1 μM). Aptamers have been described that bind their targets with $K_D$s in the picomolar (μM) range. However, aptamers useful for cell selection can bind in the range of 1 μM to 10 μM, 1 μM to 100 μM, 1 μM to 200 μM, 1 μM to 300 μM, 1 μM to 400 μM, 1 μM to 500 μM, 1 μM to 600 μM, 1 μM to 700 μM, 1 μM to 800 μM, 1 μM to 900 μM, 1 μM to 1 nM, 1 μM to 10 nM, 1 μM to 50 nM, 1 μM to 100 nM, 1 μM to 150 nM 1 μM to 200 nM, 1 μM to 250 nM, 1 μM to 300 nM, 1 μM to 350 nM, 1 μM to 400 nM, 1 μM to 450 nM, 1 μM to 500 nM, 1 μM to 550 nM, 1 μM to 600 nM, 1 μM to 650 nM, 1 μM to 700 nM, 1 μM to 750 nM, 1 μM to 800 nM, 1 μM to 850 nM, 1 μM to 900 nM, 1 μM to 950 nM, less than 500 nM to 10 μM, less than 450 nM to 10 μM, less than 400 nM to 10 μM, less than 350 nM to 10 μM, less than 300 nM to 10 μM, less than 250 nM to 10 μM, less than 200 nM to 10 μM, less than 150 nM to 10 μM, less than 100 nM to 10 μM, less than 50 nM to 10 μM, less than 100 nM to 900 μM, less than 100 nM to 800 μM, less than 100 nM to 700 μM, less than 100 nM to 600 μM, less than 100 nM to 500 μM, less than 100 nM to 400 μM, less than 100 nM to 300 μM, less than 100 nM to 200 μM, less than 100 nM to 100 μM, less than 100 nM to 50 μM, or less than 100 nM to 10 μM.

Various methods are known in the art for determining $K_D$ for an aptamer's binding to its target (i.e., CD71). Jing and Bowser, Anal. Chim. Acta 686:9-18, which is incorporated herein by reference, reviews various approaches.

Cell Selection Quality Control and Traceless Cell Selection Methods Using Cell-Selected Aptamer Pools Flow cytometry analysis along with other methods for cellular identification can be used to evaluate aptamer/cell interactions and the ability to select target cells using a given aptamer or combination of aptamers. OneComp eBeads™ (Invitrogen) can be used to prepare single-color controls for compensation, if needed. Stained biological samples can be analyzed, for example, using a MACSQuant™ Analyzer 10 (Miltenyi), Attune NxT (Invitrogen), or BD LSRFortessa™ (BD Biosciences) flow cytometer.

Traceless cell selection methods using cell-SELEX aptamer pools are described herein and demonstrated in the Examples.

Uses for Cells Selected on the Basis of Aptamer Binding

Large scale preparation or manufacturing of specific cell types is becoming increasingly useful for cellular-based therapies. The methods and compositions described herein provide an efficient approach for the isolation of specific target cell types that is readily scaled up for the large-scale isolation of cells for these and other uses.

Where the aptamers described herein can be used to isolate proliferating cells, such as cancer cells or fetal nucleated red blood cells, such isolated cells are specifically contemplated for use in cellular assays for research purposes, genetic analysis, or diagnosis of cancers (e.g., leukemias). Such cells can be manipulated and/or expanded prior to their use in such settings. Manipulations can include, as non-limiting examples, further cell sorting, stimulation with antigen, induction of differentiation, and/or genetic modification.

In some embodiments, the aptamers described herein can be used to "enrich" transferrin receptor-expressing cells in a cell population. By an enriched cell composition of such cells, it is meant that at least about 50%, about 60%, about 70%, about 80%, about 90%, about 95% or more of the cells express the transferrin receptor, or express the transferrin receptor at high levels. In some instances, the enriched composition will be a substantially pure population of cells expressing the transferrin receptor, whereby "substantially pure" it is meant at least 90% or more of the composition will be of the selected phenotype, e.g., 95%, 98%, and up to 100% of the population.

Depletion of Proliferating Cells for CAR T Cell Cancer Therapy

Currently, the generation and administration of autologous CAR T cell cancer therapy involves harvesting and genetically manipulating T cells before reintroducing the engineered cells back to patients. Prior to re-administration of manipulated T cells, it is important to remove substantially all cancerous cells to prevent the engraftment of genetically modified cancer cells and the generation of a new and possibly treatment-resistant cancer. A brief overview of CAR T cell technology is provided herein.

Chimeric Antigen Receptors (CARs) are recombinant proteins that allow T cells modified to express them to recognize a specific protein (antigen) on tumor cells. T cells engineered to express a CAR, referred to as CAR T cells, are expanded in the laboratory and then infused into the patient. After the infusion, the T cells multiply in the patient's body and, with guidance from their engineered receptor, recognize and kill cancer cells that display the antigen on their surfaces.

The first step in the process, cell harvesting, requires high purity isolation of desired cell populations. For example, it is known in the art that CAR T cells with defined 1:1 $CD4^+$ to $CD8^+$ cell populations are more potent than either pure ($CD4^+$ or $CD8^+$ only) and unselected populations in animal models of leukemia and are also very effective in human clinical trials for ALL.

T cells are typically isolated from peripheral blood mononuclear cells (PBMCs) collected by leukapheresis. The main methods for clinical-scale T cell isolation include (i) immunodepletion of undesired cells (e.g., proliferating or cancerous cells) followed by selection of T cell populations using antibody-conjugated magnetic beads (e.g., CliniMACS®) and (ii) "traceless" selection using Streptamer technology, which is based on fragment antigen-binding (Fab) constructs immobilized on magnetic beads. The aptamers described herein can be used to deplete transferrin receptor expressing cells (i.e., proliferating or cancerous cells) from the PBMCs collected by leukapheresis.

Examples of cancer that can be treated using cells prepared using CAR T cell technology include, but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; cholangiocarcinoma; choriocarcinoma; colon and rectal cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; teratocarcinoma; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phacomatoses, edema (such as that associated with brain tumors), tumors of primitive origins and Meigs' syndrome.

In addition to cancer, CAR T cells have also been generated as potential anti-HIV therapies. Recent studies by Hale et al., 2017 have shown that T cells utilizing CARs based on single-chain variable fragments (scFvs) derived from high-affinity broadly neutralizing antibodies (bNAbs) and containing second-generation co-stimulatory domains, in parallel with genetic protection from HIV can disrupt CCR5, and effectively target HIV-infected cells.

As used herein, the term "therapeutic cell composition" refers to a composition comprising a population of cells that are depleted of transferrin receptor-expressing cells (e.g., CD71 positive cells). Due to the potentially cancerous nature of transferrin receptor-expressing cells, the goal of depletion of transferrin receptor-expressing cells should be to remove all transferrin receptor-expressing cells. Such complete removal may require multiple rounds of depletion using the aptamers described herein or by use of, e.g., an anti-transferrin receptor antibody for a final round of cell depletion. It is also specifically contemplated herein that one or more additional aptamers can be used in combination with the aptamers described herein to deplete cells. For example, an aptamer that depletes monocytes and/or macrophages can be used in combination with the transferrin receptor-binding aptamers described herein. In one embodiment, the monocyte and/or macrophage binding aptamer comprises the sequence of:

```
                                          (SEQ ID NO: 55)
TTATGACGCAGCAGAAGAGTAGATGAAACGTTTTTTCGCCCGATAAAAGG

GACGTGCGTCATAA.
```

In another embodiment, the monocyte and/or macrophage binding aptamer comprises the sequence of: ATCCAGAGTGACGCAGCAGAAGAGTAGATGAAACGTTTTTTCGCCCGATAAAAG GGACGTGCGTCAGACATGGACACGGTGGCTTAGT (SEQ ID NO: 56). The therapeutic cells can then be expanded, differentiated in vitro, engineered, or formulated as desired before administration as a therapeutic cell composition.

As used herein, the term "depleting transferrin receptor-expressing cells" refers to the selective removal of cells expressing or highly expressing transferrin/CD71 from a sample comprising other cells, cell types or cell classes such that the resulting cell population lacks or has a reduced number of transferrin receptor-expressing cells. Target cells or a population thereof will generally be considered "depleted" as the term is used herein if the population includes less than 40% transferrin receptor-expressing cells (or cells with high expression of the transferrin receptor) resulting from a depletion method as described herein, and preferably includes less than 30%, less than 20%, less than 10%, less than 5%, less than 1% or more. In some embodiments, the therapeutic cell population following a depletion method as described herein will lack detectable numbers of cells expressing detectable levels of the transferrin receptor (i.e., cells that bind the aptamer). A population of cells is also "depleted" for transferrin receptor-expressing cells if the proportion of transferrin receptor-expressing cells is reduced following a depletion procedure by at least 50% relative to the proportion of transferrin receptor-expressing cells in the starting population. For such a depletion procedure, the population is "depleted" if the resulting population has a proportion of transferrin receptor-expressing cells that is reduced by at least 50%, 60%, 70%, 80%, 90%, 95%, 96%, 97%, 98%, 99% or more relative to the starting population. Cells that are depleted of transferrin receptor-expressing cells are referred to herein as "therapeutic cells" or a "therapeutic cell composition." Examples of therapeutic cell compositions depleted of TfR-expressing cells can include cell preparations enriched for NK cells, monocytes, macrophage, and the like. Similarly, the term "depletion" or "depleted" can be applied to the depletion of other cell types or cells expressing a given marker, for example, when using an aptamer that depletes monocytes and/or macrophages from the biological cell sample.

When the resulting therapeutic cells are to be genetically modified, for example production of CAR T cells, it is important to remove all transferrin receptor-expressing cells to prevent their genetic modification and potential escape from CAR T therapy. Multiple rounds of depletion and optionally one or more rounds of expansion can be used to ensure complete (i.e., 100%) removal of transferrin receptor-expressing cells. In addition, one or more rounds of depletion with a transferrin receptor antibody (e.g., in combination with aptamer-based depletion as described herein) can help to ensure the complete removal of such cells.

In one embodiment, the therapeutic cells are obtained directly from the subject to whom they are to be administered (i.e., autologous transplantation). In another embodiment, the transplantation can be non-autologous or allogeneic. As used herein, "allogeneic" refers to therapeutic cells (e.g., CAR T cells) obtained from one or more different donors of the same species, where the genes at one or more loci are not identical. For example, a therapeutic cell composition being administered to a subject can be derived from umbilical cord blood obtained from one more unrelated donor subjects, or from one or more non-identical siblings. In some embodiments, syngeneic cell populations can be used, such as those obtained from genetically identical animals, or from identical twins. In other embodiments of this aspect, the therapeutic cells are autologous cells; that is, the cells are obtained or isolated from a subject and administered to the same subject, i.e., the donor and recipient are the same.

For non-autologous transplantation, the recipient is preferably given an immunosuppressive drug to reduce the risk of rejection of the transplanted cell. Methods of administering cells include but are not limited to intradermal, intramuscular, intraperitoneal, intravenous, subcutaneous, intranasal, and epidural routes. The cells can be administered by any convenient route and can be administered together with other biologically active agents. The route of administration is preferably intravenous or intradermal. The titer of therapeutic cells to be transplanted or administered and which will be effective in the treatment of a particular disease or condition will depend on the nature of the disorder or condition and can be determined by standard clinical techniques. In addition, in vitro assays can optionally be employed to help identify optimal dosage ranges. The precise dose to be employed in the formulation will also depend on the route of administration, and the seriousness of the disease or disorder, and should be decided according to the judgment of the practitioner and each subject's circumstances.

In some respects, the methods provided herein comprise delivering a plurality of therapeutic cells or their progeny or differentiation product cells to a host tissue. In other aspects, the methods provided herein comprise delivering a plurality of cells that have been depleted of aptamer-binding cells (e.g., transferrin receptor-expressing cells). As described herein, therapeutic cell compositions following aptamer-mediated depletion of transferrin receptor-expressing cells can be delivered according to any method known in the art or can be incorporated into pharmaceutical compositions suitable for administration to a subject, e.g., for in vivo delivery to tissues, or organs of the subject.

The dosage ranges for the therapeutic cell composition includes amounts large enough to produce the desired effect, e.g., treatment of a disease or symptom thereof, e.g., cancer. The dosage should not be so large as to cause unacceptable adverse side effects. Generally, the dosage will vary with the particular characteristics of therapeutic cell composition, and with the age, condition, and sex of the patient. The dosage can be determined by one of skill in the art and, unlike traditional cell therapies, can also be adjusted by the individual physician in the event of any complication.

In some embodiments, the therapeutic cell composition is delivered for a repeated or limited amount of time. In some embodiments, the doses are given once a day, or multiple times a day. The duration of treatment depends upon the subject's clinical progress and responsiveness to therapy.

Compositions comprising a therapeutic cell population depleted of transferrin receptor-expressing cells can be delivered to target cells or tissues by surgical implantation, intravenous administration, intra-arterial administration, intraperitoneal administration, limb perfusion, (optionally, isolated limb perfusion of a leg and/or arm; see, e.g., Arruda et al., (2005) Blood 105:3458-3464), and/or direct intramuscular injection. Administration to a muscle (e.g., the diaphragm) can be by any suitable method including intravenous administration, intra-arterial administration, and/or intraperitoneal administration.

In some embodiments, one or more additional compounds can also be included with the therapeutic cell composition (i.e., a cell population depleted of aptamer-binding cells) to alleviate symptoms of a disease or to otherwise assist or support the function of the administered cells.

In some embodiments, the additional compound can be a therapeutic agent. The therapeutic agent can be selected from any class suitable for the therapeutic objective. In other words, the therapeutic agent can be selected according to the treatment objective and biological action desired. Furthermore, the active ingredients of the therapeutic agent can be mixed with optional pharmaceutical additives such as excipients or carriers which are pharmaceutically acceptable and compatible with the active ingredient.

Therapeutic cells can further comprise a targeting moiety for a tissue of interest. For example, the targeting moiety can comprise a receptor molecule, including receptors that naturally recognize a specific desired molecule of a target cell (e.g., a tumor cell). Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). In other embodiments, the targeting moiety can comprise a ligand molecule, including, for example, ligands which naturally recognize a specific desired receptor on a target cell. Such ligand molecules include ligands that have been modified to increase their specificity of interaction with a target receptor, ligands that have been modified to interact with a desired receptor not naturally recognized by the ligand, and fragments of such ligands. In other embodiments, the targeting moiety can comprise an aptamer that has not been used in the initial cell selection as described herein.

For use in the various aspects described herein, an effective amount of therapeutic cells (e.g., low or lacking expression of CD71) comprises at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, at least $1\times10^7$ cells, at least $2\times10^7$ cells, at least $3\times10^7$ cells, at least $4\times10^7$ cells, at least $5\times10^7$ cells, at least $6\times10^7$ cells, at least $7\times10^7$ cells, at least $8\times10^7$ cells, at least $9\times10^7$ cells, at least $1\times10^8$ cells, at least $2\times10^8$ cells, at least $3\times10^8$ cells, at least $4\times10^8$ cells, at least $5\times10^8$ cells, at least $6\times10^8$ cells, at least $7\times10^8$ cells, at least $8\times10^8$ cells, at least $9\times10^8$ cells, at least $1\times10^9$ cells, at least $2\times10^9$ cells, at least $5\times10^9$ cells, at least $1\times10^{10}$ cells, at least $2\times10^9$ cells, at least $5\times10^9$ cells, at least $1\times10^{10}$ cells, at least $2\times10^{10}$ cells, at least $5\times10^{10}$ cells, at least $1\times10^{11}$ cells, at least $2\times10^{11}$ cells, at least $5\times10^{11}$ cells, at least $1\times10^{12}$ cells, at least $2\times10^{12}$ cells, at least $5\times10^{12}$ cells, at least $1\times10^{13}$ cells, or multiples thereof. In some embodiments of the aspects described herein, the therapeutic cells are expanded in culture prior to administration to a subject in need thereof. In some embodiments, the therapeutic cells are CAR T cells.

In one embodiment, the term "effective amount" as used herein refers to the amount of a population of therapeutic cells (e.g., those cells having low or undetectable levels of the transferrin receptor) needed to alleviate at least one or more symptom of a disease (e.g., cancer), and relates to a sufficient amount of a composition to provide the desired effect, e.g., treat a subject having a disease, such as cancer. The term "therapeutically effective amount" therefore refers to an amount of therapeutic cells or a composition thereof that is sufficient to promote a particular effect when administered to a typical subject, such as one who has or is at risk of cancer. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

As used herein, "administered" refers to the delivery of a composition comprising therapeutic cells as described herein into a subject by a method or route which results in at least partial localization of the cell composition at a desired site. A cell composition can be administered by any appropriate route which results in effective treatment in the subject, i.e., administration results in delivery to a desired location in the subject where at least a portion of the composition delivered, i.e., at least $1\times10^4$ therapeutic cells are delivered to the desired site for a period of time. Modes of administration include injection, infusion, instillation, or ingestion. "Injection" includes, without limitation, intravenous (iv), intramuscular (im), intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebro spinal, and intrasternal injection and infusion. For the delivery of therapeutic cells, a composition thereof, or an aptamer-active agent complex, administration by injection or infusion is generally preferred.

In one embodiment, such therapeutic cells or aptamer-active agent complex as described herein are administered systemically. The phrases "systemic administration," "administered systemically", "peripheral administration" and "administered peripherally" as used herein refer to the administration of a population of therapeutic cells other than directly into a target site, tissue, or organ, such that it enters, instead, the subject's circulatory system and, thus, is subject to metabolism and other like processes.

The efficacy of a treatment comprising a therapeutic cell composition, or an aptamer-active agent complex as described herein for the treatment of a given disease can be determined by the skilled clinician. However, a treatment is considered "effective treatment," as the term is used herein, if any one or all the signs or symptoms of the disease are altered in a beneficial manner, other clinically accepted symptoms or markers of disease are improved or ameliorated, e.g., by at least 10% following treatment with the therapeutic cells. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of a given disease; or (2) relieving the disease, e.g., causing regression of symptoms; and (3) preventing or reducing the likelihood of the development of disease.

Following in vitro or ex vivo cell culture, isolation, or differentiation as described herein, isolated or enriched therapeutic cells are prepared for treatment and/or implantation. The cells are suspended in a physiologically compatible carrier, such as cell culture medium (e.g., Eagle's minimal essential media), phosphate buffered saline, or a T cell specific medium. The volume of cell suspension to be implanted will vary depending on the site of implantation, treatment goal, and cell density in the solution.

It will be appreciated by one of skill in the art that a cell composition useful for treating a given disease does not need to be a pure, homogeneous culture of, e.g., therapeutic cells lacking expression of transferrin receptor or having low expression of the transferrin receptor. Accordingly, in one embodiment, the composition administered comprises at least 2% therapeutic cells. In other embodiments, the composition comprises at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more therapeutic cells as described herein.

The cells can be administered to a subject by any appropriate route that results in delivery of the therapeutic cells to a desired location in the subject where at least a portion of the cells remain viable. It is preferred that at least 5% remain viable. In other embodiments, at least 10%, at least 20%, at least 30%, at least 40%, or at least 50%, at least 60%, at least 70%, at least 80%, at least 90%, at least 95%, at least 98%, at least 99% or more of the therapeutic cells remain viable after administration into a subject. The period of viability of the therapeutic cells after administration to a subject can be as short as a few hours, e.g., twenty-four hours, to a few days, to as long as a few weeks to months.

To accomplish these methods of administration, the therapeutic cell composition(s) can be inserted into a delivery device that facilitates introduction by injection or implantation of the therapeutic cells into the subject. Typically, the therapeutic cells are injected into the target area as a cell suspension. Alternatively, the cells can be embedded in a solid or semisolid support matrix when contained in such a delivery device.

In some embodiments, administration of a composition comprising therapeutic cells is repeated after a given interval of time (e.g., one day, three days, one week, two weeks, three weeks, one month or more. Repeated treatments can be performed, for example, to establish or maintain a threshold level of engraftment necessary to continue effective treatment, as necessary. In some embodiments, the method is repeated twice, three times, four times, five times or more.

Aptamer Therapeutics and Other Uses

Aptamers have been widely used as targeting ligands to mediate delivery of a variety of payloads to cellular or intracellular targets (e.g., HER2, nucleolin). Payloads include therapeutic drugs, imaging compounds, unstable molecules (e.g., nucleic acids). or ribonucleoproteins. These aptamer pay load complexes can be termed "aptamer-active agent complexes." In cancer therapy, aptamers can be used to facilitate delivery of therapeutics to cancer cells with high targeting efficiency. In many cancers, tumor cells upregulate specific biomarkers; targeted aptamers can guide nanomedicine systems to deliver therapeutic payloads to these cells, reducing off-target toxicity. These nanomedicine platforms include liposomes, polymeric micelles, or iron oxide nanoparticles. Efficacy of these platforms has been demonstrated both in vitro and in vivo. (See e.g., Alshaer, W. et al. Aptamer-guided nanomedicines for anticancer drug delivery. (2018) Adv. Drug Deliv. Rev. 134:122-137; Ray and White; Aptamers for Targeted Drug Delivery. (2010) *Pharmaceuticals* 3:1761-1778; Meng, H-M. et al. Aptamer-integrated DNA nanostructures for biosensing, bioimaging and cancer therapy. (2016) *Chem. Society Rev.* 45:2583-2602).

Thus, specifically contemplated herein is the use of the aptamers described herein as a drug delivery device for targeting a given drug to TfR positive cells or other tissues. Also contemplated herein is the use of such aptamers to target an active agent, such as, for example, a therapeutically active agent to TfR positive cells. In certain embodiments the aptamer is attached to the therapeutically active agent.

In another embodiment, the aptamers described herein are contemplated for use as sensors or as a theranostic. Some aptamers can undergo significant conformation change upon binding to their ligand or receptor. These switching aptamers can be labeled with a reporter molecule (e.g., a fluorophore for fluorescence detection or a redox probe for electrochemical detection) to provide a signal change upon ligand binding. In another example, aptamers can also be designed to be in duplex structures until binding to their target; binding releases a fluorescently labeled complementary strand, called a "beacon" (see e.g., Tuleuova and Revzin. Micropatterning of aptamer beacons to create cytokine-sensing surfaces. (2010) *Cell Mol. Bioeng.* 3:337-344; Iliuk, et al. Aptamer in bioanalytical applications. (2011) Anal. Chem. 83:4440-4452). The aptamers presented in this application can similarly be used to report the presence and relative number of TfR positive cells by engineering the aptamer into an aptamer reporter.

Pharmaceutical Compositions, Administration and Efficacy

Pharmaceutical or therapeutic compositions comprising an aptamer, aptamer-therapeutically active agent complex, or aptamer-depleted cells for the treatment of a given disease or disorder can contain a physiologically tolerable carrier, wherein the therapeutic agent is dissolved or dispersed therein as an active ingredient(s). In a preferred embodiment, the pharmaceutical composition is not immunogenic when administered to a mammal or human patient for therapeutic purposes. As used herein, the terms "pharmaceutically acceptable", "physiologically tolerable" and grammatical variations thereof, as they refer to compositions, carriers, diluents, and reagents, are used interchangeably and represent that the materials are capable of administration to or upon a mammal without the production of undesirable physiological effects such as nausea, dizziness, gastric upset, and the like. A pharmaceutically acceptable carrier will not promote the raising of an immune response to an agent with which it is admixed, unless so desired. The preparation of a pharmacological or pharmaceutical composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition comprising an aptamer or a population of aptamer-enriched cells for treatment of a disease or disorder can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine, and the like.

Physiologically tolerable carriers are well known in the art. Exemplary liquid carriers are sterile aqueous solutions that contain no materials in addition to the active ingredients and water or contain a buffer such as sodium phosphate at physiological pH value, physiological saline, or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of disease or a symptom thereof will depend on the nature of the disorder or condition and can be determined by standard clinical techniques.

A pharmaceutical composition as described herein can be formulated for parenteral administration, e.g., by bolus injection or continuous infusion. Formulations for injection can be presented in unit dosage form, e.g., in ampoules or in multidose containers with, optionally, an added preservative. The compositions can be suspensions, solutions, or emulsions in oily or aqueous vehicles, and can contain formulatory agents such as suspending, stabilizing, and/or dispersing agents.

Pharmaceutical compositions for parenteral administration include aqueous solutions of the active preparation in water-soluble form. Additionally, suspensions of the active ingredients can be prepared as appropriate oily or water-based injection suspensions.

Suitable lipophilic solvents or vehicles include fatty oils such as sesame oil, or synthetic fatty acid esters such as ethyl oleate, triglycerides, or liposomes. Aqueous injection suspensions can contain substances that increase the viscosity of the suspension, such as sodium carboxymethyl cellulose, sorbitol, or dextran.

Optionally, the suspension can also contain suitable stabilizers or agents that increase the solubility of the active ingredients, to allow for the preparation of highly concentrated solutions. Alternatively, the active ingredient can be in powder form for constitution with a suitable vehicle, e.g., a sterile, pyrogen-free, water-based solution, before use.

In some embodiments, a therapeutic aptamer-active agent complex can be delivered in an immediate release form. In other embodiments, the therapeutic aptamer-active agent complex composition can be delivered in a controlled-release system or sustained-release system. Controlled- or sustained-release pharmaceutical compositions can have a common goal of improving drug therapy over the results achieved by their non-controlled or non-sustained-release counterparts. Advantages of controlled- or sustained-release compositions include extended activity of the therapeutic agents, reduced dosage frequency, and increased compliance. In addition, controlled- or sustained-release compositions can favorably affect the time of onset of action or other characteristics, such as blood levels of the therapeutic agent, and can thus reduce the occurrence of adverse side effects. Controlled- or sustained-release of an active ingredient can be stimulated by various conditions, including but not limited to, changes in pH, changes in temperature, concentration or availability of enzymes, concentration or availability of water, or other physiological conditions or compounds.

In one embodiment, a pump can be used (Langer, (1990) *Science* 249:1527-1533; Sefton, (1987) *CRC Crit. Ref Biomed. Eng.* 14:201; Buchwald et al. (1980) *Surgery* 88:507; and Saudek et al. (1989) *N. Engl. J. Med.* 321:574). In another embodiment, polymeric materials can be used (see Medical Applications of Controlled Release (Langer and Wise eds., 1974); Controlled Drug Bioavailability, Drug Product Design and Performance (Smolen and Ball eds., 1984); Ranger and Peppas, (1983) *J. Macromol. Sci. Rev. Macromol. Chem.* 23:61; Levy et al. (1985) *Science* 228: 190; During et al. (1989) *Ann. Neurol.* 25:351; and Howard et al. (1989) *J. Neurosurg.* 71:105). In yet another embodiment, a controlled- or sustained-release system can be placed in proximity of a target of infection, thus requiring only a fraction of the systemic dose.

When in tablet or pill form, a pharmaceutical composition as described herein can be coated (e.g., enterically coated) to delay disintegration and absorption in the gastrointestinal tract, thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

A pharmaceutical composition as described herein can also be formulated in rectal compositions such as suppositories or retention enemas, using, for example, conventional suppository bases such as cocoa butter or other glycerides.

The appropriate dosage range for a given therapeutic agent depends upon the potency and includes amounts large enough to produce the desired effect, e.g., reduction in at least one symptom of a given disease. The dosage of the therapeutic agent should not be so large as to cause unacceptable or life-threatening adverse side effects or should be used under close supervision by a medical professional. Generally, the dosage will vary with the specific aptamer and/or formulation, and with the age, condition, and sex of the patient. The dosage can be determined by one of skill in the art and can also be adjusted by the individual physician in the event of any complication.

Typically, the dosage of a given therapeutic aptamer and/or aptamer-active agent complex, can range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 μg/kg body weight to 30 μg/kg body weight. Alternatively, the dose range will be titrated to maintain serum levels between 5 μg/mL and 30 μg/mL.

Administration of the doses recited above or as employed by a skilled clinician can be repeated for a limited and defined period of time. In some embodiments, the doses are given once a day, or multiple times a day, for example, but not limited to three times a day. Typically, the dosage regimen is informed by the half-life of the agent as well as the minimum therapeutic concentration of the agent in blood, serum or localized in a given biological tissue. In a preferred embodiment, the doses recited above are administered daily for several weeks or months. The duration of treatment depends upon the subject's clinical progress and continued responsiveness to therapy. Continuous, relatively low maintenance doses are contemplated after an initial higher therapeutic dose.

A therapeutically effective amount is an amount of an agent that is sufficient to produce a statistically significant, measurable change of a given symptom of disease (see "Efficacy Measurement" below). Such effective amounts can be gauged in clinical trials as well as animal studies for a given agent. For example, reduction of a given symptom of disease can be indicative of adequate therapeutic efficacy of an agent(s).

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. The agent can be administered systemically, if so desired.

Therapeutic compositions containing at least one therapeutic agent can be conventionally administered in a unit dose. The term "unit dose" when used in reference to a therapeutic composition refers to physically discrete units suitable as unitary dosage for the subject, each unit containing a predetermined quantity of a therapeutic agent calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as, e.g., an antibody or targeted liposome technology.

Precise amounts of active ingredient required to be administered depend on the judgment of the practitioner and are particular to each individual. However, suitable dosage ranges for systemic application are disclosed herein and depend on the route of administration. Suitable regimes for administration are also variable but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

In some embodiments, at least one additional therapeutic agent is used in combination with the aptamers or cells described herein for the treatment of a given disease.

In some embodiments, a therapeutic aptamer composition is administered to a subject concurrently with a combination therapy. As used herein, the term "concurrently" is not limited to the administration of the two or more agents at exactly the same time, but rather, it is meant that they are administered to a subject in a sequence and within a time interval such that they can act together (e.g., synergistically to provide an increased benefit than if they were administered otherwise). For example, the combination of therapeutics can be administered at the same time or sequentially in any order at different points in time; however, if not administered at the same time, they should be administered sufficiently close in time so as to provide the desired therapeutic effect, preferably in a synergistic fashion. The agents can be administered separately, in any appropriate form and by any suitable route. When each of the therapeutic agents in a combination are not administered in the same pharmaceutical composition, it is understood that they can be administered in any order to a subject in need thereof. For example, the first therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second therapeutic agent, to a subject in need thereof (or vice versa). In other embodiments, the delivery of either therapeutic agent ends before the delivery of the other agent/treatment begins. In some embodiments of either case, the treatment is more effective because of combined administration. For example, the therapeutic agents used in combination are more effective than would be seen with either agent alone. In some embodiments, delivery is such that the reduction in a symptom, or other parameter related to the disorder is greater than what would be observed with either therapeutic agent alone. The effect of such a combination can be partially additive, wholly additive, or greater than additive. The agent and/or other therapeutic agents, procedures or modalities can be administered during periods of active disease, or during a period of persistence or less active disease.

When administered in combination, one or more of the therapeutic agents can be administered in an amount or dose that is higher, lower or the same as the amount or dosage of the given agent used individually, e.g., as a monotherapy. In certain embodiments, the administered amount or dosage of a first therapeutic agent when administered in combination with a second therapeutic agent is lower (e.g., at least 20%, at least 30%, at least 40%, or at least 50%) than the amount or dosage of the first agent when used individually. In other embodiments, the amount or dosage of a first therapeutic agent, when administered in combination with a second therapeutic agent, results in a desired effect (e.g., improved cognitive functioning) is lower (e.g., at least 20%, at least 30%, at least 40%, or at least 50% lower) than the amount or dosage of the first (or second) agent required to achieve the same therapeutic effect when administered alone.

The efficacy of a treatment for a given disease can be determined by the skilled clinician. However, a treatment is considered "effective treatment," as the term is used herein, if any one or all the signs or symptoms of the given disease is/are altered in a beneficial manner, or other clinically accepted symptoms or markers of disease are improved, or ameliorated, e.g., by at least 10% following treatment with a therapeutic aptamer or a population of therapeutic cells as described herein. Efficacy can also be measured by failure of an individual to worsen as assessed by stabilization of the disease, or the need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of the disease; or (2) relieving the disease, e.g., causing regression of symptoms; and (3) preventing or reducing the likelihood of the development of the disease, or preventing secondary diseases/disorders associated with the disease.

An effective amount for the treatment of a disease means that amount which, when administered to a mammal in need thereof, is sufficient to result in effective treatment as that term is defined herein, for that disease. Efficacy of an agent can be determined by assessing physical indicators of the disease, such as, e.g., pain, fatigue, fever, and the like.

Kits

In one aspect, provided herein are kits containing any one or more of the elements disclosed in the above methods and compositions. Provided herein are kits comprising aptamers as described herein, and formulations thereof. In one embodiment, the kit comprises, consists of, or consists essentially of reagents and instructions for selecting or depleting transferrin receptor-expressing cells from a cell population. In other embodiments, the kit comprises, consists of, or consists essentially of reagents and instructions for genomic or phenotypic analysis of aptamer-selected CD71-expressing cells, generating CAR T cells from a population of cells depleted for aptamer-binding cells and administering such CAR T cells.

In certain embodiments, the kits comprise one or more solid supports or an aptamer conjugated to a solid support. Kits can also comprise columns, including but not limited to affinity chromatography columns and flow cytometry columns.

The kit can comprise cell culture or preparation reagents including labeling means, salts, growth media, serum etc.

In some embodiments, a kit comprises one or more reagents for use in a process utilizing one or more of the elements described herein. Reagents can be provided in any suitable container. For example, a kit can provide one or more reaction or storage buffers. A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10.

It is understood that the preceding detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

The following provides non-limiting Examples demonstrating and supporting the technology as described herein.

Example 1: Discovery of a Transferrin Receptor 1-Binding Aptamer for Removing Cancer Cells from Adoptive T-Cell Therapy Manufacturing Chimeric antigen receptor (CAR) T-cell therapy has gained significant traction in the oncology field, with five FDA-approved therapies to-date: four for treating relapsed or refractory (r/r) $CD19^+$ B-cell malignancies (Novartis's Kymriah®, Gilead-Kite's Yescarta™ and Tecartus™, and Bristol Myers Squibb-Juno Therapeutic's Breyanzi™) and another two for treating r/r $BCMA^+$ multiple myeloma (Bristol Myers Squibb-bluebird bio's Abecma™ and Janssen Pharmaceuticals-Legend Biotech's Carvykti™).[1-8] In these treatments, a patient's T cells journey through an elaborate manufacturing process that consists of 1) enrichment from a leukapheresis product, 2) activation ex vivo, 3) lentiviral or retroviral expression of a CAR that directs T-cell function against a tumor-associated antigen, 4) expansion to therapeutically relevant numbers, and 5) re-infusion into the patient's body for cancer elimination.[9] Given the intricate nature of this operation, there is a continual need for further innovation at each production step to reduce the costs and increase the efficacy and safety of these adoptive T-cell therapies.[10]

T-cell enrichment or selection is a pivotal steps in CAR T-cell manufacturing, as the cell composition and purity used in subsequent activation and transduction steps can influence the outcome of the therapy. For Kymriah®, Yescarta™, and Abecma™, T cells are indirectly enriched by collecting peripheral blood mononuclear cells (PBMCs) from leukapheresis product using counterflow centrifugal elutriation, which removes most monocytes, granulocytes, platelets, and residual red blood cells based on differences in cell size and density relative to lymphocytes.[11-13] However, this selection approach is unable to discriminate healthy T cells from circulating cancerous lymphocytes, meaning that tumor cells can be present in downstream manufacturing steps and thereby drive uncontrollable activation and exhaustion of the CAR T-cell product.[14] Additionally, transduction of a single leukemic B cell with the CAR gene during CAR T-cell manufacturing caused in cis epitope masking that led to a patient's relapse and eventual death.[15] These issues highlight the need for complete removal of cancerous lymphocytes during the selection step prior to further CAR T-cell manufacturing.

To address this problem, especially for patients with high circulating blast and leukemia cell counts, Tecartus™, Breyanzi™, and Carvykti™ rely on direct isolation of T cells. Whereas Tecartus™ and Carvykti™ isolates bulk $CD3^+$ T cells,[5, 16] Breyanzi™ separately isolates helper $CD4^+$ T cells and cytotoxic $CD8^+$ T cells for CAR T-cell production and later infuses the patient with a defined 1:1 composition of the subsets.[6] Breyanzi is associated with lower rates of cytokine release syndrome and neurotoxicity than Kymriah® and Yescarta™ while remaining equally effective.[2, 3, 6] However, the direct isolation of T cells is expensive, typically relying on costly antibody- or multimerized Fab-coated magnetic beads that target either the CD3, CD4, and/or CD8 T-cell markers for positive enrichment or unwanted immune cell markers for negative enrichment.[17] Furthermore, these approaches do not actively remove the cancer cells from a patient's leukapheresis product. In contrast to B-cell malignancies, malignant T cells can be difficult to separate from healthy T cells used for manufacturing CAR T cell therapies.[18], [19] Accordingly, as autologous CAR T-cell therapies are broadened to treat diverse hematological malignancies, an inexpensive and universal method for removing cancerous cells from healthy PBMCs will be imperative for their safe manufacturing.

DNA aptamers, single-stranded oligonucleotides that fold into sequence-specific secondary structures, are molecular recognition agents that can address the current deficiencies of cancer cell removal in adoptive T-cell manufacturing. Aptamers can bind their targets with affinities comparable to antibodies, but unlike antibodies they are synthesized chemically with high reproducibility and relatively low cost.[20] Aptamers can also be controllably modified at any position (5' end, 3' end, or internally) for facile immobilization onto solid supports (e.g., hydrogels) for affinity-based separations.[21] Aptamer binding to their targets can also be reversed by disrupting aptamer structure, for example, by use of a complementary sequence.[21, 22] Demonstrating these points, the inventors previously identified CD8-binding DNA aptamers and used them to isolate $CD8^+$ T cells via magnetic-activated cell sorting (MACS) with comparable purity, yield, and downstream CAR functionality as those isolated from commercial antibody-based methods.[23]

Aptamers can be selected to bind certain cell types without prior knowledge of receptor identity (i.e., receptor-agnostic panning).[24-26] The subtractive evolutionary process in which aptamers go through rounds of positive and negative selection against whole cells, termed cell-SELEX (systematic evolution of ligands by exponential enrichment), has become an attractive method for discovering aptamers that can differentiate malignant cells from healthy normal cells.[27] Given these benefits, cell-SELEX holds great promise for discovering DNA aptamers that can selectively bind and deplete circulating leukemia and lymphoma cells from PBMCs at low cost prior to CAR T-cell manufacturing.

Here, in a cell-SELEX intended to identify T-cell antigen-binding aptamers, the inventors discovered and truncated an aptamer, named tJBA8.1, that displays high-affinity binding for Jurkat T-leukemia cells. Further assays identified transferrin receptor 1 (TfR1), an iron-uptake receptor not expressed on resting immune cells but upregulated on actively dividing and cancerous cells, as the binding target of tJBA8.1. The tJBA8.1-TfR1 interaction was characterized by flow cytometry, biolayer interferometry, and competition studies with holo-transferrin, and further compare its binding properties to a previously reported TfR1-binding aptamer. The inventors further employed tJBA8.1 in MACS to remove spiked Raji B-lymphoma cells from PBMCs with high yield and minimal impact on the healthy immune cell composition. Lastly, the off-target binding of tJBA8.1 was studied and a point mutation to the aptamer sequence for affinity improvement are described. Given the broad expression of TfR1 on many cancers, including difficult to distinguish T-cell leukemias and lymphomas, it is contemplated that this method can be universally used for the depletion of circulating cancer cells from patient PBMCs prior to downstream CAR T-cell manufacturing, leading to a safer, more potent, and cost-mindful therapy.

Discovery of the Jurkat-Binding Aptamer 8.1 (JBA8.1) by Cell-SELEX and Stem Truncation to tJBA8.1

Figure 1A:
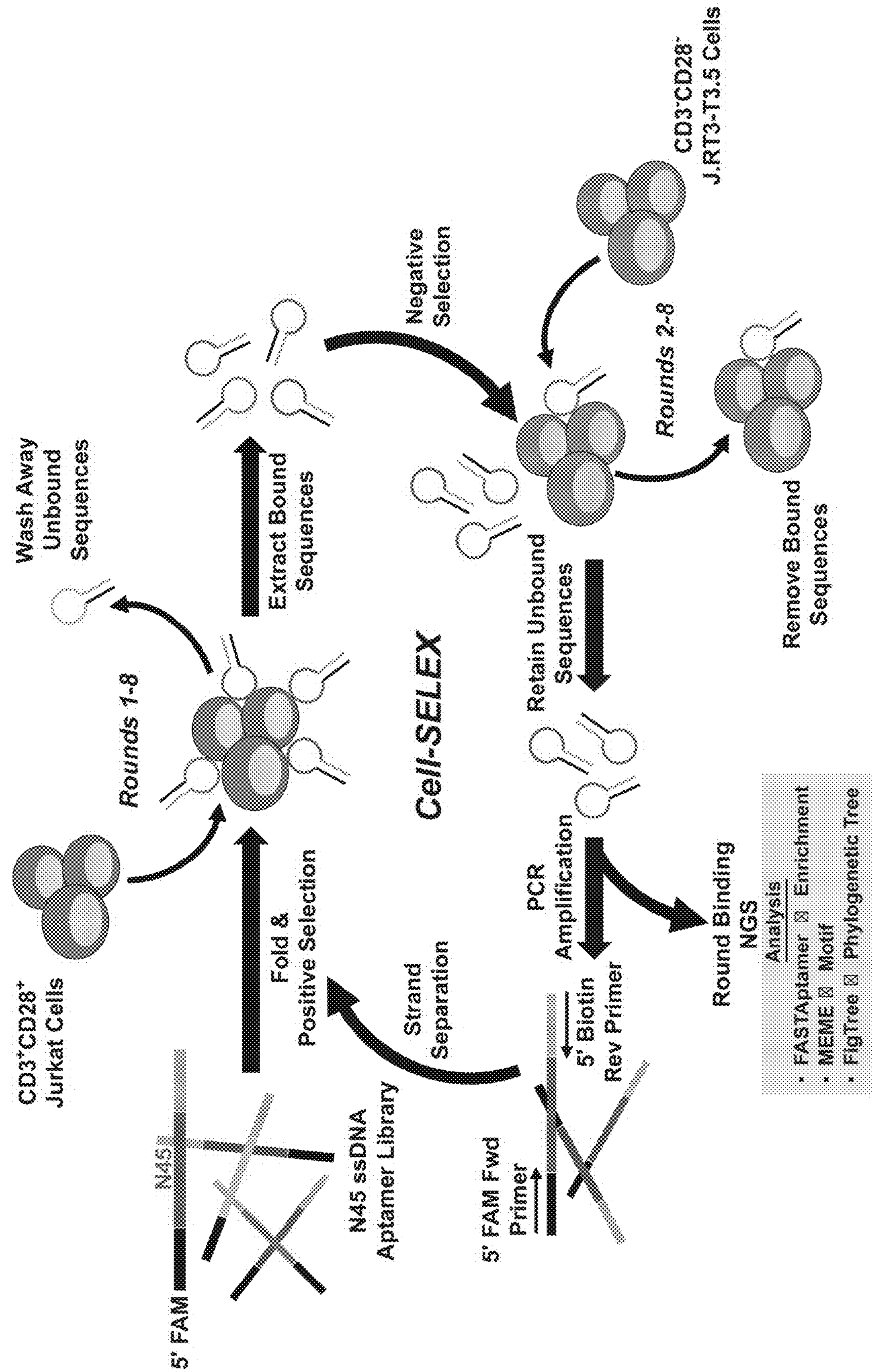
FIGS. 1A-1C. Cell-SELEX and post-SELEX truncation lead to the development of the JBA8.1 aptamer.

In an initial effort to identify aptamers that bind the human CD3 and CD28 T-cell receptors, cell-SELEX was performed using $CD3^+CD28^+$ Jurkat T-leukemia cells for positive selection and $CD3^-CD28^-$ J.RT3-T3.5 cells for negative/counter selection (FIG. 1A). The single-stranded DNA (ssDNA) library used in cell-SELEX was comprised of a 45-base pair (bp) random region flanked by two 18-bp constant regions designed for both PCR amplification between rounds and stem formation, amounting to 81 bp total. After an initial positive selection against Jurkat cells with a naive library of $10^{16}$ unique ssDNA sequences, seven additional rounds of sequential positive selection with Jurkat cells and negative selection with J.RT3-T3.5 cells were conducted with progressively increased stringency (Table 3).

TABLE 3

| Experimental conditions used in rounds of cell-SELEX. | | | | | | |
|---|---|---|---|---|---|---|
| SELEX Round | Positive Selection (Jurkat) | Negative Selection (J.RT3-T3.5) | Aptamer Pool (μM) | FBS (%) | Time (min) | # of Washes |
| 1 | $10^7$ Cells | — | 14 | — | 660 | 3 |
| 2 | $5 \times 10^6$ Cells | $10^7$ Cells | 0.5 | — | 660 | 3 |
| 3 | $4 \times 10^6$ Cells | $10^7$ Cells | 0.5 | — | 660 | 3 |
| 4 | $2 \times 10^6$ Cells | $10^7$ Cells | 0.5 | 5 | 445 | 4 |
| 5 | $1 \times 10^6$ Cells | $10^7$ Cells | 0.5 | 5 | 445 | 4 |
| 6 | $1 \times 10^6$ Cells | $10^7$ Cells | 0.5 | 10 | 445 | 5 |
| 7 | $1 \times 10^6$ Cells | $10^7$ Cells | 0.5 | 10 | 330 | 5 |
| 8 | $1 \times 10^6$ Cells | $10^7$ Cells | 0.5 | 20 | 330 | 6 |

Figure 1B:
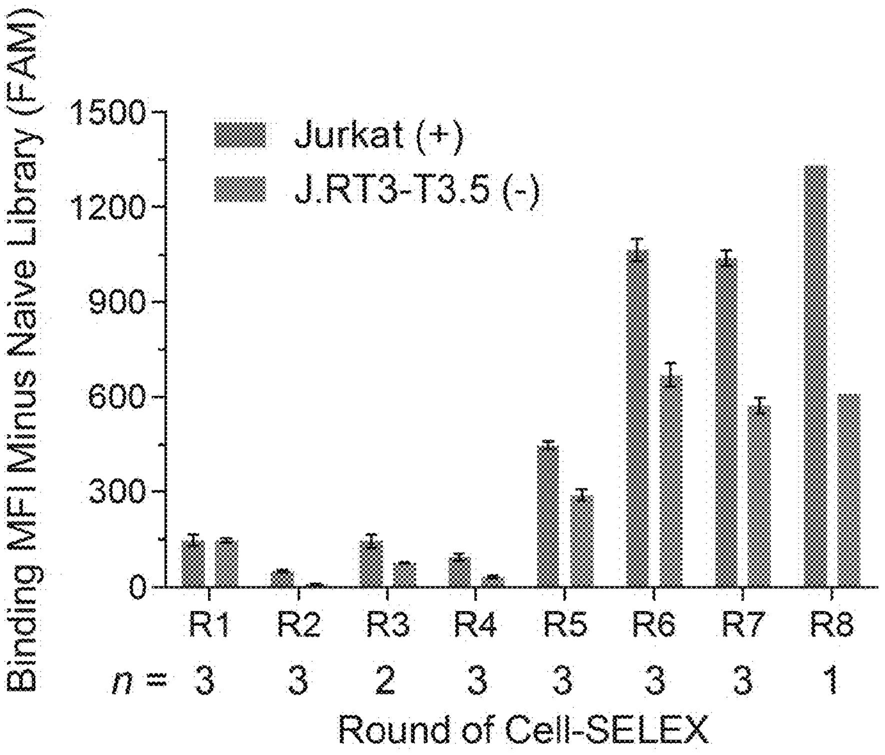

Prior to cell binding, aptamer sequences were folded by heating in DPBS supplemented with approximately 0.9 mM $CA^{2+}$ and approximately 5.5 mM $Mg^{2+}$ ions for 5 min at 95° C. followed by snap cooling on ice (See infra for details). Flow cytometry binding of aptamer pools from the individual SELEX rounds revealed substantial binding to both Jurkat and J.RT3-T3.5 cells starting in round 5 that plateaued by round 8 (FIG. 1B). While preferential binding to Jurkat cells was observed in later rounds, but differences in cell size and absolute number of receptors per cell may have biased binding to larger Jurkat cells. Nonetheless, the inventors proceeded with next generation sequencing (NGS) of the ssDNA pools from all 8 rounds using the primers detailed in Table 4 to identify the enriched cell-binding aptamers.

Figure 16A:
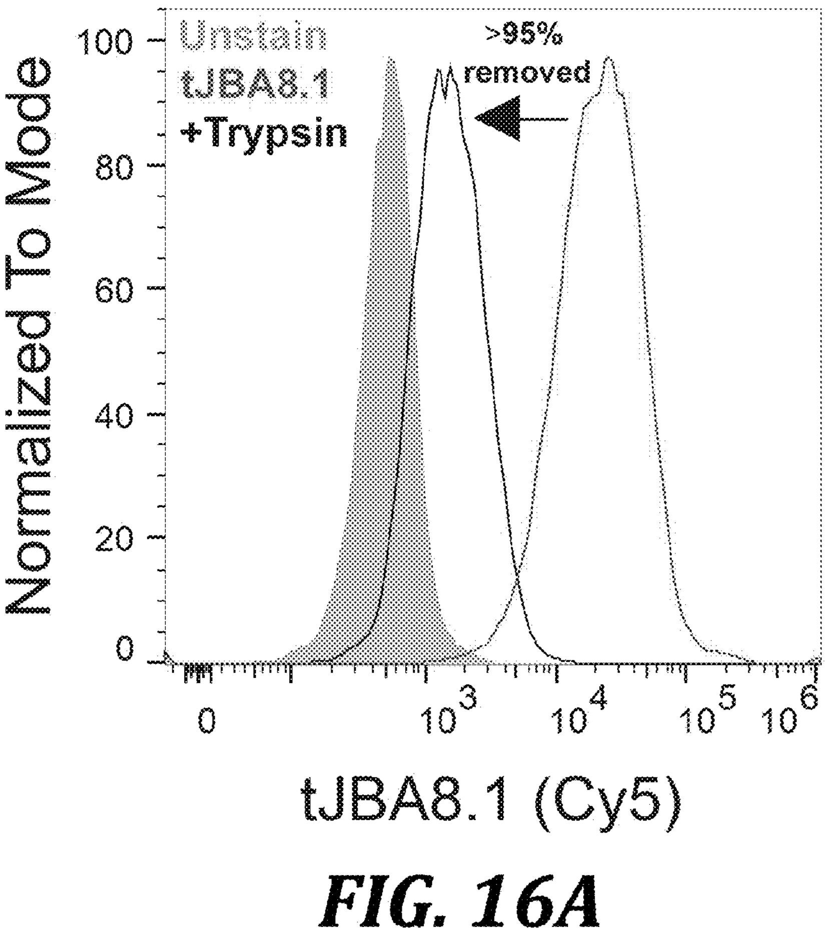
FIGS. 16A-16B. tJBA8.1 targets membrane-bound proteins on Jurkat cells.
Figure 16B:
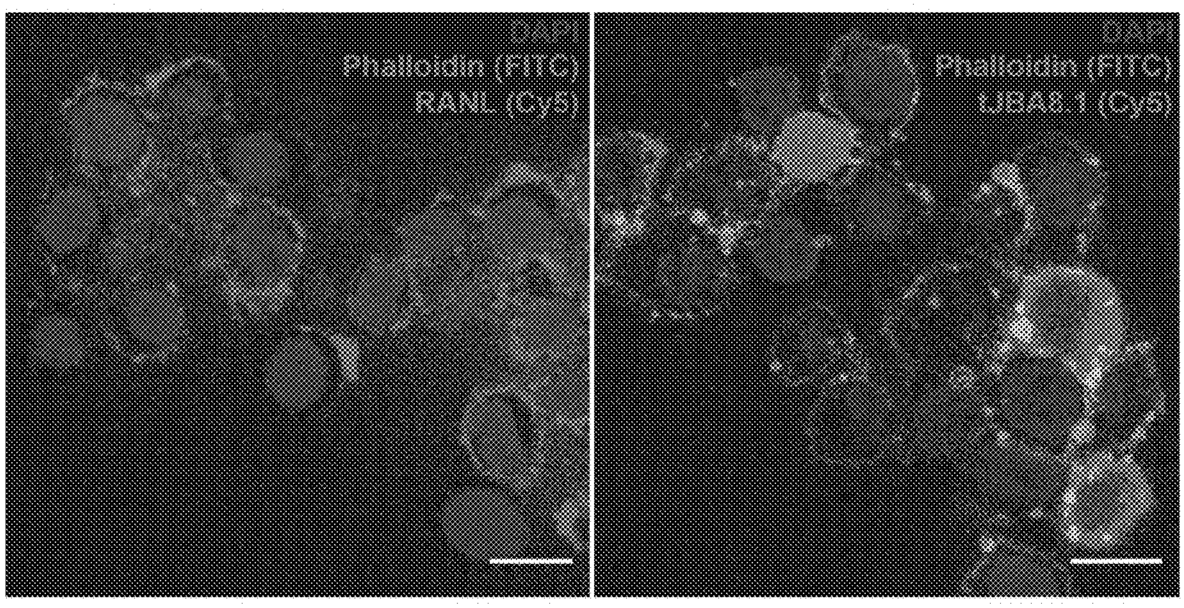

FASTAptamer™ toolkit was used to analyze NGS results and calculate fold-enrichment of unique aptamer sequences over rounds of cell-SELEX.[29] Unique sequence reads were low for rounds 1-4, reflecting high aptamer pool diversity until rounds 5-8. These results are consistent with the cell-SELEX round binding results in FIG. 1B, in which aptamer pool binding to Jurkat cells was observed starting in round 5. FigTree™ software and MEME analysis were used to generate phylogenetic trees and identify consensus motifs, respectively, for the top 50 aptamer sequences over rounds 5-8 (FIG. 16).[36,37] In round 5, top aptamer sequences were primarily characterized by one of three short motifs (Motifs 1, 2, and 3) with low individual sequence representation (<0.4%). Sequence representation progressively increased in rounds 6 and 7, with top sequences representing as much as 6.3% and 10.6% of the pool, respectively. By round 8, Motif 3 expanded to encompass the whole 45-nucleotide (nt) random region and a new 40-nt motif, Motif 5, emerged, with top aptamers belonging to each motif displaying robust tree clustering and thus high sequence similarity. Notably, the most prevalent aptamer in round 8, which belonged to Motif 3, represented 21.1% of the entire sequence pool. Table 5 lists the predicted motifs, sequences, and the round-by-round enrichment of the top 50 aptamers identified from round 8.

TABLE 4

| Primers used for next generation sequencing (NGS) of naive library (NL) and cell-SELEX rounds 1-8. The NL and Rounds 7-8 were sequenced initially, followed by Rounds 1-6 in a separate run. Accordingly, there is some overlap in the barcoded reverse primers used between the separate runs. | | | |
|---|---|---|---|
| Primer Name | SELEX Round | Sequence | Barcode (underlined) |
| Aptamer_F | NL, 1-8 | AATGATACGGCGACCACCGAGATCTACACCGAGGAG ATACCACTAAGCCACCGTGTCCA (SEQ ID NO: 57) | |
| Aptamer_R_77 | NL | CAAGCAGAAGACGGCATACGAGATGCAATTCGACAG ACCGTCGATCCAGAGTGACGCAGCA (SEQ ID NO: 58) | CGAATTGC |
| Aptamer_R_79 | 1 | CAAGCAGAAGACGGCATACGAGATTCGATTAAACAGA CCGTCGATCCAGAGTGACGCAGCA (SEQ ID NO: 59) | TTAATCGA |
| Aptamer_R_80 | 2 | CAAGCAGAAGACGGCATACGAGATGAATGGACACAG ACCGTCGATCCAGAGTGACGCAGCA (SEQ ID NO: 60) | GTCCATTC |
| Aptamer_R_81 | 3 | CAAGCAGAAGACGGCATACGAGATAGAATCAGACAG ACCGTCGATCCAGAGTGACGCAGCA (SEQ ID NO: 61) | CTGATTCT |
| Aptamer_R_82 | 4 | CAAGCAGAAGACGGCATACGAGATAACTGCCAACAG ACCGTCGATCCAGAGTGACGCAGCA (SEQ ID NO: 62) | TGGCAGTT |
| Aptamer_R_83 | 5 | CAAGCAGAAGACGGCATACGAGATAAGTAACGACAG ACCGTCGATCCAGAGTGACGCAGCA (SEQ ID NO: 63) | CGTTACTT |
| Aptamer_R_84 | 6 | CAAGCAGAAGACGGCATACGAGATACTCAATGACAGA CCGTCGATCCAGAGTGACGCAGCA (SEQ ID NO: 64) | CATTGAGT |
| Aptamer_R_78 | 7 | CAAGCAGAAGACGGCATACGAGATCAAGAGGTACAG ACCGTCGATCCAGAGTGACGCAGCA (SEQ ID NO: 65) | ACCTCTTG |
| Aptamer_R_79 | 8 | CAAGCAGAAGACGGCATACGAGATTCGATTAAACAGA CCGTCGATCCAGAGTGACGCAGCA (SEQ ID NO: 66) | TTAATCGA |

TABLE 5

Enrichment of top 50 Round 8 (R8) aptamer sequences between rounds of cell-SELEX. Fold enrichment is calculated by dividing the reads per million (RPM) of the sequence from a round by the value of the former round.

| R8 Rank | % Rep. | Motif | Random Region Sequence | SEQ ID NO: | Fold Enrichment R8/R7 | R7/R6 | R6/R5 |
|---|---|---|---|---|---|---|---|
| 1 | 21.08 | 3 | GCGTAAAGGGGGTGTTTGTGCGGTGTGGAGTG CGCGTGCTGCTGC | 67 | 6.9 | 7.8 | 19.5 |
| 2 | 11.15 | | ATCCGGGAGAGTCGTTGTGTTGAGGTCCGCCCCTGCT CGCCCGCG | 68 | 11.1 | 20.3 | |
| 3 | 6.41 | 2 | GGGGCCGCGGATGCAAACGCCCGATAGGGGGACGGC ACTGGAGCT | 69 | 0.6 | 4.1 | 89.4 |
| 4 | 5.59 | | ACCCAAACCACCAGCCGGGGATGCAAACACCGCACAG GGAACGGC | 70 | 1.3 | 6.7 | 104.6 |
| 5 | 5.07 | | AAGCGGTTTTCGGGTTCGGGTCTGGGGGTTGGGTTGT CGGCACTA | 71 | 0.8 | 15.9 | |
| 6 | 4.61 | | ACAGACAGCTGCGCCGCCGGGAGGGCACCCGGACGG GCTGGGCGG | 72 | 1.7 | 0.4 | 55.1 |
| 7 | 4.01 | 2 | ACCACAGATGCAAATGCGCGAGAGCGGGACGGTTTGC TAGGCTCA | 73 | 0.7 | 5.3 | 80.8 |
| 8 | 3.88 | 5 | GTGGGCCAAATGGATTGGATTAGGGTTGGGCCGCCC GGGAGGGGT | 74 | 0.6 | 28.2 | 51.4 |
| 9 | 3.29 | 1 | AGGCGCTAGACGCAATCCCGCAAGCGGAGCCGGATT CCCTAGTGG | 75 | 0.7 | 2.0 | 13.9 |
| 10 | 3.17 | 3 | GCATAAAGGGGGTGTTTGTGCGGTGTGGAGTGCGCGT GCTGCTGC | 76 | 20.1 | 17.4 | |
| 11 | 2.88 | 2 | GCCGGTCGCAGATGCAAATGCCCGACAGGGGGACGC GGGCTGCCA | 77 | 0.6 | 4.4 | 65.7 |
| 12 | 2.70 | 2 | CAGATGCAAATGCCTGACCAGGGAACTGCGACTGGAT GGCTCTTG | 78 | 1.0 | 5.3 | 60.4 |
| 13 | 2.26 | 1 | ATCACAGGGCTACAAGGTGCTAAACGTAAACTAGCAA GAGAACTA | 79 | 0.8 | 1.8 | 20.1 |
| 14 | 1.82 | 2 | GATGCAAATGCTCGAGAGAGGACCGGCGGCACTGGT GAACGTAGG | 80 | 1.0 | 5.6 | 70.8 |
| 15 | 1.55 | | CTCTCGGGGGGTAGGTGGGAAGGGGGCCGCCCCCTG GGTTAGGCT | 81 | 22.4 | 9.8 | |
| 16 | 1.18 | 2 | AGCGGGGATGCAAACACCCGAAAGGGGAACGGGAGC TGCGTCAAG | 82 | 1.7 | 1.1 | 73.4 |
| 17 | 0.93 | | AGGTGGCTGTGGGCGGATGGTGGGCTCGCGTGGGCG GCCACCTGA | 83 | 0.9 | 0.9 | 12.4 |
| 18 | 0.90 | | ACGTTATCCCCTTTACGGGGTCCTAGAGCCCCGTGAG TGCTCACG | 84 | 1.0 | 1.7 | 19.4 |
| 19 | 0.83 | | TCGGTGTTTATGGTGTCTGTCGGTGCGTACTCGGGGC TTCACTAG | 85 | 0.8 | 9.9 | 15.3 |
| 20 | 0.69 | 2 | TTGGAGGTGGCGGATGCAAACGCTAGACAGAGGCAC CAGCTCCAA | 86 | 0.8 | 3.9 | |
| 21 | 0.64 | | GACTGCTGTGCCACCGGGAGTGCCTTCAGCGCCGTAC GGTCTGCT | 87 | 1.2 | 0.2 | 31.9 |
| 22 | 0.63 | 1 | ACGCAGCAAGGTGCTAAACGCAATCCCGGATTCTCGT GCGTCAAG | 88 | 1.3 | 1.2 | 18.3 |
| 23 | 0.49 | 2 | GATGCAAATGCCCGAATGGGGGACGGCGGACACGGG GTGTGCCGA | 89 | 0.6 | 4.4 | |
| 24 | 0.43 | | TACGGCTTATGCTCAGAGGGGCTGTGGGCCGAGGGG AGCGTCGCG | 90 | 0.9 | 1.2 | 9.5 |

TABLE 5-continued

Enrichment of top 50 Round 8 (R8) aptamer sequences between rounds of cell-SELEX. Fold enrichment is calculated by dividing the reads per million (RPM) of the sequence from a round by the value of the former round.

| R8 Rank | % Rep. | Motif | Random Region Sequence | SEQ ID NO: | Fold Enrichment R8/R7 | R7/R6 | R6/R5 |
|---|---|---|---|---|---|---|---|
| 25 | 0.35 | | TGTAAGCCGAATGTTGGTGCTTGGGTAGGCGCCATTGTGAGCTCG | 91 | 0.8 | 3.2 | 12.8 |
| 26 | 0.33 | 3 | GCGTAAAGGGGGTGTTTGTGCGGTGTGGAGTGCGCGCGCTGCTGC | 92 | 22.3 | | |
| 27 | 0.25 | | CTGTGGGGTCACATTGGGGGACGGGACCGTGCGTGAGATCTAAGA | 93 | 2.6 | 12.6 | |
| 28 | 0.21 | | GGGTTCCGGATGTGGTGGGGCTTAGGGGGGTTTCACTGCTAGCGT | 94 | 0.5 | 5.2 | |
| 29 | 0.19 | | AAGGTTGCCATACCACCGGGAGCGTTCGAGTACGGCCTGTCGCGC | 95 | 0.6 | 0.5 | 23.3 |
| 30 | 0.18 | 1 | AGGGGTACAAGGTGTTAAACGTAAATTCTGCGCGGAGGGGAACTT | 96 | 0.8 | 1.5 | 11.0 |
| 31 | 0.16 | | GACGCAGCAGTGCCATCGGGGGGGATTTCCTTGTACGACGTCACC | 97 | 0.6 | 0.8 | 16.0 |
| 32 | 0.15 | | GTGCCATCGGGAGGCGCGAGTCCGTACGACGTCATTTGGCAAAAC | 98 | 0.8 | 0.8 | 19.3 |
| 33 | 0.14 | | AAAAGAAGCGACCGAGACCACGGATGCAAACGCCCAGGCGGGGAA | 99 | 0.7 | 2.8 | |
| 34 | 0.13 | 1 | CTGTGGCGTAATTCTGGTCGGCGGTCACGTGCGTGAGAGCTGGGG | 100 | 3.7 | 10.7 | |
| 35 | 0.11 | 1 | AGGTGTTAAACGCTAACGCCAGTTATCTTAAAGAAAGTAAACGAC | 101 | 0.5 | 1.3 | 7.5 |
| 36 | 0.11 | | TCAAGGGGTTACACGAAAAGATAGGCTTTCACGCTAGTGGGCTTG | 102 | 0.6 | 1.3 | 7.5 |
| 37 | 0.10 | | CAGATGCAAATGCCTGACCAGGGAACTGCGACTGGATGGCTCTTT | 103 | 0.7 | 1.5 | 6.4 |
| 38 | 0.09 | | CAGATGCAAATGCCTGACCAGGGAACTGCGACTGGATGGCTCTTT | 104 | 1.5 | 6.8 | |
| 39 | 0.09 | | CGAAAATTTCAAGCTTTATGCTCTAGCGCAGCGCCTCGTACCCCT | 105 | 1.8 | 1.5 | |
| 40 | 0.08 | | GGTGAAGGGCAGTGGTTTGCTGTGGTGGGCGCCCGTGAGCGTTGC | 106 | 2.2 | 6.1 | |
| 41 | 0.08 | | GGGAGTTCGGGCATGATTTGCCCTGGGGGGCACGGGAAGGTACCG | 107 | 1.0 | 7.7 | 2.7 |
| 42 | 0.08 | 1 | CGCACCAAGGCGTTAGACGGAATGGATTTGGAACTTCATGCGAAG | 108 | 0.4 | 1.3 | 6.4 |
| 43 | 0.08 | | GTTGGGCTAAGCGGAGGATGGTAATGGTGCTTGGGCAGGCGCTCA | 109 | 0.8 | 2.5 | 11.3 |
| 44 | 0.07 | 2 | CAGATGCAAATGCCTGACCAGGGAACTGCGACTTGATGGCTCTTG | 110 | 1.5 | 5.8 | |
| 45 | 0.07 | 3 | GCGCAAAGGGGGTGTTTGTGCGGTGTGGAGTGCGCGTGCTGCTGC | 111 | 20.6 | | |
| 46 | 0.07 | | GTGCCATCGGGAAGGTGTTGACCTGTACGACGTCATAGGATGGAC | 112 | 1.2 | 1.0 | |
| 47 | 0.07 | | GGGGTGTAGGGTGGGGTAGTGGGAACATTGCGTAAAGTGTAGCTC | 113 | 0.9 | 6.2 | |
| 48 | 0.06 | | ACTGTTTGTACGGAGTTAGGGTGTGCCTTTATTGCGCGGGGGGGA | 114 | 5.6 | | |

TABLE 5-continued

Enrichment of top 50 Round 8 (R8) aptamer sequences between rounds of cell-SELEX. Fold enrichment is calculated by dividing the reads per million (RPM) of the sequence from a round by the value of the former round.

| R8 Rank | % Rep. | Motif | Random Region Sequence | SEQ ID NO: | Fold Enrichment R8/R7 | R7/R6 | R6/R5 |
|---|---|---|---|---|---|---|---|
| 49 | 0.06 | | TCATTGGAGTGGGTAGGGGTGTTTGTGCGGGATGCGG TGGCTAGG | 115 | 3.4 | .4 | |
| 50 | 0.06 | 5 | GTTGGCCAAATGGATTGGATTAGGGTTGGGCCGCCCG GGAGGGGT | 116 | 1.0 | | |

Nine Jurkat-binding aptamers from round 8 listed in Table 6 and named JBA8.X (where "X" is the aptamer's rank in Table 5) were chosen for cell binding based on their representation, motif, and enrichment across rounds.

TABLE 6

Sequences of aptamers used in experiments. Aptamers were modified on their 5'-end with either 6-FAM, Cy5, or biotin-hexa-ethyleneglycol depending on the assay. The exact modifications are specified in the figures and captions. For 5' modification of tJBA8.1 with 6-FAM, a thymidine nucleotide was added at the 5' end to prevent fluorescence quenching by guanosine. Underlined nucleotides represent constant regions. Bolded text represents nucleotides that were deleted to make the truncated tJBA8.1 aptamer, and lower-case, bolded text represents nucleotides that were substituted to create either point variants of tJBA8.1 or JBA8.26.

| SEQ ID NO: | Name | Sequence |
|---|---|---|
| 117 | RANL | 5'-ATCCAGAGTGACGCAGCAAATTCCAAACTCGAGTAAGCGTAGA GCCTCTCATCGCCTCAATAATGGACACGGTGGCTTAGT-3' |
| 2 | JBA8.1 | 5'-ATCCAGAGTGACGCAGCAGCGTAAAGGGGGTGTTTGTGCGGT GTGGAGTGCGCGTGCTGCTGCTGGACACGGTGGCTTAGT-3' |
| 118 | JBA8.2 | 5'-ATCCAGAGTGACGCAGCAATCCGGGAGAGTCGTTGTGTTGAG GTCCGCCCCTGCTCGCCCGCGTGGACACGGTGGCTTAGT-3' |
| 119 | JBA8.3 | 5'-ATCCAGAGTGACGCAGCAGGGGCCGCGGATGCAAACGCCCG ATAGGGGGACGGCACTGGAGCTTGGACACGGTGGCTTAGT-3' |
| 120 | JBA8.4 | 5'-ATCCAGAGTGACGCAGCAACCCAAACCACCAGCCGGGGATG CAAACACCGCACAGGGAACGGCTGGACACGGTGGCTTAGT-3' |
| 121 | JBA8.7 | 5'-ATCCAGAGTGACGCAGCAACCACAGATGCAAATGCGCGAGA GCGGGACGGTTTGCTAGGCTCATGGACACGGTGGCTTAGT-3' |
| 122 | JBA8.8 | 5'-ATCCAGAGTGACGCAGCAGTGGGCCAAATGGATTGGATTAGG GTTGGGCCGCCCGGGAGGGGTTGGACACGGTGGCTTAGT-3' |
| 123 | JBA8.11 | 5'-ATCCAGAGTGACGCAGCAGCCGGTCGCAGATGCAAATGCCCG ACAGGGGGACGCGGGCTGCCATGGACACGGTGGCTTAGT-3' |
| 124 | JBA8.15 | 5'-ATCCAGAGTGACGCAGCACTCTCGGGGGGTAGGTGGGAAGG GGGCCGCCCCCTGGGTTAGGCTTGGACACGGTGGCTTAGT-3' |
| 125 | JBA8.17 | 5'-ATCCAGAGTGACGCAGCAAGGTGGCTGTGGGCGGATGGTGG GCTCGCGTGGGCGGCCACCTGATGGACACGGTGGCTTAGT-3' |
| 1 | tJBA8.1 | 5'-GCAGCAGCGTAAAGGGGGTGTTTGTGCGGTGTGGAGTGCGC GTGCTGCTGC-3' |
| 126 | XQ-2d | 5'-ACTCATAGGGTTAGGGGCTGCTGGCCAGATACTCAGATGGTA GGGTTACTATGAGC-3' |
| 7 | tJBA8.1 GGAGG | 5'-GCAGCAGCGTAAAGGaGGTGTTTGTGCGGTGTGGAGTGCGC GTGCTGCTGC-3' |
| 4 | tJBA8.1 GGGAG | 5'-GCAGCAGCGTAAAGGGaGTGTTTGTGCGGTGTGGAGTGCGC GTGCTGCTGC-3' |
| 127 | tJBA8.1 GGGGC | 5'-GCAGCAGCGTAAAGGGGcTGTTTGTGCGGTGTGGAGTGCGC GTGCTGCTGC-3' |

TABLE 6-continued

Sequences of aptamers used in experiments. Aptamers were modified on their 5'-end with either 6-FAM, Cy5, or biotin-hexa-ethyleneglycol depending on the assay. The exact modifications are specified in the figures and captions. For 5' modification of tJBA8.1 with 6-FAM, a thymidine nucleotide was added at the 5' end to prevent fluorescence quenching by guanosine. Underlined nucleotides represent constant regions. Bolded text represents nucleotides that were deleted to make the truncated tJBA8.1 aptamer, and lower-case, bolded text represents nucleotides that were substituted to create either point variants of tJBA8.1 or JBA8.26.

| SEQ ID NO: | Name | Sequence |
|---|---|---|
| 27 | JBA8.26 | 5'-ATCCAGAGTGACGCAGCAGCGTAAAGGGGGTGTTTGTGCGGT GTGGAGTGCGCGcGCTGCTGCTGGACACGGTGGCTTAGT-3' |

Figure 1C:
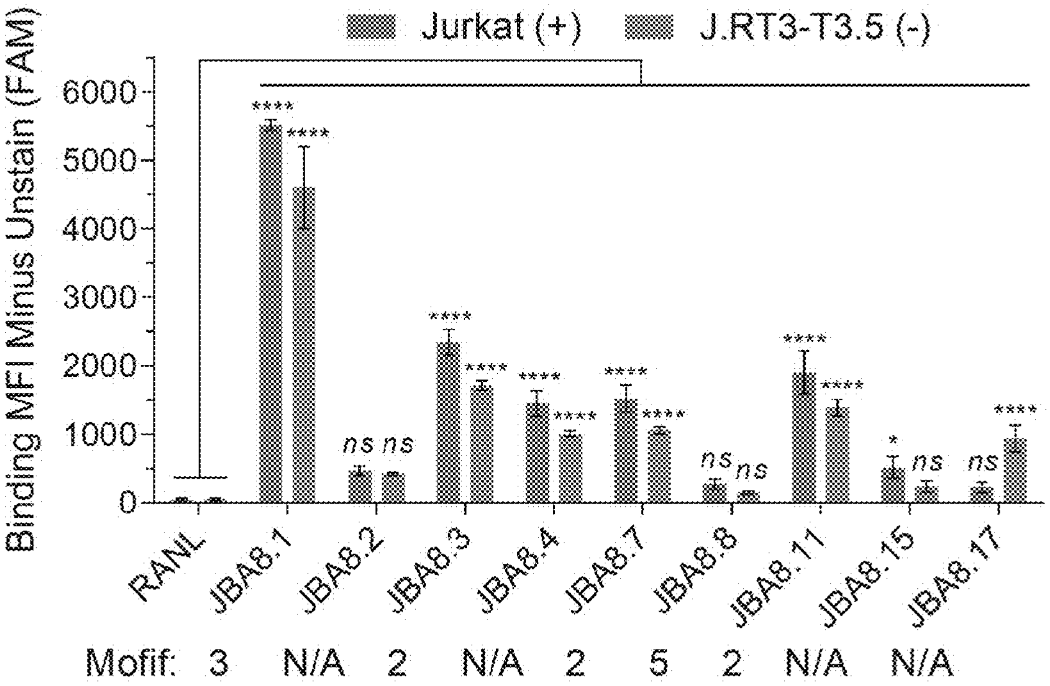

None of the selected fluorescein-labeled aptamers displayed specific binding for Jurkat cells over J.RT3-T3.5 cells, indicating that the SELEX process did not enrich CD3- or CD28-binding aptamers (FIG. 1C). Fluorescein-labeled JBA8.1 from Motif 3, JBA8.3, JBA8.7, and JBA8.11 from Motif 2, and JBA8.4 without a motif all displayed robust binding to both Jurkat and J.RT3-T3.5 cells compared to a random aptamer from the naïve library (RANL), with JBA8.1 distinguishing itself with greater than 2-fold higher binding than the other aptamers. JBA8.8 did not significantly bind to either cell line despite belonging to the 40-bp Motif 5, whereas JBA8.17 without a motif displayed preferential binding for J.RT3-T3.5 cells. Given these data, the negative selection appeared to be ineffective, possibly due to the order of positive followed by negative selection, or else insufficient number of JRT3-T3.5 cells used. The JBA8.1 aptamer was then characterized and optimized due to its pronounced binding to Jurkat T leukemic cells.

Truncation and Binding Affinity of the JBA8.1 Aptamer

Figure 2A:
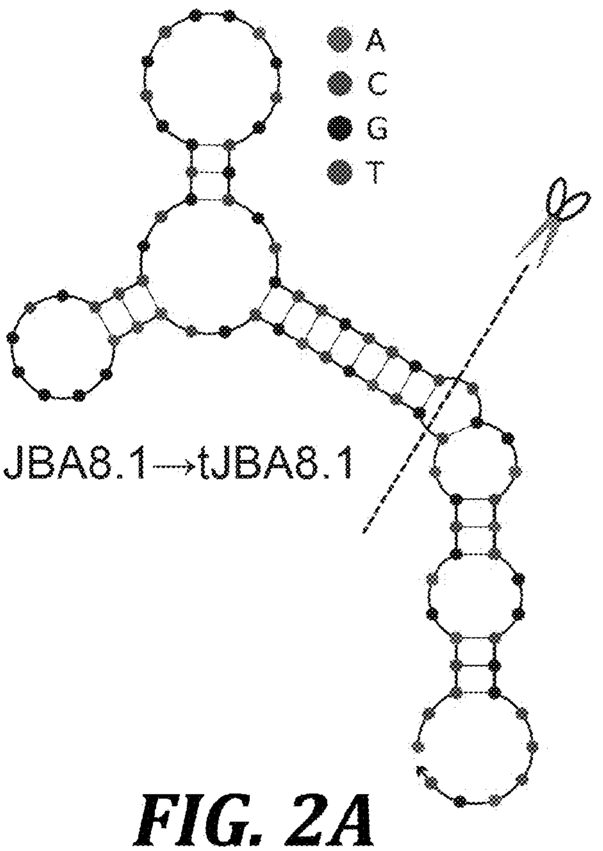
FIGS. 2A-2B. Stem truncation of JBA8.1 to tJBA8.1 minimally impacts binding affinity.
Figure 2B:
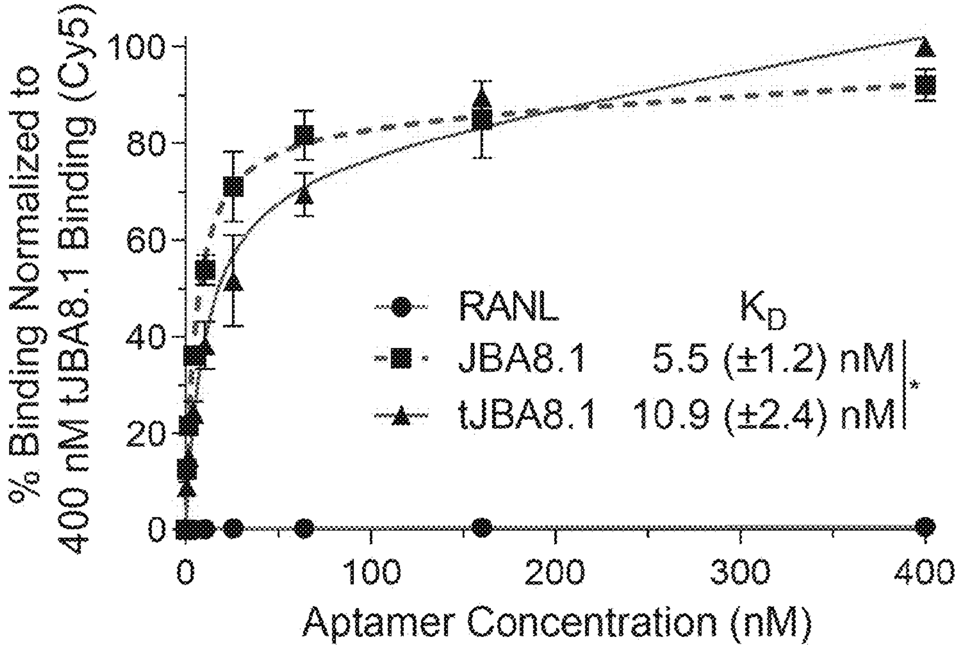

To reduce aptamer productions costs in downstream assays, the inventors first sought to truncate the JBA8.1 aptamer. Using the NUPACK™ application to predict the minimum free energy (MFE) structure of JBA8.1,[33] it was found that the simulated structure of JBA8.1 conforms well to the intended library design, with the majority of the 45-bp Motif 3 forming a multi-hairpin structure that sits on top of a stem comprised of the partially complementary 18-nt flanking primer sequences (FIG. 2A). While the stem may be important for maintaining the integrity of the Motif 3 hairpin structure, it was speculated that it does not directly contribute to aptamer binding and thus could be shortened without compromising the binding affinity of the aptamer. Accordingly, the inventors truncated the stem of tJBA8.1 sequence by removing 12 nt from the 5' constant region and all 18 nt from the 3' constant region, yielding the 51-nt tJBA8.1 aptamer sequence (FIG. 2A and Table 6). Comparing the apparent binding affinity ($K_D$) of the full-length and truncated aptamer to Jurkat cells, it was found that JBA8.1 has an apparent $K_D$ of 5.5±1.2 nM versus that of 10.9±2.4 nM for tJBA8.1, indicating that the truncation only has a minimal impact on target binding. (FIG. 2B). tJBA8.1 was selected for further receptor identification, characterization, and application studies.

Identification and Validation of Transferrin Receptor 1 (TfR1) as a Target of tJBA8.1

Figure 17A:
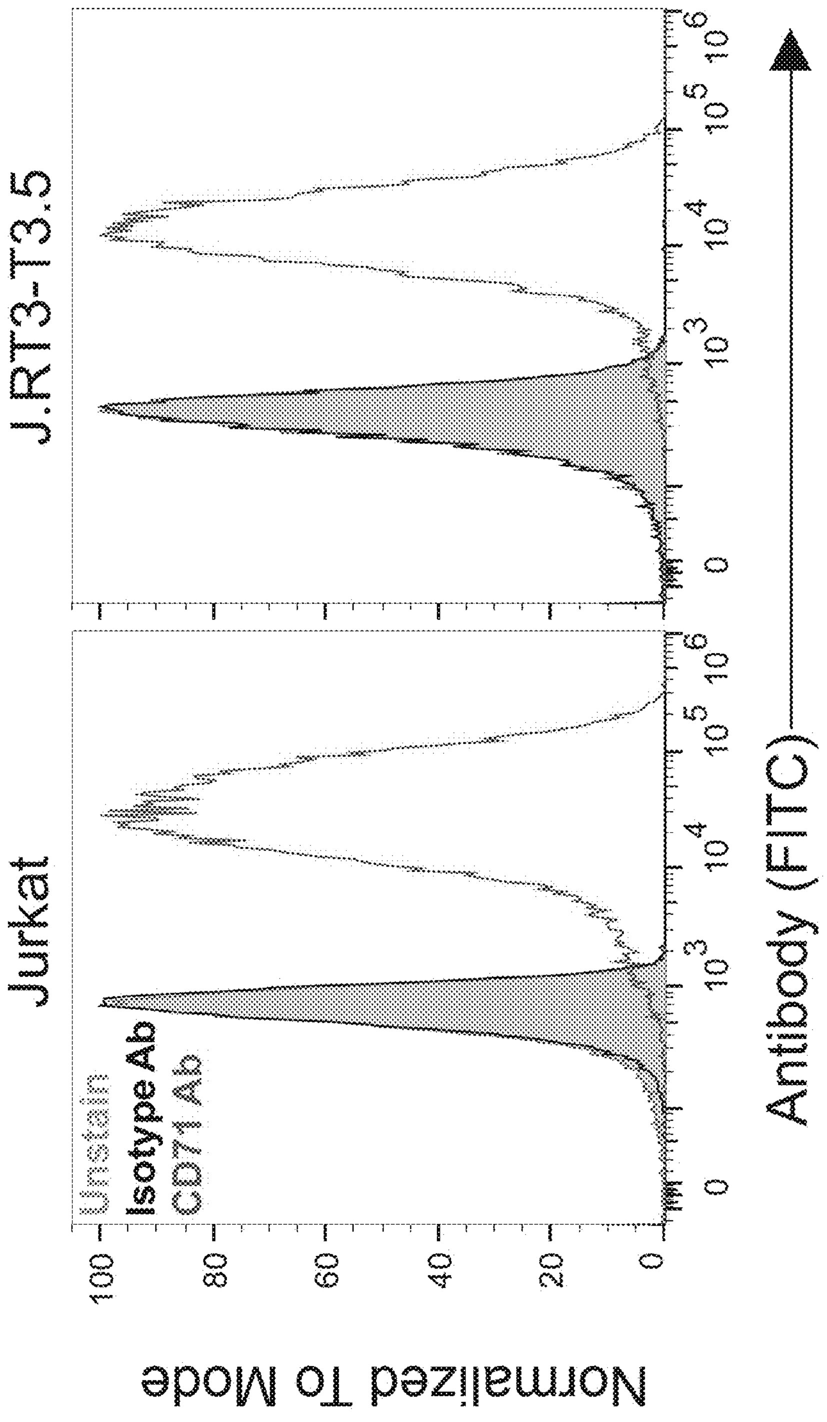
FIGS. 17A-17B. Jurkat and J.RT3-T3.5 cells robustly and differentially express TfR1.
Figure 17B:
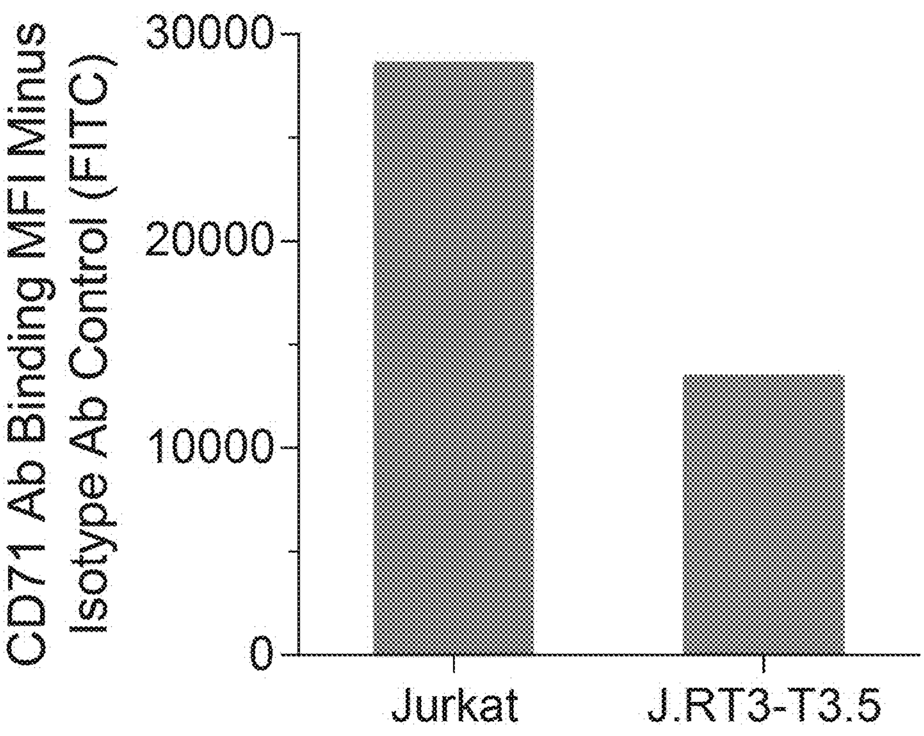

To investigate the cellular compartment and type of molecule targeted by tJBA8.1, Jurkat cells were labeled with tJBA8.1 at 4° C. followed by enzymatic treatment with trypsin, a cell-impermeable serine endopeptidase that cleaves many extracellular proteins. tJBA8.1 binding was almost completely abolished after trypsin treatment (FIG. 17A), indicating that the aptamer targets trypsin-sensitive cell membrane proteins. The localization of tJBA8.1 binding on Jurkat cells was further confirmed by confocal microscopy, which primarily showed punctate staining of the cell membrane after incubation with tJBA8.1 at 4° C. (FIG. 17B).

Having demonstrated that tJBA8.1 binds to an extracellular membrane protein, the inventors next adapted a reported aptamer-based pull-down assay designed for identification of target membrane receptors.[34] Briefly, cell membrane proteins extracted and solubilized from Jurkat cells were depleted for non-specific DNA-binding proteins using the RANL aptamer before incubation with biotinylated tJBA8.1. Aptamer-bound membrane proteins were then purified using streptavidin-coated magnetic beads and stratified by molecular weight via SDS-PAGE. Compared to a control sample that was purified with biotin-saturated streptavidin beads without tJBA8.1, two distinct protein bands that were highly enriched by tJBA8.1 were observed at approximately 200 kDa (band a) and 100 kDa (band b) (FIG. 3A). The protein bands were extracted, digested, analyzed by mass spectrometry, and matched to the human transferrin receptor protein 1 (TfR1; also known as CD71) (FIG. 3B). Specifically, peptides extracted from the higher molecular weight band (a) covered 62% of the TfR1 amino acid sequence, whereas the lower molecular weight band (b) covered 58%. The presence of two bands is consistent with the structure of TfR1, which is a homodimer composed of two disulfide-linked monomers.[35] TfR1 is a type II transmembrane glycoprotein that regulates the uptake of transferrin-bound iron needed for cellular metabolism and proliferation.[36] TfR1 is thus ubiquitously expressed at low levels on many cell types, with elevated expression on rapidly dividing cells such as activated lymphocytes and cancer cells including Jurkat cells.[37-39]

To validate that tJBA8.1 binds TfR1, short interfering RNA (siRNA) duplexes (Table 7) were used to knockdown the expression of TfR1 encoded by the TFRC gene in Jurkat cells and evaluated aptamer binding.

TABLE 7 siRNA duplexes used 1 for transferrin receptor 1 (TfR1) knockdown.

| SEQ ID NO: | Name | Sequence |
|---|---|---|
| 128 | hs.Ri.TFRC.13.1.SEQ1 | 5'-rCrArGrUrUrCrArGr ArArUrGrArUrGrGrArUr CrArArGrCTA-3' |

TABLE 7-continued siRNA duplexes used 1 for transferrin receptor 1 (TfR1) knockdown.

| SEQ ID NO: | Name | Sequence |
|---|---|---|
| 129 | hs.Ri.TFRC.13.1.SEQ2 | 5'-rUrArGrCrUrUrGrArUrCrCrArUrCrArUrUrCrUrGrArArCrUrGrCrC-3' |

Figure 18A:
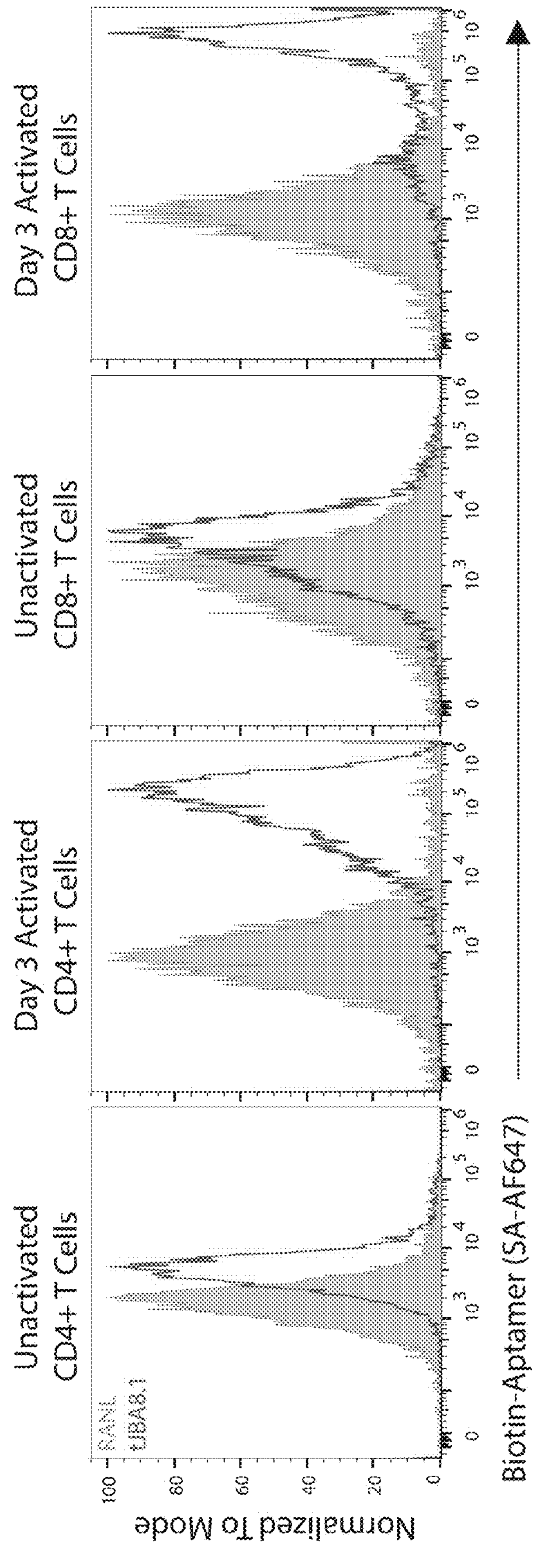
FIGS. 18A-18B. JBA8.1 and tJBA8.1 binding correlates with TfR1 upregulation on activated $CD4^+$ and $CD8^+$ T cells.
Figure 18B:
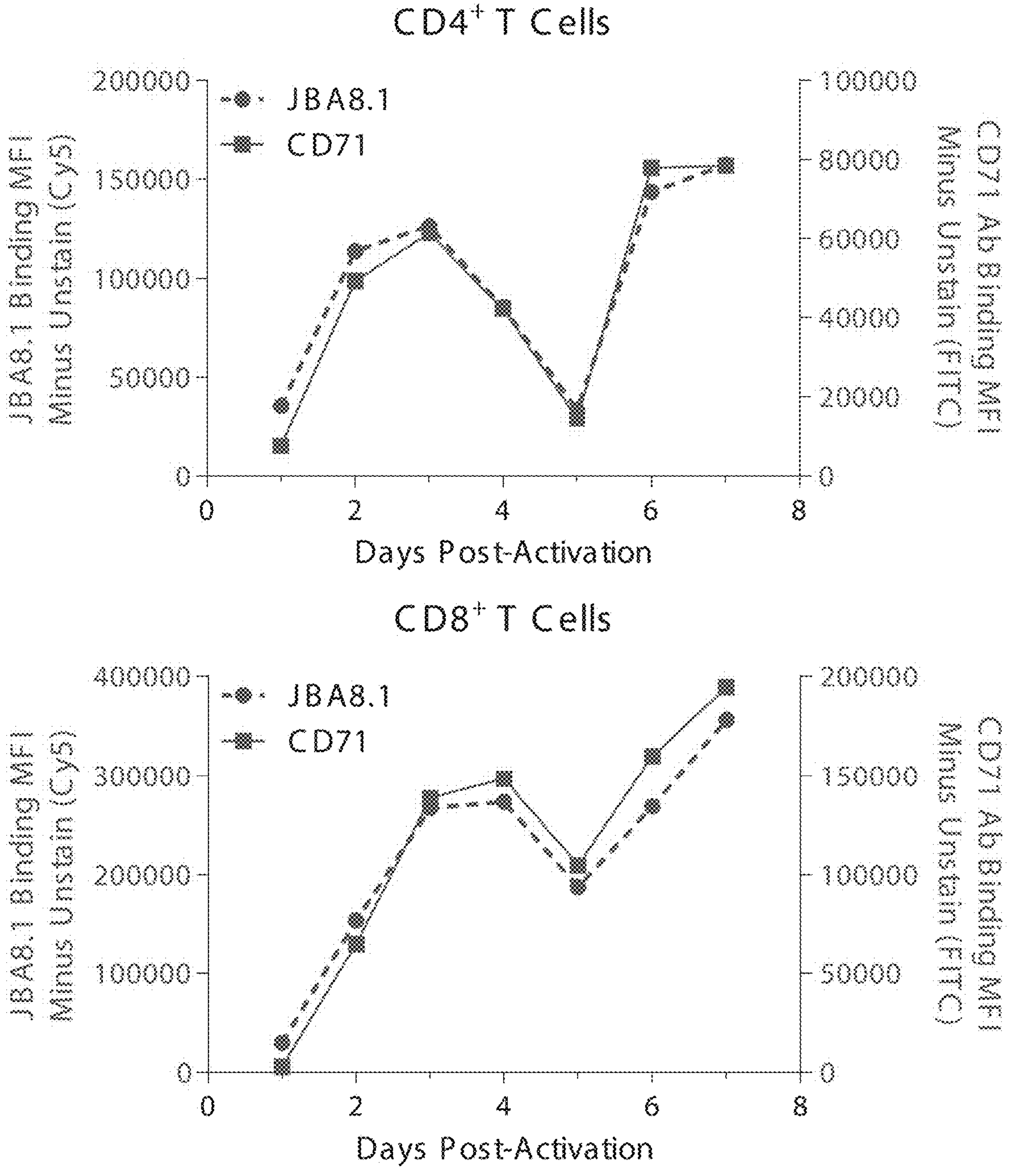

Compared to cells that were nucleofected with non-specific (NS) siRNA, cells nucleofected with TFRC siRNA had 51% reduced TfR1 expression as evaluated by anti-CD71 antibody (CD71 Ab) staining, which matched closely with the observed 49% reduction in tJBA8.1 binding (FIG. 3C). The inventors also evaluated TfR1 expression on the positive selection Jurkat cells and negative selection J.RT3-T3.5 cells used in cell-SELEX by CD71 Ab staining. In agreement with the binding profiles of the cell-SELEX aptamer pools and the individual JBA8.1 aptamer (FIG. 1B, FIG. 1D), both cell lines robustly express TfR1 (FIG. 18A), with Jurkat cells having higher expression than J.RT3-T3.5 cells (FIG. 18B). Lastly, as TfR1 is expressed negligibly on resting T cells but is upregulated upon antigen and cytokine stimulation,[38] the inventors evaluated tJBA8.1 binding to unactivated and day 3 CD3/CD28 Dynabead™-activated $CD4^+$ and $CD8^+$ T cells. For both subsets, tJBA8.1 binding was low to unactivated T cells but greatly increased after Dynabead™ activation (FIG. 19A). Furthermore, when tracking JBA8.1 binding and TfR1 expression by CD71 Ab staining on $CD4^+$ and $CD8^+$ T cells over 7 days of Dynabead™ activation, the inventors found that JBA8.1 binding kinetics correlated strongly with that of TfR1 expression (FIG. 19B). Collectively, these results confirm that TfR1 is a binding target of JBA8.1 and tJBA8.1.

Characterization of tJBA Binding to TfR1 and Competition with Other Ligands

Figure 4A:
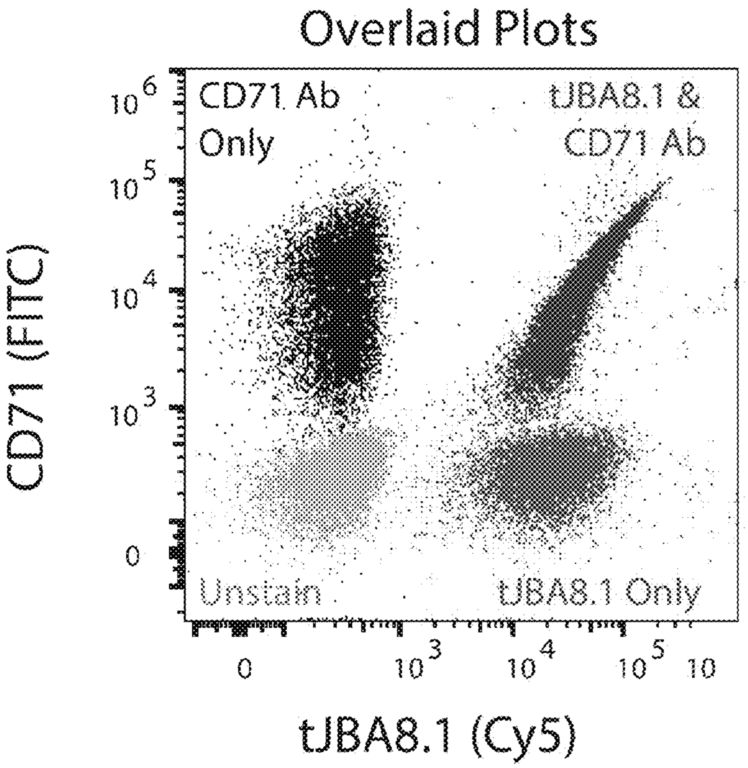
FIGS. 4A-4D. tJBA8.1 competes with holo-Tf but not antibody CY1G4 for binding to TfR1.
Figure 4B:
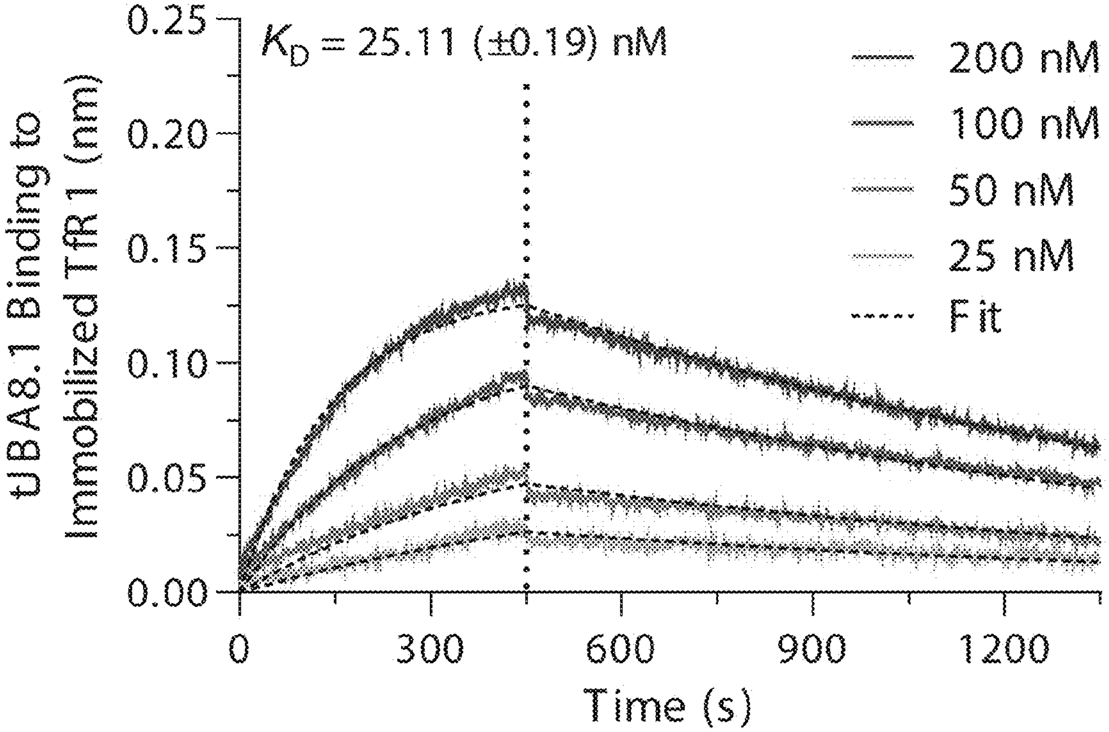

To better elucidate the interaction between tJBA8.1 and TfR1, Jurkat cells were co-stained with CD71 Ab (clone CY1G4) and tJBA8.1. A striking positive correlation was observed between CD71 Ab and tJBA8.1 staining, demonstrating that tJBA8.1 can bind TfR1 on cells simultaneously with the CD71 Ab (FIG. 4A). As binding to cells probes steady-state behavior but not binding in real-time, biolayer interferometry (BLI) was next used to directly characterize the kinetics of tJBA8.1 binding to TfR1. Recombinant biotinylated TfR1 protein was immobilized onto streptavidin BLI biosensors to avoid avidity effects from homodimeric TfR1 protein that may occur if the aptamers were immobilized instead. Whereas the RANL aptamer negative control did not associate with the TfR1 protein, tJBA8.1 bound the protein with a $K_D$ value of 25.11±0.19 nM (FIG. 4C), demonstrating fast and high-affinity binding kinetics (Table 8).

Figure 19:
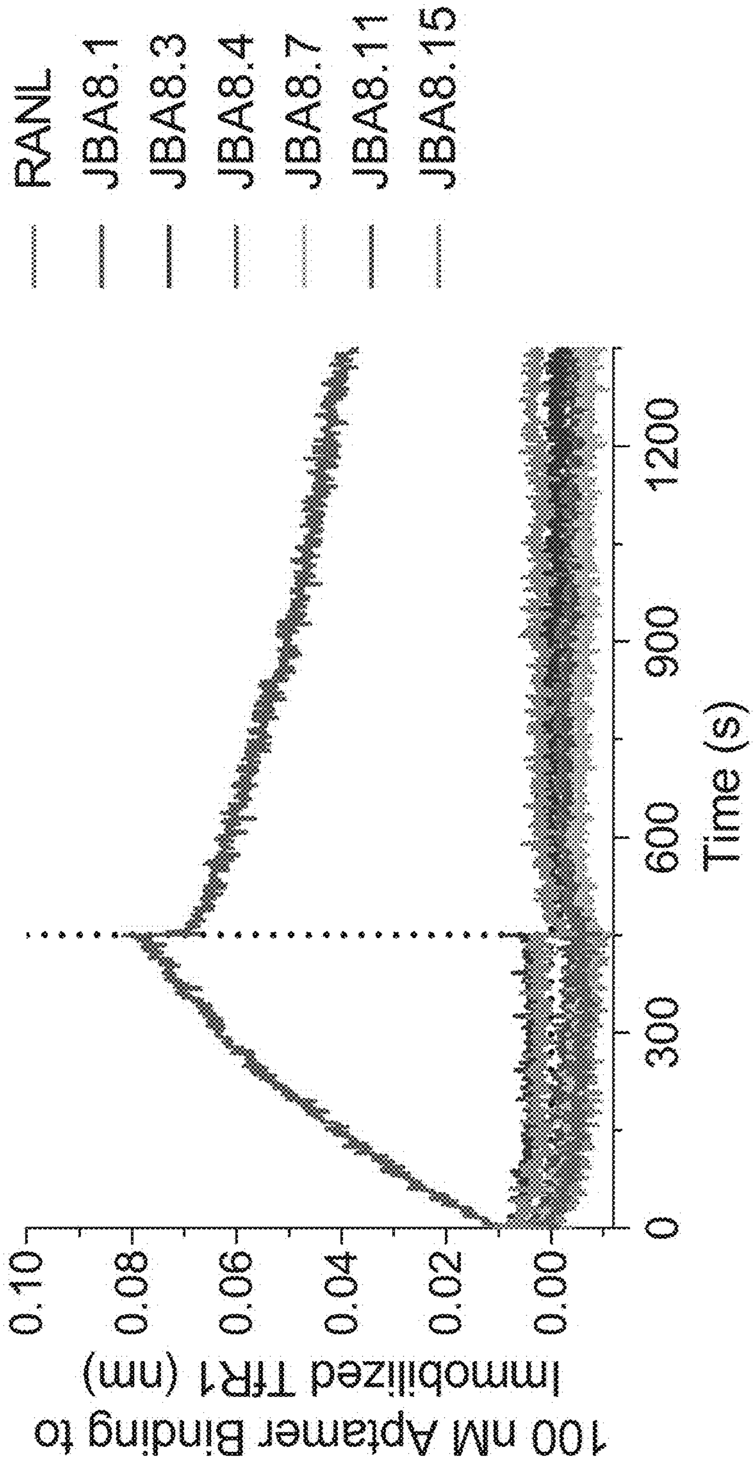
FIG. 19. Other Jurkat-binding aptamers identified from cell-SELEX do not bind TfR1. Association and dissociation kinetics of 100 mM FAM-labeled RANL, JBA8.1, JBA8.3, JBA8.4, JBA8.7, JBA8.11 and JBA8.15 to biotinylated TfR1 immobilized on streptavidin biosensors by BLI. The association phase is illustrated from 0-450 s, whereas dissociation is shown from 450-1350 s (separated by the vertical dotted line). Data are representative of n=1 independent experiment with one individual concentration of each aptamer.

Whether aptamers JBA8.3, JBA8.4, JBA8.7, JBA8.11, and JBA8.15 bind to TfR1 was also tested by BLI. Despite these aptamers displaying statistically significant binding to Jurkat cells in FIG. 1C, none of them appreciably bound TfR1 besides JBA8.1. (FIG. 19)

Figure 20A:
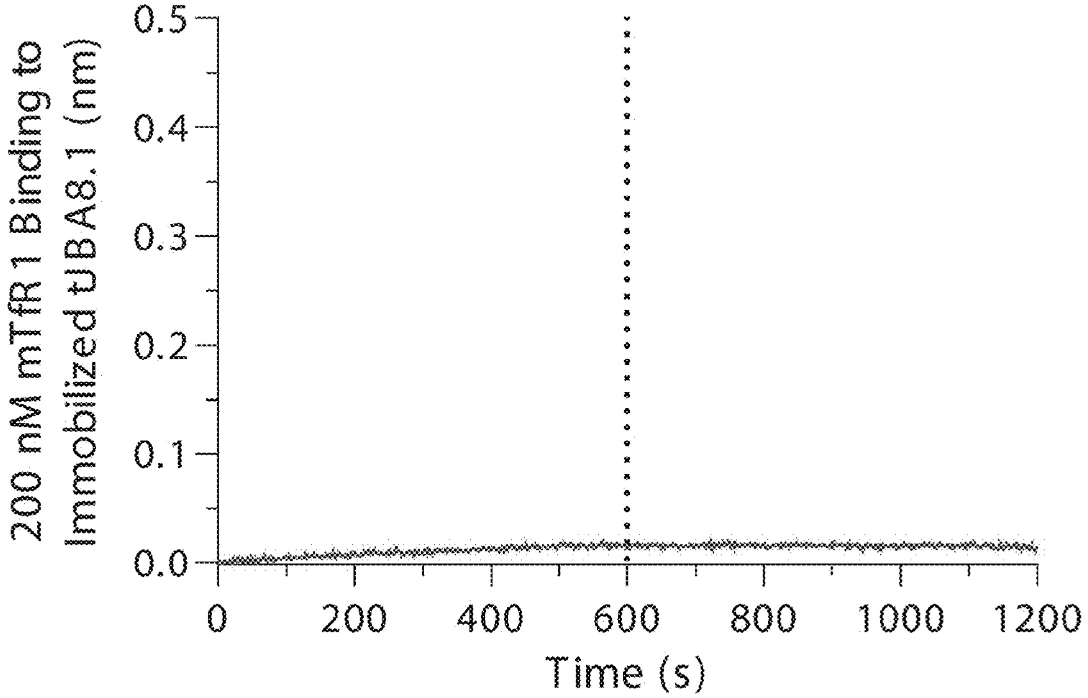
FIG. 20A-20B. tJBA8.1 does not bind mouse TfR1.
Figure 20B:
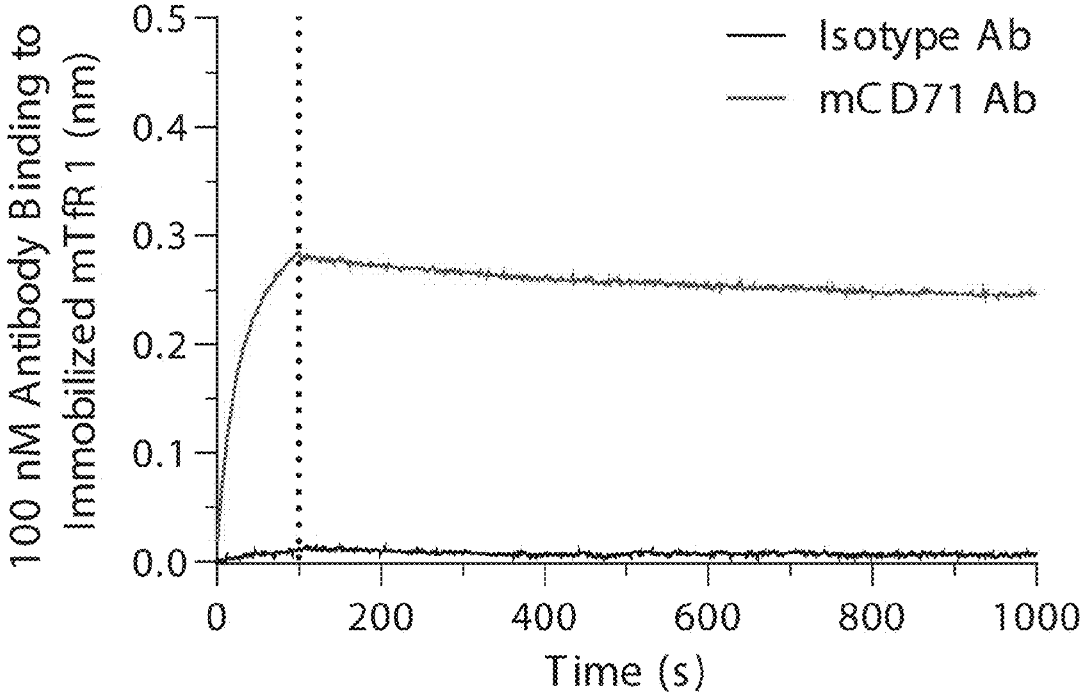

The inventors also evaluated binding of His-tagged mouse recombinant TfR1 protein to immobilized tJBA8.1 by BLI, but results were negative despite positive control antibody binding, suggesting that tJBA8.1 does not target mouse TfR1 (FIGS. 20A, 20B).

Figure 4C:
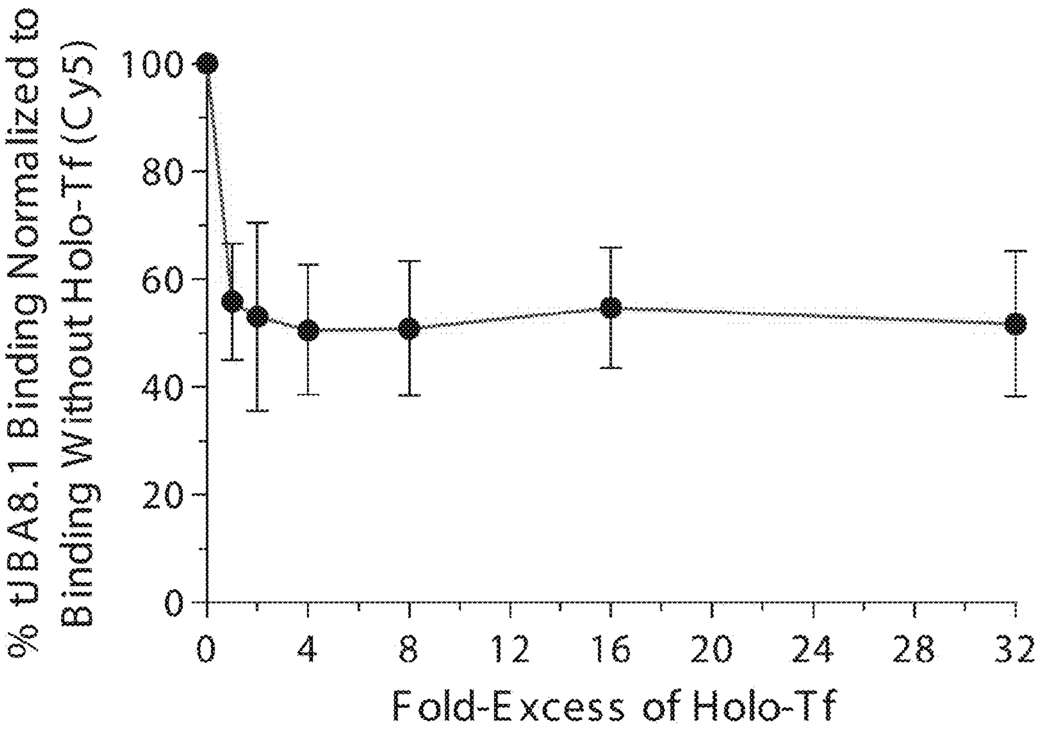
Figure 4D:
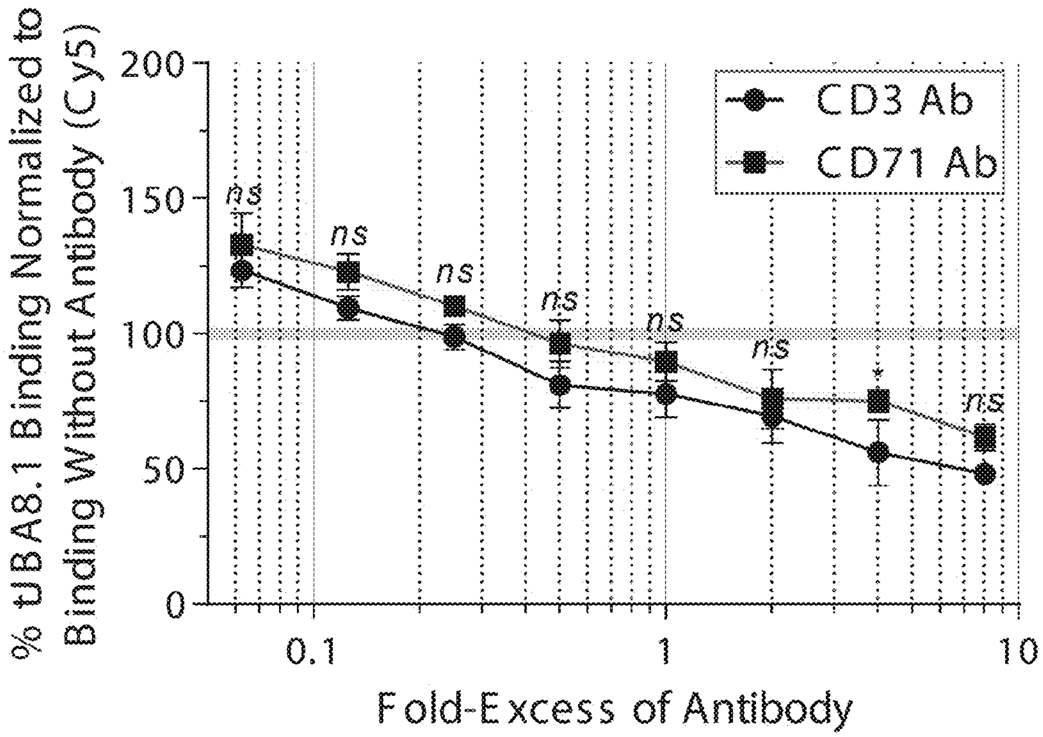

Iron is delivered intracellularly to cells via a transferrin cycle. Specifically, iron-bound transferrin (holo-Tf) binds to TfR1 for uptake, after which iron is released from transferrin under acidic endosomal pH and the resulting iron-free transferrin (apo-Tf) is recycled to the cell surface for dissociation under neutral pH.[40] As demonstrated in FIG. 4A, tJBA8.1 can stain cells simultaneously with CD71 Ab (clone CY1G4), which has been previously shown to bind a TfR1 epitope distinct from that of holo-Tf,[41] it was hypothesized that tJBA8.1 may compete with holo-Tf for binding to TfR1. To test this, Jurkat cells were co-incubated with a fixed concentration of labeled tJBA8.1 and varying concentrations of holo-Tf as a competitor. tJBA8.1 binding was reduced by half upon competition with just 1-fold excess of holo-Tf, confirming that tJBA8.1 and holo-Tf share proximal binding sites on TfR1 (FIG. 4C). However, relative tJBA8.1 binding plateaued at 50% and did not further decrease even when holo-Tf was added at 32-fold excess, indicating that tJBA8.1 has a transferrin- or TfR1-independent binding component to Jurkat cells. The inventors also conducted a similar competition assay with tJBA8.1 and the CD71 Ab (clone CY1G4) discussed previously, which is known to bind a TfR1 epitope distinct from that of holo-Tf.[41] Furthermore, the binding behavior of tJBA8.1 to Jurkat cells in the presence of various concentrations of the CD71 Ab (clone CY1G4) was statistically indistinguishable from binding in the presence of an anti-CD3 antibody (CD3 Ab) control (FIG. 4D), confirming that tJBA8.1 and the CD71 Ab (clone CY1G4) do not share an overlapping binding epitope on TfR1.

Comparison of tJBA8.1 with a Reported TfR1-Binding DNA Aptamer

Figure 21A:
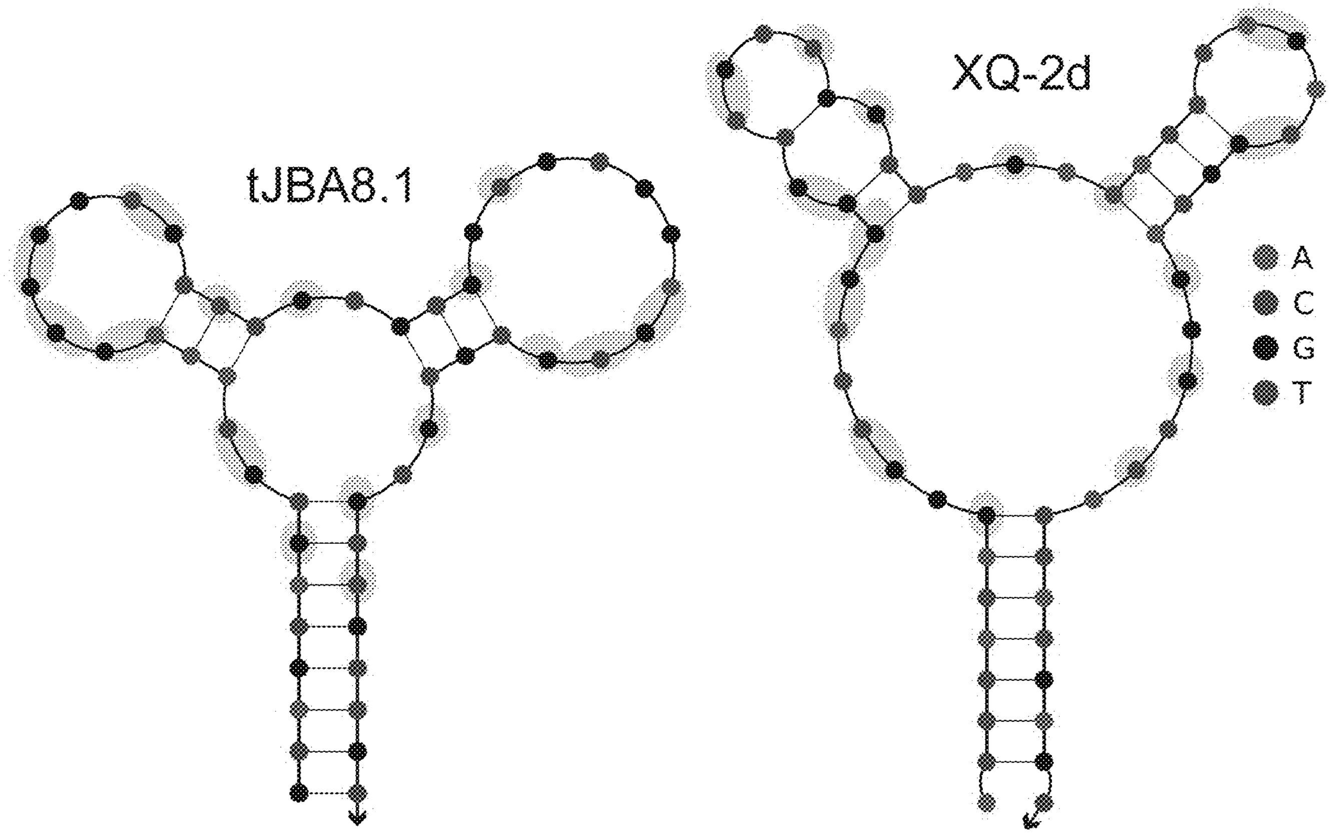
FIGS. 21A-21F. XQ-2d competes with holo-Tf for binding to TfR1.

XQ-2d is a 56-bp truncated aptamer previously discovered by the Tan group that also targets TfR1.[42,43] Aligning the variable sequence regions of tJBA8.1 and XQ-2d, the inventors observed sequence similarity between tJBA8.1 and XQ-2d, with 21 nucleotides overlapping in their respective 45-bp and 42-bp random regions (FIG. 21A). The overlapping nucleotides are mostly found within predicted hairpin structures of each aptamer, and four of them (G17, G36, T38, and G39 in XQ-2d) were previously predicted by

TABLE 8

Bio-layer interferometry (BLI) measured affinity kinetics of tJBA8.1, XQ-2d, and JBA8.26 aptamer binding to immobilized TfR1 protein. Data are mean ± standard deviation; n = 4-5 individual aptamer concentrations. Values were calculated by performing a global fit of the multi-concentration kinetic data in FIGS. 4B, 4D and FIG. 36C to a 1:1 binding model. The ratio between the dissociation rate constant ($K_{dis}$) and the association rate constant ($K_{on}$) gives the equilibrium dissociation constant ($K_D$). The goodness of fit was evaluated by a reduced chi-square ($\chi^2$) and a $R^2$ value approaching 1.

Figure 21B:
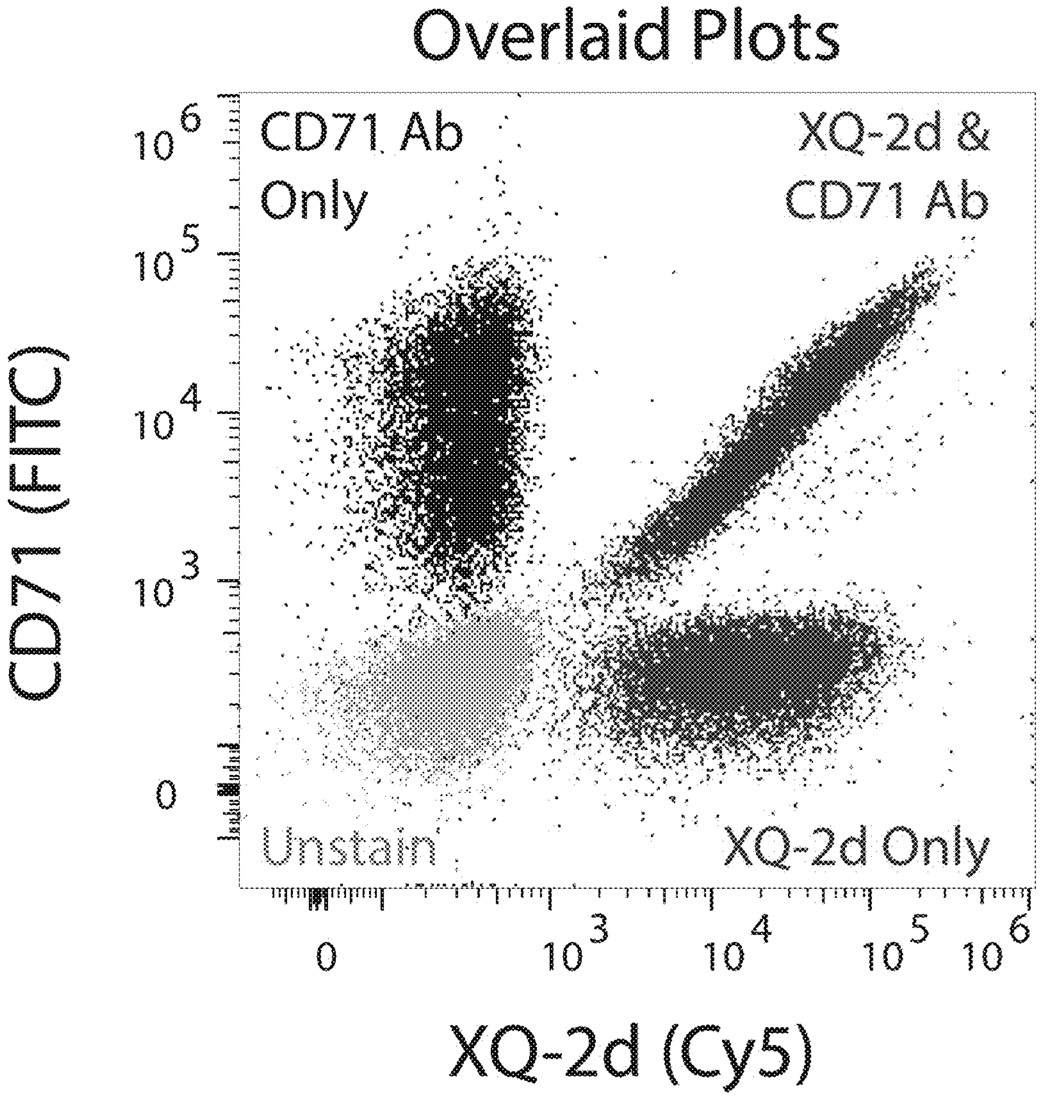
Figure 21C:
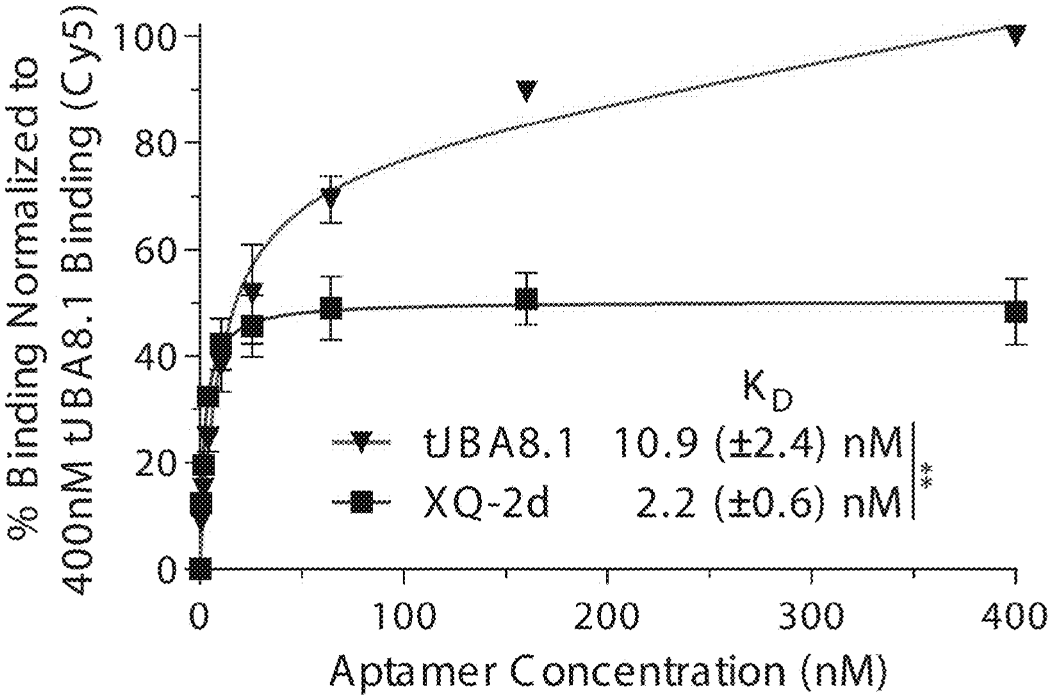
Figure 21D:
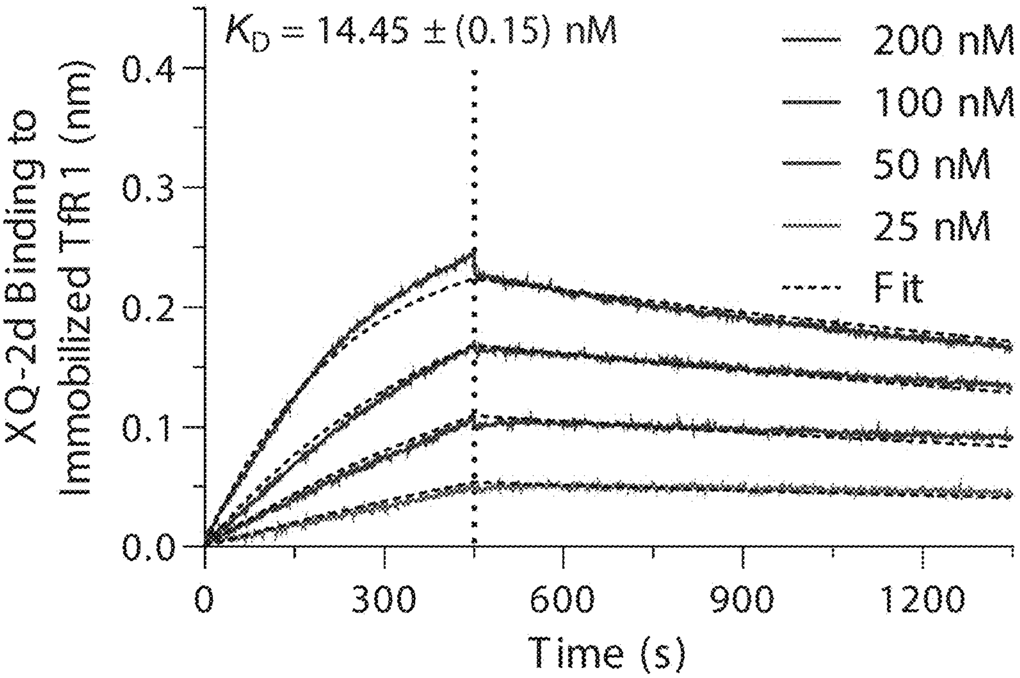
Figure 21E:
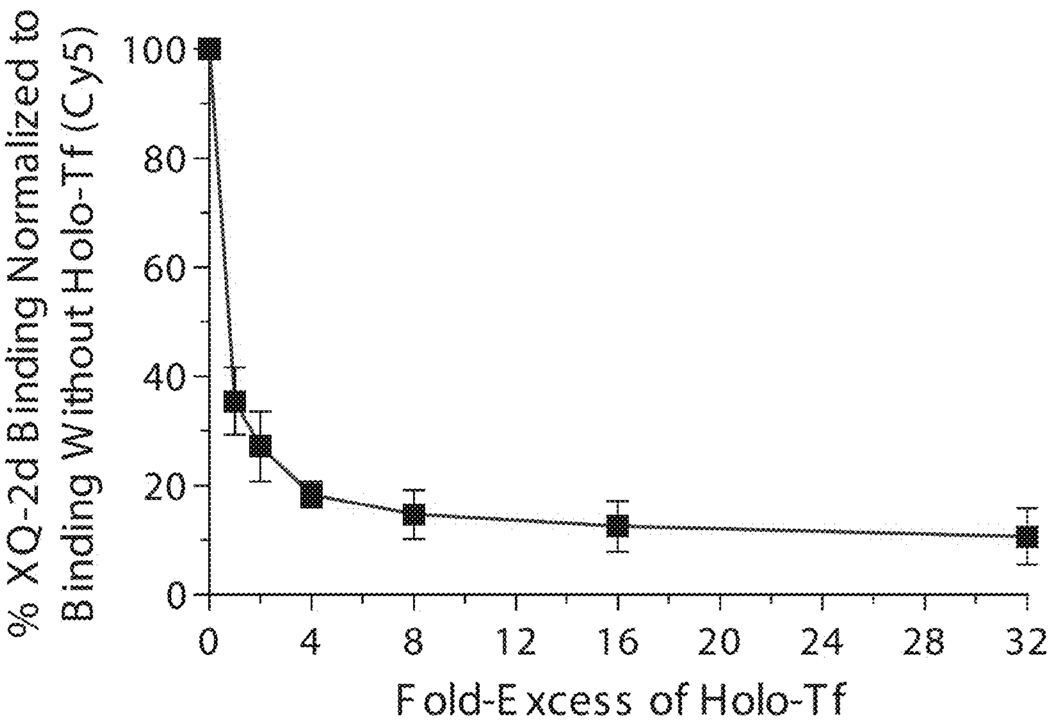
Figure 21F:
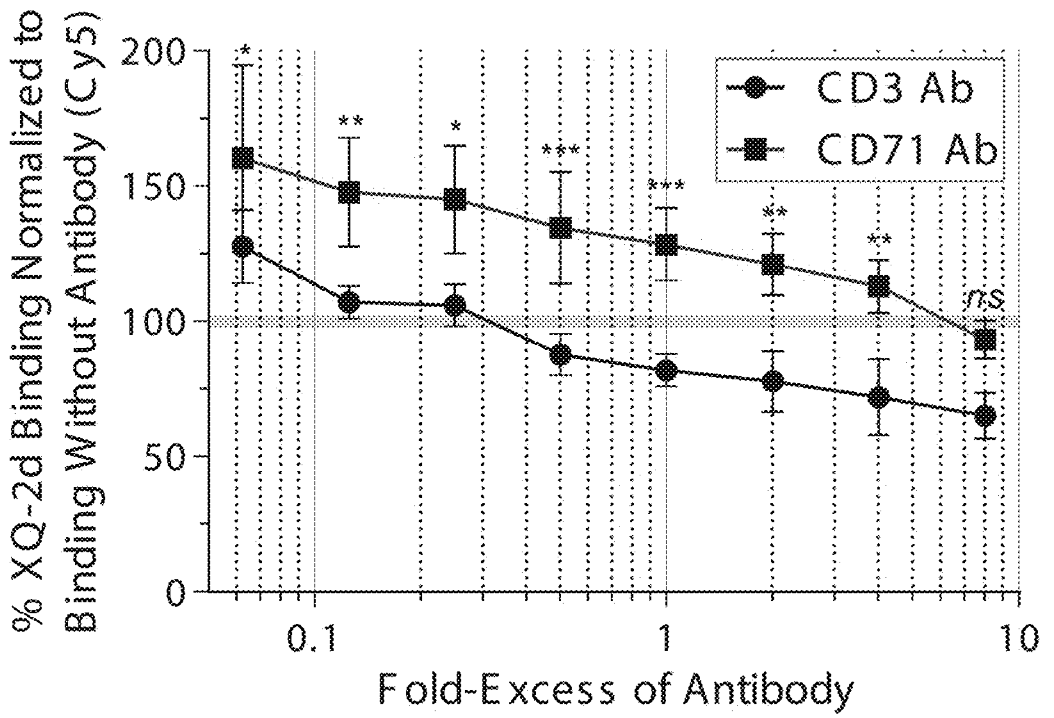

| Aptamer | $K_D$ (nM) | $K_{on}$ ($nM^{-1}s^{-1}$) × $10^{-5}$ | $K_{dis}$ ($s^{-1}$) × $10^{-4}$ | Full $\chi^2$ | Full $R^2$ |
|---|---|---|---|---|---|
| tJBA8.1 | 25.11 (±0.19) | 3.05 (±0.02) | 7.66 (±0.03) | 0.0402 | 0.9928 |
| XQ-2d | 14.45 (±0.15) | 2.06 (±0.02) | 2.97 (±0.02) | 0.1272 | 0.9939 |
| JBA8.26 | 6.87 (±0.04) | 6.24 (±0.03) | 4.29 (±0.02) | 0.0439 | 0.9968 |

molecular dynamics simulations to participate in a hydrogen bond network that drives the interaction between XQ-2d and TfR1 and produces a steric clash with holo-Tf.[43] To validate the reported TfR1-binding properties of XQ-2d and compare them to tJBA8.1, the inventors conducted the same characterization assays as shown previously for tJBA8.1. Using flow cytometry, a positive correlation between CD71 Ab and XQ2d staining on Jurkat cells was observed (FIG. 21B), and XQ-2d was found to bind Jurkat cells with an apparent $K_D$ of 2.2±0.6 nM (FIG. 21C). Compared to XQ-2d, tJBA8.1 produced a substantially higher binding signal to Jurkat cells that did not fully saturate at 400 nM, further demonstrating that tJBA8.1 may bind an additional protein expressed by Jurkat cells with lower affinity. By BLI, XQ-2d bound immobilized TfR1 with a $K_D$ value of 14.45±0.15 nM (FIG. 21D), displaying both slower association and dissociation than tJBA8.1 (Table 8). Similar to tJBA8.1, XQ-2d binding was competed off by holo-Tf but not CD71 Ab (clone CY1G4) (FIGS. 21E, 21F), although XQ-2d binding was more completely depleted by holo-Tf competition compared to tJBA8.1.

Figure 22A:
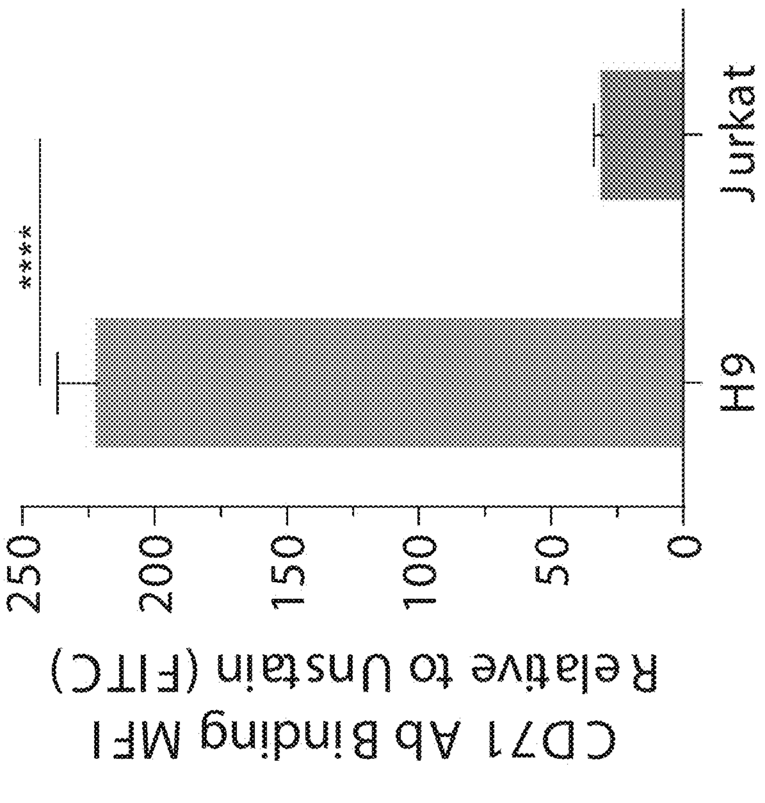
FIGS. 22A-22C. tJBA8.1 binds TfR1hi H9 cells solely through TfR1.
Figure 22B:
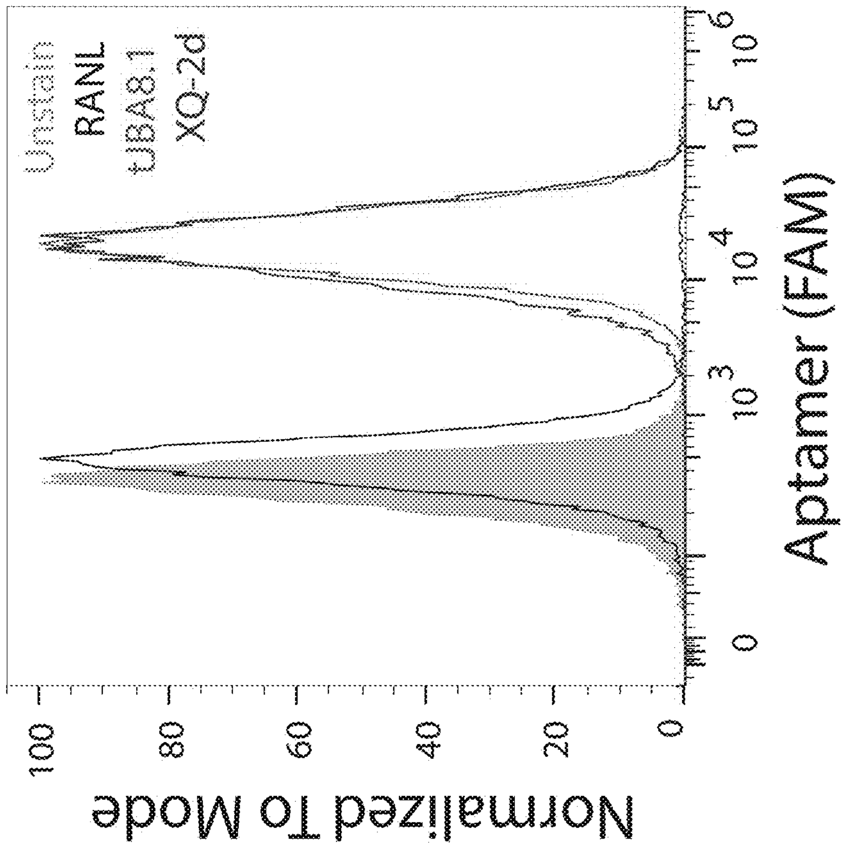
Figure 22C:
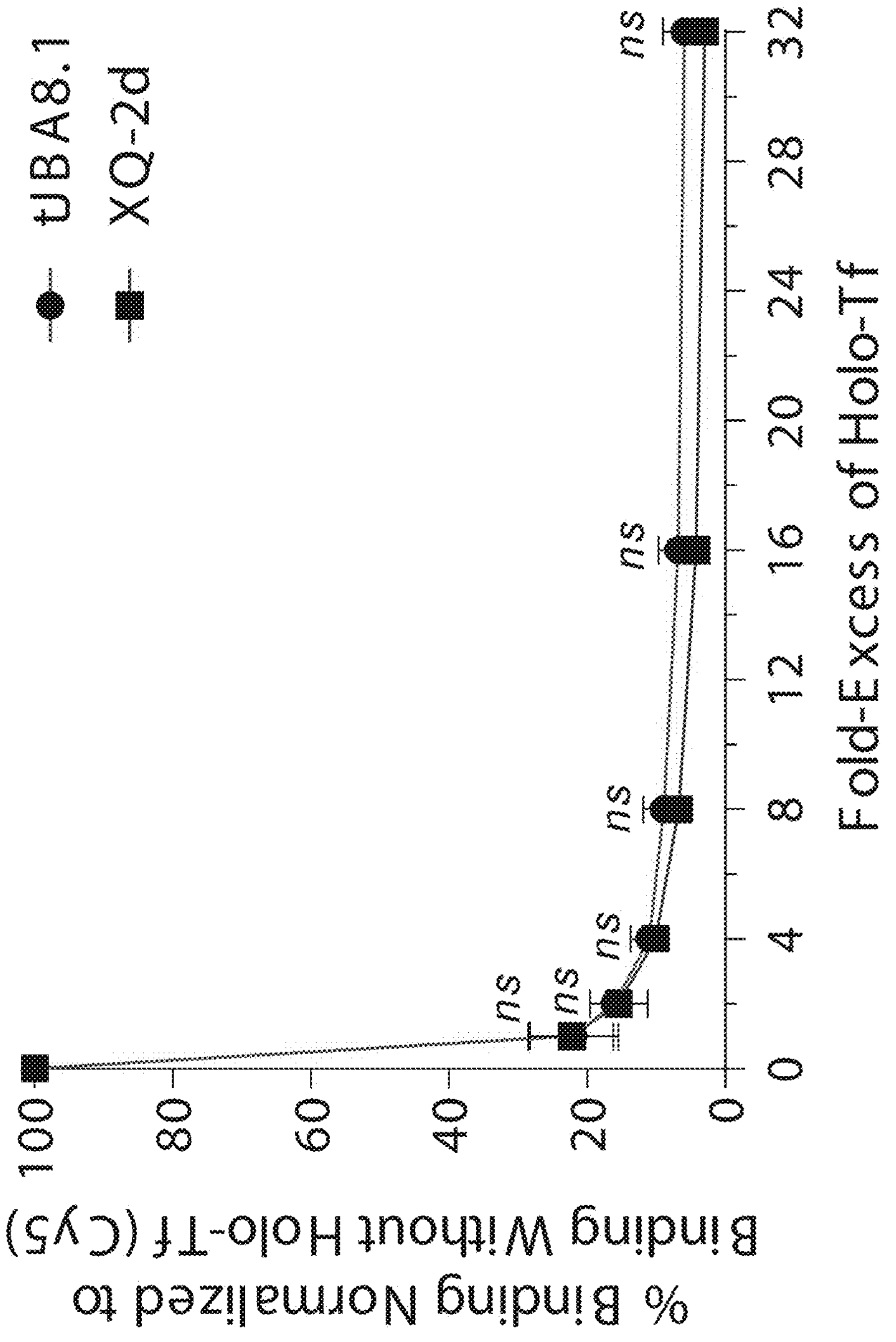
Figure 23:
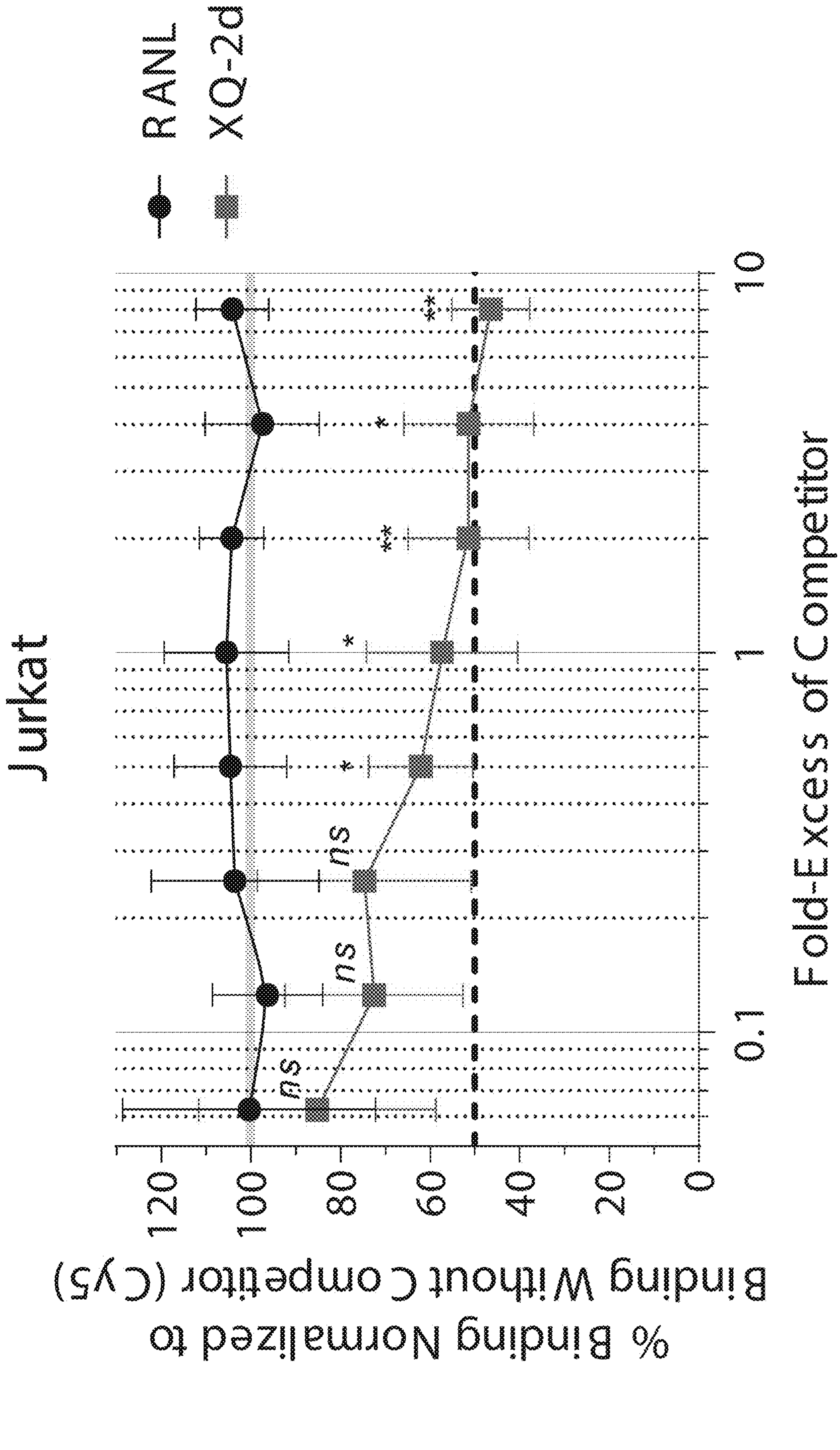
FIG. 23. tJBA8.1 and XQ-2d share a common binding epitope on TfR1. Competitive binding of 25 nM Cy5-labeled tJBA8.1 with varying fold-excess of FAM-labeled RANL and XQ-2d on Jurkat and H9 cells by flow cytometry. Binding was normalized to tJBA8.1-stained controls without competitor. Data points and error bars represent mean±standard deviation; n=3 independent experiments. ns>0.05, *P<0.05, P<0.01, *P<0.001 (ordinary two-way ANOVA with Šídík correction). Cy5, cyanine 5; FAM, 6-carboxyfluorescein.
Figure 23:
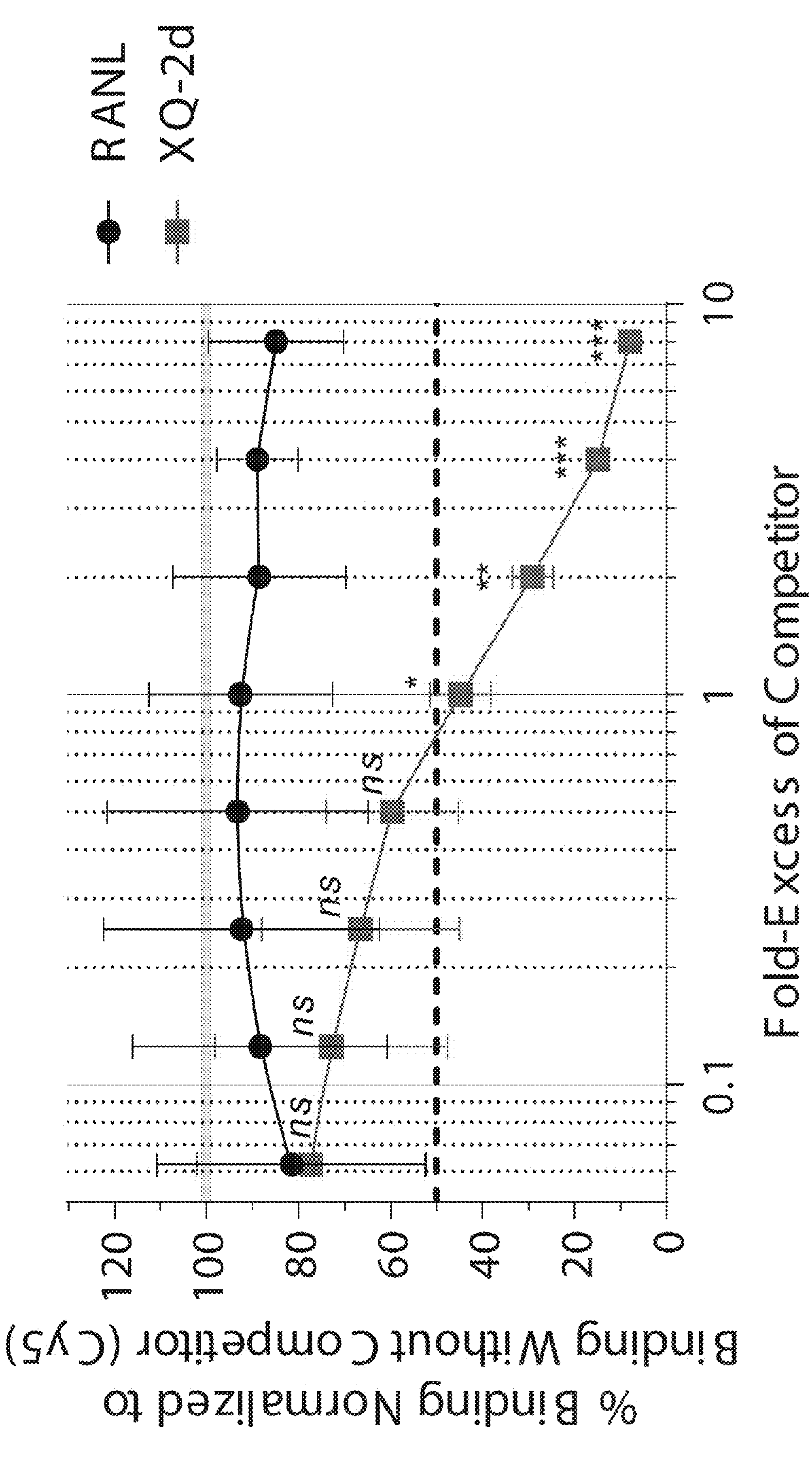

Given the discrepancies between tJBA8.1 and XQ-2d binding to Jurkat cells, the inventors also evaluated holo-Tf competition with these aptamers on H9 T-lymphoma cells, which have higher TfR1 expression than Jurkat cells and exhibit more equivalent max binding signal between tJBA8.1 and XQ-2d (FIGS. 22A, 22B). Unexpectedly, holo-Tf equivalently competed off over 90% of both tJBA8.1 and XQ-2d binding in this cell model (FIG. 22C), indicating either that H9 cells lack expression of the unidentified protein that tJBA8.1 binds independent of TfR1 or that the higher TfR1 expression on H9 cells causes TfR1-dependent binding to overshadow TfR1-independent binding. Next, competitive binding between tJBA8.1 and XQ-2d was tested on Jurkat and H9 cells relative to a RANL control. A concentration-dependent reduction in tJBA8.1 binding was observed with XQ-2d as a competitor, verifying that tJBA8.1 and XQ-2d do target a common epitope on TfR1 (FIG. 23). Furthermore, in agreement with the above holo-Tf competition results, only half of tJBA8.1 binding was competed off by high fold excess of XQ-2d on Jurkat cells whereas over 90% was competed off on H9 cells under the same conditions.

Figure 24C:
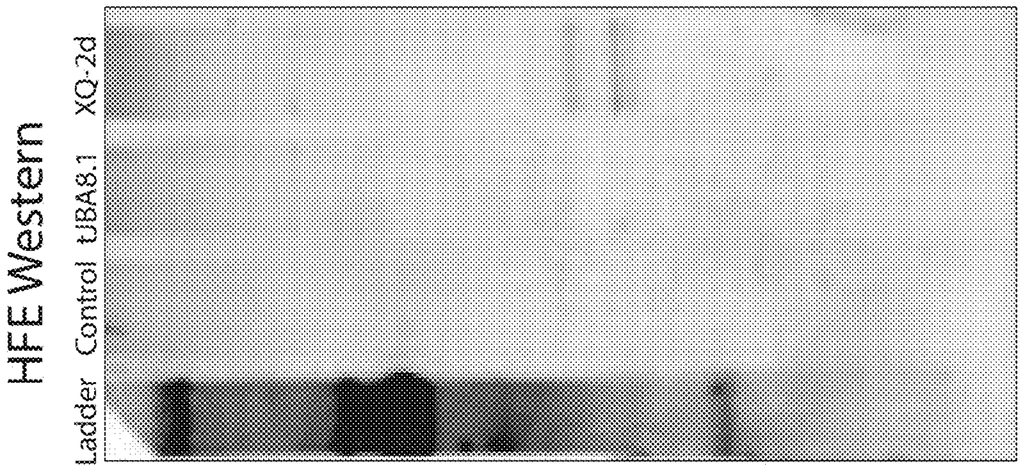
FIGS. 24A-24C. tJBA8.1 and XQ-2d differentially bind TfR1 with respect to HFE. Colloidal blue-stained 4-20% SDS-PAGE gel of Jurkat cell membrane proteins pulled down by tJBA8.1 and XQ-2d (FIG. 24A) and corresponding Western blots staining for TfR1 (FIG. 24B) and HFE (FIG. 24C). The control lanes represent proteins captured by biotin-saturated magnetic beads only. Dashed white boxes on SDS-PAGE gel designate prominently enriched proteins, most of which were identified by Western blotting (bands a-e). Band f is identified by mass spectrometry in FIG. 29A.
Figure 24B:
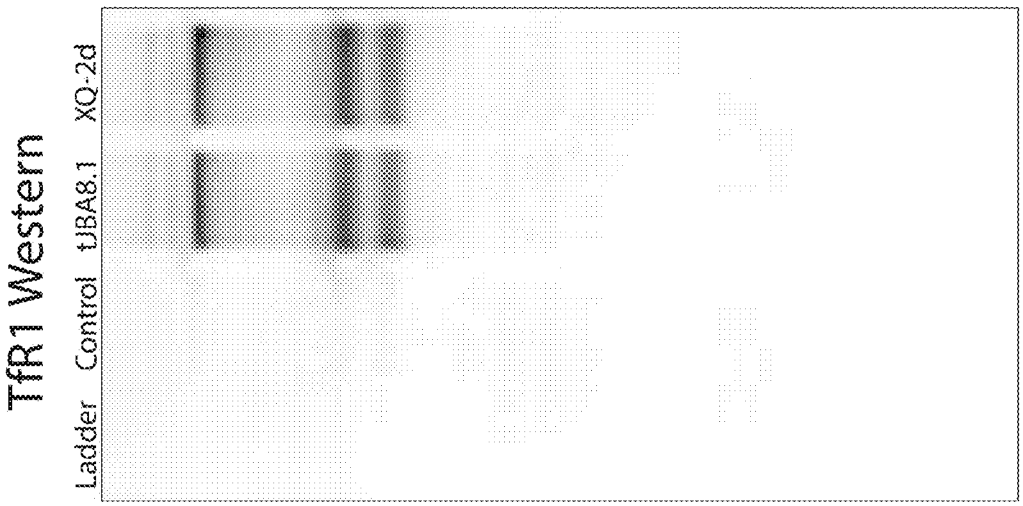

Besides holo-Tf, TfR1 has other natural ligands that may share binding epitopes with tJBA8.1. HFE is a major histocompatibility complex (MHC) class I-like membrane protein that is known to compete with holo-Tf at its TfR1-binding site to regulate iron uptake,[44-47] and mutation of HFE can cause iron overload that resembles hereditary hemochromatosis via hepatic hepcidin deficiency.[48,49] To ascertain whether tJBA8.1 and XQ-2d differentially bind TfR1 with respect to HFE, the same membrane protein pull-down assay was performed as before but also included Western blotting to examine HFE co-precipitation, if any, with aptamer-enriched TfR1. Bands with the characteristic sizes of TfR1 were highly enriched by both tJBA8.1 and XQ-2d (FIG. 24A, bands a-c), and Western blotting confirmed the presence of TfR1 in these bands (FIG. 24B). Of importance, XQ-2d uniquely enriched two protein bands, one at 35 kDa and the other slightly larger (FIG. 24A, bands d and e), and Western blotting discovered the corresponding enrichment of HFE (~40 kDa) at these molecular weights (FIG. 24C). This indicates that XQ-2d co-precipitates HFE with TfR1 whereas tJBA8.1 does not, bringing attention to differences in each aptamer's interaction with TfR1. Band f, which was uniquely enriched by tJBA8.1 and may represent the other protein that tJBA8.1 binds independent of TfR1 on Jurkat cells, will be discussed in a later section. Altogether, these results demonstrate that tJBA8.1 and XQ-2d have overlapping but distinct binding sites on TfR1.

tJBA8.1-Mediated Depletion of B-Lymphoma Cells from PBMCs

Figure 5A:
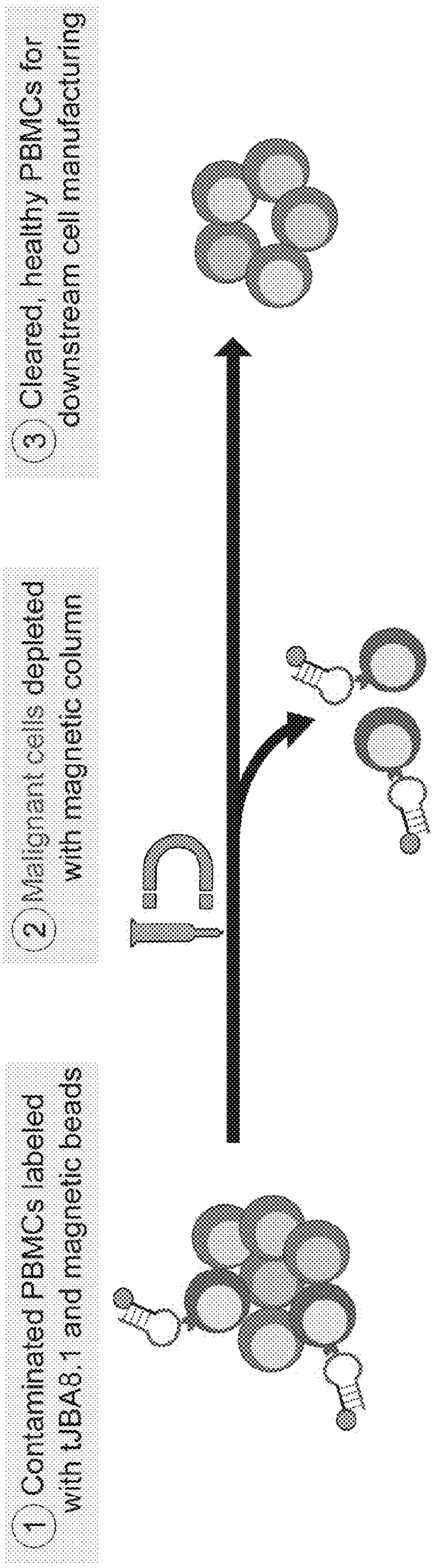
FIGS. 5A-5D. tJBA8.1 thoroughly depletes Raji B-lymphoma cells from PBMCs without compromising healthy immune cell composition.
Figure 5B:
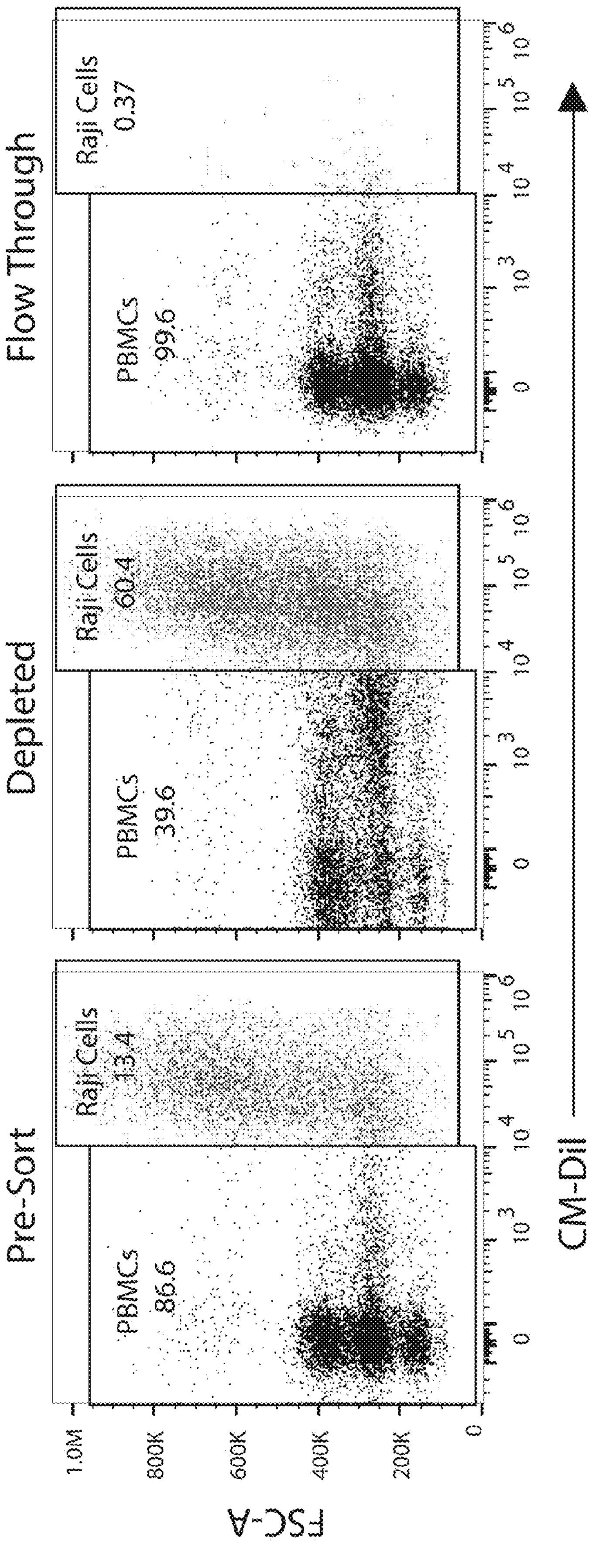
Figure 5C:
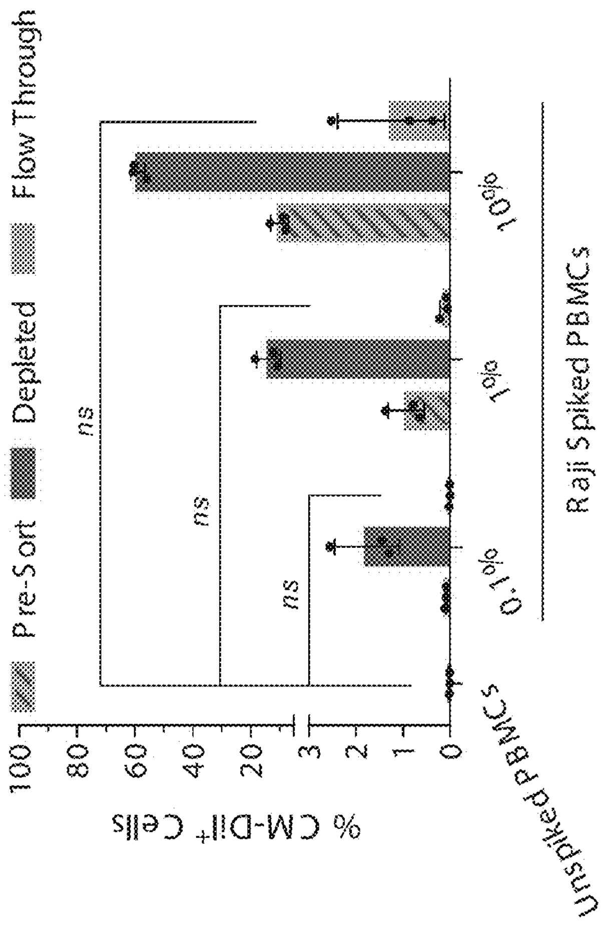
Figure 5D:
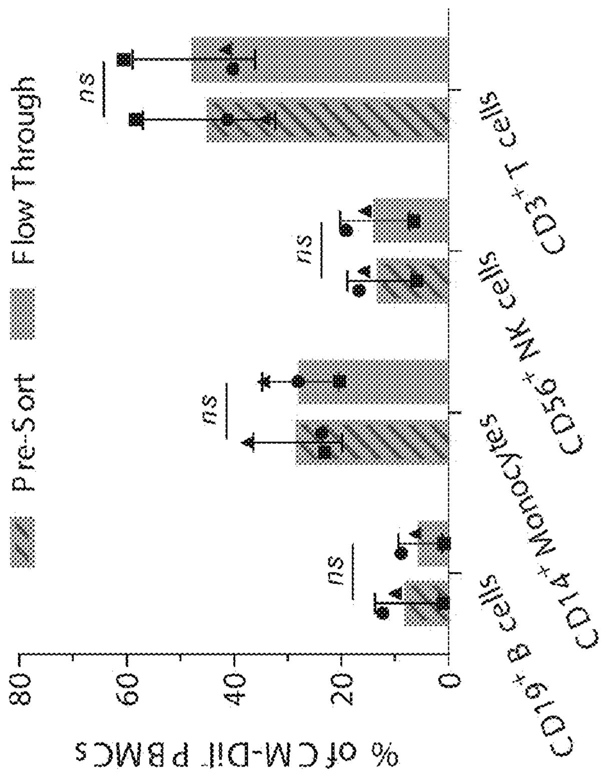
Figure 6:
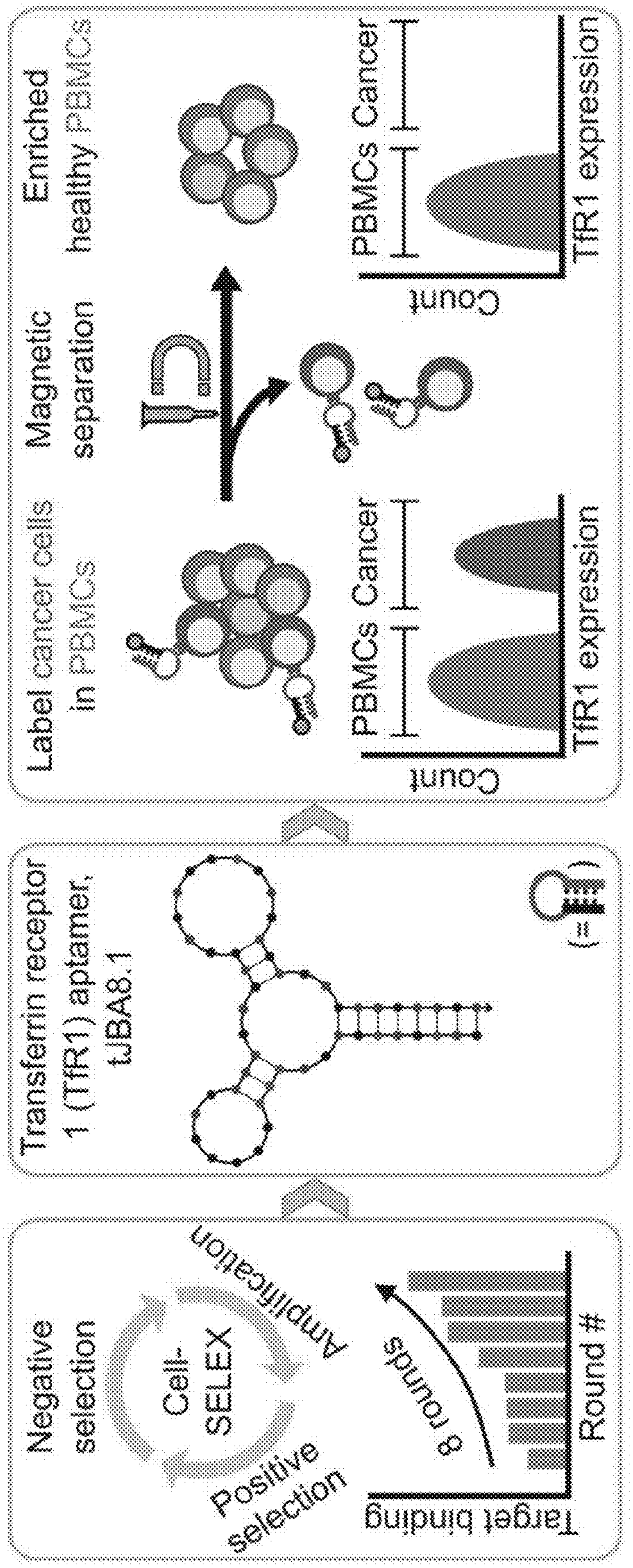
FIG. 6 is a schematic representation of the methods used to identify and test the aptamers described herein.
Figure 25A:
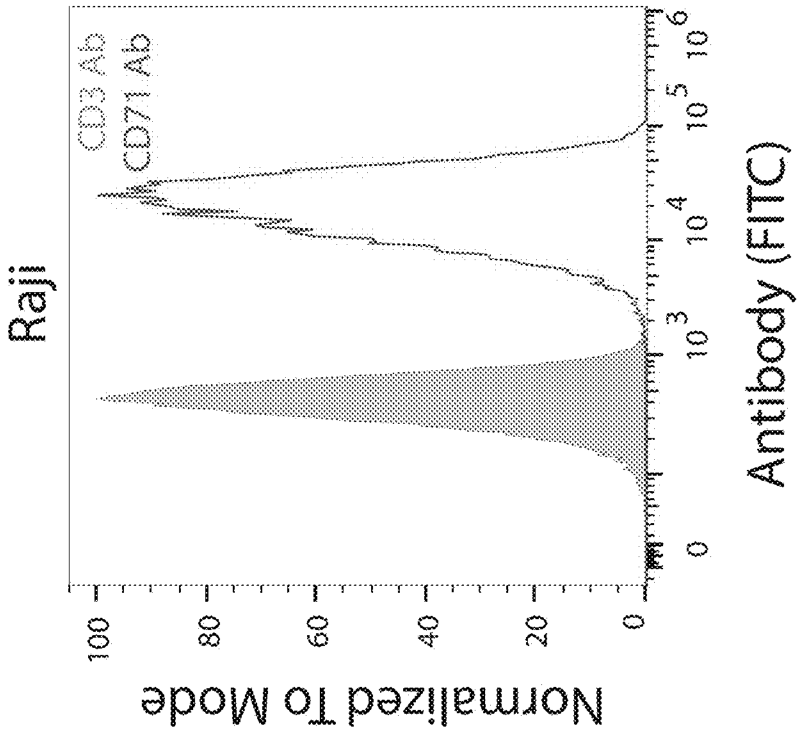
FIGS. 25A-25B. TfR1 expression distinguishes Raji B-lymphoma cells from healthy PBMCs. Flow cytometry histograms of FITC-labeled CD71 Ab binding to Raji cells (FIG. 25A) and healthy donor PBMCs (FIG. 25B). For Raji cells, a FITC-labeled anti-CD3 antibody (CD3 Ab) was used as a negative/isotype control. Histograms are representative of n=1 independent experiment. FITC, fluorescein isothiocyanate.
Figure 25B:
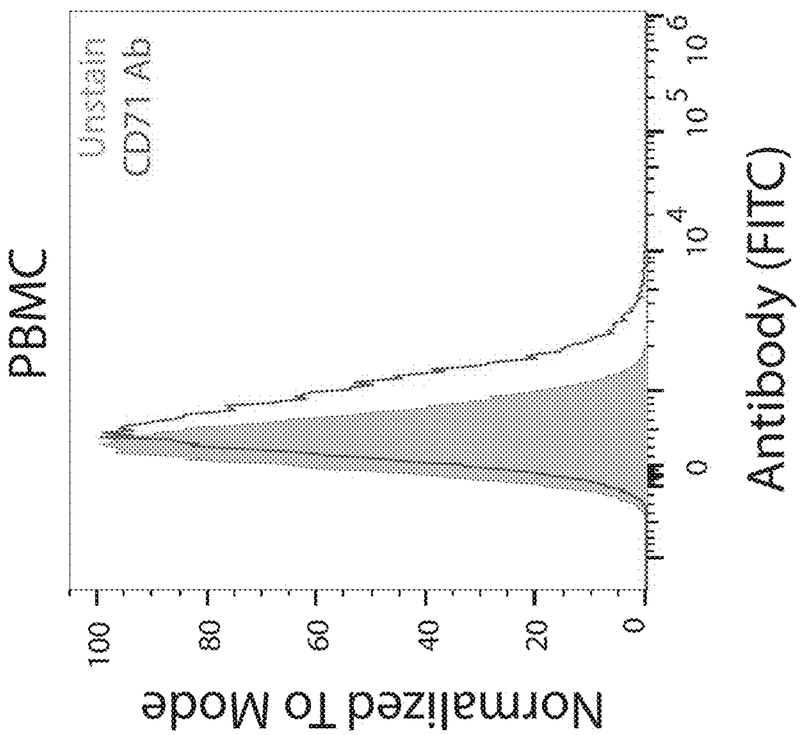
Figure 26A:
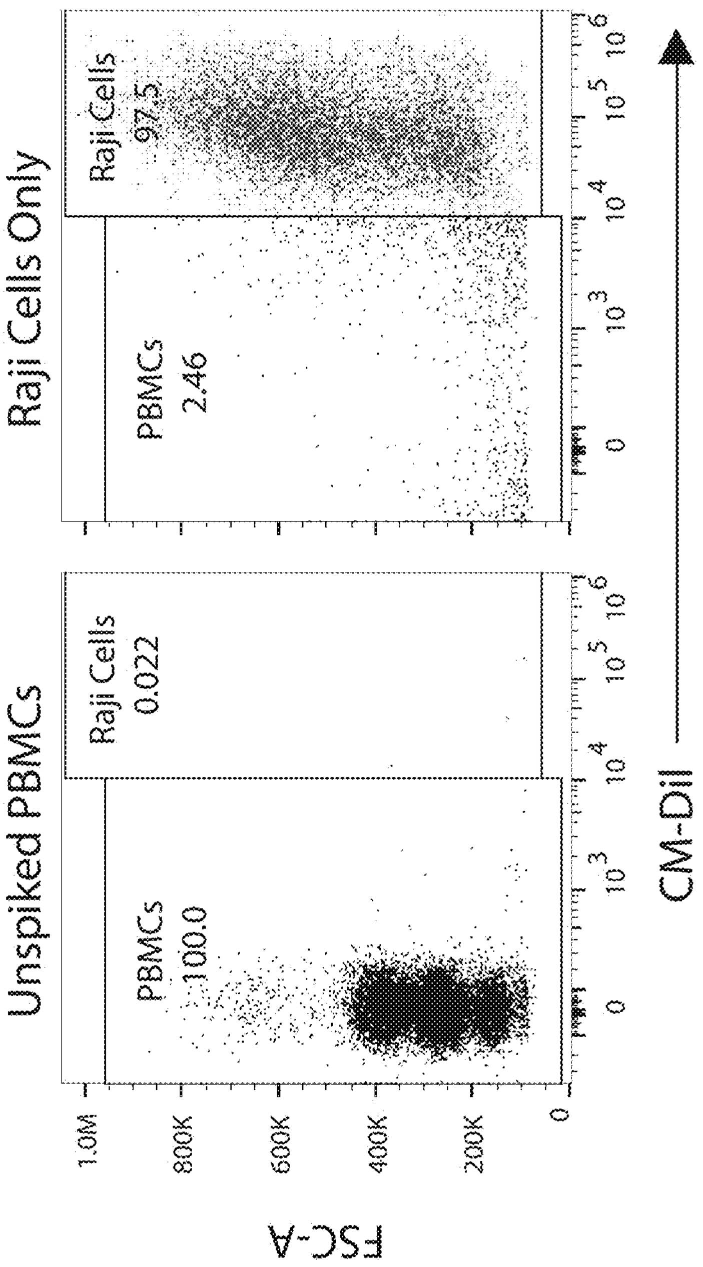
FIGS. 26A-26C. tJBA8.1 efficiently depletes Raji cells from PBMCs even at low spiked percentages.
Figure 26B:
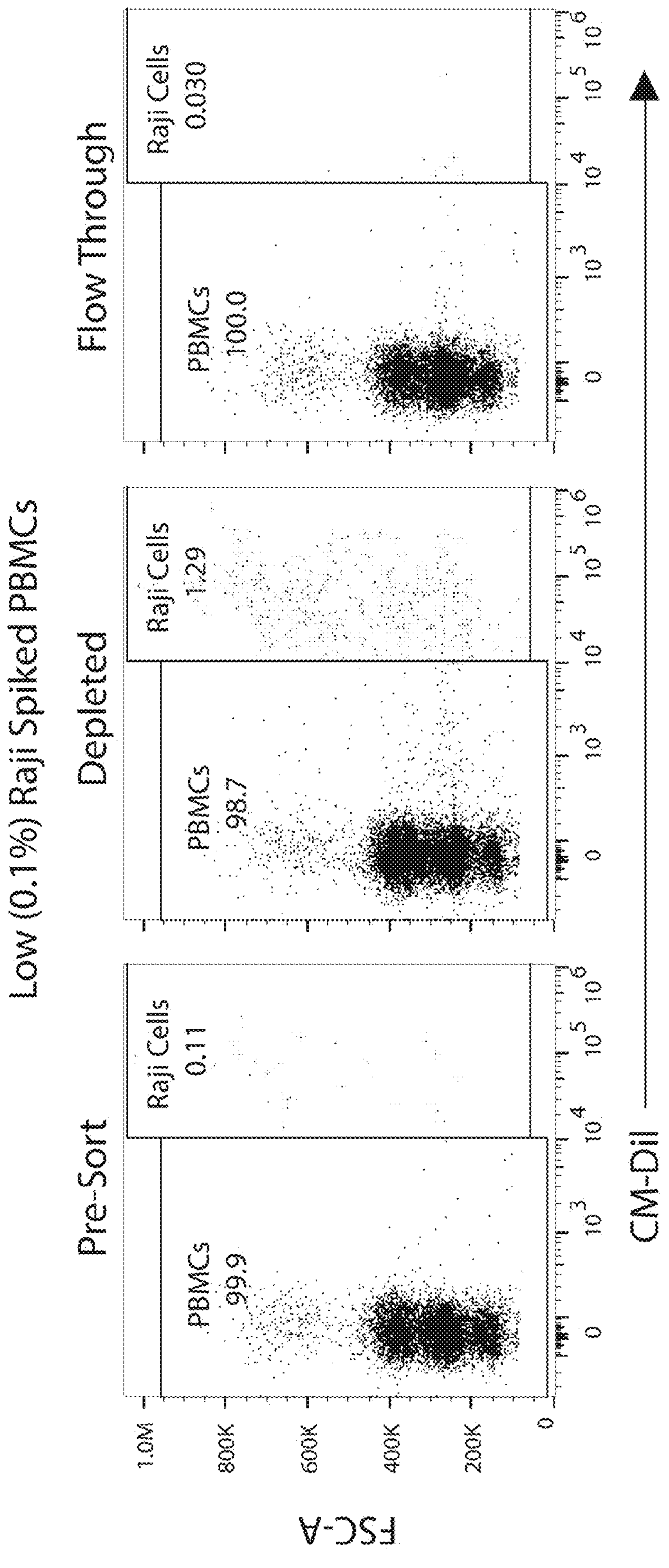
Figure 26C:
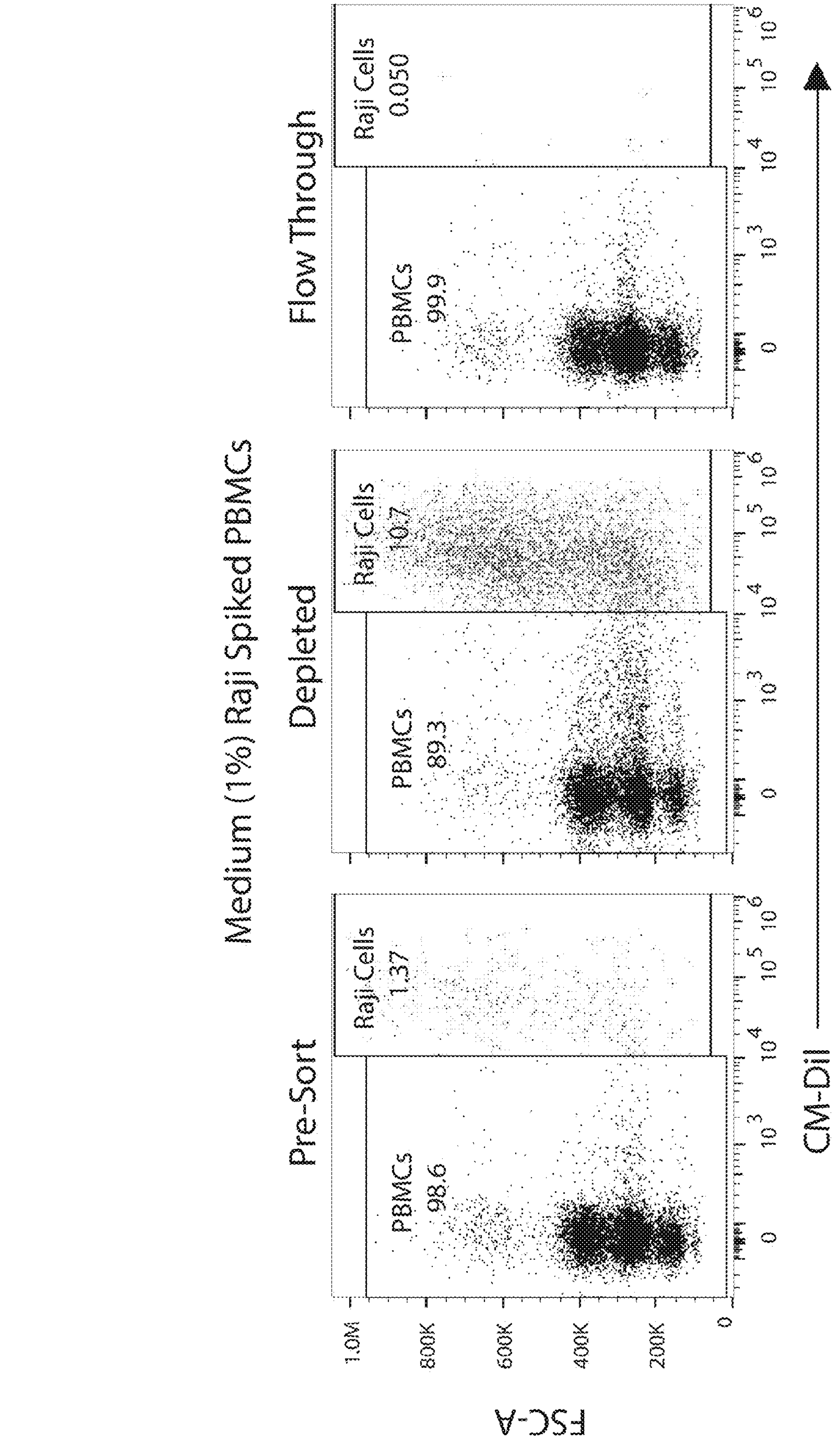
Figure 27B:
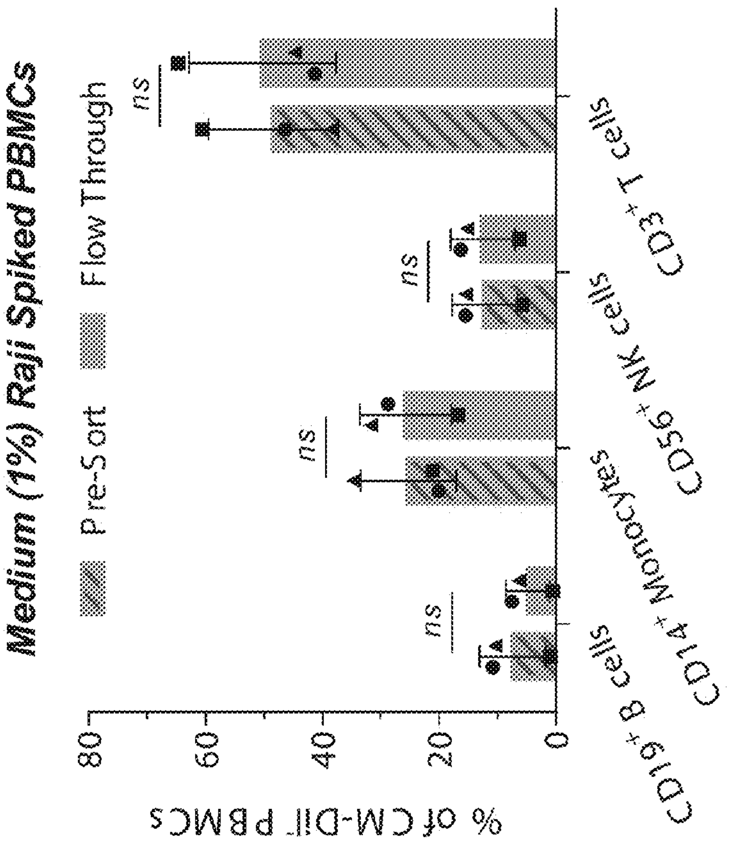
FIGS. 27A-27B. tJBA8.1-mediated depletion of Raji cells from low and medium spiked PBMCs does not affect the healthy immune cell composition. Flow cytometry analysis of the healthy immune cell composition within CM-Dil$^-$ PBMCs before (pre-sort) and after (flow through) Raji depletion from low (0.1%) (FIG. 27A) and medium (1%) (FIG. 27B) Raji spiked PBMCs. The circles, squares and triangles represent different PBMC donors from separate depletion studies. Graph bars and error bars represent mean±standard deviation; n=3 independent experiments with different PBMC donors. ns>0.05 (paired two-way ANOVA with Šídík correction). CM-Dil, chloromethylbenzamido-1,1'-dioctadecyl-3,3,3',3'-tetramethylindocarbocyanine perchlorate.
Figure 27A:
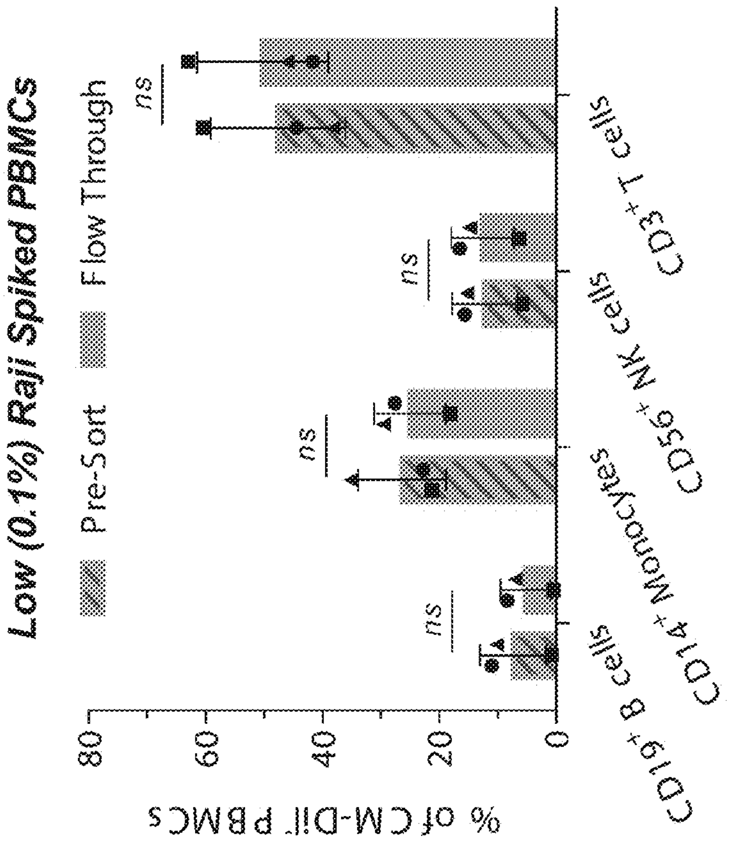

Because TfR1 is overexpressed in many cancer types including leukemias (both lymphocytic and myeloid),[50,51] lymphomas,[52,53] and myelomas,[39] and the level of TfR1 expression marks the proliferative potential of these malignant cells,[54] it was recognized that tJBA8.1 could be utilized as a malignant cell depletion agent in CAR T-cell manufacturing. The inventors therefore developed a MACS-based approach combining biotinylated tJBA8.1 and Anti-Biotin Microbeads (Miltenyi Biotec) for selective depletion of cancerous cells from PBMCs (FIG. 5A, top). Immortalized Raji B-lymphoma cells were used, which robustly express TfR1 in contrast to healthy PBMCs that have near-background expression (FIGS. 25A, 25B), to mimic cancers currently treated by FDA-approved CD19-directed CAR T-cell therapies. Raji cells were pre-labeled with a CM-Dil membrane dye for tracking purposes (FIG. 26A) and subsequently spiked into healthy PBMCs at low (~0.1%), medium (~1%), and high (~10%) percentages to reproduce circulating malignant cell heterogeneity found in patient leukapheresis populations.[55] The mixed cells were incubated with biotinylated tJBA8.1 and anti-biotin beads before separating them by magnetic separation on a column. The pre-sort, depleted, and flow through fractions were analyzed by flow cytometry to detect CM-Dil$^+$ Raji cells (FIG. 5B and FIGS. 26B, 26C). It was observed that tJAB8.1-mediated depletion effectively removed CM-Dil$^+$ Raji cells from all spiked PBMC populations, with flow-through populations that were statistically indistinguishable from un-spiked PBMC controls (FIG. 5C). Analyzing the depleted fractions, enrichment of CM-Dil$^+$ Raji cells was observed, as expected, although their purity scaled with the amount of spike cells and never peaked past 60%. As this indicates some CM-Dil$^-$ PBMCs were depleted as well, the percentages of immune cells in the CM-Dil$^-$ pre-sort and flow through fractions was further examined to determine if the PBMC composition was being impacted by the depletion process. There were no significant changes in the percentages of CD19$^+$ B cells, CD14$^+$ monocytes, CD56$^+$ NK cells, and CD3$^+$ T cells between the pre-sort and flow through fractions (FIG. 5D, FIGS. 27A, 27B), indicating that loss of CM-Dil$^-$ PBMCs in the depleted fraction was low and likely non-specific. Taken together, these data demonstrate proof-of-concept removal of TfR1$^+$ malignant cells from PBMCs using tJBA8.1, yielding healthy and uncompromised cell product that can be used in downstream CAR T-cell manufacturing with improved safety.

Elucidation of TfR1-Independent tJBA8.1 Binding and Affinity Optimization

Figure 28A:
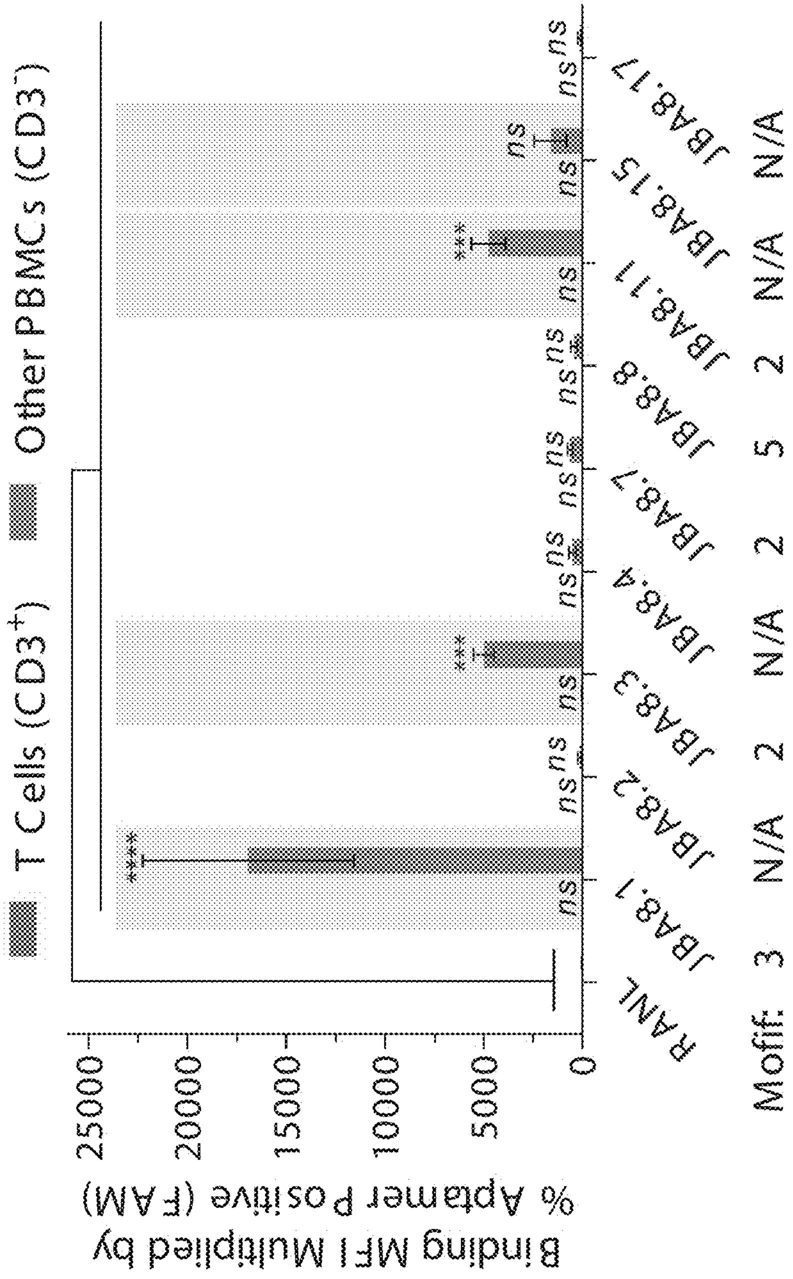
Figure 28B:
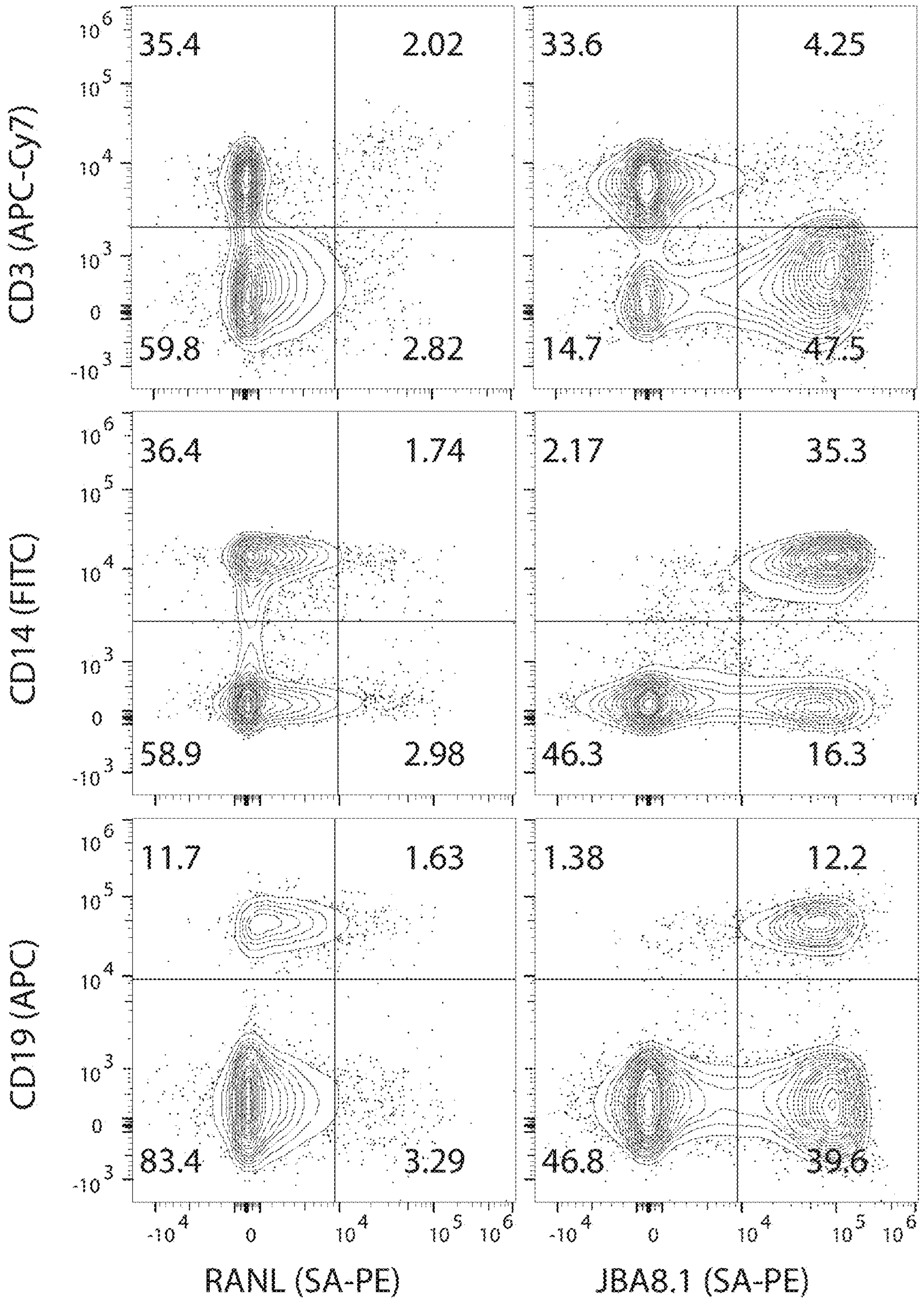
Figure 28D:
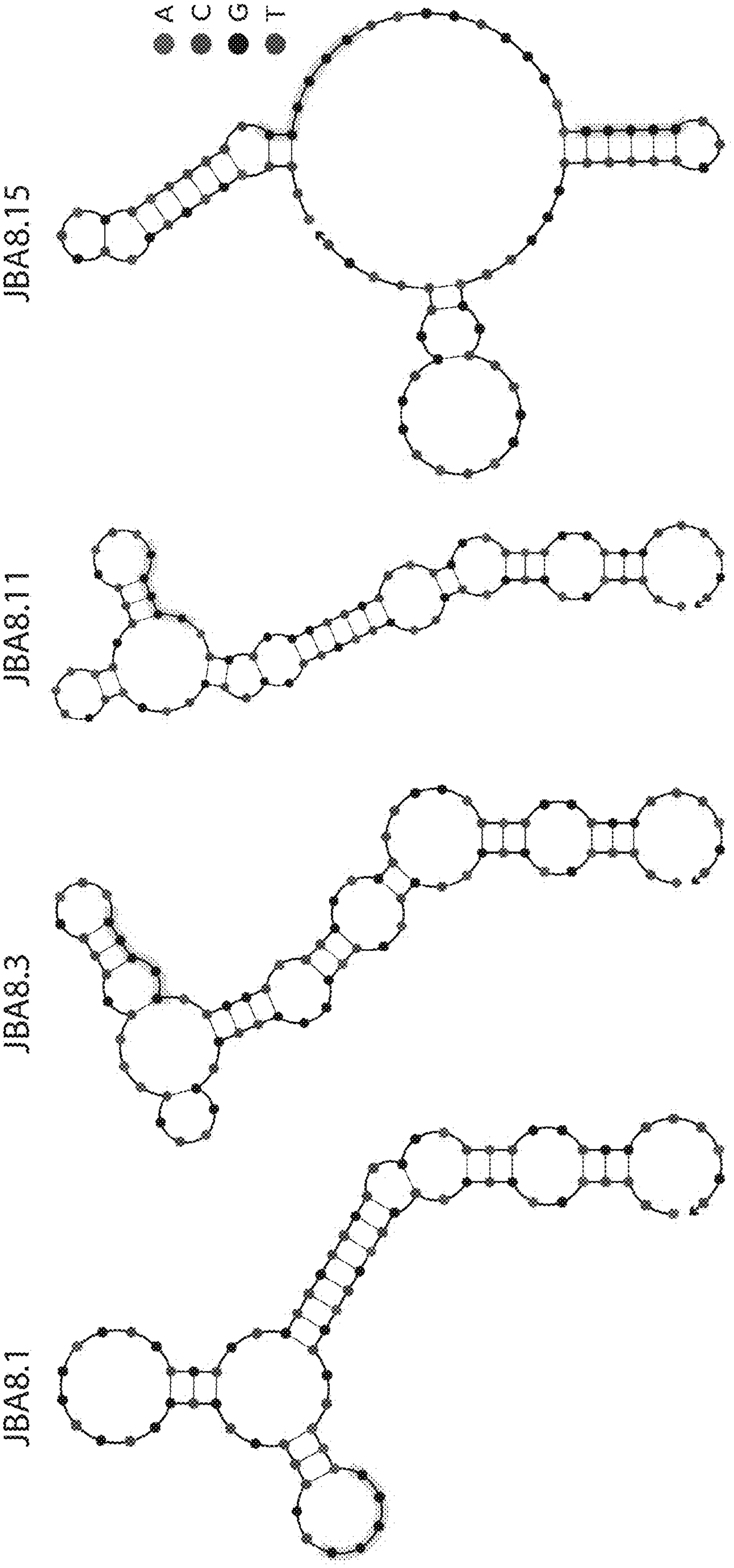

The previous binding and competition results with tJBA8.1 on Jurkat cells support the hypothesis that tJBA8.1 has a TfR1-independent binding component. Given that tJBA8.1 captured some PBMCs in depletion studies, it was speculated that tJBA8.1 can bind a subpopulation of PBMCs via the same TfR1-independent mechanism. To test this and better understand the nucleotides that contribute to this interaction, the individual full-length aptamers identified from cell-SELEX in FIG. 1C were revisited and their ability to bind PBMCs was compared. The inventors also co-stained with a CD3 Ab to distinguish binding to CD3$^+$ T cells and other CD3$^-$ PBMCs (B cells, monocytes, and the like). While none of the aptamers bound CD3$^+$ T cells, four of them (JBA8.1, JBA8.3, JBA8.11, and JBA8.15) displayed high binding to $CD3^-$ PBMCs relative to the RANL control, with JBA8.1 having the highest binding (FIG. 28A). Using JBA8.1 and a broader antibody panel for co-staining, it was found that $CD14^+$ monocytes and $CD19^+$ B cells comprised the majority of aptamer bound CD3-PBMCs (FIG. 28B). Comparing the sequences of all the individual aptamers tested, a motif of five consecutive guanine bases (GGGGG or G-quintet) that was specific to JBA8.1, JBA8.3, JBA8.11, and JBA8.15 (FIG. 28C) was identified. Interestingly, only the G-quintet motif of JBA8.1 was predicted to be single-stranded, whereas the G-quintet motifs of the other three aptamers were predicted to be partially or fully double-stranded (FIG. 28D). These results establish a potential molecular and structural basis for the TfR1-independent binding of tJBA8.1.

Figure 24A:
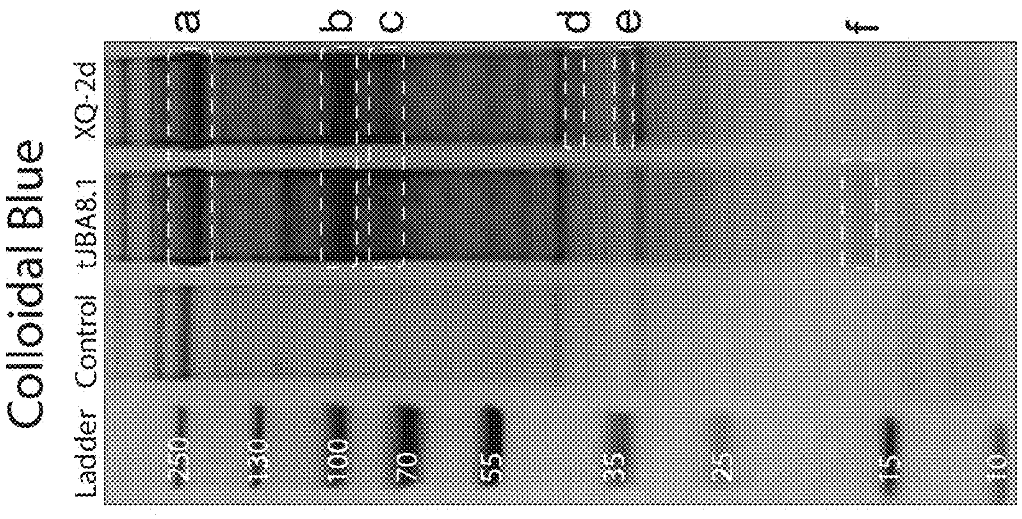
Figures 29A, 29B:
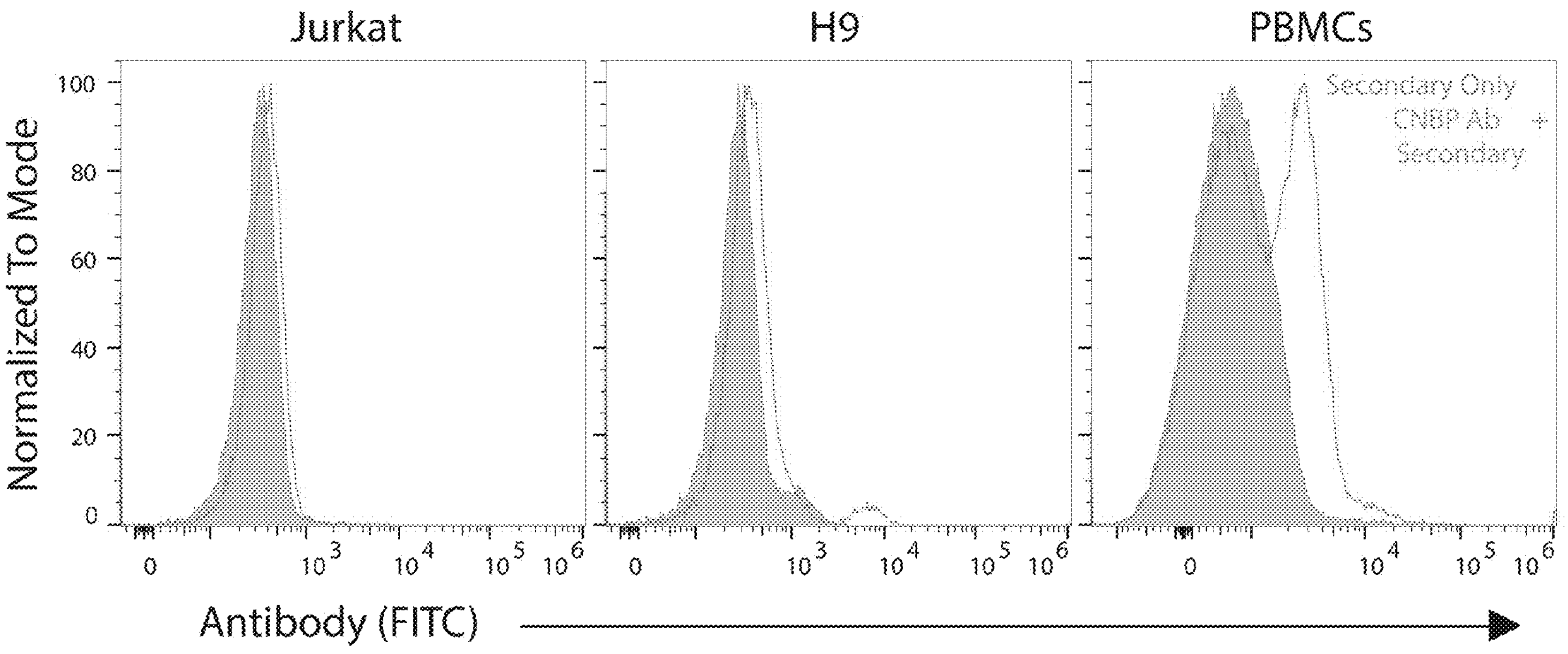
FIGS. 29A-29G. Extracellular cellular nucleic-acid binding protein (CNBP) may contribute to TfR1-independent binding of tJBA8.1.

To identify the cellular target that tJBA8.1 binds independently from TfR1, the inventors revisited the pull-down results in FIG. 24A. Besides the characteristic bands of TfR1, tJBA8.1 uniquely enriched a low molecular weight protein band at approximately 20 kDa (band f). Analyzing the band by mass spectrometry, cellular nucleic acid-binding protein (CNBP, also known as ZNF9) was identified as the top relevant protein hit, with extracted peptides covering 20% of the CNBP sequence (FIG. 29A). Of relevance to the G-quintet motif that was specifically found in the aptamers displaying TfR1-independent binding, CNBP is a highly conserved zinc-finger protein that regulates gene transcription and translation by binding to and unfolding G-rich single-stranded DNA and RNA, particularly those that form G-quadruplexes.[56-58] Consistent with this, JBA8.1, JBA8.3, JBA8.11, and JBA8.15 are predicted to form G-quadruplex structures, with anticipated involvement of the G-quintet sequence in G-quadruplex formation.[59] Furthermore, CNBP expression is elevated in cancer and monocytes,[60,61] which aligns with the TfR1-independent binding of tJBA8.1 to cancerous Jurkat cells and $CD3^-$ PBMCs. Given these associations, it is contemplated that CNBP may be contributing to the TfR1-independent binding of tJBA8.1.

Figure 29C:
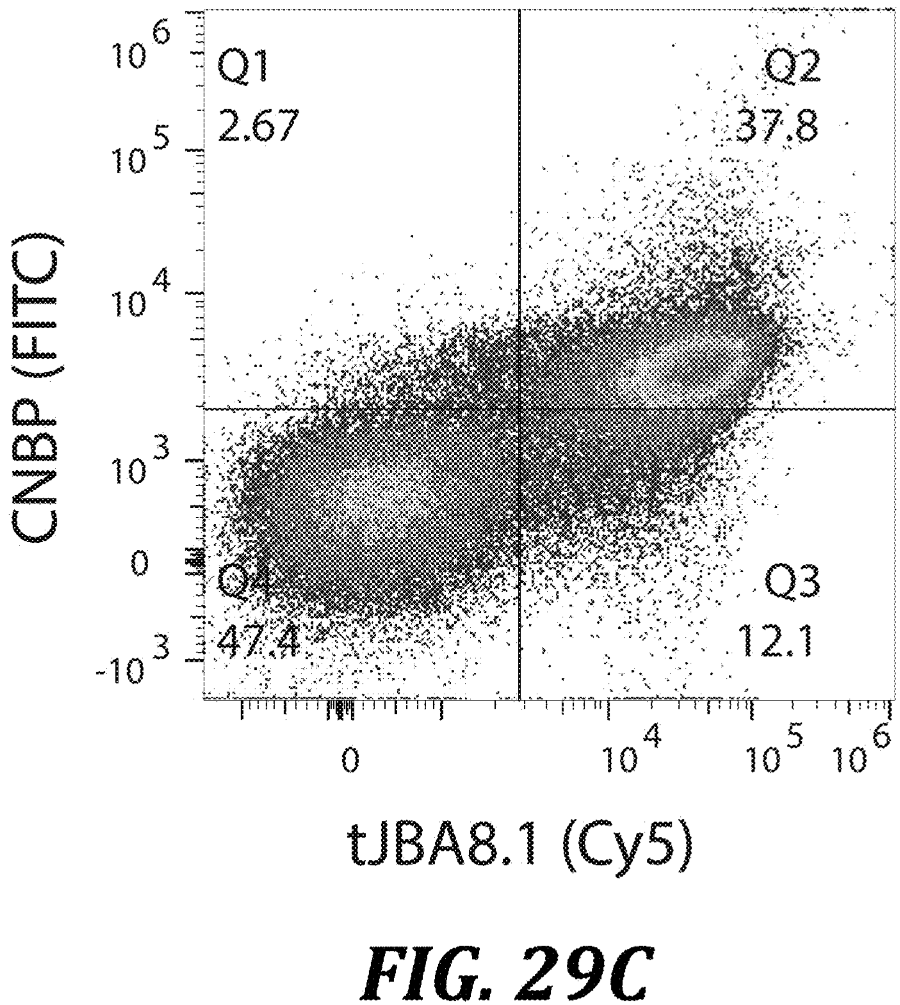
Figure 29D:
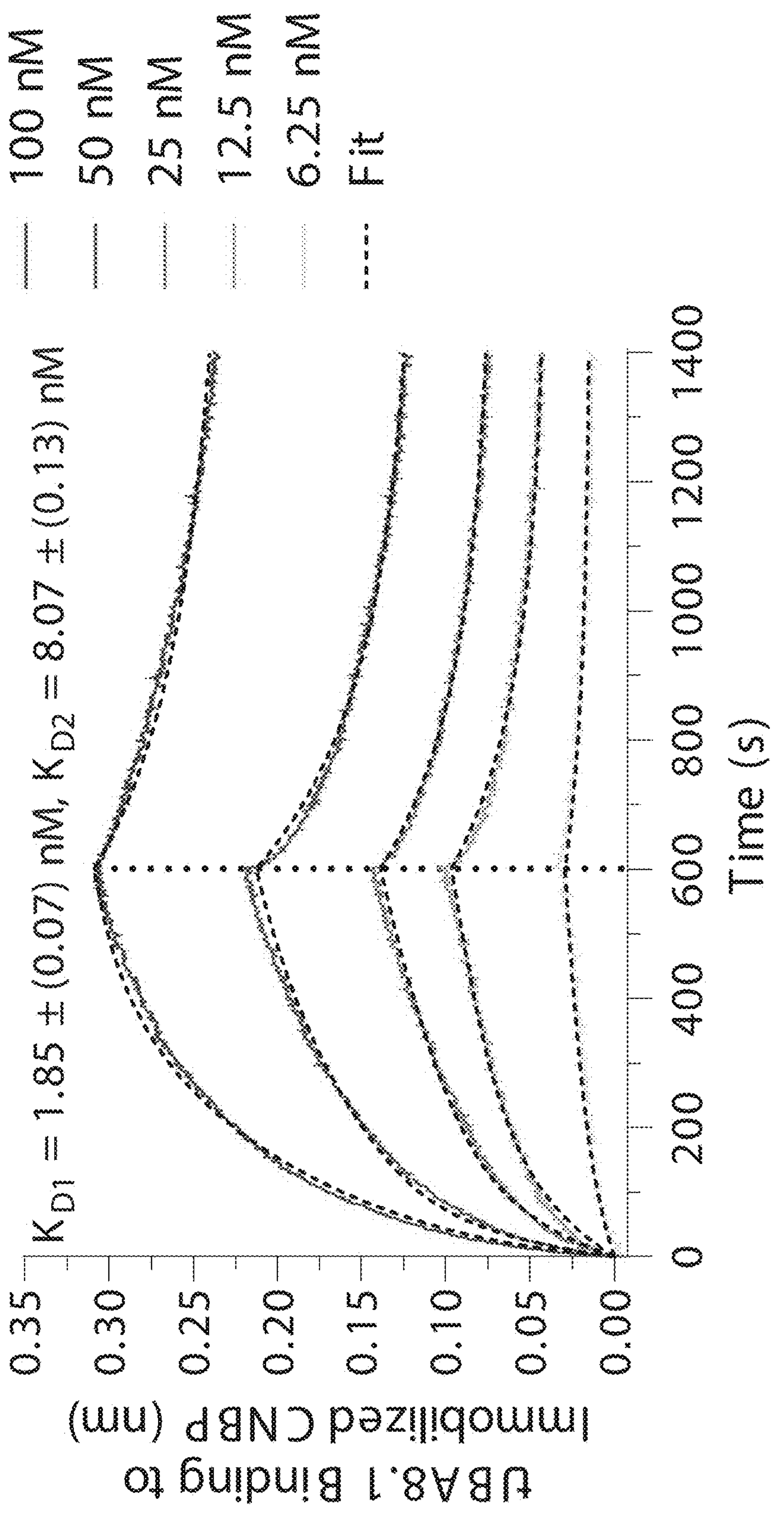
Figure 29E:
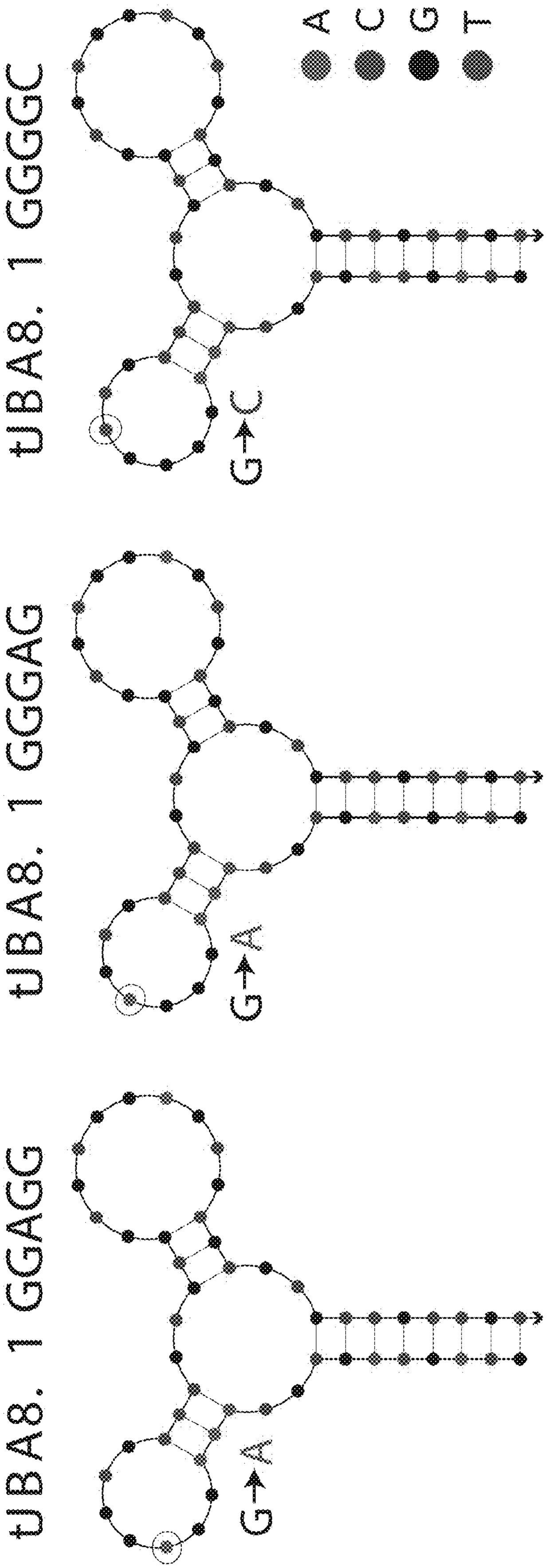
Figure 29F:
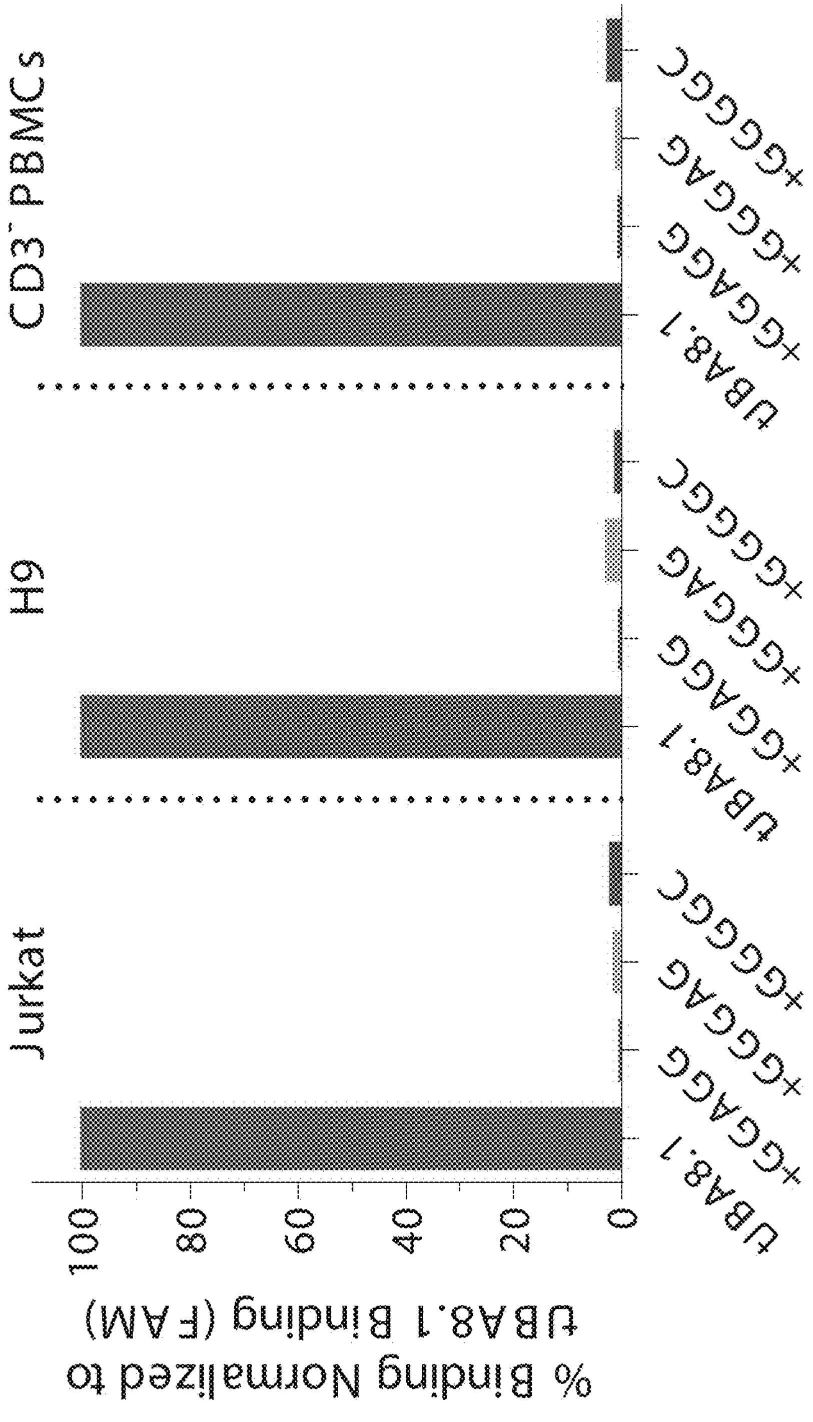
Figure 29G:
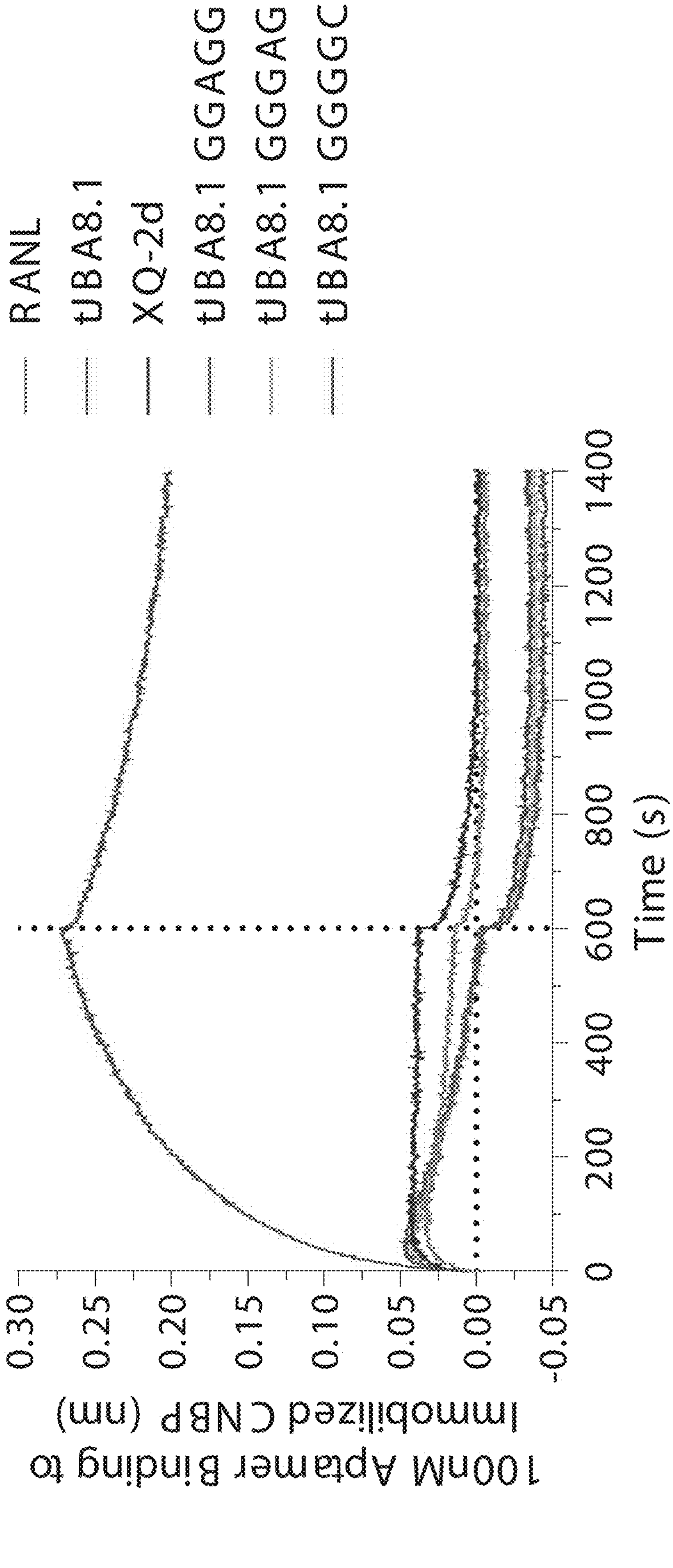

Although CNBP lacks a transmembrane domain and its subcellular localization to-date has only been documented in the cytoplasm,[57] it was hypothesized that it may be unconventionally expressed at the surface of certain cells, similar to the DNA/RNA-binding protein nucleolin that has been famously targeted by the G-quadruplex containing AS1411 aptamer.[62,63] To test this, the inventors conducted extracellular flow cytometry staining of Jurkat cells, H9 cells, and PBMCs with a monoclonal anti-CNBP antibody (clone 38F10). While extracellular expression of CNBP was not detected on Jurkat and H9 cells with this antibody clone, extracellular CNBP expression was observed on a subset of PBMCs (FIG. 29B). Further co-staining with tJBA8.1 revealed that the anti-CNBP antibody and tJBA8.1 binding on this subset of PBMCs, with positive correlation between the two stains (FIG. 29C). To more directly demonstrate tJBA8.1 binding to CNBP, the inventors immobilized recombinant His-tagged CNBP protein onto nickel-charged tris-nitrilotriacetic (Ni-NTA) BLI biosensors to mimic cell-bound CNBP and evaluated tJBA8.1 binding. tJBA8.1 bound to immobilized CNBP in a concentration-dependent manner, displaying biphasic association and dissociation curves suggestive of 2:1 heterogeneous binding interaction between tJBA8.1 and CNBP with a $K_D$m value of 1.85±0.07 nM and a $K_D$m value of 8.07±0.13 nM (FIG. 29D). The non-equilibrating association phase of these BLI curves is reminiscent of the tJBA8.1 binding curve to Jurkat cells in FIG. 2B, which failed to saturate even at 400 nM. As these results support the hypothesis of extracellular CNBP expression and tJBA8.1 binding to CNBP on cells, it was next sought to determine if perturbation of the G-quintet motif could remove tJBA8.1 binding to CNBP without impacting binding to TfR1. To this end, the inventors generated tJBA8.1 GGAGG (SEQ ID NO: 7) and tJBA8.1 GGGAG (SEQ ID NO: 4), adenine-substituted point variants of tJBA8.1 derived from low ranked aptamers in the round 8 cell-SELEX pool belonging to the same 45-bp Motif 3 as JBA8.1, and tJBA8.1 GGGGC (SEQ ID NO: 144), a cytosine-substituted point variant of tJBA8.1 that more closely resembles XQ-2d (Table 6). Importantly, the MFE secondary structures of these mutated tJBA8.1 variants were not predicted to change from tJBA8.1 (FIG. 29E). Using flow cytometry, it was found that these mutated tJBA8.1 aptamers lost all binding to Jurkat cells, H9 cells, and $CD3^-$ PBMCs, indicating that these mutations to the G-quintet motif abrogated both TfR1-dependent and independent binding of tJBA8.1 (FIG. 29F). Similarly, BLI revealed that these modified tJBA8.1 aptamers lost binding to immobilized CNBP, in addition to RANL and XQ-2d that also did not display binding (FIG. 29G). While these modifications failed to enhance the TfR1 specificity of tJBA8.1, they support the notion that tJBA8.1 binds to extracellular CNBP via its G-quintet motif.

tJBA8.1 Affinity Optimization

Figure 30A:
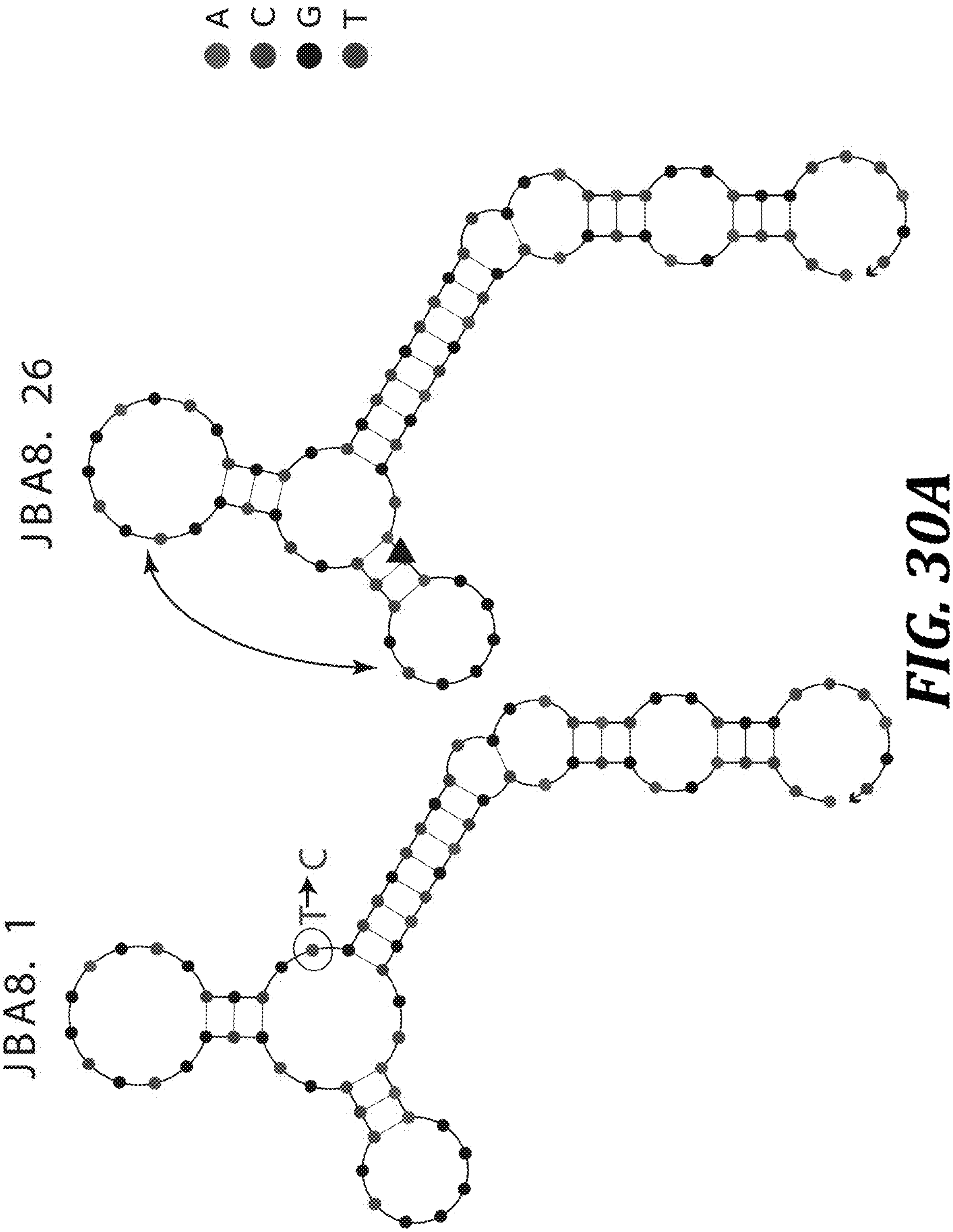
FIGS. 30A-30C. JBA8.26 is a higher affinity point variant of JBA8.1.
Figure 30B:
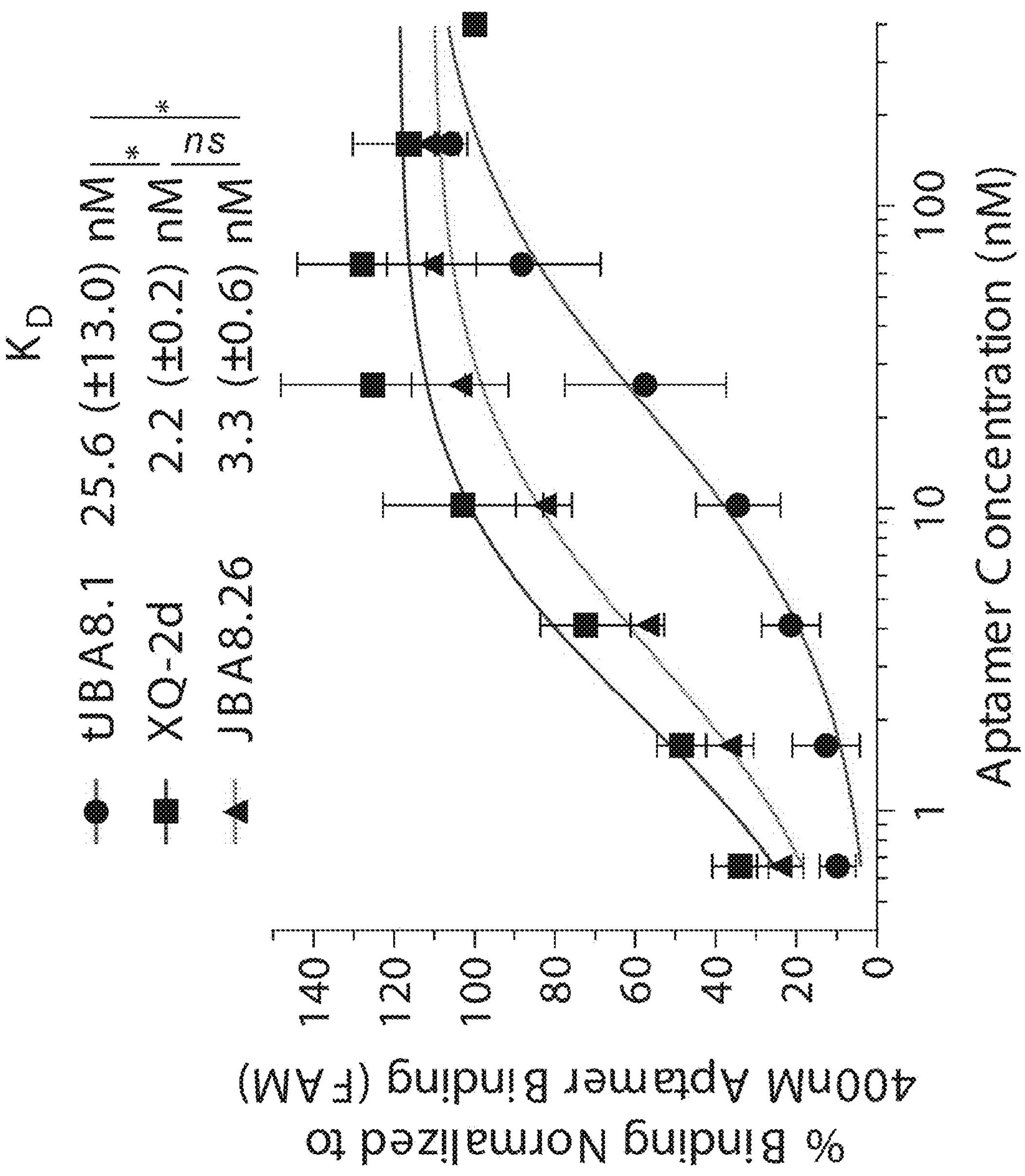
Figure 30C:
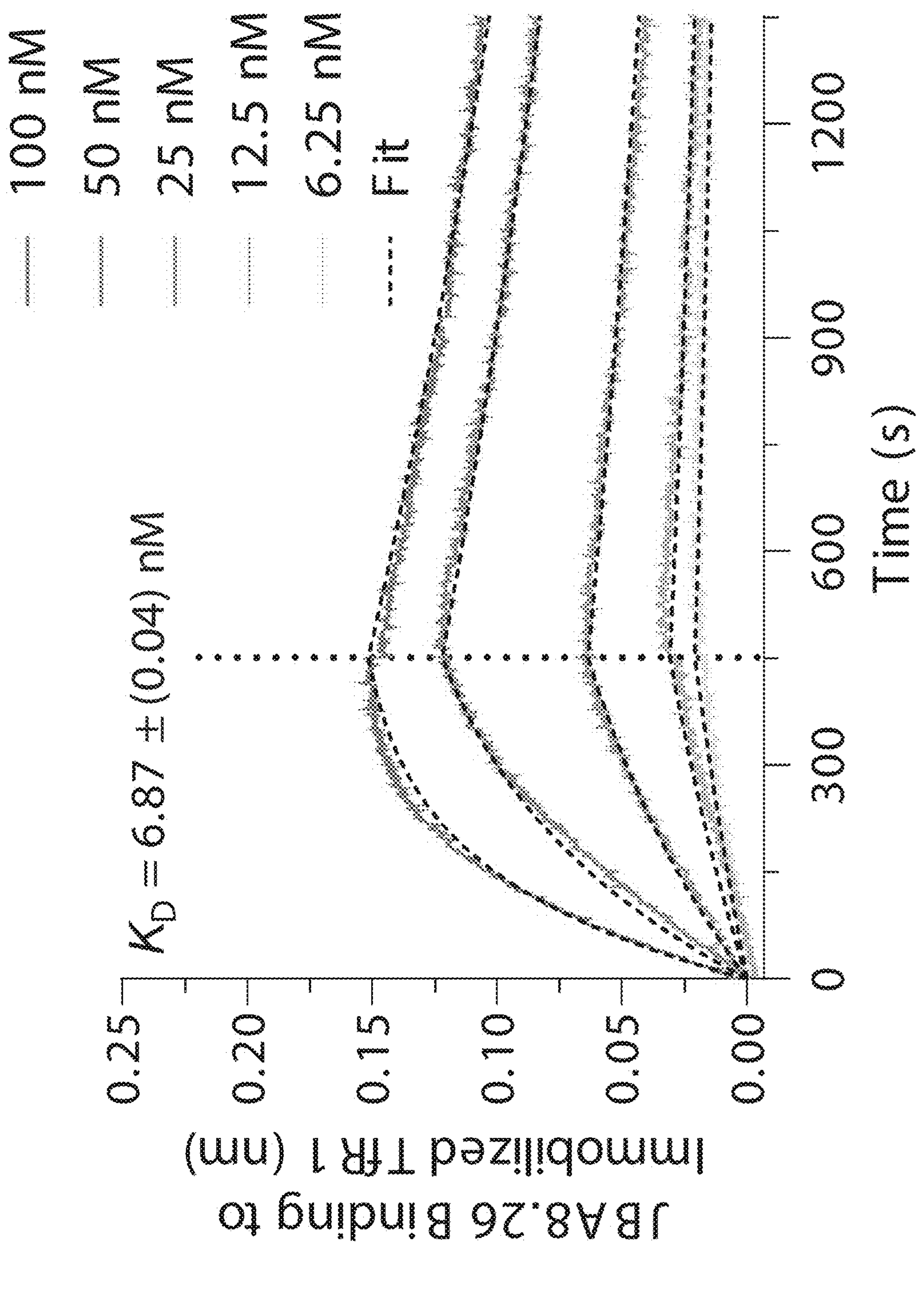
Figure 33A:
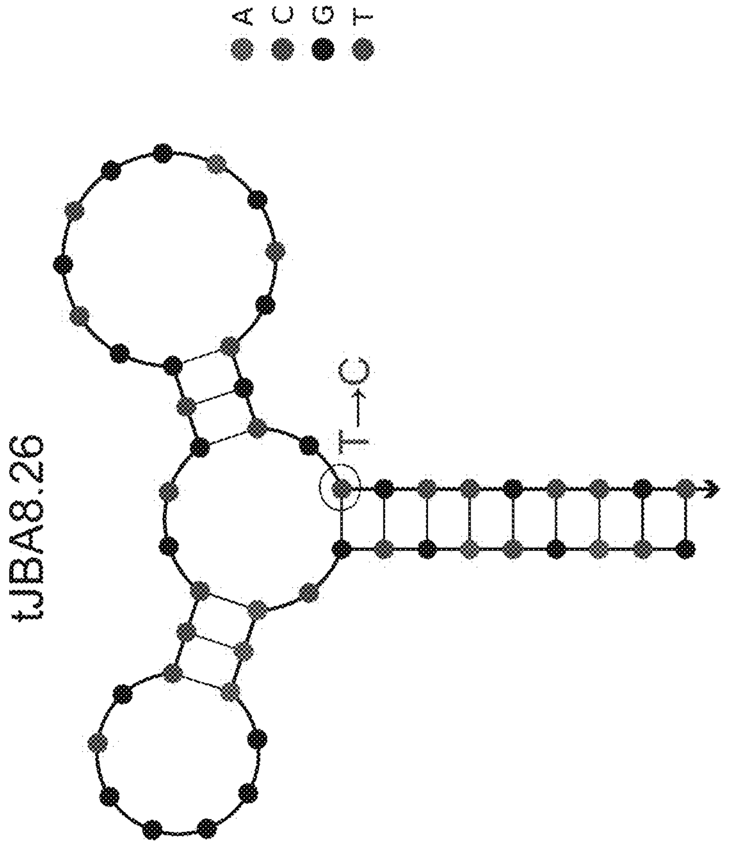
FIG. 33A-33D. Putative secondary structures of prospective aptamer sequences with improved affinity and specificity. tJBA8.26 (FIG. 33A) SEQ ID NO: 26; tJBA.1 AGGGG (FIG. 33B) SEQ ID NO: 137; tJBA8.1 GAGGG (FIG. 33C) SEQ ID NO: 138; tJBA8.1 with partially double-stranded GGGGG #1 (FIG. 33D) SEQ ID NO: 139; tJBA8.1 G29A (FIG. 33E) SEQ ID NO: 140.
Figure 33B:
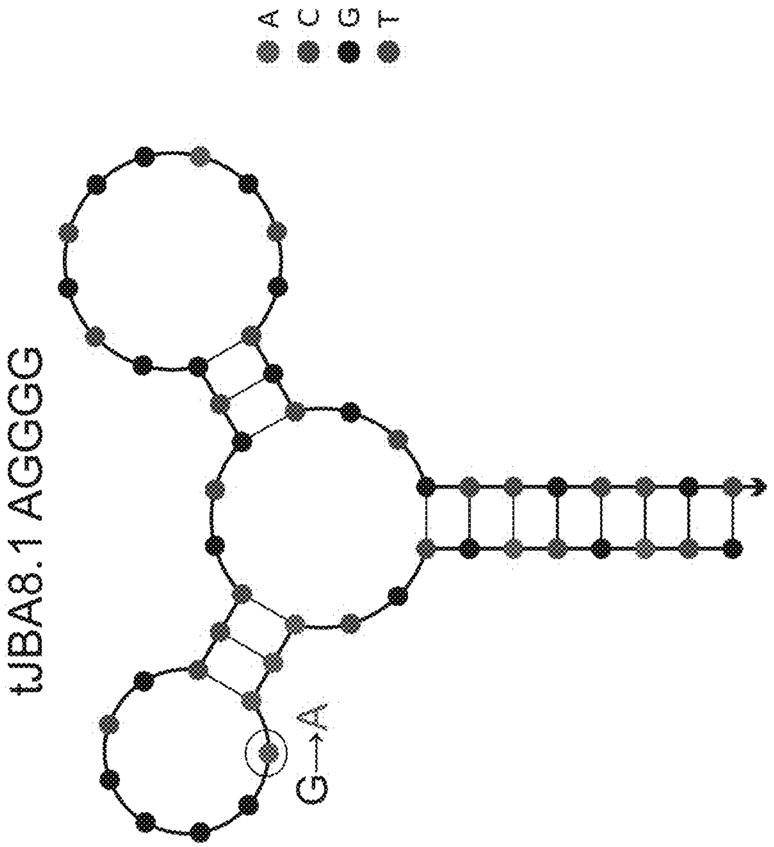
Figure 33C:
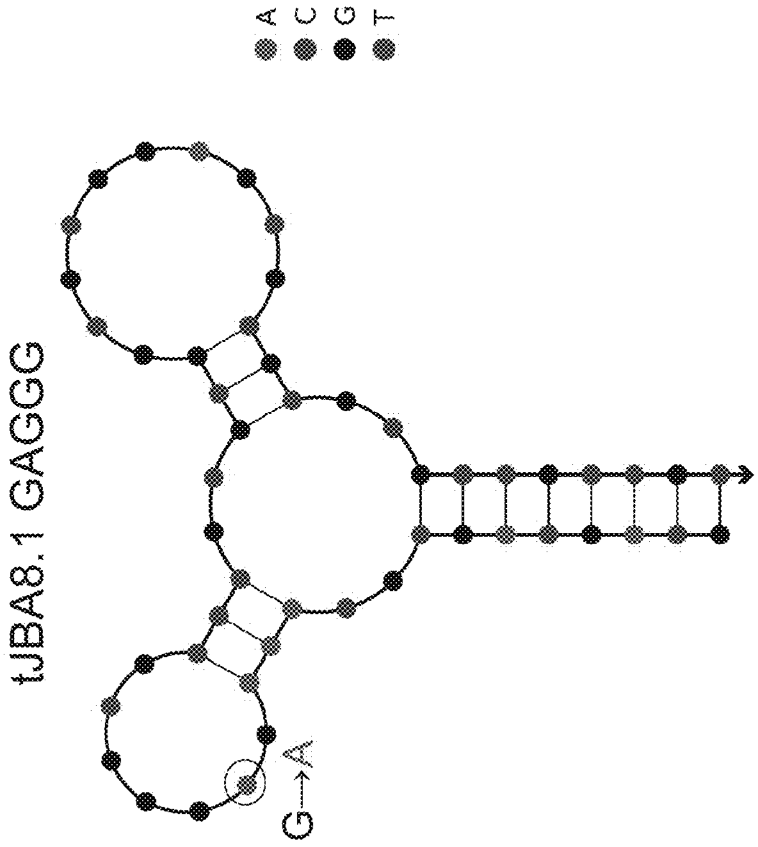
Figure 33D:
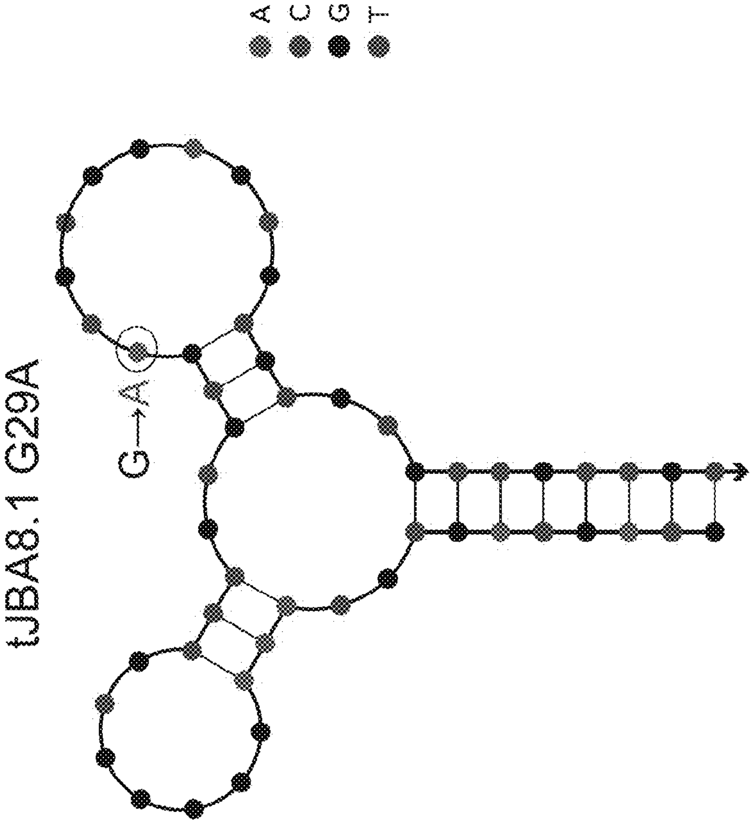

As these efforts to remove TfR1-independent binding were unsuccessful, the inventors revisited the NGS results to identify alternative Motif 3 aptamers that could have improved affinity for TfR1, which would allow one to lower the concentration of aptamer needed for effective cancer cell depletion and thereby minimize TfR1-independent binding. Besides JBA8.1, there were three other aptamers belonging to Motif 3 in the top 50 sequences of the round 8 cell-SELEX pool, namely JBA8.10, JBA8.26, and JBA8.45 (Table 5). Notably, all three aptamers were single-point variants of JBA8.1 that displayed approximately 20-fold enrichment in round 8, which was significantly greater than the 6.9-fold round 8 enrichment for JBA8.1. JBA8.26 was selected for further characterization given that it had the highest fold enrichment of the three aptamers. Analyzing the predicted MFE secondary structure of JBA8.26 by NUPACK™, it was noticed that JBA8.26 has an extended stem region compared to JBA8.1, owing to a T→C mutation that induces complementary base pairing (FIG. 30A). Interestingly, this base pairing contracts the central hairpin of the aptamer and increases the distance between the two out-branching hairpins. The inventors hypothesized that these predicted changes would increase the structural stability of JBA8.26 relative to JBA8.1 and alter its binding interaction with TfR1, elevating its affinity. Confirming this, JBA8.26 bound $TfR1^{hi}$ H9 T-lymphoma cells with an apparent $K_D$ of 3.3±0.6 nM, which was comparable to that of XQ-2d (2.2±0.2 nM) and a near 8-fold improvement compared to tJBA8.1 (25.6±13.0 nM) (FIG. 30B). Using BLI, JBA8.26 was found to bind immobilized TfR1 with a $K_D$ of 6.87±0.04 nM (FIG. 30C), displaying both a 2- to 3-fold faster association rate and a nearly 2-fold slower disassociation rate than those of tJBA8.1 tJBA8.1 (Table 8). Given these upgraded TfR1-binding kinetics, it was predicted that JBA8.26 and its future truncations, e.g., analogous to truncated tJBA8.1, will increase the partitioning efficiency of, for example, the cancer cell depletion strategy.

As expensive, living drugs that often serve as the final barrier between severely ill cancer patients and terminal disease, CAR T cells require stringent manufacturing to maximize their safety and efficacy. In rare cases, with T-cell isolation approaches currently employed in commercial therapies, malignant cells advance through the isolation process and contaminate enriched T cells, which can inadvertently exhaust produced CAR T cells or even create a cancer resistant to therapy.[14, 15] Accordingly, an inexpensive approach that actively removes cancerous cells from patient PBMCs while leaving healthy T cells untouched would be of high value to CAR T-cell manufacturing and safety.

In this work and in the studies described herein and the inventors report the discovery of a nanomolar-affinity DNA aptamer, named tJBA8.1, that binds the iron importer TfR1 overexpressed by cancer cells but not expressed by healthy PBMCs. In proof-of-concept MACS-based depletion studies, tJBA8.1 was capable of efficiently removing Raji B-lymphoma cells spiked into PBMCs at various concentrations, yielding uncontaminated, label-free PBMCs. Importantly, the composition of healthy immune cells was unaltered by the depletion steps, showing the precise partitioning afforded by tJBA8.1. This work provides a straightforward, cost-effective approach for selectively removing malignant cells before CAR T-cell production, enabling safer and more reproducible manufacturing of this precious therapy.

Comprehensive validation and characterization of aptamer binding to their cognate receptors can contribute to their widespread recognition and use. For tJBA8.1, the inventors conducted many assays to both validate its binding to TfR1 and further understand its binding site on the receptor, especially within the context of other TfR1 ligands. Notably, tJBA8.1 binding to TfR1$^+$ cells was competed off by both iron-bearing transferrin and another TfR1-binding aptamer described in the literature, XQ-2d,[42, 43] indicating that tJBA8.1 shares overlapping binding epitopes on TfR1 with these ligands. Intriguingly, in pull-down assays using cell membrane proteins, tJBA8.1 failed to co-precipitate HFE, another natural TfR1 ligand that is co-expressed on the cell surface, while XQ-2d could. This establishes a key difference in TfR1 binding between tJBA8.1 and XQ-2d, indicating that their binding interfaces are spread over multiple regions on the receptor, some of which overlap between the two aptamers while others are unique. Indeed, molecular dynamics simulations predicted that XQ-2d binds to TfR1 at two regions,[31] and only the nucleotides involved in binding to one region appear to overlap strongly with the tJBA8.1 sequence.

The inventors also demonstrated that tJBA8.1 does not bind mouse TfR1 despite the protein sharing ~75% identity in its extracellular domain with human TfR1. Mouse TfR1 has mutations at multiple residues in α helices 1, 2, and 3 of the human TfR1 helical domain bound by holo-transferrin (FIG. 31),[45] perhaps explaining why tJBA8.1 lacks binding to this protein. Also, of potential interest to tJBA8.1 binding is TfR2, a hepatic-localized homolog of TfR1 that shares approximately 47% identity in its extracellular domain with TfR1.69 TfR2 has even less conservation of the residues in a helices 1, 2, and 3 of the TfR1 helical domain (FIG. 32), suggesting that tJBA8.1 would not bind or have severely reduced affinity for TfR2.

Besides TfR1, it is likely that tJBA8.1 has other target receptors on Jurkat cells and other cell types. Aptamer binding to Jurkat cells was only partially abrogated by large molar excesses of holo-transferrin and XQ-2d, and aptamer binding to TfR1$^-$ monocytes and B cells within PBMCs was also observed. Potentially explaining some of this TfR1-independent binding, an interaction between tJBA8.1 and the DNA/RNA-binding protein CNBP was characterized. As CNBP expression has previously been documented only in the cell cytoplasm, it is reported for the first time herein probable extracellular expression of this protein on CD3$^-$ PBMCs that colocalized and correlated with TfR1-independent binding of tJBA8.1. While the monoclonal anti-CNBP antibody that was tested failed to detect extracellular CNBP expression on Jurkat cells, enriched CNBP was found in pull-down assays using tJBA8.1 and Jurkat membrane extracts. It is known that the CNBP gene encodes as many as seven alternatively spliced isoforms,[57] some of which may be selectively expressed on the cell surface of certain cells and lack epitopes for monoclonal antibody recognition. Alternatively, tJBA8.1 may be internalized by a two-part macropinocytosis mechanism that is CNBP-dependent, which has been similarly described for the nucleolin-binding AS1411 aptamer and would explain why tJBA8.1 does not greatly deplete TfR1$^-$ monocytes and B cells from PBMCs via MACS despite binding these subsets.[70]

The inventors believe that the TfR1-independent binding of tJBA8.1 is mediated by a motif of five consecutive guanines (i.e., G-quintet) which is shared by multiple aptamers identified from the cell-SLEX. This G-rich patterning may promote the formation of intramolecular or intermolecular G-quadruplexes,[59] which are know to interact with DNA/RNA-binding proteins like CNBP.[71] Initial attempts have been made to decouple this off-target binding of tJBA8.1 from its intended TfR1 binding by mutating the last three guanines in the G-quintet motif, but these changes to the tJBA8.1 sequence removed both TfR1-dependent and independent binding, suggesting that these nucleotides are important for TfR1 binding and/or tJBA8.1 structure. Despite these results, there are further strategies worth exploring, such as mutating the first two guanines of the G-quintet motif or neighboring nucleotides to make the G-quintet motif partially double stranded.

While B-lymphoma cells were used in depletion studies to mimic cancers currently treated by commercial CAR T-cell therapies, it is anticipated that the depletion strategy described herein will have a greater impact on the treatment of T-cell malignancies. Presently, autologous CAR T-cell manufacturing for treating T-cell leukemias and lymphomas is impractical since malignant T cells are often found in the peripheral blood of patients with these diseases and immunoaffinity purification approaches that target common T-cell antigens are unable to distinguish normal T cells from these malignant T cells.[18, 19] To circumvent these challenges, CAR NK cells or allogeneic CAR T cells can be used for treatment,[72, 73] but the former is difficult to manufacture at a clinical scale whereas the latter requires gene editing to prevent fatal graft-versus-host-disease and likely has limited persistence due to host-versus-graft effects. For these reasons, CAR T-cell manufacturing for T-cell malignancies would serve to benefit the most from the depletion strategy developed here, as it would allow selective harvesting of healthy autologous T cells that are otherwise unattainable. Furthermore, as T-lineage leukemias and lymphomas have been shown to have greater TfR1 expression and positivity than B-lineage counterparts,[51, 53] these cancers should be especially amenable to tJBA8.1 recognition and capture.

It is specifically contemplated that the aptamer-based malignant cell depletion strategy described here could be adapted to affinity chromatography approaches, eliminating cell processing steps associated with MACS. Chemical conjugation of aptamers to chromatography solid supports will also realize a fully-synthetic, low-cost cell depletion system, unlike the anti-biotin coupling used here that relies on expensive antibodies. As contaminating myeloid cells also inhibit the production of CAR T cells,[74] tJBA8.1 could be applied in combination with the monocyte-binding aptamer described above to elegantly deplete malignant cells and monocytes from patient PBMC concentrates in a single processing step.[75] Besides cell isolation, other applications of tJBA8.1 within CAR T-cell manufacturing are possible. The inventors previously used cationic comb polymers and polymer-lytic peptide conjugates (VIPER) for non-viral gene delivery to T cells, and low uptake was one of the limiting barriers to activated T-cell transfection.[76,77] Of relevance, the inventors show in this work that activated T cells have upregulated TfR1 expression and high tJBA8.1 binding, and TfR1 is well known to be rapidly internalized upon ligand binding via clathrin-mediated endocytosis.[40] Comb polymer and VIPER formulations could thus be decorated with tJBA8.1 to enhance their binding to activated T cells via TfR1, improving their uptake for T-cell transfection. Outside of CAR T-cell therapy, TfR1 targeting with tJBA8.1 could have implications in the detection of circulating tumor cells and the delivery of drugs across the blood-brain barrier,[78, 79] paving the way for tJBA8.1-based diagnostics and therapeutics.

Methods and Materials

Cell line and primary cell culture. The Jurkat, J.RT3-T3.5, H9, and Raji cell lines were purchased from ATCC and cultured in RPMI 1640 medium (Corning, Gibco) with 10% FBS (Life Tech). Primary healthy donor PBMCs were isolated from Leukocyte Reduction System (LRS) chambers (Bloodworks Northwest) by Ficoll-Paque™ density gradient centrifugation (GE). Positively enriched primary $CD4^+$ and $CD8^+$ T cells were gifted by Juno Therapeutics. For T-cell activation studies, T cells were thawed and stimulated 1:1 with Dynabeads™ Human T-Activator CD3/CD28 (Gibco) in RPMI 1640 10% FBS supplemented with 20 ng/mL recombinant human IL-2 (Miltenyi) for $CD8^+$ T cells, 5 ng/mL recombinant human IL-7 (Miltenyi) for $CD4^+$ T cells, and 0.5 ng/mL recombinant human IL-15 (Miltenyi) for both $CD4^+$ and $CD8^+$ T cells. Fresh media exchanges were conducted every 2-3 days to replenish cytokines, and T cells were passaged to larger plates or flasks upon reaching high densities (2-3×$10^6$ cells/mL) with visible yellow coloration of the culture media.

Oligonucleotides, PCR reagents, and recombinant proteins. Aptamer sequences used in this work are listed in Table 6. All oligonucleotides, including the randomized naïve library, primers, and individual aptamers, were synthesized by Integrated DNA Technologies with either HPLC purification (naïve library and individual aptamers) or standard desalting (primers). The FAM-labeled forward primer and biotin-labeled reverse primer used to amplify aptamer pools between rounds of cell-SELEX are as previously described.[23] dNTPs and Phusion™ High-Fidelity Polymerase used in PCR reactions were purchased from QIAGEN and NEB, respectively. Recombinant human holo-Tf used in competition studies was purchased from Sigma-Aldrich. For BLI studies, the following recombinant proteins were used: biotinylated human TfR1 (TfR-H82E5, ACROBiosystems), His-tagged mouse TfR1 (50741-M07H, Sino Biological), and His-tagged human CNBP (NBP2-22742, Novus Biologicals). Recombinant human holo-Tf used in competition studies was purchased from Sigma-Aldrich.

Flow cytometry reagents and staining. For flow cytometry cell staining and competition studies, the following dyes and antibodies were used: ZOMBIE VIOLET™ (1:500, $10^7$ cells/mL, BioLegend), CM-Dil (1:200, $10^6$ cells/mL, Invitrogen), FITC anti-human CD71 (1:100-1:200, BioLegend, CY1G4), FITC anti-human CD14 (1:100, BioLegend, M5E2), FITC anti-human CD3 antibody (1:100, BioLegend, UCHT1), APC-Cy7 anti-human CD14 (1:200, Invitrogen, 61D3), Super Bright 702 anti-human CD19 (1:100, Invitrogen, SJ25C), Super Bright 600 anti-human CD56 (1:100, Invitrogen, TULY56), PE anti-human CD3 (1:100, BioLegend, HIT3a), APC-Cy7 anti-human CD3 (1:200, BD Biosciences, SP34-2), APC anti-human CD19 (1:200, BioLegend, HIB19), and Alexa Fluor™ 647 streptavidin (1:500, BioLegend), PE streptavidin (1:500, BioLegend), mouse anti-human CNBP (1:20, Novus Biologicals, 38F10), and FITC goat anti-mouse IgG (1:100, BioLegend, Poly4053). Antibody dilutions were adjusted when used as isotype/negative controls to match the concentration of experimental antibody used, or when doing serial dilutions for competition studies.

The base wash buffer used for aptamer folding, cell staining, and washing was comprised of DPBS with calcium and magnesium (Corning; ~0.9 mM $CaCl_2$ and ~0.5 mM $MgCl_2$) further supplemented with 5 mM $MgCl_2$ (Fisher) and 25 mM D-glucose (Sigma-Aldrich). For antibody staining without aptamers, wash buffer supplemented with 1% BSA (Miltenyi) was used. For aptamer binding/staining with or without antibodies, wash buffer supplemented with 1% BSA and 0.1 mg/mL yeast tRNA (Invitrogen) was used. Wash buffer supplemented with 1% BSA was used for all wash steps. Aptamers were folded at 1 μM in wash buffer by heating the solution at 95° C. for 5 min followed by snap cooling on ice for at least 10 min before binding. For flow cytometry staining, cells were first removed from culture or thawed and washed with DPBS (Gibco) to remove residual media and serum. Cells were then incubated with live/dead ZOMBIE VIOLET™ dye diluted in DPBS for 15 min at room temperature. After live/dead staining, cells were washed with wash buffer 1% BSA to neutralize remaining ZOMBIE VIOLET™ and aliquoted into a polypropylene U-bottom 96-well plate (Corning) at 1-2×$10^5$ cells/well for immortalized cell lines and primary T cells and 2-5×$10^5$ cells/well for PBMCs. Cells were then blocked with 10 μL FcR Blocking Reagent (Miltenyi) for 5-10 min at 4° C. (only if they were to be stained with antibodies) and subsequently stained with 100 μL antibodies and/or aptamers for 20-30 min at 4° C. in the appropriate binding buffer at the indicated concentrations. For competition assays, unlabeled anti-CD3 antibody (BioLegend, UCHT1), unlabeled anti-CD71 antibody (BioLegend, CY1G4), recombinant human holo-Tf, or FAM-labeled XQ-2d were added to the primary incubation with aptamer at different concentrations. After staining, cells were washed twice with 200 μL wash buffer 1% BSA to remove excess antibodies and/or aptamers. If the aptamers or the antibodies used were biotinylated or were unlabeled, cells underwent a further incubation with 100 μL of fluorescently labeled secondary for 20-30 min at 4° C. in wash buffer 1% BSA and subsequently washed twice as before. Fully stained cells were lightly fixed in 200 μL wash buffer 1% BSA further supplemented with 0.1-0.2% PFA (Alfa Aesar) and immediately analyzed on an Attune™ NxT Cytometer (Invitrogen). If required, unstained and single-stained cell controls were used for compensation.

Cell-SELEX. The experimental design of cell-SELEX used in this study is summarized in FIG. 1A and Table 3. This selection process is modified from a published protocol.[27] The inventors started with an input of 10 nmol randomized naïve library, which theoretically provides ~$10^{16}$ unique sequences. Each sequence consists of a N45 random region, flanked by 18 nt constant region. A total volume of 700 μL of the naïve library was used (~14 μM) for incubation in the first round of SELEX, whereas 0.2 nmol aptamer pools in 400 μL (~0.2 μM, ~$10^{14}$ sequences) were used in subsequent rounds. In positive selection steps across SELEX rounds, decreasing amounts of Jurkat cells were resuspended with the aptamer pools in wash buffer supplemented with 0.1 mg/mL yeast tRNA, 0.1% BSA, and increasing concentrations of FBS and incubation at 4° C. Aptamer-bound Jurkat cells were then washed in an increasing number of times with wash buffer before aptamers were eluted from the cells by heating at 95° C. for 10 min in 500 μL water (only first round since there was no negative selection) or wash buffer with 0.1 mg/mL yeast tRNA and 0.1% BSA. Cell debris from the elution step was spun down and pelleted and heat-eluted aptamers were refolded simultaneously by centrifugation at 13,100×g for 5 min at 4° C., and the supernatant with refolded aptamers was collected for immediate PCR amplification (only first round) or for negative selection. In negative selection steps across SELEX rounds, the heat-eluted and refolded aptamer pools were incubated with 106 J.RT3.T3.5 cells at 4° C. for the corresponding time that was used in positive selection. Aptamer-bound J.RT3-T3.5 cells were removed by centrifugation, and the supernatant with unbound aptamer pool was collected for PCR amplification. After each SELEX round, the PCR cycle number required to amplify the aptamer pools was optimized. For preparation of ssDNA aptamer pools from the PCR product, the amplified double-stranded DNA (dsDNA) pool was captured via the biotinylated reverse strand using High Capacity Neutravidin™ Agarose Resin (Thermo Fisher), and the FAM-labeled forward single stranded DNA (ssDNA) was then selectively eluted from the reverse strand using 200 mM sodium hydroxide. The eluted forward ssDNA was desalted into water using a NAP-5 desalting column (GE Healthcare), dried using a Speed-Vac™ concentrator (Thermo Fisher), and resuspended and folded at 1 μM in wash buffer for the next round of SELEX.

Next generation sequencing (NGS) and sequence analysis. The aptamer pools from each SELEX round were amplified using the barcoded primers listed in Table 4 and sequenced on the MiSeq™ System (Illumina) using a MiSeq™ Reagent kit v2 (300 cycles). FASTAptamer™ v1.0.3 toolkit was used to analyze the FASTA files from sequencing.[29] Specifically, FASTAptamer-Count™ was first used to measure the reads for each unique sequence and rank the sequences by abundance (reads per million or RPM), and FASTAptamer-Enrich™ was then used to analyze the fold-enrichment of each unique sequence across adjacent rounds (e.g., RPM om Round Y divided by RPM om Round X; or later rounds over earlier rounds). MEME™ suite v5.3.3 Motif Discovery tool was used to find recurring motifs within the top 50 aptamers sequences in rounds 5-8 with the following settings: zero or one site per sequence for motif distribution, 0-order model of sequences for the background model, minimum motif width of 6 bases, maximum motif width of 45 bases, minimum sites per motif of 2, maximum sites per motif of 50, and search given strand only.[31] Phylogenetic trees of the top 50 aptamer sequences in rounds 5-8 were generated using the FigTree™ v1.4.3 graphical viewer to map sequence similarities and differences.[30] The NUPACK™ web application was used to predict the minimum free energy structure of aptamer sequences at 4° C. with 137 mM $Na^+$ and 5.5 mM $Mg^{++}$ concentrations.[33]

Subcellular localization of aptamer binding by trypsin flow and confocal imaging. The localization of tJBA8.1 binding on Jurkat cells at 4° C. was evaluated by both flow cytometry and confocal imaging. In the flow cytometry assay, Jurkat cells were first stained with Cy5-labeled tJBA8.1 as described above. After washing away unbound aptamer 50 μL of 0.25% trypsin or wash buffer with 1% BSA was then added to the cells for a 5-min incubation at 37° C. Immediately after incubation, 200 μL RPMI 1640 10% FBS was added to the cells (a 4-time trypsin volume) was added to the cells to neutralize trypsin enzymatic activity, and the cells were washed with 200 μL of wash buffer with 1% BSA before fixation in wash buffer 1% BSA further supplemented with 0.2% PFA. The change in Cy5-labeled tJBA8.1 binding on the Jurkat cell surface due to trypsin treatment was evaluated by flow cytometry.

For confocal imaging of tJBA8.1 subcellular compartment binding at 4° C., 15-mm round glass cover slips (Bellco Glass) were first sanitized in 95% ethanol for 5 min and subsequently dried over a 24-well plate for 15 min. Cover slips were next coated with 150 μL of 10 μg/mL poly-D-lysine (Sigma) for 2 hr at 37° C. in a 24-well plate. Meanwhile, $5\times10^6$ Jurkat cells were washed twice with wash buffer 1% BSA and stained with 300 μL of 200 nM Cy5-labeled RANL or tJBA8.1 aptamer in binding buffer for 30 min at 4° C. After aptamer binding, excess aptamer was removed by washing the cells twice with 200 μL of wash buffer 1% BSA, and the cells were resuspended in 200 μL wash buffer 1% BSA fir cover slip plating. For this, poly-D-lysine-coated-cover slips were washed once with 1 mL water in a 24-well plate to remove excess poly-D-lysine before adding cells. Jurkat cells were adhered to the coated cover slips by centrifugation at 650×g for 10 min at 4° C. After cell attachment, the excess buffer was aspirated, and adhered cells were fixed with 200 μL of 0.4% PFA for 10 min at room temperature. Fixative was washed off the cell-coated cover slips three times with 1 ml DPBS for 1 min each, and fixed cells were then permeabilized with 200 μL of 0.1% Triton X-100 (Sigma) for 10 min at room temperature. After washing as before FITC Phalloidin (1:100, Invitrogen) and DAPI (300 nM, Thermo fisher) in 200 μL DPBS were applied onto the fixed and permeabilized cells for 30 min at room temperature. Stained cells were then washed as before except in longer 5-min increments, and the stained cell-coated glass cover slips were mounted onto larger microscope slides (Fisher) with 10 μL polyvinyl acetate. Fluorescent images were taken at 60× magnification on a Leica SP8× confocal microscope and imaging processing, and overlaying was performed using Fiji/ImageJ.[82]

Target receptor pull-down and identification. About 85 million Jurkat cells (aptamer target cells) were used for each group. The membrane protein extraction and target purification process were modified from a previously published method.[34] Jurkat cell were washed three times in DPBS to remove media-derived proteins and then lysed foe 30 min at 4° C. with end-over-end mixing in ~3.3 mL hypotonic buffer comprised of 10 mM Tris-HCl (pH 7.5) supplemented EDTA-free cOmplete™ Protease Inhibitor Cocktail (Roche) and 1 mM phenylmethylsulfonyl fluoride. The resulting cell membrane debris were pelleted at 16,000×g for 15 min at 4° C. and washed 3 times with 3.3 ml of the same hypotonic buffer to remove released intracellular proteins. The membrane pellets were then each resuspended in 1 mL of wash buffer containing 1% Triton X-100, and same concentration of protease inhibitors and 1 mM PMSF to extract and solubilize membrane proteins. The extraction took place at 4° C. with end-for-end mixing for 30 minutes followed by a brief 5 min sonication in an ice water bath. Afterward, the samples were centrifuged as before and the supernatant containing the extracted proteins was collected and stored at −80° C. until next step or used immediately.

Once processed, the extract was first "pre-cleared." The extracts (1 mL) were thawed and spiled with 100 nM biotin RANL and 0.1 mg/mL yeast tRNA as anionic blocker. After incubating for 30 min at 4° C. with end-to-end mixing, 200 μL (2 mg) of MyOne™ Streptavidin C1 Dynabeads™ (Thermo Fisher) were added to the extracts and incubated for another 15 min at 4° C. to magnetically remove RANL-bound proteins. For the tJBA8.1 group, the pre-cleared extract was spiked with 0.1 mg/mL salmon sperm DNA (Invitrogen) as an additional anionic blocker and 100 nM biotinylated tJBA8.1. After incubating for 30 min at 4° C. with end-over-end mixing, 150 μL (1.5 mg) Streptavidin Dynabeads™ were added to the binding reaction and incubated for another 15 min at 4° C. to capture tJBA8.1-bound proteins. For the control group, 150 μL (1.5 mg) Streptavidin Dynabeads™ were instead saturated with 50 nmol biotin and added to the pre-cleared extract for a 30-min incubation at 4° C. Afterwards, the beads for both groups were washed 5 times for 5 min each with 1 mL cold wash buffer with 0.01% Triton X-100 to remove unbound proteins. To minimize the stripping off streptavidin from the beads, the captured membrane proteins were mildly eluted by heating the beads for 15 min at 47° C. for 15 minutes in loading buffer composed of 1× Laemmli sample buffer (containing SDS) supplemented with 4.6 M urea, 2.5% 2-mercaptoethanol, 10 mM EDTA, and 0.1% Triton X-100. Eluted proteins were stored at −80° C. unless used immediately.

After removing the Streptavidin Dynabeads™ from the supernatant, the eluted proteins (25 μL) were loaded onto a Novex™ Wedge 8% Tris-Glycine gel (Invitrogen) and separated by electrophoresis. The gel was stained with Colloidal Blue Staining Kit (Invitrogen) and imaged on a Gel Doc EZ system. Enriched bands were excised, and the excised band samples were digested, desalted, and subjected to tandem mass spectrometry (Orbitrap Elite). The data was analyzed with Proteome Discoverer™ 2.2 against Uniprot Human database.

siRNA knockdown study. Some $10^6$ Jurkat cells in logarithmic growth phase were nucleofected with a Human T cell Nucleofector™ Kit (Lonza) with program settings X-001 following the manufacturer instruction. 30 pmol of TFRC1 (Table 7) and NS siRNA (non-specific scrambled control) were used. After nucleofection, the cells were incubated for 22 hours and stained with Cy5 tJBA8.1 and FITC antihuman CD71 antibody. The aptamer staining and CD71 expression was evaluated with flow cytometry.

BLI. BLI studies were performed on an Octet RED96™ instrument (Sartorius) using either streptavidin or Ni-NTA biosensors (Sartorius). The sample buffer used for equilibration, loading, rinse, baseline, association, and dissociation steps was comprised of wash buffer supplemented with 1% BSA, 0.1 mg/mL yeast tRNA, 0.1 mg/mL salmon sperm DNA, and 0.01% Tween-20. All steps were performed at 25° C. with sample agitation at 1000 r.p.m. Biosensors were allowed to equilibrate in buffer for at least 10 min before loading. Loading thresholds were optimized for each capture ligand and analyte used. For streptavidin biosensors, 25 nM recombinant biotinylated human TfR1 was loaded until a 3.5 nm threshold and 50 nM biotinylated aptamers were loaded until a 0.5 nm threshold before performing rinse and baseline steps in buffer alone for 100 s each. For Ni-NTA biosensors, 150 nM recombinant His-tagged mouse TfR1 was loaded until a 0.7 nm threshold and 300 nM recombinant His-tagged human CNBP was loaded until a 3 nm threshold before performing cross-linking with 0.1 M EDC+ 0.025 M NHS in water for 60 s to stabilize the capture protein. The cross-linking reaction was quenched with 1 M ethanolamine pH 8.5 for 60 s before performing rinse and baseline steps as before. Afterwards, loaded sensors were associated with appropriate analytes at concentrations and times indicated in the figures and figure legends. Lastly, sensors were transferred to wells containing buffer alone for dissociation. Data analysis was done on the Octet™ Data Analysis 9.0 software (Sartorius). Association and dissociation curves were normalized to sensors that received capture ligand alone, and kinetic constants were calculated for datasets with several analyte concentrations by conducting a global fit of the association and dissociation curves to a 1:1 or 2:1 heterogeneous ligand binding model. The quality of the fit was evaluated using $R^2$ and $\chi^2$ values which are listed in Table 8 for the applicable datasets along with the calculated kinetic constants.

Aptamer, recombinant protein, and antibody competition studies. Jurkat or H9 cells were incubated with Cy5- or FAM-labeled aptamers at 25 nM with or without various fold-increased concentrations of competitor aptamers, FITC anti-human CD71 antibody or recombinant holo-transferrin proteins for 30 minutes at 4° C. Cells were washed 2 times with wash buffer with 1% BSA and fixed in wash buffer with 1% BSA and 0.2% PFA. Changes in aptamer binding affected by the competitors was evaluated on flow cytometer.

Western blotting. Western blotting was used to identify human TfR1 and HFE protein in the aptamer purified protein mixture. Aptamer-bound membrane proteins were first purified using the pull-down process described above with 100 nM biotinylated tJBA8.1 and XQ-2d. Eluted proteins (5 μL) were loaded on Novex™ WedgeWell™ 4-20% Tris-Glycine gel (Invitrogen) and separated by SDS-PAGE. Separated proteins were then blotted on a PVDF membrane (Bio-Rad) under 50 V for 3 hours on ice. Blotted membranes were subsequently blocked in TBST buffer (20 mM Tris, 150 mM NaCl, 0.1% Tween-20 at pH 7.5) supplemented with 3% BSA at room temperature for 1 hour. After blocking, membranes were washed twice with TBST for 5 min each before cutting into separate matched lanes for the different stains. Separated membranes were then stained with rabbit anti-human TfR1 (1:1000, Cell signaling, D7G9X) or rabbit anti-human HFE (1:1000, Abcam, EPR6750) diluted in TBST supplemented with 1% BSA overnight at 4° C. with gentle shaking. After primary incubation, the membranes were washed for 5 minutes 3 times with TBST and stained with secondary antibody, HRP-conjugated anti-rabbit IgG (1:5000, Sigma-Aldrich, A6154) diluted with TBST supplemented with 1% BSA for 1 hr at room temperature with gentle shaking. After secondary incubation, the membranes were then washed 3 times as before with TBST and imaged using SuperSignal™ West Pico PLUS substrate (Thermo Fisher) on a Xenogen™ IVIS (PerkinElmer) imager with small binning, aperture of f/2, and 10-60 s of exposure.

Raji cell depletion from PBMCs. Raji cells ($5\times10^6$) were first pre-stained with Vybrant™ CM-Dil dye (1:200 or 5 μM, Invitrogen) in serum-free RPMI 1640 medium at $10^6$ cells/mL for 30 min at room temperature. After washing the stained cells twice with wash buffer, approximately $3\times10^4$, $3\times10^5$, and $3\times10^6$ CM-Dil stained Raji cells were spiked into three aliquots of $30\times10^6$ freeze-thawed PBMCs to achieve 0.1%, 1%, and 10% spiked cell percentages. The mixed PBMC-Raji cells were then each stained with 500 μL 80 nM biotinylated tJBA8.1 in wash buffer supplemented with 0.5% BSA and 0.1 mg/mL yeast tRNA for 30 min at 4° C. Meanwhile, three aliquots of 150 μL Anti-Biotin MicroBeads (Miltenyi) were blocked in 500 μL of the same buffer for 30 min at 4° C. to prevent non-specific interactions. After staining, each group of aptamer-labeled mixed cells was washed once with wash buffer 0.5% BSA 0.1 mg/mL yeast tRNA and resuspended in 650 μL of the blocked microbead-containing solution for a 15-min incubation at 4° C. After attaching the microbeads to the aptamer-labeled cells, each group of fully labeled mixed cells was washed once as before and resuspended in 1 mL wash buffer 0.5% BSA 0.1 mg/mL yeast tRNA.

Prior to Raji cell depletion, three LS Columns (Miltenyi) were anchored onto a separation magnet (QuadroMACS Separator, Miltenyi) and each was washed once with 3 mL cold wash buffer with 0.5% BSA and 0.1 mg/mL yeast tRNA. Each column was equipped with a 30 μm Pre-Separation Filter (Miltenyi) before applying the full labeled mixed cells. The Raji cell-depleted PBMCs in the flow through were collected, and each filter-equipped column was washed three times with 3 mL cold wash buffer and 0.5% BSA into the same flow through collection tube. The captured Raji cells were collected by removing the columns from the magnet and flushing each with 5 mL autoMACS Rinsing Solution (Miltenyi, 2 mM EDTA) further supplemented with 3 mM EDTA (Invitrogen) and 0.5% BSA using a plunger. The cell composition in each fraction and corresponding depletion efficiencies were determined by antibody staining and flow cytometry.

Protein sequence alignment of TfR1 with mouse ortholog and hepatic homolog. Protein sequence alignment of human TfR1 (UniProt entry P02786; SEQ ID NO: 144) with mouse TfR1 (UniProt entry Q62351; SEQ ID NO: 146) and human TfR2 (UniProt entry Q9UP52; SEQ ID NO: 145) was performed with Clustal Omega v1.2.4.83,84. The percent identity between the extracellular domain of human TfR1 (residues 89-760) with each of the extracellular domains of mouse TfR1 (residues 89-763) and human TfR2 (residues 105-801) was calculated in the same program.

Statistical analysis. Data are expressed as mean±standard deviation (s.d.), unless otherwise stated, and the number of biological and technical replicates is specified in the figure legends. A two-tailed t-test was used for hypothesis testing when comparing only two populations. ANOVA was used for hypothesis testing comparing more than two populations to each other. Paired hypothesis testing was sometimes performed to account for large donor-to-donor, or experimental (e.g., nucleofection) variability. To correct for multiple comparisons, Tukey's test or Dunnett's test was used to adjust the P values when every mean was compared to every other mean or a control mean, respectively, whereas Šidík correction was used to adjust P values when select sets of means were compared, assuming independence. If comparisons could not be assumed independent from each other Bonferroni correction were used instead of Šidík correction to adjust the P values. Tested differences were considered significant if $P<0.05$. Unless otherwise stated in the methods, graphing and statistical tests were performed using GraphPad™ Prism v6.01 (GraphPad Software Inc.) for Windows

REFERENCES (1) Maude, et al. Tisagenlecleucel in Children and Young Adults with B-Cell Lymphoblastic Leukemia. *New Engl. J. Med.* 2018, 378(5), 439-448.

(2) Schuster, et al. Tisagenlecleucel in Adult Relapsed or Refractory Diffuse Large B-Cell Lymphoma. *New Engl. J. Med.* 2018, 380(1), 45-56.

(3) Neelapu, et al. Axicabtagene Ciloleucel CAR T-Cell Therapy in Refractory Large B-Cell Lymphoma. *New Engl. J. Med.* 2017, 377(26), 2531-2544.

(4) Locke, et al. Long-Term Safety and Activity of Axicabtagene Ciloleucel in Refractory Large B-Cell Lymphoma (ZUMA-1): A Single-Arm, Multicentre, Phase 1-2 Trial. *Lancet Oncol.* 2019, 20(1), 31-42.

(5) Wang, et al. KTE-X19 CAR T-Cell Therapy in Relapsed or Refractory Mantle-Cell Lymphoma. *New Engl. J. Med.* 2020, 382(14), 1331-1342.

(6) Abramson, et al. Lisocabtagene Maraleucel for Patients with Relapsed or Refractory Large B-Cell Lymphomas (TRANSCEND NHL 001): A Multicentre Seamless Design Study. *Lancet* 2020, 396(10254), 839-852.

(7) Munshi, et al. Idecabtagene Vicleucel in Relapsed and Refractory Multiple Myeloma. *New Engl. J. Med.* 2021, 384(8), 705-716.

(8) Berdeja, et al. Ciltacabtagene Autoleucel, a B-Cell Maturation Antigen-Directed Chimeric Antigen Receptor T-Cell Therapy in Patients with Relapsed or Refractory Multiple Myeloma (CARTITUDE-1): A Phase 1b/2 Open-Label Study. *Lancet* 2021, 398(10297), 314-324.

(9) Vormittag, et al. A Guide to Manufacturing CAR T Cell Therapies. *Curr. Opin. Biotech.* 2018, 53, 164-181.

(10) Cardle, et al. Biomaterials in Chimeric Antigen Receptor T-Cell Process Development. *Accounts Chem. Res.* 2020, 53(9), 1724-1738.

(11) Powell, et al. Efficient Clinical-Scale Enrichment of Lymphocytes for Use in Adoptive Immunotherapy Using a Modified Counterflow Centrifugal Elutriation Program. *Cytotherapy* 2009, 11(7), 923-935.

(12) Maude, et al. Chimeric Antigen Receptor T Cells for Sustained Remissions in Leukemia. *New Engl. J. Med.* 2014, 371(16), 1507-1517.

(13) Iyer, et al. Industrializing Autologous Adoptive Immunotherapies: Manufacturing Advances and Challenges. *Front. Med.* 2018, 5, 150.

(14) Hoffmann, et al. Differences in Expansion Potential of Naive Chimeric Antigen Receptor T Cells from Healthy Donors and Untreated Chronic Lymphocytic Leukemia Patients. *Front. Immunol.* 2018, p 1956.

(15) Ruella, et al. Induction of Resistance to Chimeric Antigen Receptor T Cell Therapy by Transduction of a Single Leukemic B Cell. *Nat. Med.* 2018, 24(10), 1499-1503.

(16) Jie, et al. Exploratory Trial of a Biepitopic CAR T-Targeting B Cell Maturation Antigen in Relapsed/Refractory Multiple Myeloma. *Proc. Natl. Acad. Sci.* 2019, 116(19), 9543-9551.

(17) Miltenyi, et al. High Gradient Magnetic Cell Separation with MACS. *Cytometry* 1990, 11(2), 231-238.

(18) Alcantara, et al. CAR T-Cells for T-Cell Malignancies: Challenges in Distinguishing between Therapeutic, Normal, and Neoplastic T-Cells. *Leukemia* 2018, 32(11), 2307-2315.

(19) Fleischer, et al. Targeting T Cell Malignancies Using CAR-Based Immunotherapy: Challenges and Potential Solutions. *J. Hematol. Oncol.* 2019, 12(1), 141.

(20) Zhou, and Rossi, Aptamers as Targeted Therapeutics: Current Potential and Challenges. *Nat. Rev. Drug Disc.* 2017, 16(6), 440.

(21) Zhang, et al. Programmable Hydrogels for Controlled Cell Catch and Release Using Hybridized Aptamers and Complementary Sequences. *J. Am. Chem. Soc.* 2012, 134(38), 15716-15719.

(22) Rusconi, et al. RNA Aptamers as Reversible Antagonists of Coagulation Factor IXa. *Nature* 2002, 419, 90-94.

(23) Kacherovsky, et al. Traceless Aptamer-Mediated Isolation of CD8+ T Cells for Chimeric Antigen Receptor T-Cell Therapy. *Nat. Biomed. Eng.* 2019, 3(10), 783-795.
(24) Robertson, and Joyce, Selection in Vitro of an RNA Enzyme That Specifically Cleaves Single-Stranded DNA. *Nature* 1990, 344, 467-468.
(25) Tuerk, and Gold, Systematic Evolution of Ligands by Exponential Enrichment: RNA Ligands to Bacteriophage T4 DNA Polymerase. *Science* 1990, 249 (4968), 505-510.
(26) Ellington, and Szostak, In Vitro Selection of RNA Molecules That Bind Specific Ligands. *Nature* 1990, 346, 818-822.
(27) Sefah, et al. Development of DNA Aptamers Using Cell-Selex. *Nature Protoc.* 2010, 5, 1169-1185.
(28) Weiss, and Stobo, Requirement for the Coexpression of T3 and the T Cell Antigen Receptor on a Malignant Human T Cell Line. *J. Exp. Med.* 1984, 160(5), 1284-1299.
(29) Alam, et al. FASTAptamer: A Bioinformatic Toolkit for High-Throughput Sequence Analysis of Combinatorial Selections. *Mol. Ther. Nucleic Acids* 2015, 4(3), e230.
(30) Rambaut, FigTree-Version 1.4. 3, a Graphical Viewer of Phylogenetic Trees. Computer program distributed by the author, website: http://tree.bio.ed.ac.uk/software/figtree. 2016.
(31) Bailey, et al. MEME Suite: Tools for Motif Discovery and Searching. *Nucl. Acids Res.* 2009, 37, W202-W208.
(32) Gold, et al. Aptamer-Based Multiplexed Proteomic Technology for Biomarker Discovery. *PLOS ONE* 2010, 5(12), e15004.
(33) Zadeh, et al. NUPACK: Analysis and Design of Nucleic Acid Systems. *J. Compt. Chem.* 2011, 32 (1), 170-173.
(34) Shangguan, et al. Cell-Specific Aptamer Probes for Membrane Protein Elucidation in Cancer Cells. *J. Proteome Res.* 2008, 7(5), 2133-2139.
(35) Montemiglio, et al. Cryo-EM Structure of the Human Ferritin-Transferrin Receptor 1 Complex. *Nat. Commun.* 2019, 10, 1121.
(36) Tortorella, and Karagiannis, Transferrin Receptor-Mediated Endocytosis: A Useful Target for Cancer Therapy. *J. Mem. Biol.* 2014, 247, 291-307.
(37) Gatter, et al. Transferrin Receptors in Human Tissues: Their Distribution and Possible Clinical Relevance. *J. Clin. Path.* 1983, 36(5), 539-545.
(38) Caruso, A.; Licenziati, S.; Corulli, M.; Canaris, A. D.; De Francesco, M. A.; Fiorentini, S.; Peroni, L.; Fallacara, F.; Dima, F.; Balsari, A.; Turano, A. Flow Cytometric Analysis of Activation Markers on Stimulated T Cells and Their Correlation with Cell Proliferation. *Cytometry* 1997, 27, 71-76.
(39) Yeh, et al. Transferrin Binding by Peripheral Blood Mononuclear Cells in Human Lymphomas, Myelomas and Leukemias. *Vox Sanguinis* 1984, 46(4), 217-223.
(40) Mayle, et al. The Intracellular Trafficking Pathway of Transferrin. *Biochimica et Biophysica Acta* (BBA)—*Gen. Subjects* 2012, 1820(3), 264-281.
(41) Boumsell, et al. Anti-CD71 Monoclonal Antibodies and Uses Thereof for Treating Malignant Tumor Cells. U.S. Pat. No. 8,409,573 B2, Apr. 2, 2013.
(42) Wu, et al. DNA Aptamer Selected against Pancreatic Ductal Adenocarcinoma for In Vivo Imaging and Clinical Tissue Recognition. *Theranostics* 2015, 5(9), 985-994.
(43) Wu, et al. Elucidation and Structural Modeling of CD71 as a Molecular Target for Cell-Specific Aptamer Binding. *J. Am. Chem, Soc.* 2019, 141(27), 10760-10769.
(44) Bennett, et 1. Crystal Structure of the Hereditary Haemochromatosis Protein HFE Complexed with Transferrin Receptor. *Nature* 2000, 403, 46-53.
(45) Cheng, et al. Structure of the Human Transferrin Receptor-Transferrin Complex. *Cell* 2004, 116 (4), 565-576.
(46) Feder, et al. The Hemochromatosis Gene Product Complexes with the Transferrin Receptor and Lowers Its Affinity for Ligand Binding. *Proc. Natl Acad. Sci.* 1998, 95(4), 1472-1477.
(47) Waheed, et al. Regulation of Transferrin-Mediated Iron Uptake by HFE, the Protein Defective in Hereditary Hemochromatosis. *Proc. Natl. Acad. Sci.* 2002, 99(5), 3117-3122.
(48) Feder, et al. A Novel MHC Class I-like Gene Is Mutated in Patients with Hereditary Haemochromatosis. *Nat. Genet.* 1996, 13(4), 399-408.
(49) Schmidt, et al. The Transferrin Receptor Modulates Hfe-Dependent Regulation of Hepcidin Expression. *Cell Metabol.* 2008, 7(3), 205-214.
(50) Scott, et al. Membrane Transferrin Receptor (TfR) and Nuclear Proliferation-Associated Ki-67 Expression in Hemopoietic Malignancies. *Leukemia* 1988, 2(7), 438-442.
(51) Ploszynska, et al. Cytometric Evaluation of Transferrin Receptor 1 (CD71) in Childhood Acute Lymphoblastic Leukemia. *Folia Histochem. Cytobio.* 2012, 50 (2), 304-311.
(52) Habeshaw, et al. Correlation of Transferrin Receptor Expression with Histological Class and Outcome in Non-Hodgkin Lymphoma. *Lancet* 1983, 321(8323), 498-501.
(53) das Gupta, and Shah, Correlation of Transferrin Receptor Expression with Histologic Grade and Immunophenotype in Chronic Lymphocytic Leukemia and Non-Hodgkin's Lymphoma. *Hematol. Pathol.* 1990, 4(1), 37-41.
(54) Kozlowski, et al. Transferrin Receptor Expression on AML Blasts Is Related to Their Proliferative Potential. *Brit. J. Haematol.* 1988, 69(2), 275-280.
(55) Allen, et al. Autologous Lymphapheresis for the Production of Chimeric Antigen Receptor T Cells. *Transfusion* 2017, 57 (5), 1133-1141.
(56) Armas, et al. Cellular Nucleic Acid Binding Protein Binds G-Rich Single-Stranded Nucleic Acids and May Function as a Nucleic Acid Chaperone. *J. Cell. Biochem.* 2008, 103(3), 1013-1036.
(57) Benhalevy, D.; Gupta, S. K.; Danan, C. H.; Ghosal, S.; Sun, H. W.; Kazemier, H. G.; Paeschke, K.; Hafner, M.; Juranek, S. A. The Human CCHC-Type Zinc Finger Nucleic Acid-Binding Protein Binds G-Rich Elements in Target MRNA Coding Sequences and Promotes Translation. *Cell Reports* 2017, 18 (12), 2979-2990.
(58) David, et al. CNBP Controls Transcription by Unfolding DNA G-Quadruplex Structures. *Nucl. Acids Res.* 2019, 47(15), 7901-7913.
(59) Kikin, et al. QGRS Mapper: A Web-Based Server for Predicting G-Quadruplexes in Nucleotide Sequences. *Nucl. Acids Res.* 2006, 34(suppl_2), W676-W682.
(60) Lee, et al. CNBP Controls Tumor Cell Biology by Regulating Tumor-Promoting Gene Expression. *Mol. Carcinog.* 2019, 58(8), 1492-1501.
(61) Liu, et al. Alternative Splicing Analysis in Human Monocytes and Macrophages Reveals MBNL1 as Major Regulator. *Nucl. Acids Res.* 2018, 46(12), 6069-6086.
(62) Hovanessian, et al. The Cell-Surface-Expressed Nucleolin Is Associated with the Actin Cytoskeleton. *Exp. Cell Res.* 2000, 261(2), 312-328.

(63) Bates, et al. Antiproliferative Activity of G-Rich Oligonucleotides Correlates with Protein Binding*. *J. Biol. Chem.* 1999, 274(37), 26369-26377.
(64) Wilner, et al. An RNA Alternative to Human Transferrin: A New Tool for Targeting Human Cells. *Mol. Ther. Nucl. Acids* 2012, 1, e21.
(65) Zhang, et al. A DNA Aptameric Ligand of Human Transferrin Receptor Generated by Cell-SELEX. *Int. J. Mol. Sci.* 2021, 22(16), 8923.
(66) Zhang, et al. Transferrin Receptor-Mediated Internalization and Intracellular Fate of Conjugates of a DNA Aptamer. *Mol. Ther. Nuc. Acids* 2022, 27, 1249-1259.
(67) Ruigrok, et al. Characterization of Aptamer-Protein Complexes by X-Ray Crystallography and Alternative Approaches. *Internat. J. Mol. Sci.* 2012, 13(8), 10537-10552.
(68) Kacherovsky. Discovery and Characterization of Spike N-Terminal Domain-Binding Aptamers for Rapid SARS-CoV-2 Detection. *Angewandte Chemie International Edition* 2021, 60 (39), 21211-21215.
(69) Worthen, and Enns, The Role of Hepatic Transferrin Receptor 2 in the Regulation of Iron Homeostasis in the Body. *Front. Pharmacol.* 2014, 5, 34.
(70) Reyes-Reyes, et al. A New Paradigm for Aptamer Therapeutic AS1411 Action: Uptake by Macropinocytosis and Its Stimulation by a Nucleolin-Dependent Mechanism. *Cancer Res.* 2010, 70 (21), 8617-8629.
(71) Roxo, et al. G-Quadruplex-Forming Aptamers-Characteristics, Applications, and Perspectives. *Molecules* 2019, 24 (20), 3781.
(72) Finney, et al. CD19 CAR T Cell Product and Disease Attributes Predict Leukemia Remission Durability. *J. Clin. Invest.* 2019, 129(5), 2123-2132.
(73) Bersenev, CAR-T Cell Manufacturing: Time to Put It in Gear. *Transfusion* 2017, 57(5), 1104-1106.
(74) Cooper, et al. An "off-the-Shelf" Fratricide-Resistant CAR-T for the Treatment of T Cell Hematologic Malignancies. *Leukemia* 2018, 32(9), 1970-1983.
(75) Xu, et al. 2B4 Costimulatory Domain Enhancing Cytotoxic Ability of Anti-CD5 Chimeric Antigen Receptor Engineered Natural Killer Cells against T Cell Malignancies. *J. Hematol. Oncol.* 2019, 12(1), 49.
(76) Stroncek, et al. Myeloid Cells in Peripheral Blood Mononuclear Cell Concentrates Inhibit the Expansion of Chimeric Antigen Receptor T Cells. *Cytotherapy* 2016, 18(7), 893-901.
(77) Sylvestre, et al. Identification of a DNA Aptamer That Binds to Human Monocytes and Macrophages. *Bioconj. Chem.* 2020, 31(8), 1899-1907.
(78) Olden, et al. Cationic Polymers for Non-Viral Gene Delivery to Human T Cells. *J. Control. Release* 2018, 282, 140-147.
(79) Olden, et al. Identifying Key Barriers in Cationic Polymer Gene Delivery to Human T Cells. *Biomater. Sci.* 2019, 7(3), 789-797.
(80) Biglione, et al. Optimizing Circulating Tumor Cells' Capture Efficiency of Magnetic Nanogels by Transferrin Decoration. *Polymers* 2018, 10(2), 174.
(81) Li, et al. Enhanced in Vivo Blood-Brain Barrier Penetration by Circular Tau-Transferrin Receptor Bifunctional Aptamer for Tauopathy Therapy. *J. Am. Chem. Soc.* 2020, 142(8), 3862-3872.
(82) Schindelin, et al: An Open-Source Platform for Biological-Image Analysis. *Nat. Methods* 2012, 9(7), 676-682.
(83) Goujon, et al. A New Bioinformatics Analysis Tools Framework at EMBL-EBI. *Nucl. Acids Res.* 2010, 38 (suppl_2), W695-W699.
(84) Sievers, et al. Fast, Scalable Generation of High-Quality Protein Multiple Sequence Alignments Using Clustal Omega. *Mol. Syst. Biol.* 2011, 7(1), 539.

Example 2: Traceless Multiplexed Cell Isolation System with Aptamers

Summary: Cell isolation systems that purify cells without masking the receptors with labeling materials are beneficial for both scientific studies and pharmaceutical applications. While methods that tracelessly isolate one cell type at a time have been reported using engineered antigen binding fragments and aptamers, a multiplexed cell isolation system with removable labeling reagent is still needed. To address this, two aptamer sequences were used along with their designated complementary strands (antidotes) to tracelessly isolate two target cell types from a single specimen. This technology is useful in circumstances where the source of cells is limited for repeated positive selection of multiple cell types, such as CAR T cell manufacturing that requires both $CD4^+$ and $CD8^+$ T cells from patients that have undergone one or more cytotoxic chemotherapies. In this study, the inventors tested the feasibility of multiplexed traceless cell isolation with JBA8.1 and A3t aptamers. JBA8.1 is a previously developed CD71 protein binder that can target activated T cells and some cancer cell lines. A3t is a previously reported CD8 protein binder used for traceless isolation of CD8 T cells from peripheral blood mononuclear cells (PBMCs). The inventors modified JBA8.1 (into JBA1.2) and developed an antidote that is orthogonal to A3t strand displacement. The JBA1.2 and its antidote were first incorporated into a cell isolation system to separate activated T cells based on their CD71 expression levels. Moving forward, JBA1.2 was tested in combination of A3t to isolate activated $CD4^+$ T cells and resting $CD8^+$ T cells. Orthogonal strand displacements were used to elute these cells into separate fractions after one staining procedure.

Positive Cell Isolation Technology with Removable Targeting Ligand

Isolation systems that purify cells without masking their receptors with purification agents are necessary in biomedical fields such as cell signaling pathways research and are desirable for clinical adoptive cell therapies. Reported traceless cell isolation methods using engineered antigen binding fragments or aptamers have been limited to processing a single cell type at a time. There remains an unmet need for cell isolation processes that rapidly sort for multiple target cell types. Here, two aptamers were utilized along with their designated complementary strands (reversal agents) to tracelessly isolate two cell types from a mixed cell population with one aptamer labeling step and two sequential cell elution steps with reversal agents. A CD71-binding aptamer (rvCD71apt) was engineered and reversal agent pair to be used simultaneously with our previously-reported traceless purification approach using CD8 aptamer (rvCD8apt) and its reversal agent. The compatibility of the two aptamer displacement mechanisms was verified by flow cytometry, and the feasibility of incorporating rvCD71apt with a magnetic solid state. rvCD71apt was then combined with rvCD8apt to respectively isolate activated $CD4^+$ T cells and resting $CD8^+$ cells by eluting these target cells into separate fractions with orthogonal strand displacements. This is the first demonstration of isolating different cell types using two aptamers and reversal agents at the same time. Potentially, different or more aptamers can be included into this traceless multiplexed isolation system for diverse applications with shortened operation time and lower production cost.

Current Development of Removable Targeting Ligands

Immunoaffinity-based cell isolation methods are effective ways to purify specific cell types and include fluorescent-activated cell sorting (FACS)[1], magnetic cell separation[2], and cell affinity chromatography[3,4]. In contrast to separation methods based on physical differences (e.g., size, density) between cells that often result in lower isolation resolution[5,6], immunoaffinity-based methods rely on labeling cell surface proteins with antibodies or antibody fragments to differentiate between cell populations. The labeled cells are then separated from non-labeled cells using solid supports such as magnetic beads or agarose resins. In positive selection strategies, the desired cells are directly labeled for isolation, whereas in negative selection strategies, the undesired cells are labeled for removal from the desired cells. Positive selections usually result in high purity of target cells[7,8] but with certain surface proteins still bound by the ligands and solid supports. Negative selections rely on a panel of antibodies and result in residue-free target cell products but often with reduced purity and yield dependent on sample variability[9,10]. Since the antibodies and solid supports used for isolation can potentially induce unwanted immunogenicity[11], block cell signaling pathways[12], and impact cell proliferation[13], cells isolated for cell therapy applications such as stem cell transplantation[14] and adoptive T cell therapy[15,16] are ideally free of cell labeling materials. Thus, there has been a focus in the art on developing positive isolation strategies that employ removable selection agents[17].

Fab-Streptamer® is a "quasi-traceless" protein-based isolation system using modified Fabs (antigen binding fragments) that have lower binding affinity to targets in monovalent form and higher affinity as multivalent complexes. Fabs fused with Strep-Tag peptides[18,19] will form high affinity tetramers in the presence of Strep-Tactin[20], a mutated streptavidin, through non-covalent interaction. The interaction between Fab-Strep-Tag® and Strep-Tactin® is reversable upon competition with high affinity D-biotin for Strep-Tactin® binding. Upon release from Strep-Tactin®, the monovalent Fab has reduced affinity for target and will then separate from the target spontaneously. This technology has been used to purify proteins[21], as well as to isolate cells in clinical adoptive cell therapy manufacturing[4, 22-24]. However, D-biotin is a universal target releasing agent in this system. Isolating multiple cell types with Fab-Streptamer® is therefore a time-consuming process that requires repeated staining and dissociating steps for different targets.

Gao and coworkers developed a DNA nanotechnology method for reversible antibody labeling and sorting of targets by functionalizing antibodies with DNA oligonucleotides consisting of a toehold for on-demand displacement and a targeting probe for anchoring onto the solid state[25]. Multiple targets can be captured using an antibody cocktail with subsets subsequently recovered by sequence-dependent strand displacement initiated at the toehold domain to detach antibodies from solid supports. This elegant approach has been applied to isolate multiple immune cell types from mouse splenocytes with high purity and allows fast sequential isolation of multiple cell types with a single staining step[26], but the end product still bound by antibodies. In addition, antibodies are a relatively costly and thermosensitive reagent.

Aptamers are short, folded single-stranded DNA or RNA oligonucleotides that bind to a wide range of targets including cell surface protein receptors. Typically selected from in vitro library screening, aptamers have comparable to antibodies affinity and specificity, but have the benefits of reversible binding, lower production cost, faster and more consistent manufacturing process [27-29]. Aptamer binding can be reversed either by universal reagents, such as DNases, ion chelators, and competitors,[30-32] or by complementary nucleic acid strands, also called reversal agents. When the reversal agent anneals to portions of the aptamer, part of the folded aptamer may be displaced, losing its structure essential for binding. This unique characteristic of aptamers has been utilized in various applications. For example, the Ch-9.3t RNA aptamer which serves as an anticoagulant by targeting factor IXa, can be neutralized using a chemically modified RNA sequence complementary to its loop structure[33]. Another example is E07, an EGFR targeting RNA aptamer that was incorporated into FACS and MACS (magnetic-activated cell sorting) systems to isolate $EGFR^+$ epidermoid carcinoma cells. These $EGFR^+$ target cells were incubated with E07 reversal agent for aptamer removal, and were suitable for downstream studies on EGFR-related pathways[34]. One can also design highly effective reversal agents by implementing an overhang sequence, also referred to as a toehold, on either the 5'- or 3'-end of the aptamer. With the assistance of toehold-initiated annealing, the strand displacement rate constant can be significantly increased[35,36]. For example, a CD8 receptor-binding aptamer, A3t, has been previously developed with an 8 nucleotides (nt) toehold for isolating $CD8^+$ T cells from PBMCs. With 20 minutes of incubation using reversal agent at room temperature, over 90% of the DNA aptamer is removed from cells. The isolated $CD8^+$ T cells are free of labeling materials and are ideal for manufacturing adoptive cell therapeutic products[16].

Presented herein is a demonstration of the isolation of multiple cell types from a single selection process by using multiple aptamers paired with their reversal agents. To achieve this, different DNA toeholds were introduced into two targeting aptamers so that two cell types can be captured together upon aptamers binding and then sequentially eluted with reversal agents. Aptamers tolerate sequence modifications at the regions not essential for receptor binding. First, an existing CD71-binding aptamer, JBA8.1[37], was modified to carry a suitable toehold and a displaceable stem structure for reversal agent annealing and branch migration. The new variant was named as rvCD71apt (reversible CD71 aptamer). The corresponding reversal agent was optimized to achieve robust strand displacement. When immobilized on magnetic beads, the rvCD71apt/reversal agent pair separate bulk-stimulated PBMCs into different selection fractions based on their CD71 expression level. Next, rvCD71apt was combined with a previously reported CD8 aptamer used for cell isolation, A3t (renamed as rvCD8apt, reversible CD8 aptamer)[16], as a traceless multiplex cell sorting system for purifying activated $CD4^+$ T cells and resting $CD8^+$ cells. In the future, this isolation system can be expanded to incorporate different and/or more aptamers and reversal agent pairs and applied to various types of solid supports for diverse applications.

Materials and Methods

Cell Preparation

Jurkat cell (human T-ALL) culture was maintained in RPMI 1640 media (Corning) supplemented with 10% FBS (Life Tech). Primary human PBMCs were Ficoll™-enriched apheresis product purchased from Bloodworks Northwest.

CD4+ T cell and CD8+ T cell subtypes were isolated from PBMCs using negative cell isolation kits (Miltenyi) to obtain cells without antibody and magnetic bead residue. T cells were stimulated with recombinant cytokines (Miltenyi) and CD3/CD28 stimulation Dynabeads™ (Invitrogen) on day 0. CD4+ T cell culture media consisted of RPMI 1640 media with 10% FBS, recombinant human (rh) IL-7 (5 ng/mL) and IL-15 (0.5 ng/mL). CD8+ T cell culture media consisted of RPMI 1640 with 10% FBS, and rhIL-2 (20 ng/mL) and rhIL-15 (0.5 ng/mL). Unless stated otherwise, the stimulation beads were removed by pipetting cells with p1000 tips and separated on a magnetic rack on day 9. The cells were kept in the complete culture media containing cytokines for expansion until day 21. For bulk-stimulated PBMCs, the T cell fraction in PBMCs was used to calculate the amount of stimulation beads and cytokine needed.

Flow Cytometry and Staining Reagents

The following live/dead staining dye and antibodies were used for staining cells: Zombie Violet (1:500 in 100 μL containing $10^6$ cells, BioLegend), FITC-antihuman CD71 (1:100, BioLegend, CY1G4), Super Bright 702-antihuman CD56 (1:100, Invitrogen, TULY56), APC-Cy7-antihuman CD14 (1:200, Molecular probes, 6ID3), Super Bright 600-antihuman CD19 (1:100, Invitrogen, SJ25C1), PE-antihuman CD3 (1:100, BioLegend, HIT3a), APC-antihuman CD8a (1:100, BioLegend, RPA-T8), FITC-antihuman CD8a (1:100, BioLegend, RPA-T8), APC-Cy7-antihuman CD4 (1:100, BioLegend, RPA-TA), FITC-streptavidin (1:500, BioLegend), Alexa Fluor 647-streptavidin (1:500, BioLegend), and PE-streptavidin (1:500, BioLegend).

In the aptamer staining process, wash buffer and binding buffer were used for washing and staining. Wash buffer, which contains 137 mM $Na^+$ and 5.5 mM $Mg^{2+}$, was made with 500 mL DPBS (with calcium and magnesium, Corning) plus 2.5 mL 1 M $MgCl_2$ (Fisher) and 2.25 g D-glucose (Sigma-Aldrich). Binding buffer was made of wash buffer supplemented with 0.1 mg/mL yeast tRNA (Invitrogen) and 1% BSA (Miltenyi), unless stated otherwise. Aptamers were labeled with either FAM (6-carboxyfluorescein) fluorophore or biotin. To anneal aptamers, the DNA was adjusted to 1 μM in wash buffer and heated at 95° C. for 5 min followed by snap chilling on ice for at least 15 min. The cell staining process was kept at 4° C. to avoid aptamer internalization. RAN aptamer, a sequence that does not bind to any target cell types in this study, was used as control. The cell-associated fluorescence from aptamer binding was analyzed with an Attune NxT cytometer (Invitrogen).

Oligonucleotide Design

Customized oligonucleotides, including aptamers and antidotes were ordered from Integrated DNA Technology (IDT). Modifications of JBA8.1 was done partially with NUPACK™ web application.[16] The settings for annealed aptamer structures were 137 mM $Na^+$ and 5.5 mM $Mg^{2+}$, and temperature at 4° C. The settings for antidote annealing were the same cation concentrations, with temperature at 25° C. The application simulates aptamer and antidote-annealed aptamer structures when sequences folded into their thermally stable structures.

Aptamer Displacement with Reversal Agents

The cells were first stained with targeting aptamers, and then washed with wash buffer to remove unbound aptamers. Based on previously optimized aptamer displacement conditions,[16] the inventors used 100× concentration of agents (e.g., applying 100 nM reversal agent to cells stained with 1 nM aptamer) for incubations at room temperature for 10-20 min.[16] The reversal agents were first heated at 37° C. in water bath for 5 min, and then applied to the aptamer-stained cells. After washing off the displaced DNA strands, the remaining aptamer binding was evaluated by flow cytometry.

rvCD7Apt Cell Sorting with MACS

Bulk-stimulated PBMCs were used in the rvCD71apt MACS (Miltenyi) cell sorting studies. Cells were activated using the method described in section above on day 0. The CD3/CD28 stimulation beads were removed on day 3 by a magnetic rack. 50 million stimulated PBMCs were first applied to an LS column (Miltenyi) anchored on a magnetic separator (Miltenyi) to remove cells with residual stimulation beads. The resulting cells were stained with 1 mL 40 nM biotinylated aptamer in wash buffer with 0.5% BSA and 0.1 mg/mL yeast tRNA for 30 minutes at 4° C. After staining, the cells were washed and labeled with 150 μL anti-biotin Microbeads (Miltenyi) in the same buffer with 15 min incubation at 4° C. 30 μL of anti-biotin Microbead stock solution was used for every 10 million total cells. The labeled cells were spun down and resuspended in buffer to remove excess beads. In the meantime, an LS column was rinsed with wash buffer containing 0.5% BSA and 0.1 mg/mL tRNA to reduce non-specific interactions. After the labeled cells were applied to the column for isolation, the column was washed 3 times with wash buffer containing 0.5% BSA. 1 mL of 4 μM pre-warmed reversal agent (100×) in wash buffer with 0.5% BSA was then applied to the column. An initial 600 μL of reversal agent solution was passed through the column and the remaining volume was trapped in the column with a Luer lock plug. The reversal agent solution was incubated in the column for 10 minutes at room temperature, after which the plug was removed, and the column was washed 3 times for cell collection. The remaining cells that were not eluted by reversal agent displacement, were collected by taking the LS column off the magnetic separator and flushed with wash buffer with a plunger. The CD71 expression and cell type of the isolated cells in each fraction were evaluated by antibody staining and flow cytometry.

Removing Un-Eluted Cells with Dextran Sulfate

Activated CD4+ T cells were isolated and cultured using the method described in section 2.1. Resting CD8+ T cells were isolated using the method described section 2.1. Both cell types were first stained with Zombie Violet™ live/dead staining dye, followed by 60 nM biotinylated rvCD71apt or 5 nM biotinylated rvCD8apt labeling (0.2 million cells in 100 μL 5 binding buffer) for 20 min at 4° C. The surface bound biotinylated aptamer was then labeled with secondary staining, streptavidin-AF647, at 4° C. for 15 min. The cells were washed and incubated in dextran sulfate (6.5-10 kDa, Sigma Aldrich) dissolved in wash buffer with 0.5% BSA at 0, 0.16, 0.31, 0.63, 1.25, 2.5, 5, 10, and 12 mM at room temperature for 20 min, with or without 6 μM rvCD71apt reversal agent or 0.5 μM rvCD8apt reversal agent. The cells were washed, fixed with wash buffer with 1% BSA and 0.1% PFA (paraformaldehyde), and then analyzed by flow cytometry. The AF647 fluorescence associated with cells due to aptamer binding was normalized to the control group without dextran sulfate and the reversal agents.

Traceless Multiflexed Cell Isolation with Serial Reversal Agent Elution

About 45-50 million pre-sort cells consisting of activated CD4+ T cells and PBMCs were washed with DPBS and 0.5% BSA and resuspended in 900 μL binding buffer. In this mixed cell population, the CD4+CD71+ cells (activated CD4+ T cells) were rvCD71apt target cells, while the CD8+ cells (mostly resting CD8+ T cells) were rvCD8apt target cells. This mixed population was pre-cleared using 1 mg MyOne™ Streptavidin C1 Dynabeads™ (Invitrogen) to remove non-specific binding cells by incubation at room temperature for 20 min, followed by bead removal using a magnetic rack (MagRack™ 6, GE). The cleared cells were set on ice during beads preparation. To prepare the isolation beads, 0.64 mg Dynabeads™ were washed and resuspended in 640 μL wash buffer with 0.5% BSA and 0.1 mg/mL yeast tRNA. The beads were incubated in the buffer for at least 20 min at 4° C. to reduce non-specific interaction. Dynabeads™ (0.6 mg) were transferred into 500 μL of 60 nM biotinylated rvCD71apt in wash buffer with 0.5% BSA and 0.1 mg/mL yeast tRNA. The remaining 0.04 mg Dynabeads™ were transferred into 500 μL of 5 nM biotinylated rvCD8apt in the same buffer. These streptavidin beads were incubated with the biotinylated aptamers for 15 min at 4° C. for aptamer immobilization to take place. The aptamer-labeled beads were washed and resuspended in 50 μL wash buffer with 0.5% BSA and 0.1 mg/mL yeast tRNA.

To isolate the target cells, the aptamer-beads were incubated with the cleared cells for 30 min at 4° C. and separated on the magnetic rack. The cell-aptamer-bead complex was applied to the magnetic rack to isolate the bead-labeled target cells. The unbound cells were removed by gentle washing. The rvCD71apt reversal agent (1 mL of 6 μM) in wash buffer with 0.5% BSA was pre-heated at 37° C., and then applied to the cell-aptamer-bead complex. The solution was incubated at room temperature for 20 min on rotation to displace rvCD71apt. The beads were then thoroughly washed to collect the activated $CD4^+$ T cells. Next, 10 mM dextran sulfate was applied for 20 min at room temperature to wash off the un-eluted activated $CD4^+$ T cells. After rinsing dextran sulfate off the cells with wash buffer 0.5% BSA, the solution of 0.5 μM rvCD8apt reversal agent in 1 mL wash buffer containing 0.5% BSA was applied for 15 minutes at room temperature and then collected through washing. The remaining cells were collected along with the magnetic beads. All incubations were done in DNA lo-bind tubes (Fisher) on rotation. The washing steps implemented between each incubation procedure were done by using wash buffer and 0.5% BSA. The cell compositions collected in each step were evaluated by flow cytometry after staining with human CD71, CD4, and CD8 antibodies.

The purity of target cells collected in the reversal agent elution steps is the percentage of cells within the population gates. rvCD71apt target cells were gated on $CD4^+CD71^+$ cells. rvCD8apt target cells were gated on $CD8^+$ cells. The yield of the target cells is defined as the target cell number counted in the reversal agent elution steps divided by total target cell number counted in the pre-clearing, reversal agent elution, dextran sulfate wash steps, as well as the number of cells that were not captured by the aptamers and were not eluted by the reversal agents.

Statistical Analysis

Data are shown as mean±s.d of 3 biological replicates unless stated otherwise. Two-tailed unpaired t test was used to compare two populations. If there were more than two populations, one-way ANOVA was used to test the hypothesis. Tukey's test was used for multiple comparison in which every mean was compared to every other means. If $P<0.05$ after adjustments, the difference is considered significant. Graphing and statistical analysis was performed on GraphPad Prism 6 for Windows, version 6.01.

Results

Modification of CD71-Binding Aptamer to Achieve Multiplexed Sorting

Figures 11A, 11B:
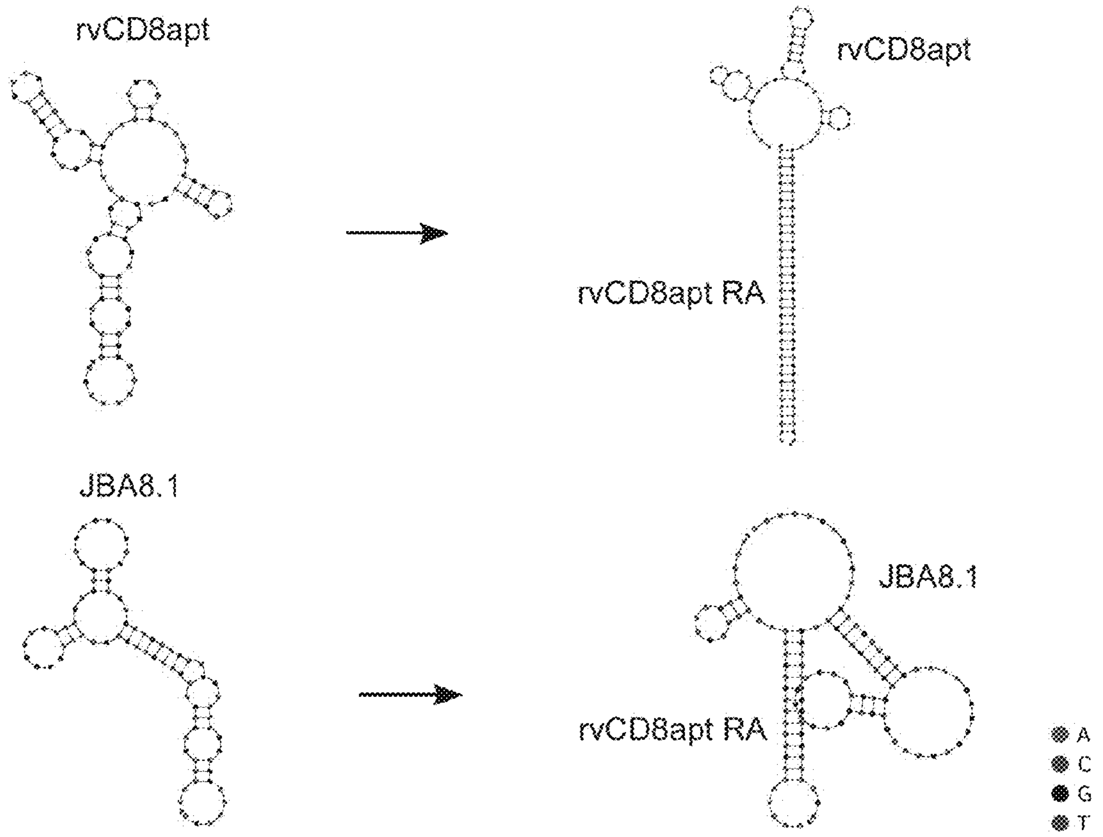
FIGS. 11A-11D. JBA8.1 sequence overlapped with rvCD8apt led to strand displacement by rvCD8apt reversal agent.
Figure 11D:
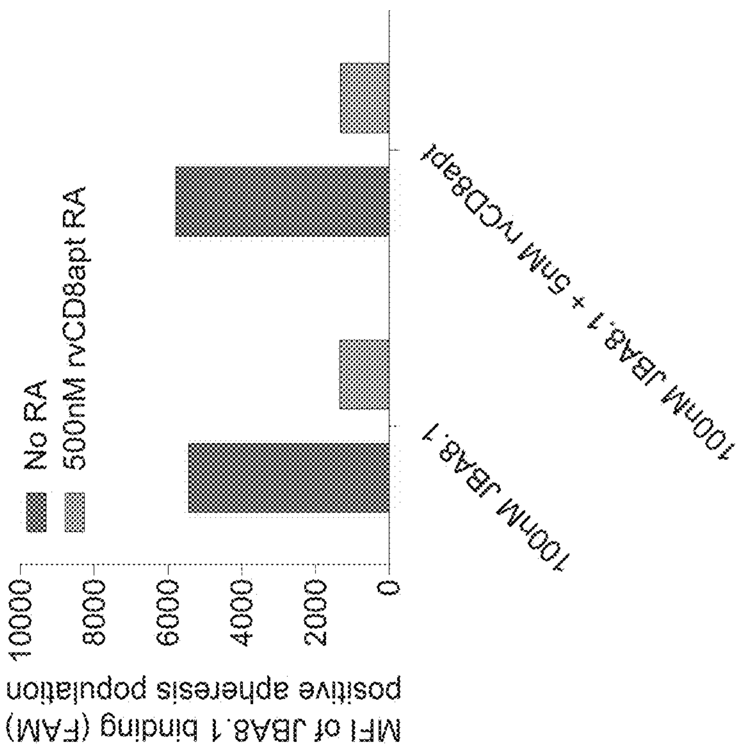
Figure 11C:
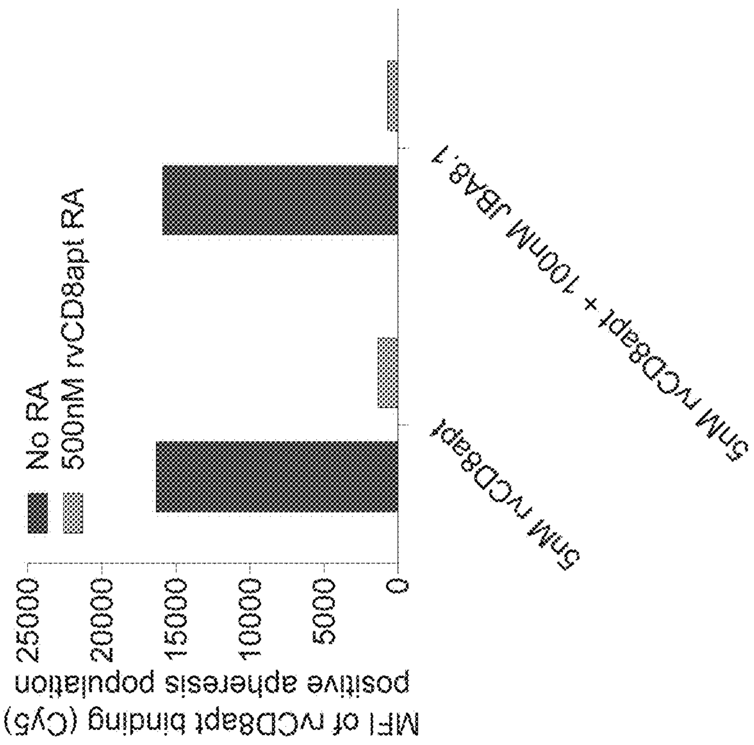

In order to isolate two cell populations from a single aptamer-based selection procedure, two aptamers were needed that could specifically disrupted by their reversal agent sequences. Two aptamers were selected: JBA8.1, a CD71 (also called transferrin receptor 1)-binding aptamer[37], and A3t, a CD8 receptor-binding aptamer[16]. To elute target cells from these individual aptamers, complementary strands (reversal agents) were required that specifically reverse the folded structure of corresponding aptamer sequences. JBA8.1, however, shares overlapped sequences in its stem structure with A3t, renamed to rvCD8apt (reversible CD8 aptamer) for this work (FIG. 11A). Therefore, the rvCD8apt reversal agent was expected to interfere with JBA8.1 by annealing near its 3'-end (FIG. 11B). It was confirmed that rvCD8apt reversal agent reverses binding of both rvCD8apt (FIG. 11C) and JBA8.1 (FIG. 11D) to their receptors using flow cytometry with apheresis cells containing the target cells of both aptamers. According to the 2-dimensional DNA structure simulations and flow cytometry results, the crucial binding structure of JBA8.1 was susceptible to the annealing of a 14 nt sequence; residues 65-78 of SEQ ID NO: 2) near its 3'-end to the rvCD8apt reversal agent. Therefore, distinctive changes were made in the stem region of JBA8.1, which was highly similar to the one of rvCD8apt, by mutating 17 bases (FIG. 1A, red). Changing these sequences also de-stabilized the overall structure of JBA8.1 by increasing the free energy of DNA folding from −27.08 kcal/mol to −22.71 kcal/mol which was expected to increase the possibility of branch migration. Toehold annealing is an effective way to initiate strand displacement of oligonucleotides in a controlled manner[35, 39, 40]. To implement a toehold domain, the 5'- and 3'-overhang sequences were removed, and added an 8 nt unique toehold to the 3'-end of the JBA8.1 (FIG. 1A, blue). This new variant was named rvCD71apt (reversible CD71 aptamer). While JBA8.1 was reported to bind CD71-expressing Jurkat cells with apparent $K_D$ around 5.5 nM[37], rvCD71apt binds to the same cell line with apparent $K_D$ around 35.2 nM (FIG. 1B). Although rvCD71apt binds to $CD71^+$ Jurkat cells with a decreased affinity, the binding was resistant to rvCD8apt reversal agent annealing. When treated with 100× molar excess rvCD8apt reversal agent, rvCD71apt binding showed no significant difference in binding to $CD71^+$ Jurkat cells compared to the control group without reversal agent incubation (FIG. 1C).

TABLE 9

Dual selection aptamer and antidote sequences. The underlined sequences are the toehold structures.

| Name | Sequence |
|---|---|
| RAN SEQ ID NO: 117 | 5'-ATCCAGAGTGACGCAGCAAATTCCAAACTC GAGTAAGCGTAGAGCCTCTCATCGCCTCAATA ATGGA CACGGTGGCTTAGT-3' |
| JBA8.1 SEQ ID NO: 2 | 5'-ATCCAGAGTGACGCAGCAGCGTAAAGGGGG TGTTTGTGCGGTGTGGAGTGCGCGTG CTGCTGCTG GACACGGTGGCTTAGT-3' |
| JBA1.2 SEQ ID NO: 130 | 5'-GGAGTCACACGCATTAGCGTAAAGGGGGTGT TTGTGCGGTGTGGAGTGCGCGTGCT AATGCTGGAG TGTTTCCCAGGACCC-3' |
| A3t SEQ ID NO: 131 | 5'-CCAGAGTGACGCAGCAACAGAGGTGTAGAAG TACACGTGAACAAGCTTGAAATTGTCT CTGACAGAG GTGGACACGGTGGCTTTTAGT-3' |
| JBA1.2 antidote (21 nt) SEQ ID NO: 132 | 5'-GGGTCCTGGGAAACACTCCAG-3' |

TABLE 9-continued

Dual selection aptamer and antidote sequences. The underlined sequences are the toehold structures.

| Name | Sequence |
|---|---|
| JBA1.2 antidote (28 nt) SEQ ID NO: 133 | 5'-GGGTCCTGGGAAACACTCCAGCATTAGC-3' |
| JBA1.2 antidote (33 nt) SEQ ID NO: 134 | 5'-GGGTCCTGGGAAACACTCCAGCATTAGCACGCG-3' |
| JBA1.2 antidote (51 nt) SEQ ID NO: 135 | 5'-GGGTCCTGGGAAACACTCCAGCATTAGCACGCGCACTCCACACCGCACAAA-3' |
| A3t antidote SEQ ID NO: 136 | 5'-ACTAAAAGCCACCGTGTCCACCTCTGTCAGAGACAA-3' |

Optimization of Reversal Agent and Toehold Sequence for rvCD71Apt

Next, the rvCD71apt system was optimized for reversibility by testing different reversal agents and different G-C content in the aptamer toehold sequences. Reversal agents with various lengths (21, 28, 33, and 51 nt) were designed for branch migration from the toehold placed on the 3'-end to various sites on rvCD71apt (FIG. 8A, Table 9). Jurkat cells were labeled with rvCD71apt and then incubated labeled cells with reversal agent (100× aptamer) at room temperature. The 33 nt reversal agent, which theoretically reaches the branched loop, showed the highest displacement with 71.9% aptamer binding reduction. Interestingly, the 51 nt reversal agent, which has 18 extra bases on top of the 33 nt reversal agent sequence, only showed 44.5% reduction on aptamer binding fluorescent intensity (FIG. 8A). Although longer reversal agent strands have lower theoretical binding free energies[35], the 51 nt reversal agent might be blocked by steric hindrance on the protein-aptamer complex. Potential conformational changes[41] in CD71 protein or in rvCD71apt itself are also factors that are unaccounted by the 2-dimensional DNA structure simulation.

Figure 7A:
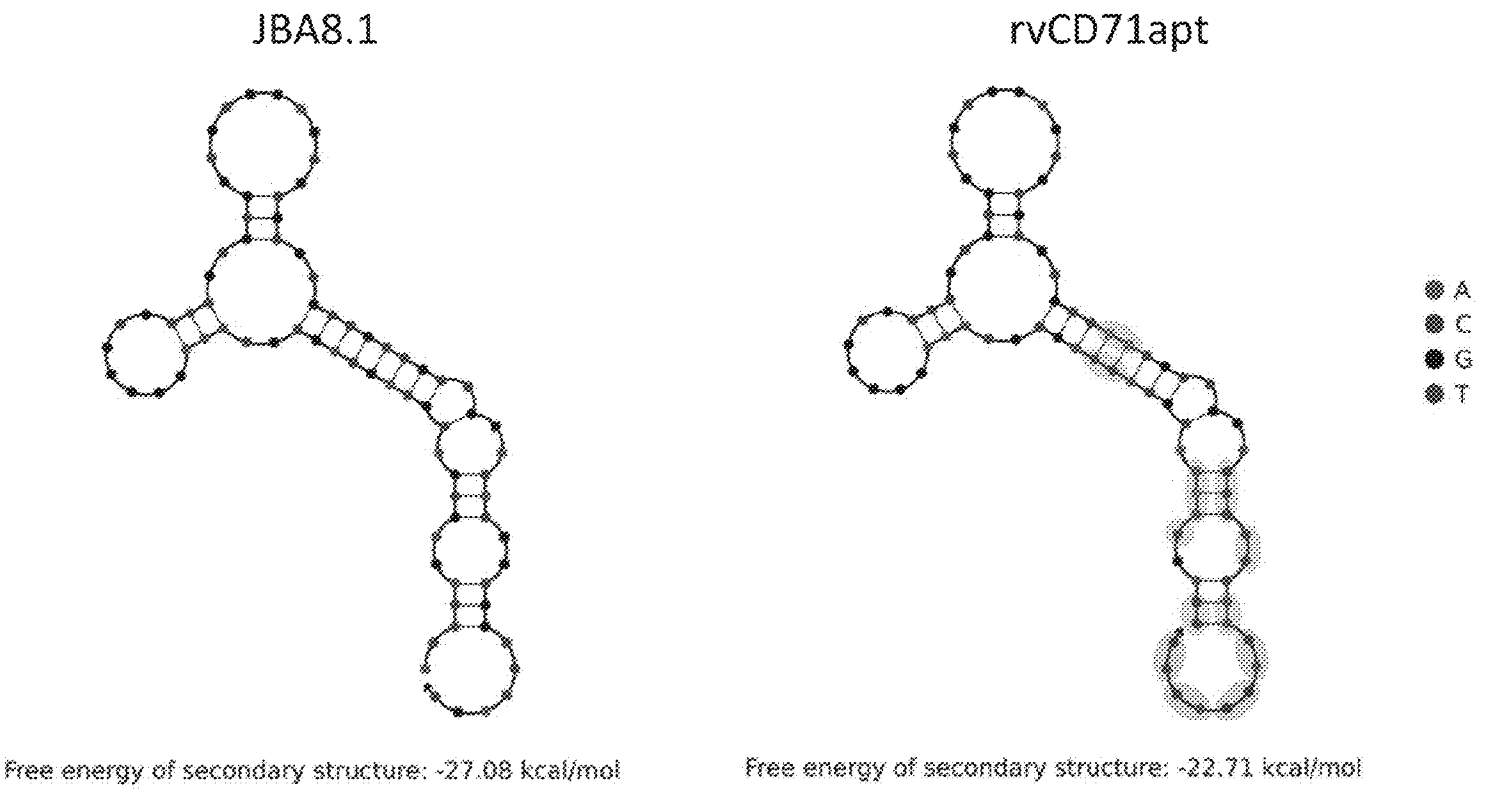
FIGS. 7A-7C. rvCD71apt design.
Figure 7C:
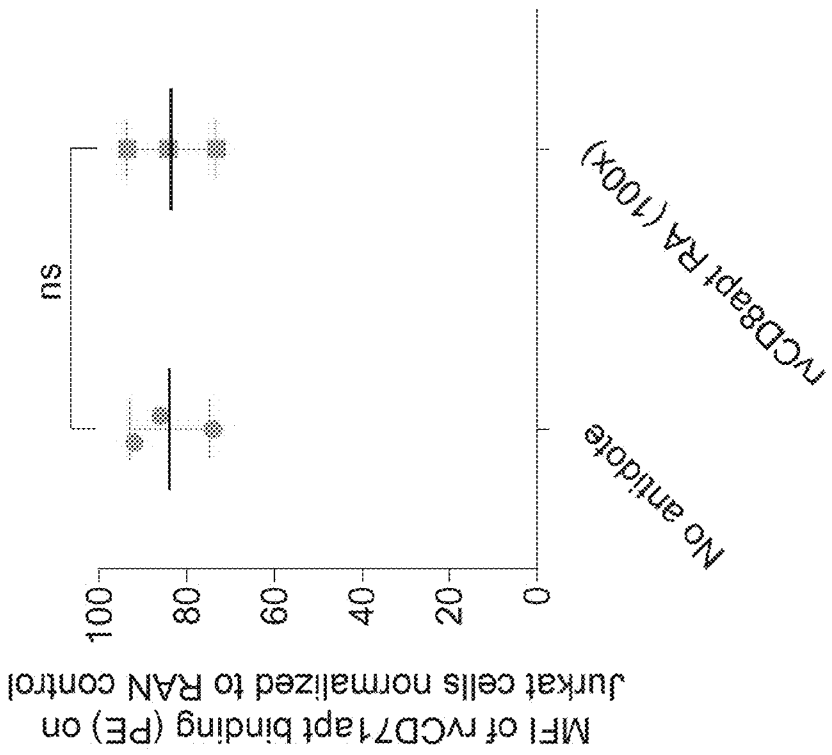
Figure 7B:
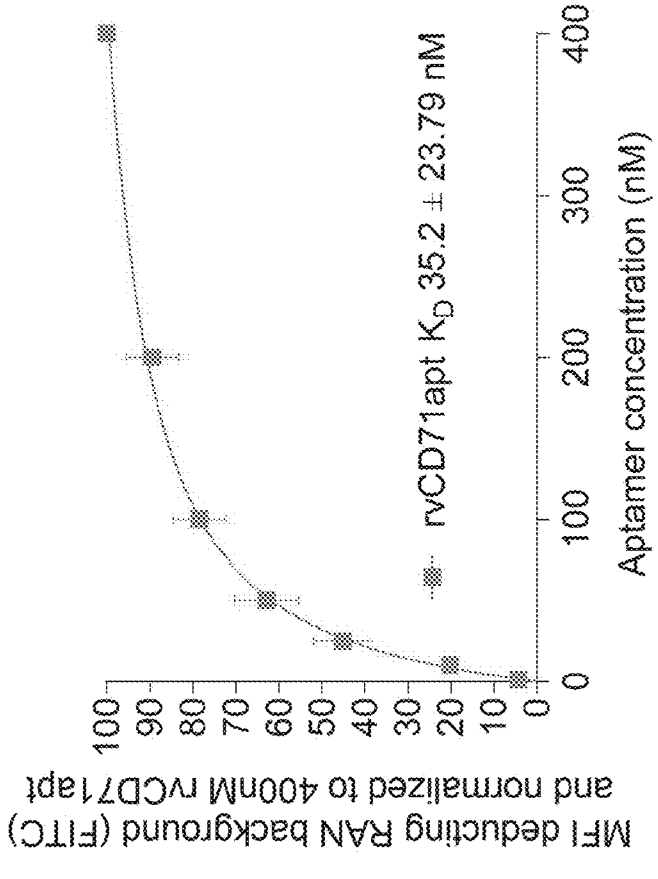
Figures 8B, 8C:
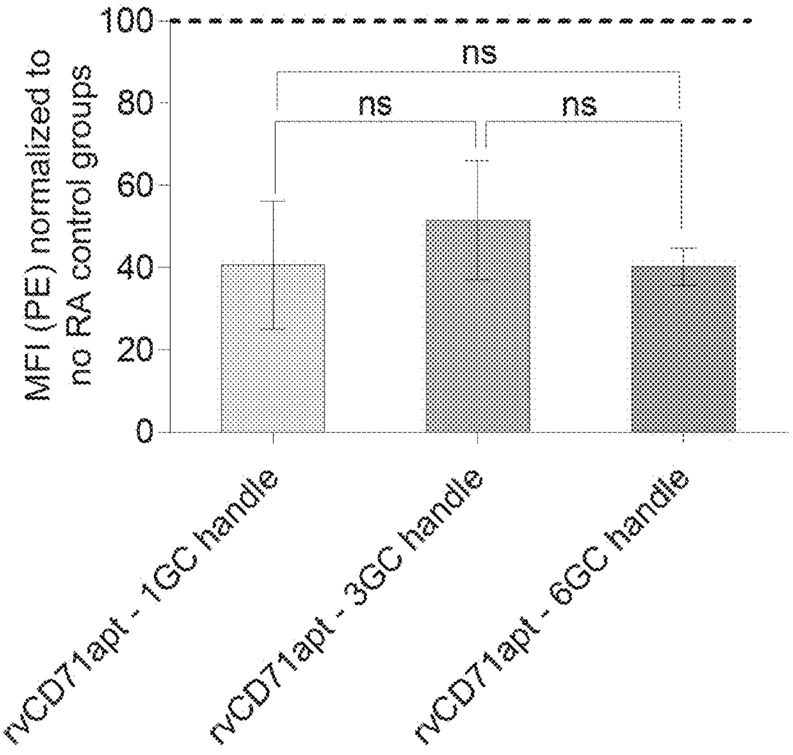
Figure 8D:
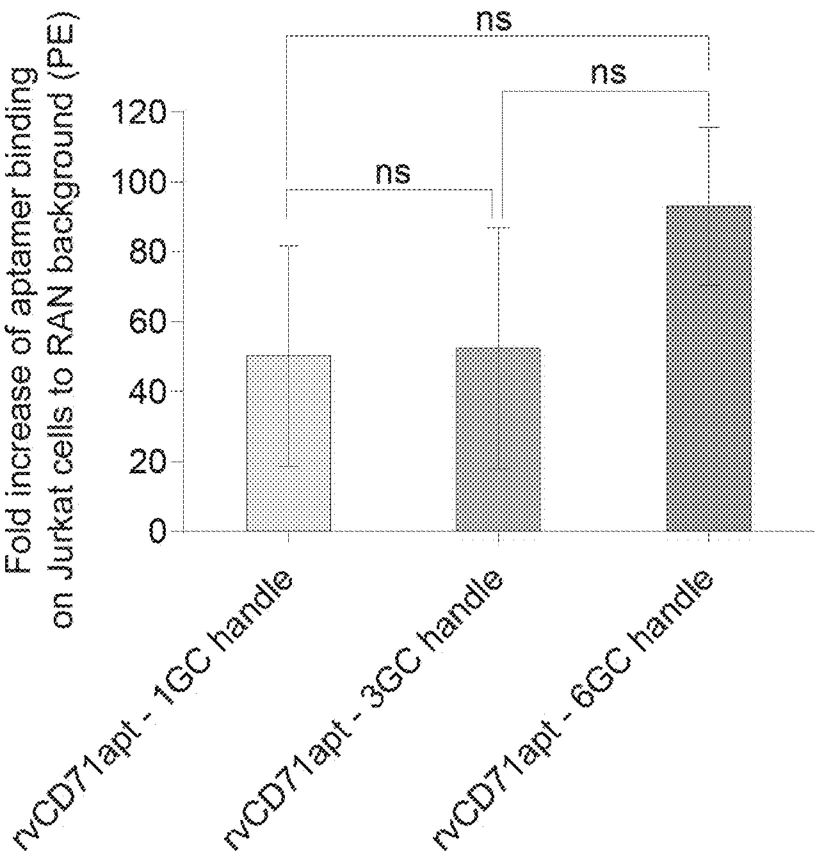

Next the impact of G-C content in the aptamer toehold sequence on strand displacement efficacy was explored. Toeholds with higher G-C content favor faster annealing rate of complementary strands due to their lower binding free energy[35]. Three rvCD71apt sequences were designed containing 8 nt toeholds with different G-C content (FIG. 8B) and tested the aptamers for binding to Jurkat cells followed by reversal agent-mediated reversal using their corresponding 33 nt reversal agents. Unexpectedly, better strand displacement was not observed from the cells using higher G-C content toeholds (FIG. 8C). It is likely that the incubation time, reversal agent concentration, and temperature applied in this experiment was sufficient for maximum reversal agent annealing to take place, negating any effect from the G-C pairs. In addition, swapping out different toehold sequences did not alter the binding of rvCD71apt significantly when staining cells with a fixed concentration at 20 nM. However, as rvCD71apt with 1 and 3 GC in the toehold sequence showed lower mean binding fluorescence intensity than rvCD71apt with 6 GC toehold (FIG. 8D), the study was continued using rvCD71apt with the 6 GC toehold as shown in FIG. 7A.

Compatibility of rvCD71Apt and rvCD8Apt Aptamer/Reversal Agent Pairs

Figure 9A:
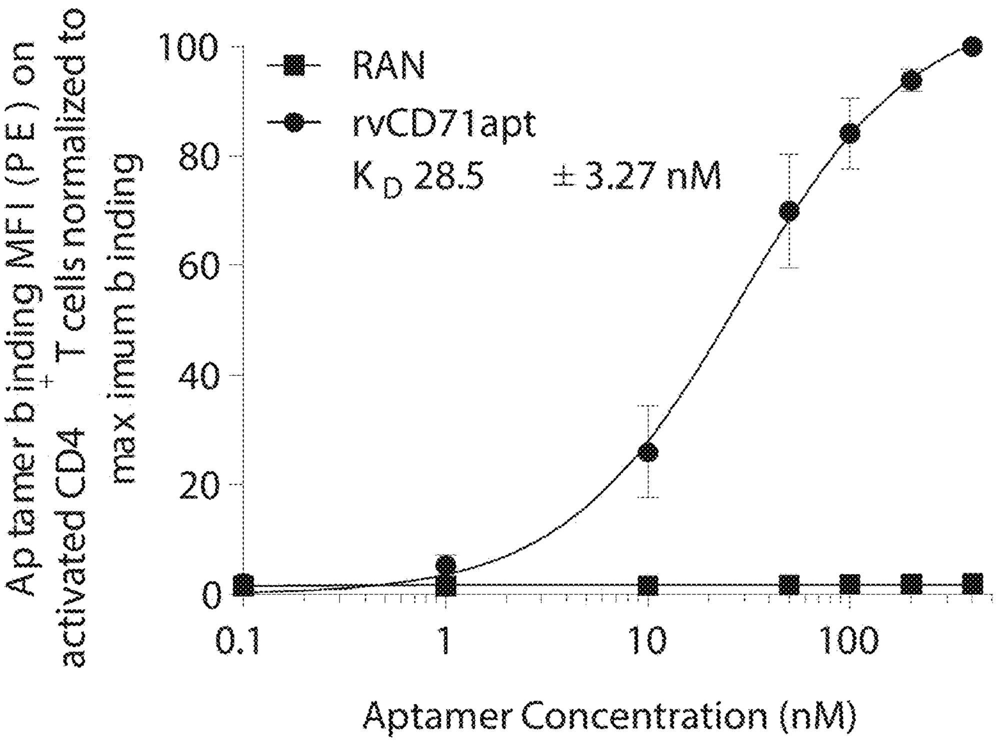
FIGS. 9A-9C. Reversal agent-specific disruption of aptamer binding. rvCD71apt binding on (FIG. 9A) activated CD4$^+$ T cells and (FIG. 9B) CD8$^+$ T cells using biotinylated aptamers followed by streptavidin-PE staining. Data are shown as mean±s.d., n=3.
Figure 9B:
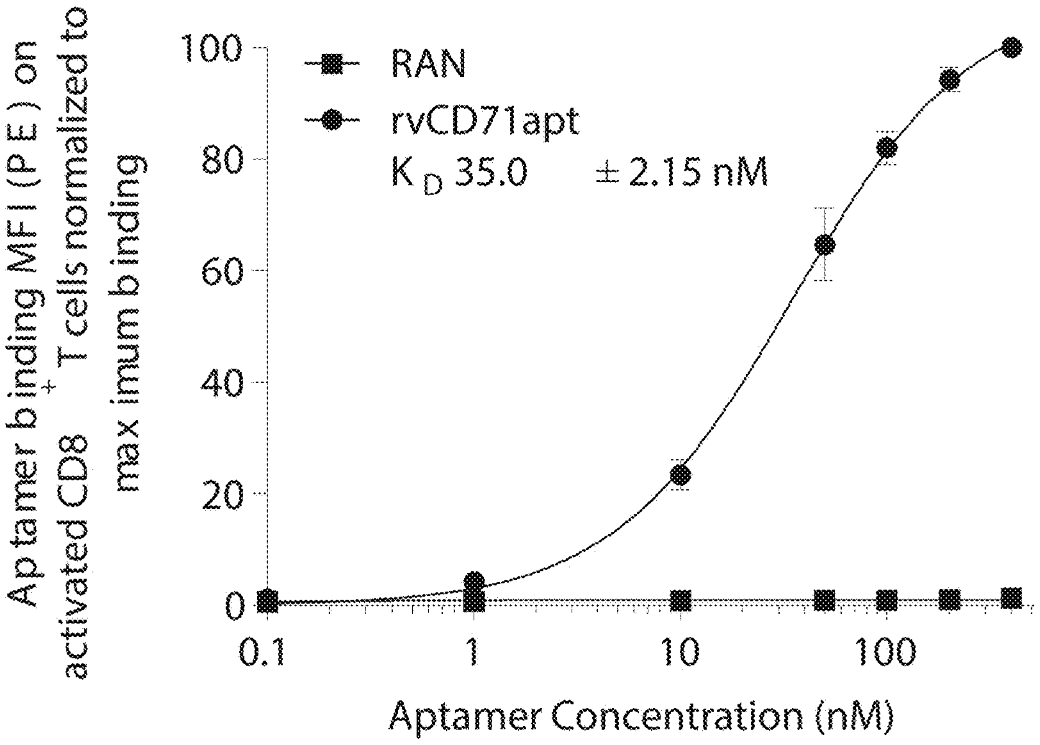
Figure 9C:
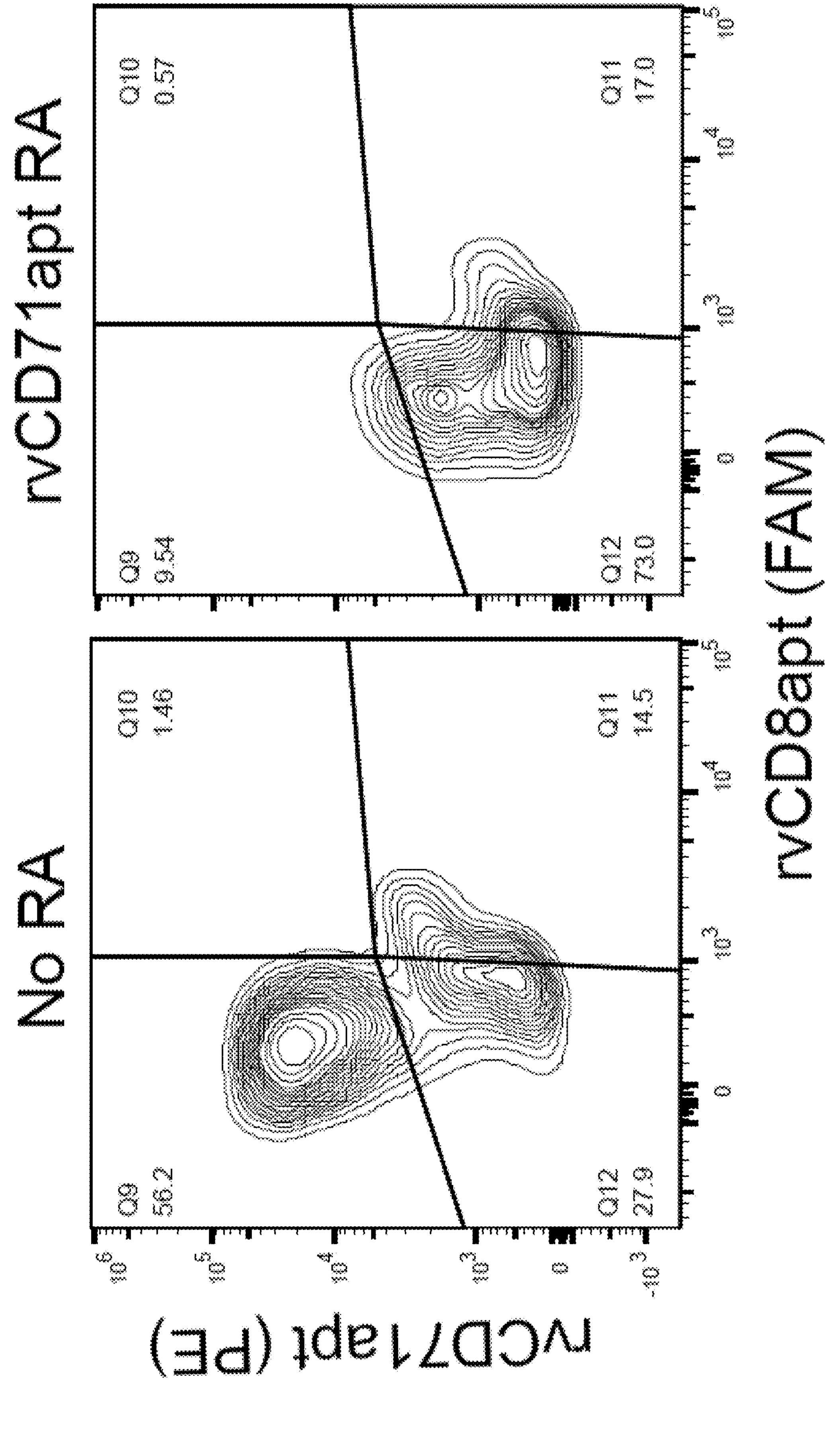
Figure 9C:
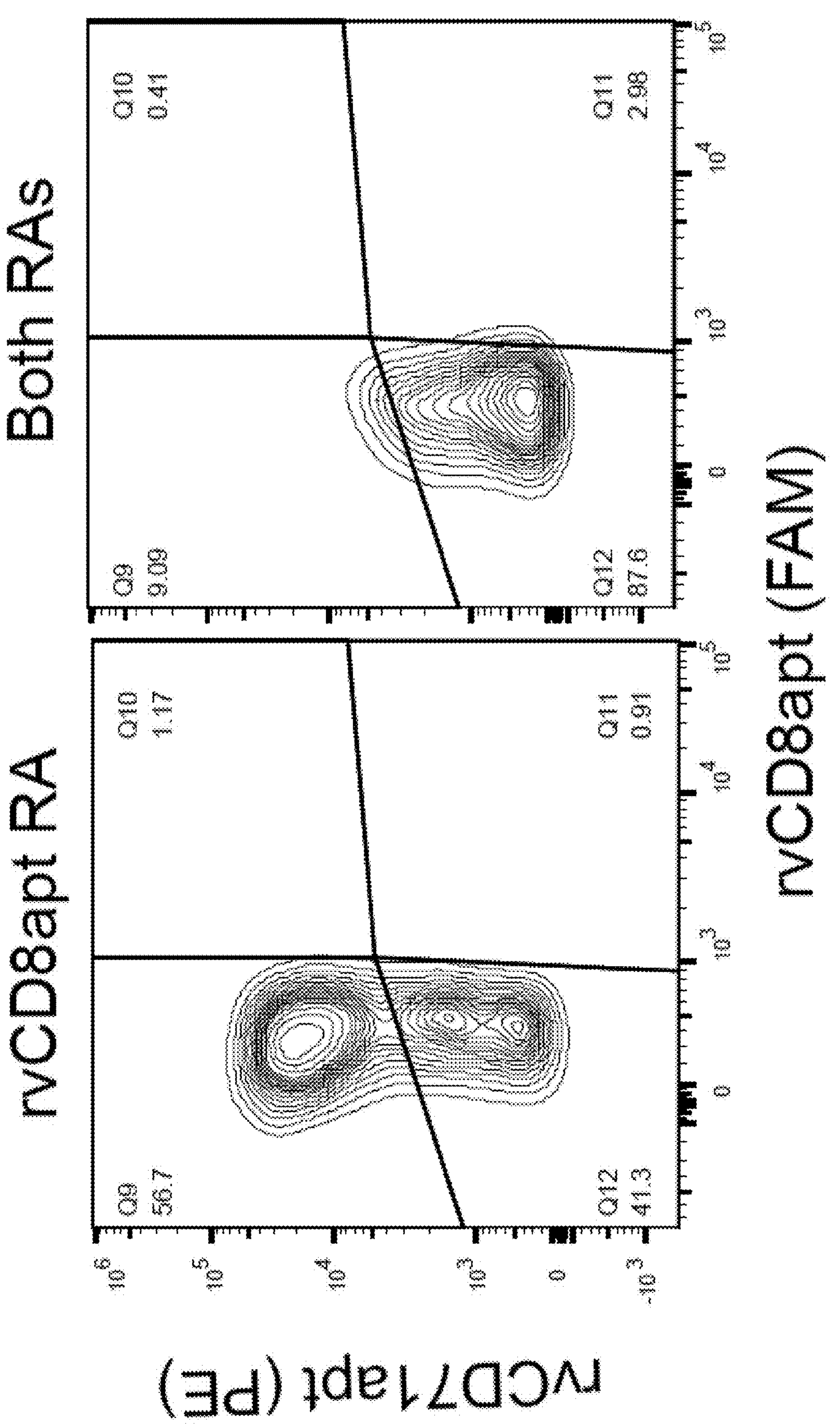

The compatibility between rvCD71apt, rvCD8apt, and their corresponding reversal agent sequences is crucial for isolating target cells at high purity with sequential elution. Here, sequence-specific displacement by the two reversal agents using flow cytometry was evaluated. It had been previously demonstrated that rvCD8apt with its reversal agent can be used for traceless isolation of $CD8^+$ T cells[16]. rvCD71apt targets CD71 receptor, which is expressed by proliferating, activated T cells but not by resting T cells[42]. rvCD71apt binds with high affinity to both activated $CD4^+$ and $CD8^+$ T cells, with apparent $K_D$ around 28.5 nM and 35 nM, respectively (FIGS. 9A and 9B). Therefore, sequence-specific reversal agent displacement was evaluated by staining a mixed population containing activated $CD4^+$ T cells and resting $CD8^+$ T cells with 20 nM rvCD71apt and 5 nM rvCD8apt, followed by reversal agent displacement. 20 nM rvCD71apt was used, a concentration close to its apparent $K_D$, to ensure sufficient labeling on activated $CD4^+$ T cells while avoiding non-specific binding. rvCD8apt was used at 5 nM in this staining procedure since it was previously shown to be adequate in a cell isolation procedure[16]. Application of a single reversal agent specifically reduced binding of the target aptamer without affecting the other aptamer sequence. Application of both reversal agents simultaneously successfully removed binding of both aptamers from their target cells. These results show that the rvCD71apt reversal agent and rvCD8apt reversal agent can disrupt their target aptamer's structure without interfering the other aptamer. In addition, the two reversal agents showed complementary displacement without non-specific annealing even when incubated at high concentration in the same well (2 μM rvCD71apt reversal agent; 0.5 μM rvCD8apt reversal agent) (FIG. 9C).

rvCD71Apt and Reversal Agent Separate PBMCs into Cell Populations Base on CD71 Expression Level Biotinylated rvCD71apt and its reversal agent were incorporated into the MACS® system (Miltenyi) for cell isolation, which utilizes anti-biotin superparamagnetic particles to anchor ligand-labeled cells in a column with application of magnetic field. MACS with aptamer labeling for isolating $CD8^+$ T cells at high purity have been used previously[16]. Therefore, this system was chosen to test the feasibility of cell isolation with rvCD71apt.

Figure 12A:
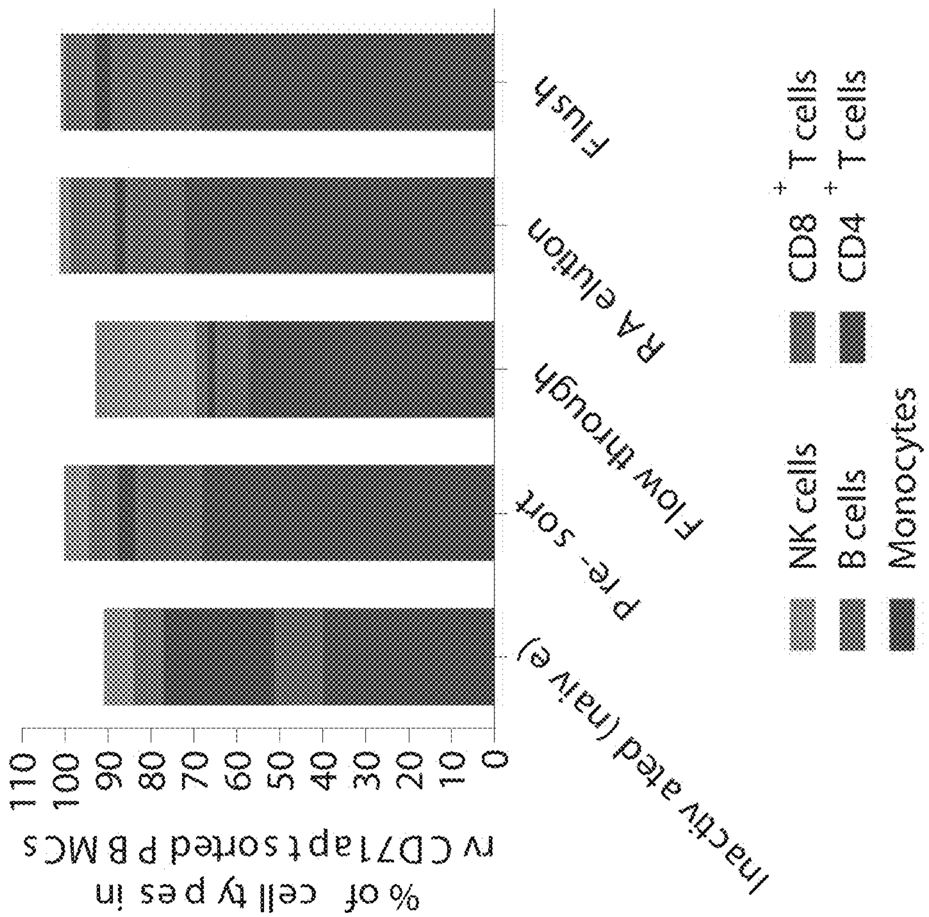
FIGS. 12A-12D. Sorting bulk stimulated PBMCs with rvCD71apt.
Figure 12B:
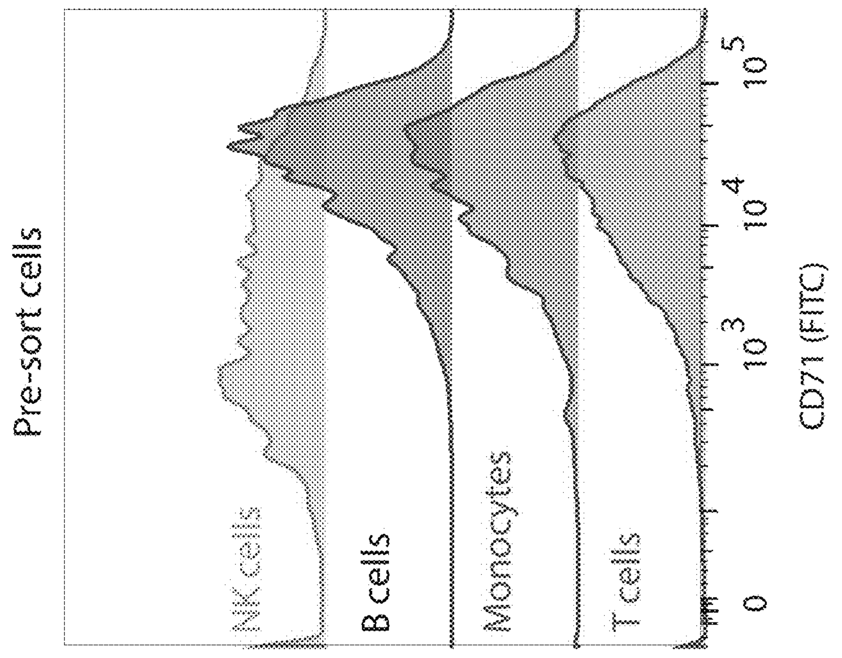
Figure 12C:
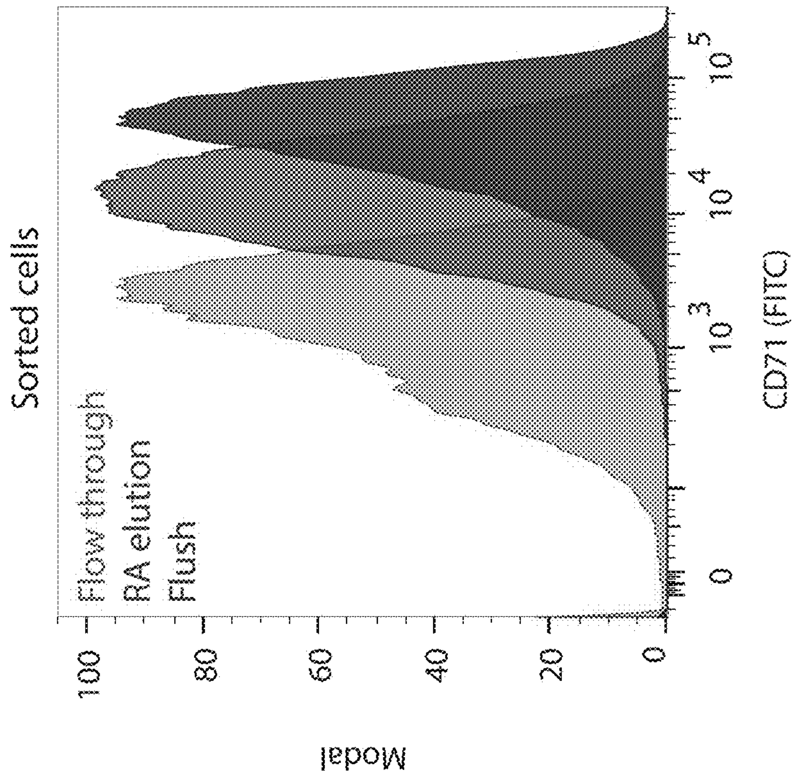

To generate cells for sorting, bulk PBMCs were treated with cytokines and CD3/CD28 stimulation beads for 3 days. On day 3, the cells were first washed to remove stimulation beads named pre-sort fraction). During this stimulation process, the fraction of non-T cell (i.e., NK cells, B cells, and monocytes) populations reduced while the T cells preferentially proliferated, resulting in 83% T cells in the total pre-sort population (FIG. 12A). All the stimulated PBMC populations express CD71 receptor to varying levels, with NK cells showing the lowest CD71 expression (FIG. 12B). The stimulated PBMCs were stained with biotinylated rvCD71apt, labeled with magnetic anti-biotin Microbeads (Miltenyi), and applied to the magnetic MACS column for separation. As expected, NK cells enrichment was seen in the fraction that was not captured by the column (named flow through fraction) due to their lower CD71 expression (FIG. 12A). The cells that were retained in the column were then incubated with rvCD71apt reversal agent at 100× aptamer concentration. A population of cells were released from the column upon reversal agent treatment (named reversal agent elution fraction). The rest of the cells not eluted by reversal agent incubation were flushed out of the column with buffer (named flush fraction). Strikingly, an over 2 orders of magnitude difference was found in CD71 expression measured by fluorescent intensity on flow cytometry between the sorted cell fractions. The cells in the flow through fraction expressed the lowest CD71 which led to insufficient physical support to counter the gravity flow of washes. The cells that were retained in the column despite reversal agent elution showed the highest CD71 expression. The cells being eluted from the column with reversal agent strand displacement had intermediate CD71 expression (FIG. 12C).

An Aptamer-Based Multiplexed System for Traceless Cell Selection

Figure 12D:
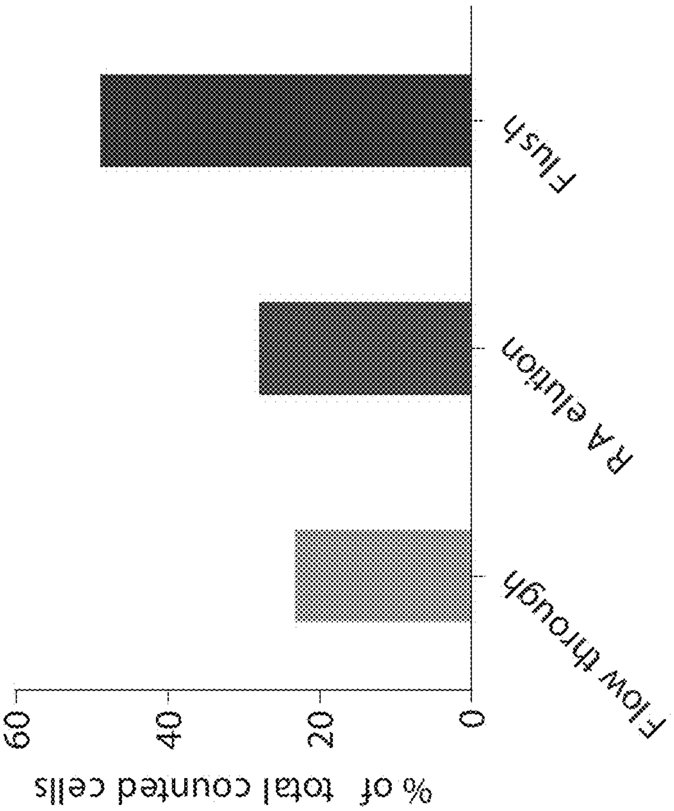

The amount of cells retained in the MACS column after reversal agent treatment led to consideration of using a different isolation method (FIG. 12D), in which the strand displacement step takes place in a rotating enclosed solution rather than a static state. Other groups have previously reported use of the micrometer-sized superparamagnetic Dynabeads® (Invitrogen) for fluorescent bead[25] and cell[26] sorting that relies on effective DNA gate strand displacements.

Figure 10A:
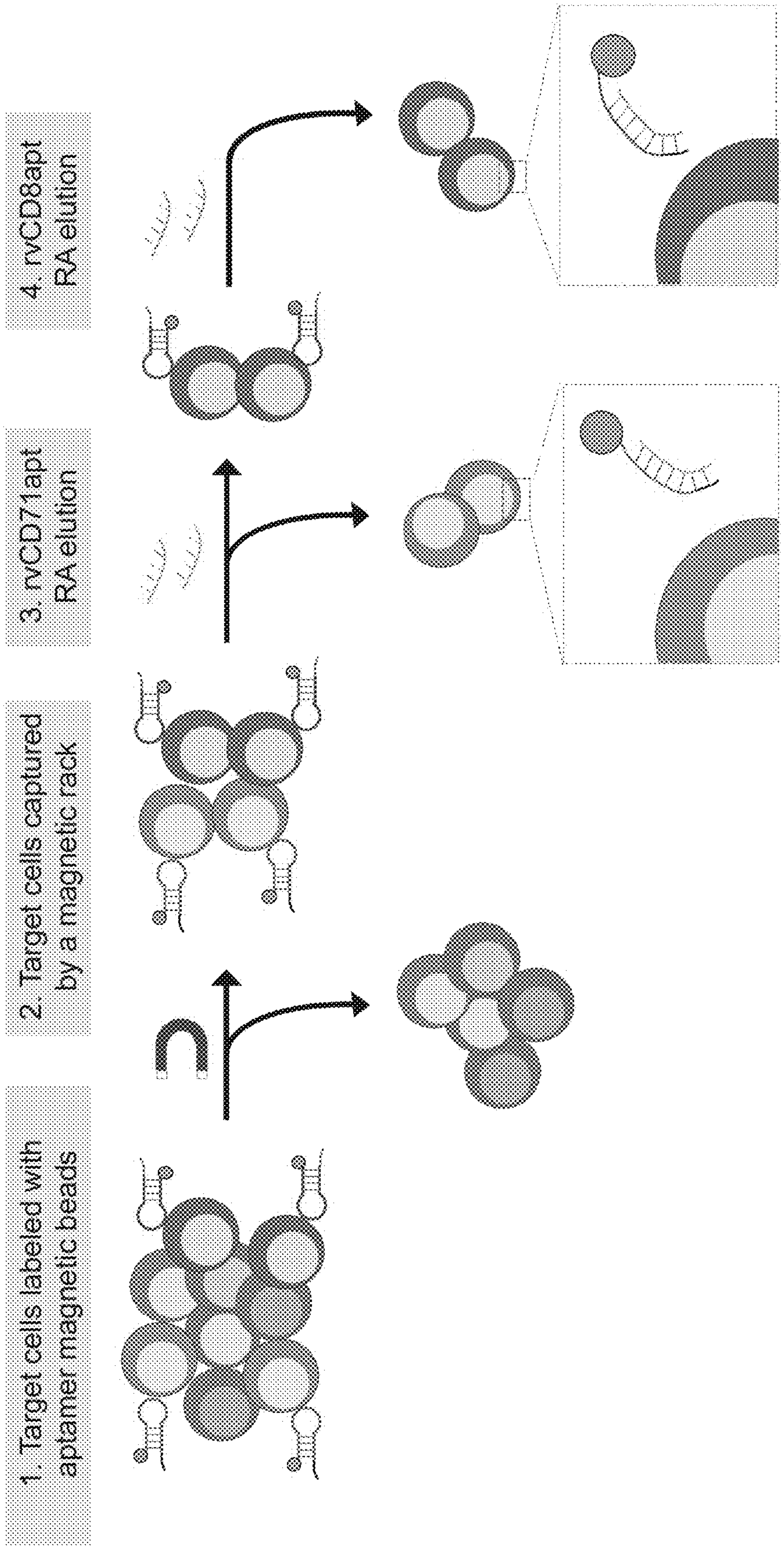
FIGS. 10A-10D. Multiplexed cell isolation using aptamer reversal agent elution.
Figure 10B:
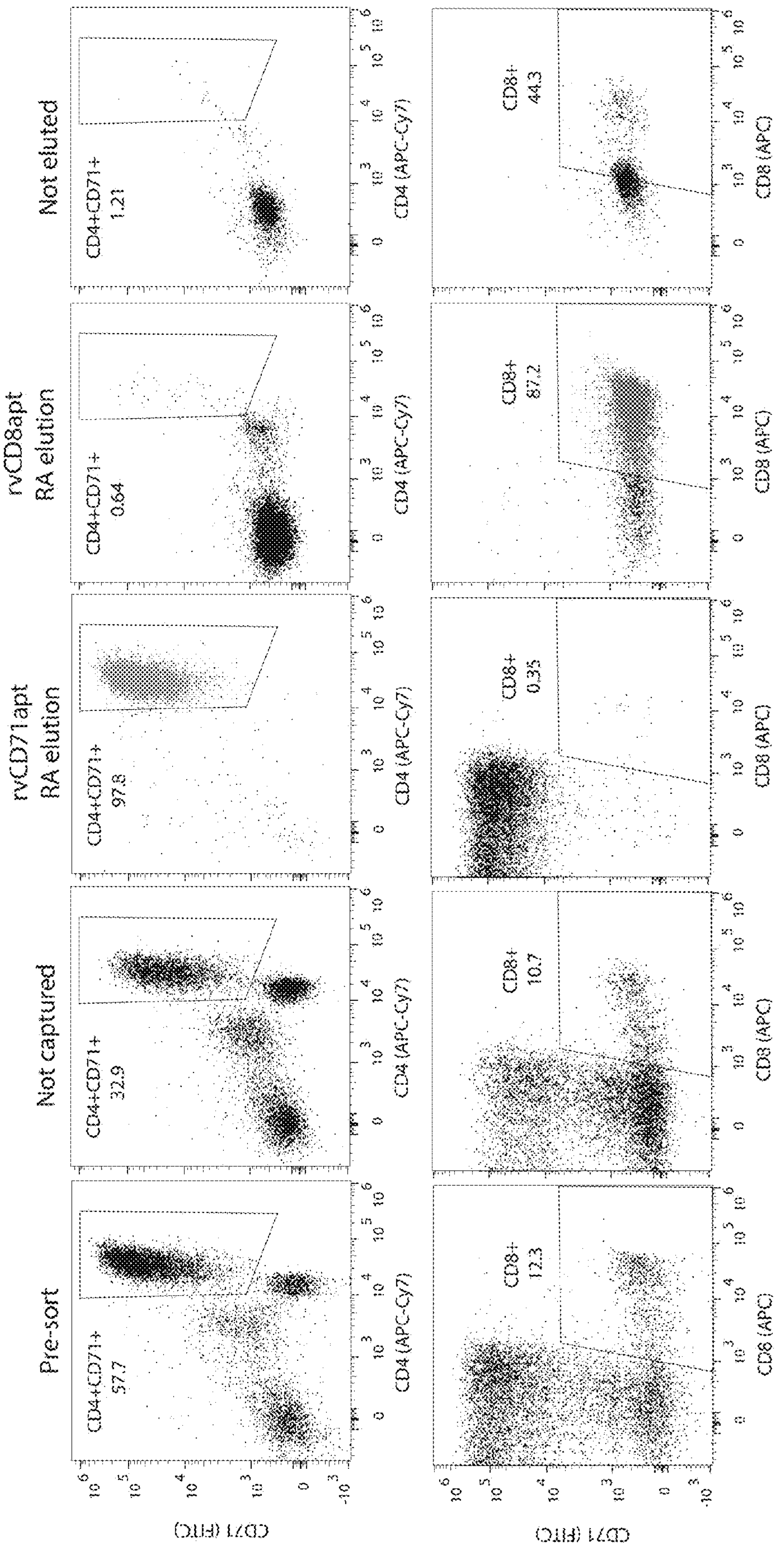
Figure 10C:
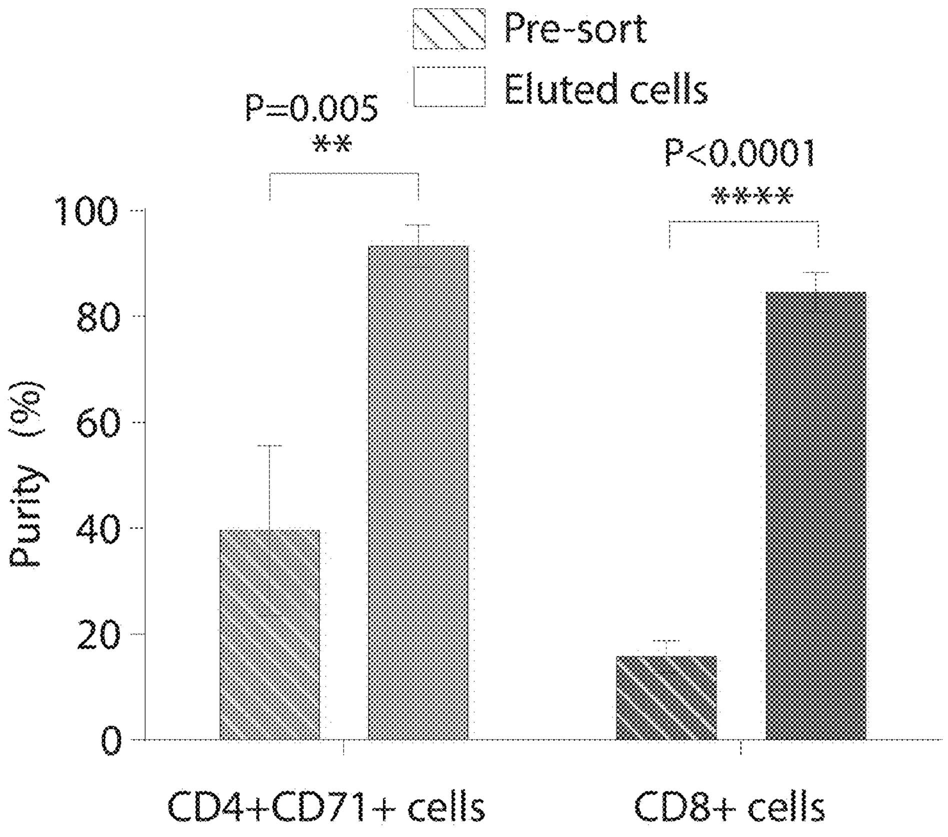
Figure 13A:
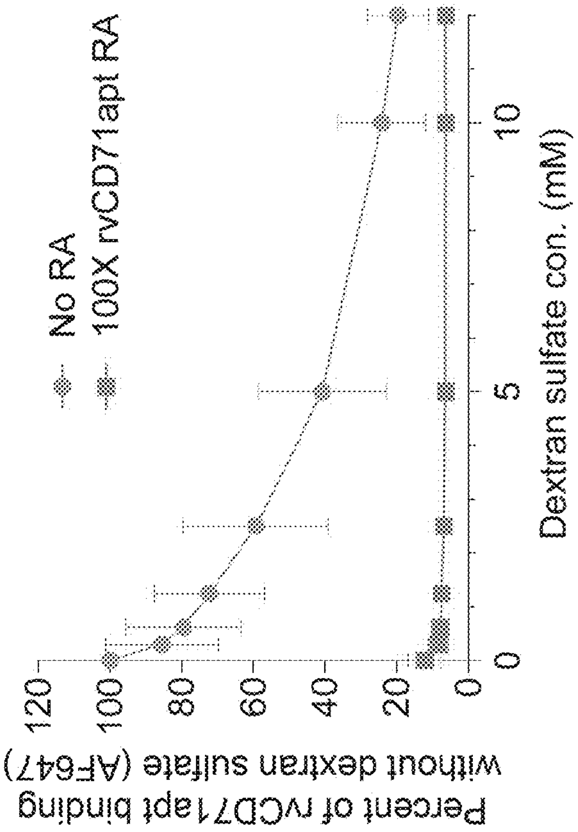
FIGS. 13A-13B. Flow cytometry evaluation of dextran sulfate impacting aptamer binding. (A) $CD4^+$ T cells were activated using rhIL-7, rhIL-15, and human CD3/CD28 activation beads. The activated $CD4^+$ T cells were stained with 60 nM biotinylated rvCD71apt before exposed to various concentrations of dextran sulfate with or without 6 μM rvCD71apt reversal agent. rvCD71apt binding was evaluated using Streptavidin AF647 as secondary staining. Data are shown as mean±s.d., n=3. (B) $CD8^+$ T cells were stained with 5 nM biotinylated rvCD8apt before exposed to various concentrations of dextran sulfate with or without 500 nM rvCD8apt reversal agent. rvCD8apt binding was evaluated using Streptavidin AF647 as secondary staining. Data are shown as mean±s.d., n=3. AF647: Alexa Fluor 647; RA: reversal agent.
Figure 13B:
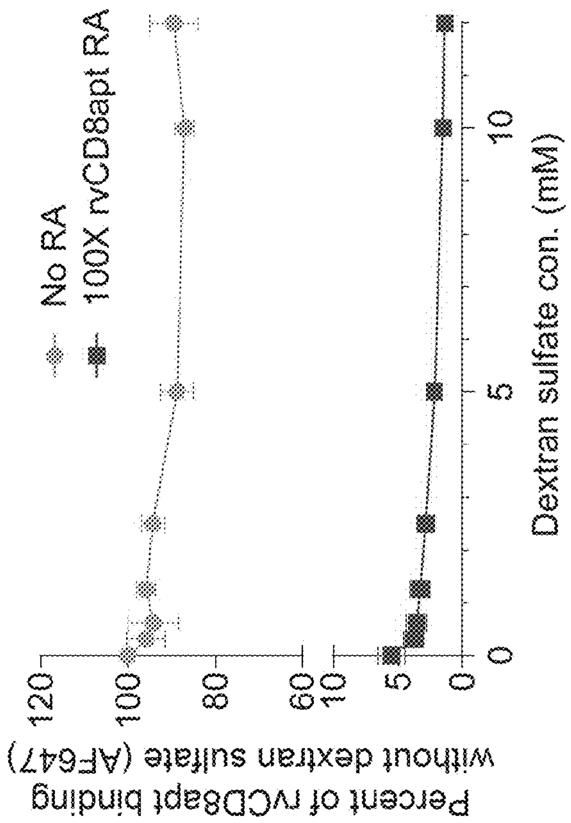

Therefore, multiplexed cell isolation was tested using MyOne™ Streptavidin C1 Dynabeads™ (Invitrogen) labeled with rvCD71apt and rvCD8apt aptamers (FIG. 10A). Biotinylated rvCD71apt and biotinylated rvCD8apt were first incubated with the Streptavidin Dynabeads™ to generate rvCD71apt-labeled and rvCD8apt-labeled solid supports. The aptamer-functionalized beads were then applied to a mixed cell population (i.e., pre-sort fraction) that consisted of activated $CD4^+$ T cell-spiked PBMCs with a goal of using rvCD71apt and rvCD8apt to isolate activated $CD4^+$ T cells and $CD8^+$ T cells, respectively. The labeled target cells were applied to a magnetic Eppendorf tube rack (MagRack™ 6, GE), such that target cells were retained on the side of the tube due to magnetic force, while the un-labeled or un-sufficiently anchored cells were washed away (i.e., not captured fraction). Activated $CD4^+$ T cells were eluted first with rvCD71apt reversal agent incubation (i.e., rvCD71apt reversal agent elution fraction). Next, the excess DNA and un-eluted activated $CD4^+$ T cells were rinsed away using dextran sulfate solution, a anionic polysaccharide commonly used to reduce both non-specific background (at low concentrations) and targeted aptamer binding (at high concentrations) (FIGS. 13A and 13B)[43,44]. rvCD8apt reversal agent was then applied to the column for $CD8^+$ T cell elution (i.e., rvCD8apt reversal agent elution fraction). Lastly, the remaining bead-labeled cells were collected by resuspending with buffer (i.e., not eluted fraction). Cells were collected from each fraction to be stained with antibodies to determine cell phenotype (FIG. 10B). rvCD71apt target cells were gated as $CD4^+CD71^+$. rvCD8apt target cells were gated as $CD8^+$ cells. It was found that rvCD71apt reversal agent eluted activated $CD4^+$ T cells at high purity of 93.3% and rvCD8apt reversal agent eluted $CD8^+$ cells at 84.6% purity (FIG. 10C). These results demonstrated that aptamer-specific reversal agent elution can be used to isolate multiple cell types in a sequential and traceless manner.

Figure 10D:
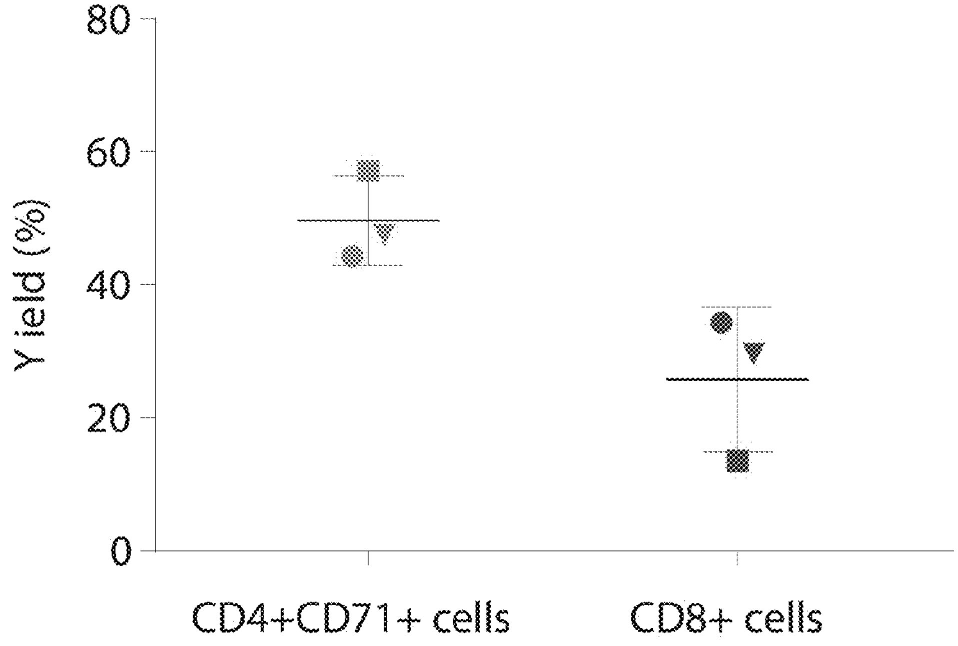
Figure 14:
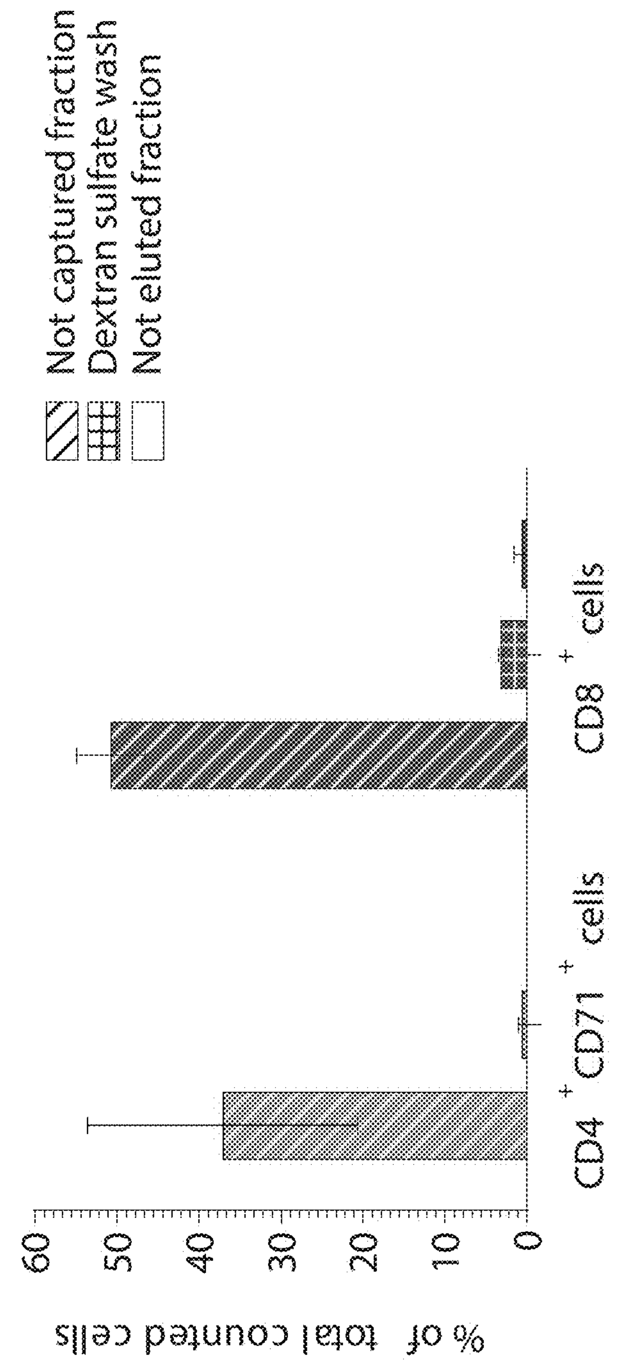
FIG. 14. Percentage of the target cells counted in different fractions divided by the total cell counts in all fractions combined in the traceless multiplexed isolation system. Data are shown as mean±s.d., n=3.
Figure 15:
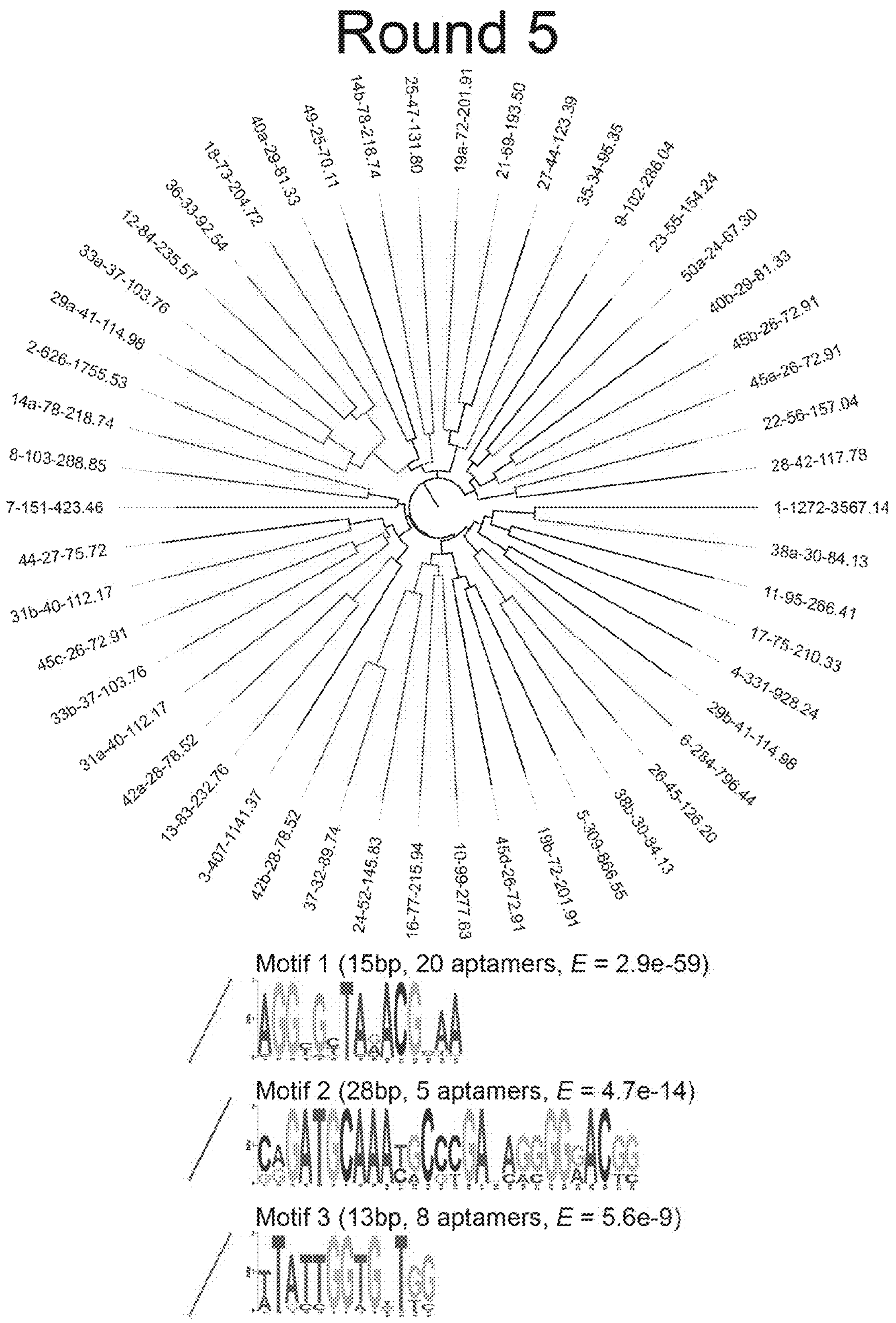
FIG. 15. Phylogenetic trees of the top 50 aptamers from rounds 5-8 of Jurkat cell-SELEX and emerging consensus motifs. Phylogenetic trees were generated with FigTree™ software, and statistically significant binding motifs were predicted using MEME analysis (MEME-suite.org). Phylogenetic trees are colored to denote aptamers belonging to identified motifs. Branch labels denote the aptamer rank followed by raw reads and reads per million.
Figure 15:
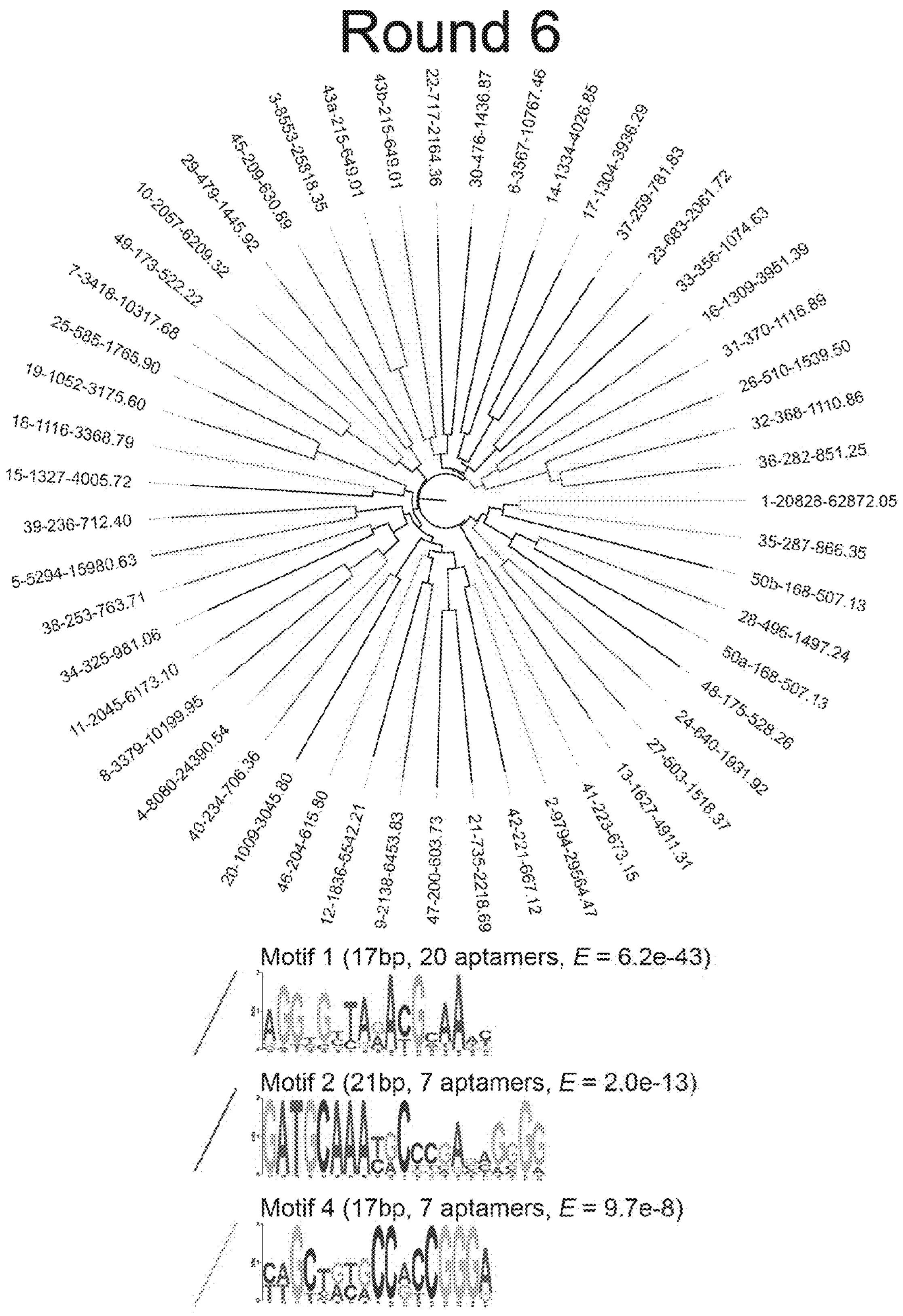
Figure 15:
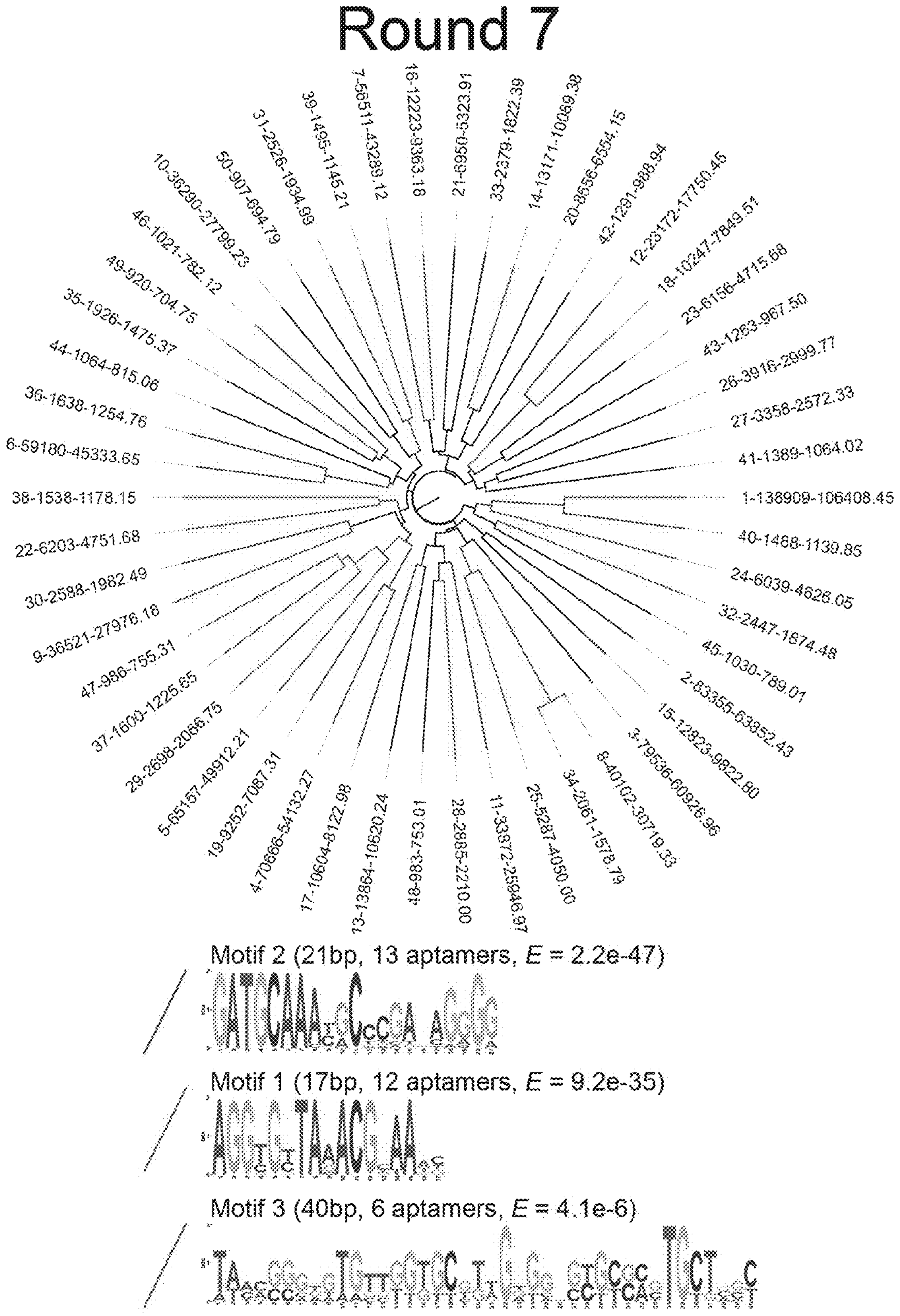

In contrast to the MACS system, most of the target cells were effectively from the aptamer-functionalized Dynabeads™ (not eluted fraction in FIG. 10D). However, despite the high purity and effective collection of traceless activated $CD4^+$ T cells and $CD8^+$ cells (mostly resting $CD8^+$ T cells) sorted by this method, it was noticed that a significant fraction of target cells was not retained by the magnetic beads (not captured fraction in FIG. 10B and FIG. 14). Unlike the insufficient reversal agent displacement issue observed with the MACS system (FIG. 12D), cells were not anchored securely by the Dynabeads™ MyOne™ Streptavidin C1 and GE MagRack™ 6 system. Consequently, the yield of target cells isolated from reversal agent elution was only 49.7% of total $CD4^+CD71^+$ cells and 25.7% of total $CD8^+$ cells (FIG. 10D). This is likely due to insufficient strength afforded by the magnetic separation since we have titrated and applied excessive aptamer and streptavidin beads to saturate the binding events in each staining step. However, only less than 1% of the input target cells remained attached on the Dynabeads after reversal agent strand displacement (FIG. 10D). The efficient recovery can be attributed to the free-floating state of cells and beads during the elution steps, which likely makes aptamers more accessible to the reversal agent sequences.

The most common strategy to achieve traceless cell isolation is by capturing undesired cells with a panel of staining reagents, which often results in insufficient yield and purity[9, 10, 17]. There is therefore significant interest in developing removable affinity agents to capture target cells, including recombinant proteins and synthetic oligonucleotides. Cell sorting systems using Fab-Streptamer® complexes can achieve cell purity over 90%22, 23, 45, with yields between 10-60%22 when used to isolate cell types that require multiple marker labeling such as T cell subsets[22,45]. MACS-based cell isolation method using a single aptamer and reversal agent pair to purify one target cell type has been reported to provide high isolation purity of around 95%[16,34]. Herein, a new isolation method has been demonstrated using two pairs of aptamers and reversal agents as cell type-releasing DNA gates[25,26] to capture and to serially elute activated $CD4^+$ T cells and $CD8^+$ cells with 85-93% purity without repeated staining and sorting steps (FIG. 10C).

Non-specific cell binding to the solid support is a potential factor in reduced purity. Dynabeads™ are superparamagnetic beads coated with polystyrene which has been reported to non-specifically bind to cells[46,47]. Another potential factor that might cause reduced purity is unintentional physical removal of captured cells from the beads by pipetting or by charge repulsion due to the application of anionic reagents. This is a concern especially in the $CD8^+$ cell elution step, which occurs after CD71 reversal agent elution, as any un-eluted $CD71^+$ cells would have less aptamer binding and be retained less securely by the beads. Since there was only a small amount of $CD71^+$ (<1%) cells observed in the rvCD8apt reversal agent elution fraction (FIG. 10B), the remaining $CD8^-$ cells contamination likely comes from non-specific association with the beads, despite our inclusion of following components to reduce non-specific cell adsorption: pre-clearing, dextran sulfate rinse, and anionic blockers. A surface coating with less interaction with the cell surface, such as poly (ethylene glycol) or zwitterionic polymers, could help improve cell purity from this method[48].

In the process of developing the multiplexed cell isolation method, a varying yield of target cells was noticed between different donors (FIG. 10D). The choice of magnetic separation system directly impacts the immobilization of cells on the side of the tubes during washing steps. On the other hand, the expression level of target receptors, CD71 and CD8 protein, dictates the beads attachment to the cell surface. Since receptor expression is a donor-dependent and uncontrollable factor, the use of stronger magnets or different bead sizes are points of future optimization.

In sum, the inventors have demonstrated the feasibility of aptamer-based, traceless isolation of two target cell types from a single cell sorting procedure. The inventors first modified a reported CD71-binding aptamer, rvCD71apt, so that it was suitable for cell retention on the solid supports and independent reversal agent elution of the bound targets. They also optimized the reversal agent for this aptamer that could trigger rapid and efficient strand displacement to reverse target binding. It was also demonstrated that rvCD71apt could separate CD71+ cells in PBMCs according to their CD71 expression level. rvCD71apt was then with rvCD8 apt and traceless serial elution of activated CD4+ T cells (rvCD71apt target) and resting CD8+ cells (rvCD8apt target) from mixed cell populations was demonstrated. The two reversal agent elution steps successfully displaced most target cells captured on the Dynabeads™ through strand displacement with 93% and 85% mean target cells purity. Theoretically, this approach can be scaled up for isolation of even more cell populations with the development of additional orthogonal aptamer-reversal agent pairs. This study shows that as long as the aptamers and reversal agents are designed properly, the multiplexed isolation system can be versatile for a wide range of applications and different setups.

REFERENCES

1. Bonner, et al. Fluorescence Activated Cell Sorting. *Rev. Sci. Instrum.* 43, 404-409 (1972).
2. Thiel, et al. Immunomagnetic cell sorting-pushing the limits. *Immunotechnology* (1998) doi:10.1016/S1380-2933(98)00010-4.
3. Kumar, and Srivastava. Cell separation using cryogel-based affinity chromatography. *Nat. Protoc.* (2010) doi:10.1038/nprot.2010.135.
4. Mohr, et al. Efficient immunoaffinity chromatography of lymphocytes directly from whole blood. *Sci. Rep.* 8, 16731 (2018).
5. Timonen, and Saksela. Isolation of human NK cells by density gradient centrifugation. *J. Immunol. Methods* (1980) doi:10.1016/0022-1759(80)90133-7.
6. Chen, et al. Incorporation of lateral microfiltration with immunoaffinity for enhancing the capture efficiency of rare cells. *Sci. Rep.* (2020) doi:10.1038/s41598-020-71041-7.
7. Marek, et al. Magnetic cell sorting: A fast and effective method of concurrent isolation of high purity viable astrocytes and microglia from neonatal mouse brain tissue. *J. Neurosci. Methods* (2008) doi:10.1016/j.jneumeth.2008.08.016.
8. Øren, et al. A comparative study of immunomagnetic methods used for separation of human natural killer cells from peripheral blood. *J. Immunol. Methods* (2005) doi:10.1016/j.jim.2005.04.022.
9. Tondreau, et al. Isolation of BM mesenchymal stem cells by plastic adhesion or negative selection: phenotype, proliferation kinetics and differentiation potential. *Cytotherapy* 6, 372-379 (2004).
10. Lyons, et al. Microarray analysis of human leucocyte subsets: The advantages of positive selection and rapid purification. *BMC Genomics* (2007) doi:10.1186/1471-2164-8-64.
11. Harding, et al. The immunogenicity of humanized and fully human antibodies. *MAbs* (2010) doi:10.4161/mabs.2.3.11641.
12. Elkord, et al. Human monocyte isolation methods influence cytokine production from in vitro generated dendritic cells. *Immunology* (2005) doi:10.1111/j.1365-2567.2004.02076.x.
13. Laghmouchi, et al. Long-term in vitro persistence of magnetic properties after magnetic bead-based cell separation of T cells. *Scand. J. Immunol.* (2020) doi:10.1111/sji.12924.
14. Zhu, and Murthy. Stem cell separation technologies. *Curr. Opin. Chem. Eng.* (2013) doi:10.1016/j.coche.2012.11.002.
15. Ying, et al. A safe and potent anti-CD19 CAR T cell therapy. *Nat. Med.* (2019) doi:10.1038/s41591-019-0421-7.
16. Kacherovsky, et al. Traceless aptamer-mediated isolation of CD8+ T cells for chimeric antigen receptor T-cell therapy. Nat. Biomed. Eng. (2019) doi:10.1038/s41551-019-0411-6.
17. Cardle, et al. Biomaterials in chimeric antigen receptor T-cell process development. *Acc. Chem. Res.* (2020) doi:10.1021/acs.accounts.0c00335.
18. Schmidt, and Skerra. The random peptide library-assisted engineering of a c-terminal affinity peptide, useful for the detection and purification of a functional ig Fv fragment. *Protein Eng. Des. Sel.* (1993) doi:10.1093/protein/6.1.109.
19. Schmidt, et al. Molecular interaction between the strep-tag affinity peptide and its cognate target, streptavidin. *J. Mol. Biol.* (1996) doi:10.1006/jmbi.1996.0061.
20. Korndorfer. Improved affinity of engineered streptavidin for the Strep-tag II peptide is due to a fixed open conformation of the lid-like loop at the binding site. *Protein Sci.* (2002) doi:10.1110/ps.4150102.
21. Schmidt and Skerra. The Strep-tag system for one-step purification and high-affinity detection or capturing of proteins. *Nat. Protoc.* (2007) doi:10.1038/nprot.2007.209.
22. Stemberger, et al. Novel serial positive enrichment technology enables clinical multiparameter cell sorting. *PLoS One* (2012) doi:10.1371/journal.pone.0035798.
23. Neudorfer, et al. Reversible HLA multimers (Streptamers) for the isolation of human cytotoxic T lymphocytes functionally active against tumor- and virus-derived antigens. *J. Immunol. Methods* (2007) doi:10.1016/j.jim.2007.01.001.
24. Odendahl, et al. Clinical-scale isolation of 'minimally manipulated' cytomegalovirus-specific donor lymphocytes for the treatment of refractory cytomegalovirus disease. *Cytotherapy* (2014) doi:10.1016/j.jcyt.2014.05.023.
25. Probst, et al. Rapid multitarget immunomagnetic separation through programmable DNA linker displacement. *J. Am. Chem. Soc.* (2011) doi:10.1021/ja2072324.
26. Dahotre, et al. Individually addressable and dynamic DNA gates for multiplexed cell sorting. *Proc. Natl. Acad. Sci.* U.S.A (2018) doi:10.1073/pnas.1714820115.
27. Tuerk and Gold. Systematic evolution of ligands by exponential enrichment: RNA ligands to bacteriophage T4 DNA polymerase. *Science* (80-.). (1990) doi:10.1126/science.2200121.
28. Ellington and Szostak. In vitro selection of RNA molecules that bind specific ligands. *Nature* (1990) doi:10.1038/346818a0.
29. Zhou and Rossi. Aptamers as targeted therapeutics: Current potential and challenges. *Nat. Rev. Drug Disc.* (2017) doi:10.1038/nrd.2016.199.
30. Walter, et al. Aptamers as affinity ligands for downstream processing. *Eng. Life Sci.* (2012) doi:10.1002/elsc.201100197.

31. Li, et al. Aptamer Displacement Reaction from Live-Cell Surfaces and Its Applications. *J. Am. Chem. Soc.* (2019) doi:10.1021/jacs.9b07191.
32. Chen, et al. Regenerative nanooctopus based on multivalent-aptamer-functionalized magnetic microparticles for effective cell capture in whole blood. *Anal. Chem.* (2019) doi:10.1021/acs.analchem.8b05432.
33. Rusconi, et al. Antidote-mediated control of an anticoagulant aptamer in vivo. *Nat. Biotechnol.* (2004) doi: 10.1038/nbt1023.
34. Gray, et al. Aptamers as Reversible Sorting Ligands for Preparation of Cells in Their Native State. *Cell Chem. Biol.* (2020) doi:10.1016/j.chembiol.2019.12.004.
35. Zhang and Winfree. Control of DNA strand displacement kinetics using toehold exchange. *J. Am. Chem. Soc.* (2009) doi:10.1021/ja906987s.
36. Zhang and Seelig. Dynamic DNA nanotechnology using strand-displacement reactions. *Nat. Chem.* (2011) doi: 10.1038/nchem.957.
37. Cheng, et al. [Submitted] Discovery of a transferrin receptor 1-binding aptamer for removing cancer cells from adoptive T-cell therapy manufacturing. (2022).
38. Zadeh, et al. A. NUPACK: Analysis and design of nucleic acid systems. *J. Comput. Chem.* (2011) doi: 10.1002/jcc.21596.
39. Yang, et al. Regulation of DNA Strand Displacement Using an Allosteric DNA Toehold. *J. Am. Chem. Soc.* (2016) doi:10.1021/jacs.6b08794.
40. Hao, et al. Programmable Live-Cell CRISPR Imaging with Toehold-Switch-Mediated Strand Displacement. *Angew. Chemie-Int. Ed.* (2020) doi:10.1002/anie.202009062.
41. Gelinas, et al. Embracing proteins: Structural themes in aptamer-protein complexes. *Curr. Opin. Struct. Biol.* (2016) doi:10.1016/j.sbi.2016.01.009.
42. Motamedi, et al. Correlation of transferrin receptor (CD71) with Ki67 expression on stimulated human and mouse T cells: The kinetics of expression of T cell activation markers. *J. Immunol. Methods* (2016) doi: 10.1016/j.jim.2016.08.002.
43. Gold, et al. Aptamer-based multiplexed proteomic technology for biomarker discovery. *PLoS One* (2010) doi: 10.1371/journal.pone.0015004.
44. Yoon, et al. Isolation of Foreign Material-Free Endothelial Progenitor Cells Using CD31 Aptamer and Therapeutic Application for Ischemic Injury. *PLoS One* 10, e0131785 (2015).
45. Mohr, et al. Minimally manipulated murine regulatory T cells purified by reversible Fab Multimers are potent suppressors for adoptive T-cell therapy. *Eur. J. Immunol.* (2017) doi:10.1002/eji.201747137.
46. Jackson, et al. Binding of human endothelium to Ulex europaeus I-coated Dynabeads: application to the isolation of microvascular endothelium. *J. Cell Sci.* (1990) doi:10.1242/jcs.96.2.257.
47. Janssenand Rios. Non-specific cell binding characteristics of para-magnetic polystyrene microspheres used for antibody-mediated cell selection. *J. Immunol. Methods* (1989) doi:10.1016/0022-1759(89)90173-7.
48. Chen, et al. Functional polymer surfaces for controlling cell behaviors. *Materials Today* (2018) doi:10.1016/j.mattod.2017.07.002.

Example 3: Prospective Aptamer Sequences for Improving tJBA8.1 Affinity and Specificity The following variant aptamer sequences are specifically contemplated for improvements in affinity and/or specificity for binding to transferrin receptor 1/CD71.

Figure 34A:
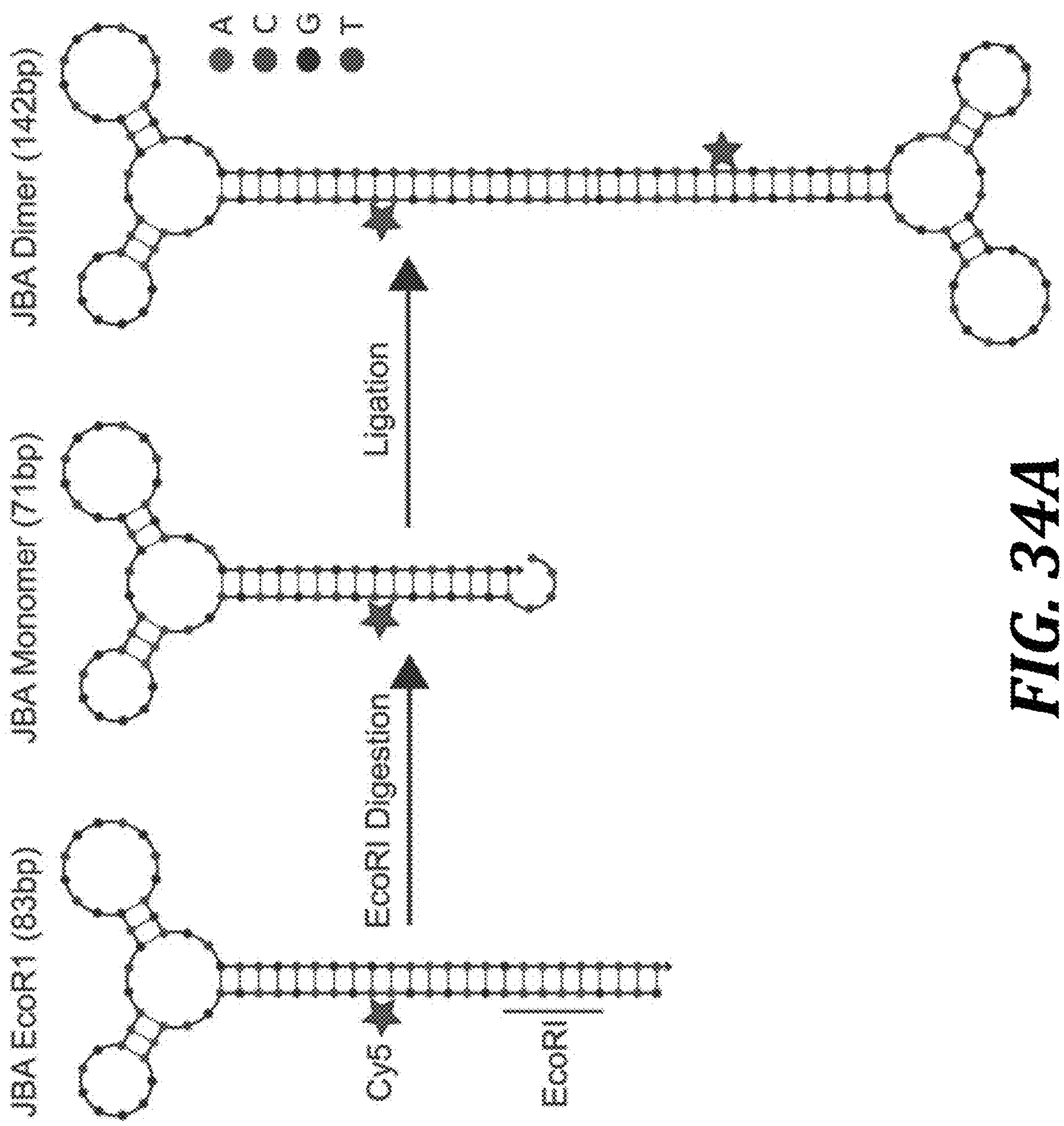
FIGS. 34A-34B. JBA dimer binds Jurkat cells with high affinity.
Figure 34B:
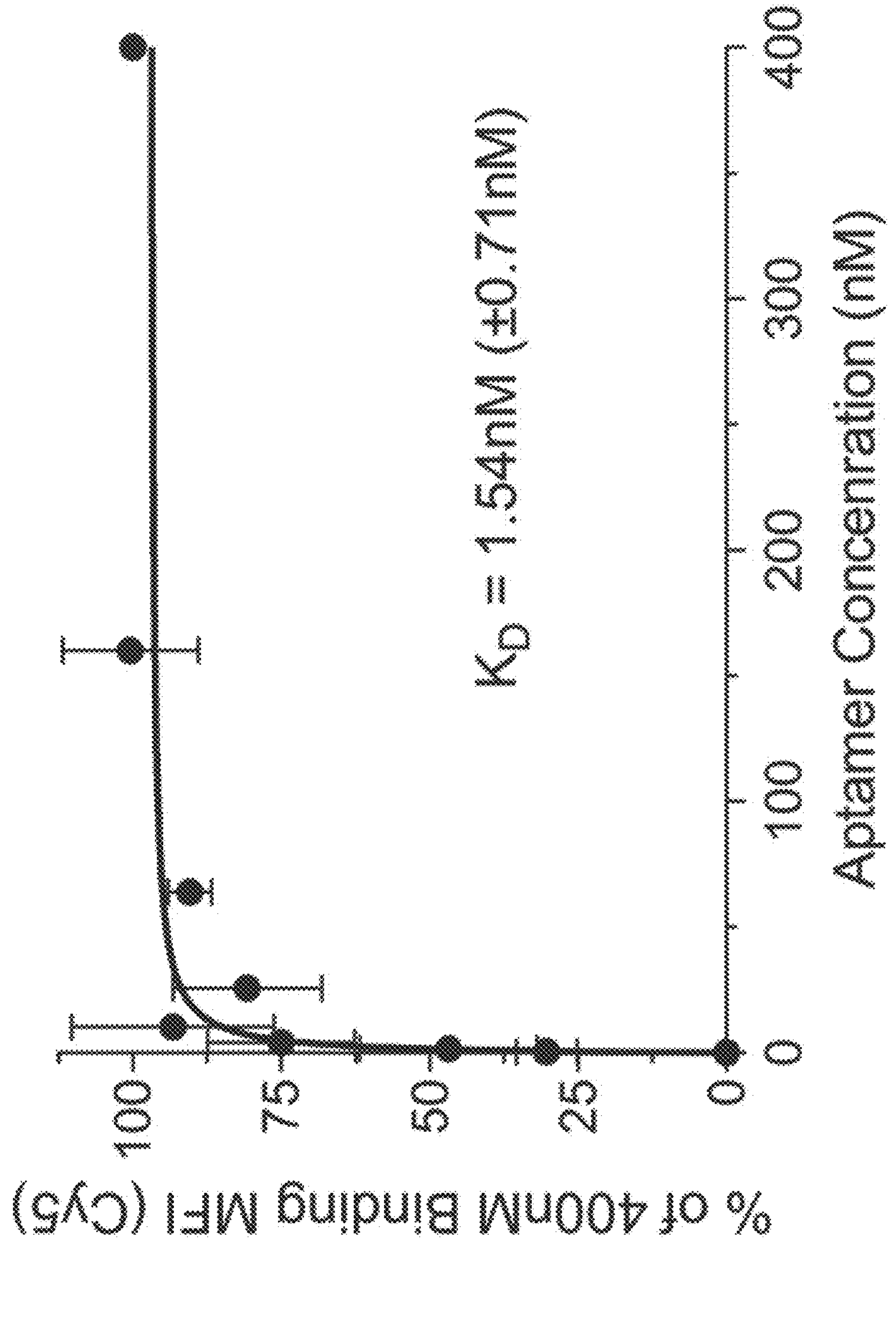

```
1. Truncated JBA8.26
                    (tJBA8.26; SEQ ID NO: 26; FIG. 34A)
GCAGCAGCGTAAAGGGGGTGTTTGTGCGGTGTGGAGTGCGCGCGCTGCTGC
It should be noted that this is truncated in the
same way as tJBA8.1.

2. "tJBA8.1 AGGGG"
                              (SEQ ID NO: 137; FIG. 34B)
GCAGCAGCGTAAAAGGGGTGTTTGTGCGGTGTGGAGTGCGCGTGCTGCTGC

3. "tJBA8.1 GAGGG"
                              (SEQ ID NO: 138; FIG. 34C)
GCAGCAGCGTAAAGAGGGTGTTTGTGCGGTGTGGAGTGCGCGTGCTGCTGC

4. tJBA8.1 G29A
                                         (SEQ ID NO: 139)
GCAGCAGCGTAAAGGGGGTGTTTGTGCGATGTGGAGTGCTCTGTCTGCTGC
```

Example 4: Aptamer tJBA8.26 Mediates Delivery into TfR1-Expressing Raji (Human B Lymphocyte) Cells Aptamer tJBA8.26 sequence: GCAGCAGCGTAAAGGGGGTGTTTGTGCGG TGTGGAGTGCGCGCGCTGCTGC (SEQ ID NO: 26) was fused to a drug loading overhang (DLO) (sequence GCAGAAGAAGAAGAAGAAGAAGAAGAAGAACG; SEQ ID NO: 140). The DLO can be used to load drugs such as nucleic acid binders or nucleic acids with complementary sequences to the DLO. As a model drug, complementary sequence to the DLO with a fluorescein label was used in this example. As a control, a mutated tJBA8.26 sequence was used. The specific sequences used are shown below:

```
tJBA8.26.DLO
                                          SEQ ID NO: 141
GCAGCAGCGTAAAGGGGGTGTTTGTGCGGTGTGGAGTGCGCGCGCTGCTGC

GCAGAAGAAGAAGAAGAAGAAGAAGAAGAACG

mtJBA8.26.DLO
                                          SEQ ID NO: 142
GCAGCAGCGTAAAGGAAGTGTTTGTGCGGTGTGGAGTGCGCGCGCTGCTGC

GCAGAAGAAGAAGAAGAAGAAGAAGAAGAACG

Complementary strand for DLO-fluorescein
                                          SEQ ID NO: 143
CGTTCTTCTTCTTCTTCTTCTTCTTCTTCTGC
```

Aptamers were folded and annealed with the labeled complementary strand in one step at 10 μM by incubating at 95° C. for 5 min, and snap cooling on ice for 10 min in Wash Buffer (WB). (FIG. 36) The aptamer constructs were then incubated at 4° C. or 37° C. for 20 min with Raji cells in Binding Buffer (WB+0.1 mg/mL tRNA+1% BSA). Aptamer association with the cells was analyzed by flow cytometry. tJBA8.26 showed high binding at 4° C. with increased cell association at 37° C., a temperature permissible for cell internalization. (FIG. 37A) In contrast, minimal mutant tJBA8.26 association was observed with Raji cells. Internalization of the aptamers was assessed by treating aptamer bound cells with 0.25% Trypsin, that cleaves Tfr1 from the cell surface. In this case, observed fluorescence is due to internalized aptamer complex. Percent internalization was calculated as a ratio of MFI of Trypsin treated cells/MFI of untreated cells. (FIG. 37A) Thus, tJBA8.26 can facilitate binding and internalization of associated drug cargo into TfR1-expressing cells.

The invention claimed is:

1. A composition comprising an aptamer that selectively binds to human CD71, wherein the aptamer comprises a sequence comprising SEQ ID NO: 32, wherein the aptamer can further comprise a number (N) of nucleotides at each end wherein each nucleotide is selected independently, and wherein each N comprises from 3 nt to 40 nt, from 3 nt to 30 nt, from 3 nt to 20 nt, or from 3 nt to 10 nt.

2. The composition of claim 1, wherein the aptamer comprises SEQ ID NO: 1 (tJBA8.1), SEQ ID NO: 2 (JBA8.1), SEQ ID NO: 26 (tJBA8.26), or SEQ ID NO: 27 (JBA8.26).

3. The composition of claim 1, wherein the aptamer comprises a central loop region, wherein a stem formed by base pairing of nucleotides from the 5' and 3' ends of the aptamer projects from the central loop region, and wherein first and second stem loops project from the central loop region.

4. The composition of claim 3, wherein the central loop region comprises nucleotides 8-11, 23-26, and 41-44 of SEQ ID NO: 1; or wherein the central loop region comprises nucleotides 9-11, 23-26, and 41-43 of SEQ ID NO: 26.

5. The composition of claim 4, wherein nucleotides 8 and 44, 11 and 23, and 26 and 41 are base paired to each other, respectively; or wherein nucleotides 9 and 43, 11 and 23, and 26 and 41 are base paired to each other, respectively.

6. The composition of claim 1, wherein the aptamer is attached to a solid support or phase-changing agent.

7. The composition of claim 1, wherein the aptamer further comprises a detectable moiety, a label, a tag, or a probe.

8. The composition of claim 1, further comprising a pharmaceutically acceptable carrier.

9. A method for preparing a composition depleted of cells expressing CD71, the method comprising:

contacting a biological sample comprising a desired cell population with a composition of claim 1, under conditions and for a time permitting binding of the aptamer to human CD71 expressed on the cells in said sample; and separating cells bound to the aptamer from the cells not bound to the aptamer, thereby providing a preparation of cells depleted in human CD71 expressing cells for use in generating a therapeutic cell composition.

10. A method for preparing T cells to be used in generating a therapeutic cell composition, the method comprising:

contacting a biological sample comprising T cells with a composition of claim 1 under conditions and for a time permitting binding of the aptamer to human CD71 expressed on cells in said sample; and separating cells bound to the aptamer from cells not bound to the aptamer, thereby providing a preparation of T cells depleted in human CD71 expressing cells, for use in generating a therapeutic cell composition.

11. The method of claim 10, wherein the aptamer is bound to a solid support.

12. The method of claim 10, wherein the T cells are genetically modified either prior to or after separation and optionally wherein the genetic modification comprises introducing a nucleic acid construct encoding a chimeric antigen receptor.

13. A method for depleting human CD71-expressing cells from a biological sample comprising a plurality of cell types, the method comprising:

contacting a biological sample comprising a plurality of cell types with a composition of claim 1 under conditions and for a time permitting binding of the aptamer to human CD71 expressed on cells in said sample; and separating cells bound to the aptamer from cells not bound to the aptamer, thereby providing a preparation depleted of human CD71 expressing cells from the biological sample.

14. The method of claim 13, wherein the cell preparation depleted of CD71 expressing cells comprises NK cells, monocytes, or macrophage.

15. A method for isolating cells expressing human CD71, the method comprising:

contacting a biological sample comprising human CD71-expressing cells with a composition of claim 1 under conditions and for a time permitting binding of the aptamer to human CD71 expressed on cells in said sample; and separating cells bound to the aptamer from cells not bound to the aptamer, thereby isolating cells expressing human CD71 from the biological sample.

16. The method of claim 15, wherein the isolated cells are tumor cells or fetal nucleated red blood cells.

17. A method of treating a cancer or an immune-related disease in a human subject, the method comprising: administering the T cells depleted of the cells expressing human CD71 produced by the method of claim 10 or an engineered or differentiated cell thereof to the subject in need thereof, thereby treating the disease.

18. A method of delivering a therapeutic agent, the method comprising administering a composition of claim 1, wherein the aptamer is attached to a therapeutic drug, a formulation comprising a therapeutic drug, or a therapeutic cell.

19. The method of claim 18, wherein the therapeutic drug is a nucleic acid or a ribonucleoprotein.

20. The method of claim 18, wherein the delivery comprises receptor-mediated transcytosis.

* * * * *

SEQUENCE LISTING

```
Sequence total quantity: 148
SEQ ID NO: 1            moltype = DNA  length = 51
FEATURE                 Location/Qualifiers
source                  1..51
                        mol_type = other DNA
                        organism = synthetic construct
SEQUENCE: 1
gcagcagcgt aaagggggtg tttgtgcggt gtggagtgcg cgtgctgctg c           51

SEQ ID NO: 2            moltype = DNA  length = 81
FEATURE                 Location/Qualifiers
source                  1..81
                        mol_type = other DNA
                        organism = synthetic construct
SEQUENCE: 2
atccagagtg acgcagcagc gtaaaggggg tgtttgtgcg gtgtggagtg cgcgtgctgc  60
tgctggacac ggtggcttag t                                            81

SEQ ID NO: 3            moltype = DNA  length = 51
FEATURE                 Location/Qualifiers
source                  1..51
                        mol_type = other DNA
                        organism = synthetic construct
SEQUENCE: 3
gcagcaacgt aaagggggtg tttgtgcggt gtggagtgcg cgtgctgctg c           51

SEQ ID NO: 4            moltype = DNA  length = 51
FEATURE                 Location/Qualifiers
source                  1..51
                        mol_type = other DNA
                        organism = synthetic construct
SEQUENCE: 4
gcagcagcgt aaagggagtg tttgtgcggt gtggagtgcg cgtgctgctg c           51

SEQ ID NO: 5            moltype = DNA  length = 51
FEATURE                 Location/Qualifiers
source                  1..51
                        mol_type = other DNA
                        organism = synthetic construct
SEQUENCE: 5
gcagcagcgt aaagggggtg tttgtgcggt gtggagtgcg cgtgctgcta c           51

SEQ ID NO: 6            moltype = DNA  length = 51
FEATURE                 Location/Qualifiers
source                  1..51
                        mol_type = other DNA
                        organism = synthetic construct
SEQUENCE: 6
gcagcagcgt aaagggggtg tttgtgcagt gtggagtgcg cgtgctgctg c           51

SEQ ID NO: 7            moltype = DNA  length = 51
FEATURE                 Location/Qualifiers
source                  1..51
                        mol_type = other DNA
                        organism = synthetic construct
SEQUENCE: 7
gcagcagcgt aaaggaggtg tttgtgcggt gtggagtgcg cgtgctgctg c           51

SEQ ID NO: 8            moltype = DNA  length = 51
FEATURE                 Location/Qualifiers
source                  1..51
                        mol_type = other DNA
                        organism = synthetic construct
SEQUENCE: 8
gcagcagcgt aaagggggtg tttgtgcggt gtgaagtgcg cgtgctgctg c           51

SEQ ID NO: 9            moltype = DNA  length = 51
FEATURE                 Location/Qualifiers
source                  1..51
                        mol_type = other DNA
                        organism = synthetic construct
SEQUENCE: 9
gcagcagcgt aaagggggtg tttgtgcggt gtggagtgcg cgtgctactg c           51

SEQ ID NO: 10           moltype = DNA  length = 51
FEATURE                 Location/Qualifiers
source                  1..51
                        mol_type = other DNA
```

```
                       organism = synthetic construct
SEQUENCE: 10
gcagcagcgt aaagggggtg tttatgcggt gtggagtgcg cgtgctgctg c           51

SEQ ID NO: 11          moltype = DNA  length = 51
FEATURE                Location/Qualifiers
source                 1..51
                       mol_type = other DNA
                       organism = synthetic construct
SEQUENCE: 11
gcagcagcgt aaagggggtg tttgtgcggt gtggagtgca cgtgctgctg c           51

SEQ ID NO: 12          moltype = DNA  length = 51
FEATURE                Location/Qualifiers
source                 1..51
                       mol_type = other DNA
                       organism = synthetic construct
SEQUENCE: 12
gcagcagcgt aaagggggtg tttgtgcggt atggagtgcg cgtgctgctg c           51

SEQ ID NO: 13          moltype = DNA  length = 51
FEATURE                Location/Qualifiers
source                 1..51
                       mol_type = other DNA
                       organism = synthetic construct
SEQUENCE: 13
gcagcagcgt aaagggggtg tttgtgcggt gtggagtgcg catgctgctg c           51

SEQ ID NO: 14          moltype = DNA  length = 51
FEATURE                Location/Qualifiers
source                 1..51
                       mol_type = other DNA
                       organism = synthetic construct
SEQUENCE: 14
gcagcagcat aaagggggtg tttgtgcggt gtggagtgcg cgtgctgctg c           51

SEQ ID NO: 15          moltype = DNA  length = 51
FEATURE                Location/Qualifiers
source                 1..51
                       mol_type = other DNA
                       organism = synthetic construct
SEQUENCE: 15
gcagcagcgt aaagggggtg tttgtgcggt ttggagtgcg cgtgctgctg c           51

SEQ ID NO: 16          moltype = DNA  length = 51
FEATURE                Location/Qualifiers
source                 1..51
                       mol_type = other DNA
                       organism = synthetic construct
SEQUENCE: 16
gcagcagcgt aaagggggtg tttgtgctgt gtggagtgcg cgtgctgctg c           51

SEQ ID NO: 17          moltype = DNA  length = 51
FEATURE                Location/Qualifiers
source                 1..51
                       mol_type = other DNA
                       organism = synthetic construct
SEQUENCE: 17
gcagcatcgt aaagggggtg tttgtgcggt gtggagtgcg cgtgctgctg c           51

SEQ ID NO: 18          moltype = DNA  length = 51
FEATURE                Location/Qualifiers
source                 1..51
                       mol_type = other DNA
                       organism = synthetic construct
SEQUENCE: 18
gcagcagctt aaagggggtg tttgtgcggt gtggagtgcg cgtgctgctg c           51

SEQ ID NO: 19          moltype = DNA  length = 51
FEATURE                Location/Qualifiers
source                 1..51
                       mol_type = other DNA
                       organism = synthetic construct
SEQUENCE: 19
gcagcagcgt aaagggggtg tttgtgcggt gtgtagtgcg cgtgctgctg c           51

SEQ ID NO: 20          moltype = DNA  length = 51
FEATURE                Location/Qualifiers
source                 1..51
```

```
                         mol_type = other DNA
                         organism = synthetic construct
SEQUENCE: 20
gcagcagcgt aaagggggtg tttgtgcggt gtggagtgcg cgtgctgctg a           51

SEQ ID NO: 21            moltype = DNA  length = 51
FEATURE                  Location/Qualifiers
source                   1..51
                         mol_type = other DNA
                         organism = synthetic construct
SEQUENCE: 21
gcagcagcgt aaagggggtg tttgtgcggt gtggagtgcg tgtgctgctg c           51

SEQ ID NO: 22            moltype = DNA  length = 51
FEATURE                  Location/Qualifiers
source                   1..51
                         mol_type = other DNA
                         organism = synthetic construct
SEQUENCE: 22
gcagcagcgt aaagggggtg tttgtgcggt gtggagtgtg cgtgctgctg c           51

SEQ ID NO: 23            moltype = DNA  length = 51
FEATURE                  Location/Qualifiers
source                   1..51
                         mol_type = other DNA
                         organism = synthetic construct
SEQUENCE: 23
gcagcagcgt aaagggggtg tttgtgtggt gtggagtgcg cgtgctgctg c           51

SEQ ID NO: 24            moltype = DNA  length = 51
FEATURE                  Location/Qualifiers
source                   1..51
                         mol_type = other DNA
                         organism = synthetic construct
SEQUENCE: 24
gcagcagcgt aaagggggtg tttgtgcggt gtggagtgcg cgtgctgctg t           51

SEQ ID NO: 25            moltype = DNA  length = 51
FEATURE                  Location/Qualifiers
source                   1..51
                         mol_type = other DNA
                         organism = synthetic construct
SEQUENCE: 25
gcagcagcgc aaagggggtg tttgtgcggt gtggagtgcg cgtgctgctg c           51

SEQ ID NO: 26            moltype = DNA  length = 51
FEATURE                  Location/Qualifiers
source                   1..51
                         mol_type = other DNA
                         organism = synthetic construct
SEQUENCE: 26
gcagcagcgt aaagggggtg tttgtgcggt gtggagtgcg cgcgctgctg c           51

SEQ ID NO: 27            moltype = DNA  length = 81
FEATURE                  Location/Qualifiers
source                   1..81
                         mol_type = other DNA
                         organism = synthetic construct
SEQUENCE: 27
atccagagtg acgcagcagc gtaaaggggg tgtttgtgcg gtgtggagtg cgcgcgctgc  60
tgctggacac ggtggcttag t                                            81

SEQ ID NO: 28            moltype = DNA  length = 51
FEATURE                  Location/Qualifiers
source                   1..51
                         mol_type = other DNA
                         organism = synthetic construct
SEQUENCE: 28
gcagcagcgt aaagggggtg tttgtgcggt gtggagtgcg cgtgcggctg c           51

SEQ ID NO: 29            moltype = DNA  length = 51
FEATURE                  Location/Qualifiers
source                   1..51
                         mol_type = other DNA
                         organism = synthetic construct
SEQUENCE: 29
gcagcagcgt aaagggggtg tttgggcggt gtggagtgcg cgtgctgctg c           51

SEQ ID NO: 30            moltype = DNA  length = 51
```

```
FEATURE                Location/Qualifiers
source                 1..51
                       mol_type = other DNA
                       organism = synthetic construct
SEQUENCE: 30
gcagcagcgt aaagggggtg tgtgtgcggt gtggagtgcg cgtgctgctg c          51

SEQ ID NO: 31          moltype = DNA  length = 51
FEATURE                Location/Qualifiers
source                 1..51
                       mol_type = other DNA
                       organism = synthetic construct
SEQUENCE: 31
gcagcagcgt agagggggtg tttgtgcggt gtggagtgcg cgtgctgctg c          51

SEQ ID NO: 32          moltype = DNA  length = 51
FEATURE                Location/Qualifiers
source                 1..51
                       mol_type = other DNA
                       organism = synthetic construct
SEQUENCE: 32
gcagcancnn anaggnngtg tntnngnngt ntgnagtgnn nnngcnnctn n          51

SEQ ID NO: 33          moltype = DNA  length = 51
FEATURE                Location/Qualifiers
source                 1..51
                       mol_type = other DNA
                       organism = synthetic construct
SEQUENCE: 33
gcagcancgt aaagggggtg tttgtgcggt gtggagtgcg cgtgctgctg c          51

SEQ ID NO: 34          moltype = DNA  length = 51
FEATURE                Location/Qualifiers
source                 1..51
                       mol_type = other DNA
                       organism = synthetic construct
SEQUENCE: 34
gcagcagcnt aaagggggtg tttgtgcggt gtggagtgcg cgtgctgctg c          51

SEQ ID NO: 35          moltype = DNA  length = 57
FEATURE                Location/Qualifiers
source                 1..57
                       mol_type = other DNA
                       organism = synthetic construct
SEQUENCE: 35
gcagcagcag cagcgnaaag ggggtgtttg tgcggtgtgg agtgcgcgtg ctgctgc    57

SEQ ID NO: 36          moltype = DNA  length = 51
FEATURE                Location/Qualifiers
source                 1..51
                       mol_type = other DNA
                       organism = synthetic construct
SEQUENCE: 36
gcagcagcgt anagggggtg tttgtgcggt gtggagtgcg cgtgctgctg c          51

SEQ ID NO: 37          moltype = DNA  length = 51
FEATURE                Location/Qualifiers
source                 1..51
                       mol_type = other DNA
                       organism = synthetic construct
SEQUENCE: 37
gcagcagcgt aaaggnggtg tttgtgcggt gtggagtgcg cgtgctgctg c          51

SEQ ID NO: 38          moltype = DNA  length = 51
FEATURE                Location/Qualifiers
source                 1..51
                       mol_type = other DNA
                       organism = synthetic construct
SEQUENCE: 38
gcagcagcgt aaagggngtg tttgtgcggt gtggagtgcg cgtgctgctg c          51

SEQ ID NO: 39          moltype = DNA  length = 51
FEATURE                Location/Qualifiers
source                 1..51
                       mol_type = other DNA
                       organism = synthetic construct
SEQUENCE: 39
gcagcagcgt aaagggggtg tntgtgcggt gtggagtgcg cgtgctgctg c          51
```

```
SEQ ID NO: 40          moltype = DNA  length = 51
FEATURE                Location/Qualifiers
source                 1..51
                       mol_type = other DNA
                       organism = synthetic construct
SEQUENCE: 40
gcagcagcgt aaagggggtg tttntgcggt gtggagtgcg cgtgctgctg c           51

SEQ ID NO: 41          moltype = DNA  length = 51
FEATURE                Location/Qualifiers
source                 1..51
                       mol_type = other DNA
                       organism = synthetic construct
SEQUENCE: 41
gcagcagcgt aaagggggtg tttgngcggt gtggagtgcg cgtgctgctg c           51

SEQ ID NO: 42          moltype = DNA  length = 51
FEATURE                Location/Qualifiers
source                 1..51
                       mol_type = other DNA
                       organism = synthetic construct
SEQUENCE: 42
gcagcagcgt aaagggggtg tttgtgnggt gtggagtgcg cgtgctgctg c           51

SEQ ID NO: 43          moltype = DNA  length = 51
FEATURE                Location/Qualifiers
source                 1..51
                       mol_type = other DNA
                       organism = synthetic construct
SEQUENCE: 43
gcagcagcgt aaagggggtg tttgtgcngt gtggagtgcg cgtgctgctg c           51

SEQ ID NO: 44          moltype = DNA  length = 51
FEATURE                Location/Qualifiers
source                 1..51
                       mol_type = other DNA
                       organism = synthetic construct
SEQUENCE: 44
gcagcagcgt aaagggggtg tttgtgcggt ntggagtgcg cgtgctgctg c           51

SEQ ID NO: 45          moltype = DNA  length = 51
FEATURE                Location/Qualifiers
source                 1..51
                       mol_type = other DNA
                       organism = synthetic construct
SEQUENCE: 45
gcagcagcgt aaagggggtg tttgtgcggt gtgnagtgcg cgtgctgctg c           51

SEQ ID NO: 46          moltype = DNA  length = 51
FEATURE                Location/Qualifiers
source                 1..51
                       mol_type = other DNA
                       organism = synthetic construct
SEQUENCE: 46
gcagcagcgt aaagggggtg tttgtgcggt gtggagtgng cgtgctgctg c           51

SEQ ID NO: 47          moltype = DNA  length = 51
FEATURE                Location/Qualifiers
source                 1..51
                       mol_type = other DNA
                       organism = synthetic construct
SEQUENCE: 47
gcagcagcgt aaagggggtg tttgtgcggt gtggagtgcn cgtgctgctg c           51

SEQ ID NO: 48          moltype = DNA  length = 51
FEATURE                Location/Qualifiers
source                 1..51
                       mol_type = other DNA
                       organism = synthetic construct
SEQUENCE: 48
gcagcagcgt aaagggggtg tttgtgcggt gtggagtgcg ngtgctgctg c           51

SEQ ID NO: 49          moltype = DNA  length = 51
FEATURE                Location/Qualifiers
source                 1..51
                       mol_type = other DNA
                       organism = synthetic construct
SEQUENCE: 49
gcagcagcgt aaagggggtg tttgtgcggt gtggagtgcg cntgctgctg c           51
```

```
SEQ ID NO: 50          moltype = DNA  length = 51
FEATURE                Location/Qualifiers
source                 1..51
                       mol_type = other DNA
                       organism = synthetic construct
SEQUENCE: 50
gcagcagcgt aaagggggtg tttgtgcggt gtggagtgcg cgngctgctg c           51

SEQ ID NO: 51          moltype = DNA  length = 51
FEATURE                Location/Qualifiers
source                 1..51
                       mol_type = other DNA
                       organism = synthetic construct
SEQUENCE: 51
gcagcagcgt aaagggggtg tttgtgcggt gtggagtgcg cgtgcngctg c           51

SEQ ID NO: 52          moltype = DNA  length = 51
FEATURE                Location/Qualifiers
source                 1..51
                       mol_type = other DNA
                       organism = synthetic construct
SEQUENCE: 52
gcagcagcgt aaagggggtg tttgtgcggt gtggagtgcg cgtgctnctg c           51

SEQ ID NO: 53          moltype = DNA  length = 51
FEATURE                Location/Qualifiers
source                 1..51
                       mol_type = other DNA
                       organism = synthetic construct
SEQUENCE: 53
gcagcagcgt aaagggggtg tttgtgcggt gtggagtgcg cgtgctgctn c           51

SEQ ID NO: 54          moltype = DNA  length = 51
FEATURE                Location/Qualifiers
source                 1..51
                       mol_type = other DNA
                       organism = synthetic construct
SEQUENCE: 54
gcagcagcgt aaagggggtg tttgtgcggt gtggagtgcg cgtgctgctg n           51

SEQ ID NO: 55          moltype = DNA  length = 64
FEATURE                Location/Qualifiers
source                 1..64
                       mol_type = other DNA
                       organism = synthetic construct
SEQUENCE: 55
ttatgacgca gcagaagagt agatgaaacg ttttttcgcc cgataaaagg gacgtgcgtc  60
ataa                                                               64

SEQ ID NO: 56          moltype = DNA  length = 88
FEATURE                Location/Qualifiers
source                 1..88
                       mol_type = other DNA
                       organism = synthetic construct
SEQUENCE: 56
atccagagtg acgcagcaga agagtagatg aaacgttttt tcgcccgata aaagggacgt  60
gcgtcagaca tggacacggt ggcttagt                                     88

SEQ ID NO: 57          moltype = DNA  length = 59
FEATURE                Location/Qualifiers
source                 1..59
                       mol_type = other DNA
                       organism = synthetic construct
SEQUENCE: 57
aatgatacgg cgaccaccga gatctacacc gaggagatac cactaagcca ccgtgtcca   59

SEQ ID NO: 58          moltype = DNA  length = 61
FEATURE                Location/Qualifiers
source                 1..61
                       mol_type = other DNA
                       organism = synthetic construct
SEQUENCE: 58
caagcagaac acggcatacg agatgcaatt cgacagaccg tcgatccaga gtgacgcagc  60
a                                                                  61

SEQ ID NO: 59          moltype = DNA  length = 61
FEATURE                Location/Qualifiers
source                 1..61
```

```
                        mol_type = other DNA
                        organism = synthetic construct
SEQUENCE: 59
caagcagaag acggcatacg agattcgatt aaacagaccg tcgatccaga gtgacgcagc  60
a                                                                   61

SEQ ID NO: 60           moltype = DNA  length = 61
FEATURE                 Location/Qualifiers
source                  1..61
                        mol_type = other DNA
                        organism = synthetic construct
SEQUENCE: 60
caagcagaag acggcatacg agatgaatgg acacagaccg tcgatccaga gtgacgcagc  60
a                                                                   61

SEQ ID NO: 61           moltype = DNA  length = 61
FEATURE                 Location/Qualifiers
source                  1..61
                        mol_type = other DNA
                        organism = synthetic construct
SEQUENCE: 61
caagcagaag acggcatacg agatagaatc agacagaccg tcgatccaga gtgacgcagc  60
a                                                                   61

SEQ ID NO: 62           moltype = DNA  length = 61
FEATURE                 Location/Qualifiers
source                  1..61
                        mol_type = other DNA
                        organism = synthetic construct
SEQUENCE: 62
caagcagaag acggcatacg agataactgc caacagaccg tcgatccaga gtgacgcagc  60
a                                                                   61

SEQ ID NO: 63           moltype = DNA  length = 61
FEATURE                 Location/Qualifiers
source                  1..61
                        mol_type = other DNA
                        organism = synthetic construct
SEQUENCE: 63
caagcagaag acggcatacg agataagtaa cgacagaccg tcgatccaga gtgacgcagc  60
a                                                                   61

SEQ ID NO: 64           moltype = DNA  length = 61
FEATURE                 Location/Qualifiers
source                  1..61
                        mol_type = other DNA
                        organism = synthetic construct
SEQUENCE: 64
caagcagaag acggcatacg agatactcaa tgacagaccg tcgatccaga gtgacgcagc  60
a                                                                   61

SEQ ID NO: 65           moltype = DNA  length = 61
FEATURE                 Location/Qualifiers
source                  1..61
                        mol_type = other DNA
                        organism = synthetic construct
SEQUENCE: 65
caagcagaag acggcatacg agatcaagag gtacagaccg tcgatccaga gtgacgcagc  60
a                                                                   61

SEQ ID NO: 66           moltype = DNA  length = 61
FEATURE                 Location/Qualifiers
source                  1..61
                        mol_type = other DNA
                        organism = synthetic construct
SEQUENCE: 66
caagcagaag acggcatacg agattcgatt aaacagaccg tcgatccaga gtgacgcagc  60
a                                                                   61

SEQ ID NO: 67           moltype = DNA  length = 46
FEATURE                 Location/Qualifiers
source                  1..46
                        mol_type = other DNA
                        organism = synthetic construct
SEQUENCE: 67
gcgtaaaggg gggtgtttgt gcggtgtgga gtgcgcgtgc tgctgc                  46

SEQ ID NO: 68           moltype = DNA  length = 45
FEATURE                 Location/Qualifiers
```

```
source                  1..45
                        mol_type = other DNA
                        organism = synthetic construct
SEQUENCE: 68
atccgggaga gtcgttgtgt tgaggtccgc ccctgctcgc ccgcg                  45

SEQ ID NO: 69           moltype = DNA  length = 45
FEATURE                 Location/Qualifiers
source                  1..45
                        mol_type = other DNA
                        organism = synthetic construct
SEQUENCE: 69
ggggccgcgg atgcaaacgc ccgatagggg gacggcactg gagct                  45

SEQ ID NO: 70           moltype = DNA  length = 45
FEATURE                 Location/Qualifiers
source                  1..45
                        mol_type = other DNA
                        organism = synthetic construct
SEQUENCE: 70
acccaaacca ccagccgggg atgcaaacac cgcacaggga acggc                  45

SEQ ID NO: 71           moltype = DNA  length = 45
FEATURE                 Location/Qualifiers
source                  1..45
                        mol_type = other DNA
                        organism = synthetic construct
SEQUENCE: 71
aagcggtttt cgggttcggg tctgggggtt gggttgtcgg cacta                  45

SEQ ID NO: 72           moltype = DNA  length = 45
FEATURE                 Location/Qualifiers
source                  1..45
                        mol_type = other DNA
                        organism = synthetic construct
SEQUENCE: 72
acagacagct gcgccgccgg gagggcaccc ggacgggctg ggcgg                  45

SEQ ID NO: 73           moltype = DNA  length = 45
FEATURE                 Location/Qualifiers
source                  1..45
                        mol_type = other DNA
                        organism = synthetic construct
SEQUENCE: 73
accacagatg caaatgcgcg agagcgggac ggtttgctag gctca                  45

SEQ ID NO: 74           moltype = DNA  length = 45
FEATURE                 Location/Qualifiers
source                  1..45
                        mol_type = other DNA
                        organism = synthetic construct
SEQUENCE: 74
gtgggccaaa tggattggat tagggttggg ccgcccggga ggggt                  45

SEQ ID NO: 75           moltype = DNA  length = 45
FEATURE                 Location/Qualifiers
source                  1..45
                        mol_type = other DNA
                        organism = synthetic construct
SEQUENCE: 75
aggcgctaga cgcaatcccg caagcggagc cggattccct agtgg                  45

SEQ ID NO: 76           moltype = DNA  length = 45
FEATURE                 Location/Qualifiers
source                  1..45
                        mol_type = other DNA
                        organism = synthetic construct
SEQUENCE: 76
gcataaaggg ggtgtttgtg cggtgtggag tgcgcgtgct gctgc                  45

SEQ ID NO: 77           moltype = DNA  length = 45
FEATURE                 Location/Qualifiers
source                  1..45
                        mol_type = other DNA
                        organism = synthetic construct
SEQUENCE: 77
gccggtcgca gatgcaaatg cccgccaggg ggacgcgggc tgcca                  45

SEQ ID NO: 78           moltype = DNA  length = 45
```

```
FEATURE                 Location/Qualifiers
source                  1..45
                        mol_type = other DNA
                        organism = synthetic construct
SEQUENCE: 78
cagatgcaaa tgcctgacca gggaactgcg actggatggc tcttg                    45

SEQ ID NO: 79           moltype = DNA  length = 45
FEATURE                 Location/Qualifiers
source                  1..45
                        mol_type = other DNA
                        organism = synthetic construct
SEQUENCE: 79
atcacagggc tacaaggtgc taaacgtaaa ctagcaagag aacta                    45

SEQ ID NO: 80           moltype = DNA  length = 45
FEATURE                 Location/Qualifiers
source                  1..45
                        mol_type = other DNA
                        organism = synthetic construct
SEQUENCE: 80
gatgcaaatg ctcgagagag gaccggcggc actggtgaac gtagg                    45

SEQ ID NO: 81           moltype = DNA  length = 45
FEATURE                 Location/Qualifiers
source                  1..45
                        mol_type = other DNA
                        organism = synthetic construct
SEQUENCE: 81
ctctcggggg gtaggtggga agggggccgc cccctgggtt aggct                    45

SEQ ID NO: 82           moltype = DNA  length = 45
FEATURE                 Location/Qualifiers
source                  1..45
                        mol_type = other DNA
                        organism = synthetic construct
SEQUENCE: 82
agcggggatg caaacacccg aaaggggaac gggagctgcg tcaag                    45

SEQ ID NO: 83           moltype = DNA  length = 45
FEATURE                 Location/Qualifiers
source                  1..45
                        mol_type = other DNA
                        organism = synthetic construct
SEQUENCE: 83
aggtggctgt gggcggatgg tgggctcgcg tgggcggcca cctga                    45

SEQ ID NO: 84           moltype = DNA  length = 45
FEATURE                 Location/Qualifiers
source                  1..45
                        mol_type = other DNA
                        organism = synthetic construct
SEQUENCE: 84
acgttatccc ctttacgggg tcctagagcc ccgtgagtgc tcacg                    45

SEQ ID NO: 85           moltype = DNA  length = 45
FEATURE                 Location/Qualifiers
source                  1..45
                        mol_type = other DNA
                        organism = synthetic construct
SEQUENCE: 85
tcggtgttta tggtgtctgt cggtgcgtac tcggggcttc actag                    45

SEQ ID NO: 86           moltype = DNA  length = 45
FEATURE                 Location/Qualifiers
source                  1..45
                        mol_type = other DNA
                        organism = synthetic construct
SEQUENCE: 86
ttggaggtgg cggatgcaaa cgctagacag aggcaccagc tccaa                    45

SEQ ID NO: 87           moltype = DNA  length = 45
FEATURE                 Location/Qualifiers
source                  1..45
                        mol_type = other DNA
                        organism = synthetic construct
SEQUENCE: 87
gactgctgtg ccaccgggag tgccttcagc gccgtacggt ctgct                    45
```

```
SEQ ID NO: 88          moltype = DNA  length = 45
FEATURE                Location/Qualifiers
source                 1..45
                       mol_type = other DNA
                       organism = synthetic construct
SEQUENCE: 88
acgcagcaag gtgctaaacg caagcccgga ttctcgtgcg tcaag                  45

SEQ ID NO: 89          moltype = DNA  length = 45
FEATURE                Location/Qualifiers
source                 1..45
                       mol_type = other DNA
                       organism = synthetic construct
SEQUENCE: 89
gatgcaaatg cccgaatggg ggacggcgga cacggggtgt gccga                  45

SEQ ID NO: 90          moltype = DNA  length = 45
FEATURE                Location/Qualifiers
source                 1..45
                       mol_type = other DNA
                       organism = synthetic construct
SEQUENCE: 90
tacggcttat gctcagaggg gctgtgggcc gaggggagcg tcgcg                  45

SEQ ID NO: 91          moltype = DNA  length = 45
FEATURE                Location/Qualifiers
source                 1..45
                       mol_type = other DNA
                       organism = synthetic construct
SEQUENCE: 91
tgtaagccga atgttggtgc ttgggtaggc gccattgtga gctcg                  45

SEQ ID NO: 92          moltype = DNA  length = 45
FEATURE                Location/Qualifiers
source                 1..45
                       mol_type = other DNA
                       organism = synthetic construct
SEQUENCE: 92
gcgtaaaggg ggtgtttgtg cggtgtggag tgcgcgcgct gctgc                  45

SEQ ID NO: 93          moltype = DNA  length = 45
FEATURE                Location/Qualifiers
source                 1..45
                       mol_type = other DNA
                       organism = synthetic construct
SEQUENCE: 93
ctgtggggtc acattggggg acgggaccgt gcgtgagatc taaga                  45

SEQ ID NO: 94          moltype = DNA  length = 45
FEATURE                Location/Qualifiers
source                 1..45
                       mol_type = other DNA
                       organism = synthetic construct
SEQUENCE: 94
gggttccgga tgtggtgggg cttagggggg tttcactgct agcgt                  45

SEQ ID NO: 95          moltype = DNA  length = 45
FEATURE                Location/Qualifiers
source                 1..45
                       mol_type = other DNA
                       organism = synthetic construct
SEQUENCE: 95
aaggttgcca taccaccggg agcgttcgag tacggcctgt cgcgc                  45

SEQ ID NO: 96          moltype = DNA  length = 45
FEATURE                Location/Qualifiers
source                 1..45
                       mol_type = other DNA
                       organism = synthetic construct
SEQUENCE: 96
aggggtacaa ggtgttaaac gtaaattctg cgcggagggg aactt                  45

SEQ ID NO: 97          moltype = DNA  length = 45
FEATURE                Location/Qualifiers
source                 1..45
                       mol_type = other DNA
                       organism = synthetic construct
SEQUENCE: 97
gacgcagcag tgccatcggg ggggatttcc ttgtacgacg tcacc                  45
```

```
SEQ ID NO: 98          moltype = DNA  length = 45
FEATURE                Location/Qualifiers
source                 1..45
                       mol_type = other DNA
                       organism = synthetic construct
SEQUENCE: 98
gtgccatcgg gaggcgcgag tccgtacgac gtcatttggc aaaac                  45

SEQ ID NO: 99          moltype = DNA  length = 45
FEATURE                Location/Qualifiers
source                 1..45
                       mol_type = other DNA
                       organism = synthetic construct
SEQUENCE: 99
aaaagaagcg accgagacca cggatgcaaa cgcccaggcg gggaa                  45

SEQ ID NO: 100         moltype = DNA  length = 45
FEATURE                Location/Qualifiers
source                 1..45
                       mol_type = other DNA
                       organism = synthetic construct
SEQUENCE: 100
ctgtggcgta attctggtcg gcggtcacgt gcgtgagagc tgggg                  45

SEQ ID NO: 101         moltype = DNA  length = 45
FEATURE                Location/Qualifiers
source                 1..45
                       mol_type = other DNA
                       organism = synthetic construct
SEQUENCE: 101
aggtgttaaa cgctaacgcc agttatctta aagaaagtaa acgac                  45

SEQ ID NO: 102         moltype = DNA  length = 45
FEATURE                Location/Qualifiers
source                 1..45
                       mol_type = other DNA
                       organism = synthetic construct
SEQUENCE: 102
tcaaggggtt acacgaaaag ataggctttc acgctagtgg gcttg                  45

SEQ ID NO: 103         moltype = DNA  length = 45
FEATURE                Location/Qualifiers
source                 1..45
                       mol_type = other DNA
                       organism = synthetic construct
SEQUENCE: 103
cagatgcaaa tgcctgacca gggaactgcg actggatggc tcttt                  45

SEQ ID NO: 104         moltype = DNA  length = 45
FEATURE                Location/Qualifiers
source                 1..45
                       mol_type = other DNA
                       organism = synthetic construct
SEQUENCE: 104
cagatgcaaa tgcctgacca gggaactgcg actggatggc tcttt                  45

SEQ ID NO: 105         moltype = DNA  length = 45
FEATURE                Location/Qualifiers
source                 1..45
                       mol_type = other DNA
                       organism = synthetic construct
SEQUENCE: 105
cgaaaatttc aagctttatg ctctagcgca gcgcctcgta cccct                  45

SEQ ID NO: 106         moltype = DNA  length = 45
FEATURE                Location/Qualifiers
source                 1..45
                       mol_type = other DNA
                       organism = synthetic construct
SEQUENCE: 106
ggtgaagggc agtggtttgc tgtggtgggc gcccgtgagc gttgc                  45

SEQ ID NO: 107         moltype = DNA  length = 45
FEATURE                Location/Qualifiers
source                 1..45
                       mol_type = other DNA
                       organism = synthetic construct
SEQUENCE: 107
```

```
gggagttcgg gcatgatttg ccctgggggg cacgggaagg taccg                45

SEQ ID NO: 108          moltype = DNA  length = 45
FEATURE                 Location/Qualifiers
source                  1..45
                        mol_type = other DNA
                        organism = synthetic construct
SEQUENCE: 108
cgcaccaagg cgttagacgg aatggatttg gaacttcatg cgaag                45

SEQ ID NO: 109          moltype = DNA  length = 45
FEATURE                 Location/Qualifiers
source                  1..45
                        mol_type = other DNA
                        organism = synthetic construct
SEQUENCE: 109
gttgggctaa gcggaggatg gtaatggtgc ttgggcaggc gctca                45

SEQ ID NO: 110          moltype = DNA  length = 45
FEATURE                 Location/Qualifiers
source                  1..45
                        mol_type = other DNA
                        organism = synthetic construct
SEQUENCE: 110
cagatgcaaa tgcctgacca gggaactgcg acttgatggc tcttg                45

SEQ ID NO: 111          moltype = DNA  length = 45
FEATURE                 Location/Qualifiers
source                  1..45
                        mol_type = other DNA
                        organism = synthetic construct
SEQUENCE: 111
gcgcaaaggg ggtgtttgtg cggtgtggag tgcgcgtgct gctgc                45

SEQ ID NO: 112          moltype = DNA  length = 45
FEATURE                 Location/Qualifiers
source                  1..45
                        mol_type = other DNA
                        organism = synthetic construct
SEQUENCE: 112
gtgccatcgg gaaggtgttg acctgtacga cgtcatagga tggac                45

SEQ ID NO: 113          moltype = DNA  length = 45
FEATURE                 Location/Qualifiers
source                  1..45
                        mol_type = other DNA
                        organism = synthetic construct
SEQUENCE: 113
ggggtgtagg gtggggtagt gggaacattg cgtaaagtgt agctc                45

SEQ ID NO: 114          moltype = DNA  length = 45
FEATURE                 Location/Qualifiers
source                  1..45
                        mol_type = other DNA
                        organism = synthetic construct
SEQUENCE: 114
actgtttgta cggagttagg gtgtgccttt attgtgtggg gggga                45

SEQ ID NO: 115          moltype = DNA  length = 45
FEATURE                 Location/Qualifiers
source                  1..45
                        mol_type = other DNA
                        organism = synthetic construct
SEQUENCE: 115
tcattggagt gggtaggggt gtttgtgcgg gatgcggtgg ctagg                45

SEQ ID NO: 116          moltype = DNA  length = 45
FEATURE                 Location/Qualifiers
source                  1..45
                        mol_type = other DNA
                        organism = synthetic construct
SEQUENCE: 116
gttggccaaa tggattggat tagggttggg ccgcccggga ggggt                45

SEQ ID NO: 117          moltype = DNA  length = 81
FEATURE                 Location/Qualifiers
source                  1..81
                        mol_type = other DNA
                        organism = synthetic construct
```

```
SEQUENCE: 117
atccagagtg acgcagcaaa ttccaaactc gagtaagcgt agagcctctc atcgcctcaa  60
taatggacac ggtggcttag t                                            81

SEQ ID NO: 118         moltype = DNA  length = 81
FEATURE                Location/Qualifiers
source                 1..81
                       mol_type = other DNA
                       organism = synthetic construct
SEQUENCE: 118
atccagagtg acgcagcaat ccgggagagt cgttgtgttg aggtccgccc ctgctcgccc  60
gcgtggacac ggtggcttag t                                            81

SEQ ID NO: 119         moltype = DNA  length = 81
FEATURE                Location/Qualifiers
source                 1..81
                       mol_type = other DNA
                       organism = synthetic construct
SEQUENCE: 119
atccagagtg acgcagcagg ggccgcggat gcaaacgccc gataggggga cggcactgga  60
gcttggacac ggtggcttag t                                            81

SEQ ID NO: 120         moltype = DNA  length = 81
FEATURE                Location/Qualifiers
source                 1..81
                       mol_type = other DNA
                       organism = synthetic construct
SEQUENCE: 120
atccagagtg acgcagcaac ccaaaccacc agccggggat gcaaacaccg cacagggaac  60
ggctggacac ggtggcttag t                                            81

SEQ ID NO: 121         moltype = DNA  length = 81
FEATURE                Location/Qualifiers
source                 1..81
                       mol_type = other DNA
                       organism = synthetic construct
SEQUENCE: 121
atccagagtg acgcagcaac cacagatgca aatgcgcgag agcgggacgg tttgctaggc  60
tcatggacac ggtggcttag t                                            81

SEQ ID NO: 122         moltype = DNA  length = 81
FEATURE                Location/Qualifiers
source                 1..81
                       mol_type = other DNA
                       organism = synthetic construct
SEQUENCE: 122
atccagagtg acgcagcagt gggccaaatg gattggatta gggttgggcc gcccgggagg  60
ggttggacac ggtggcttag t                                            81

SEQ ID NO: 123         moltype = DNA  length = 81
FEATURE                Location/Qualifiers
source                 1..81
                       mol_type = other DNA
                       organism = synthetic construct
SEQUENCE: 123
atccagagtg acgcagcagc cggtcgcaga tgcaaatgcc cgacaggggg acgcgggctg  60
ccatggacac ggtggcttag t                                            81

SEQ ID NO: 124         moltype = DNA  length = 81
FEATURE                Location/Qualifiers
source                 1..81
                       mol_type = other DNA
                       organism = synthetic construct
SEQUENCE: 124
atccagagtg acgcagcact ctcggggggt aggtgggaag ggggccgccc cctgggttag  60
gcttggacac ggtggcttag t                                            81

SEQ ID NO: 125         moltype = DNA  length = 81
FEATURE                Location/Qualifiers
source                 1..81
                       mol_type = other DNA
                       organism = synthetic construct
SEQUENCE: 125
atccagagtg acgcagcaag gtggctgtgg gcggatggtg ggctcgcgtg ggcggccacc  60
tgatggacac ggtggcttag t                                            81

SEQ ID NO: 126         moltype = DNA  length = 56
FEATURE                Location/Qualifiers
source                 1..56
```

```
                        mol_type = other DNA
                        organism = synthetic construct
SEQUENCE: 126
actcataggg ttaggggctg ctggccagat actcagatgg tagggttact atgagc      56

SEQ ID NO: 127          moltype = DNA  length = 51
FEATURE                 Location/Qualifiers
source                  1..51
                        mol_type = other DNA
                        organism = synthetic construct
SEQUENCE: 127
gcagcagcgt aaaggggctg tttgtgcggt gtggagtgcg cgtgctgctg c           51

SEQ ID NO: 128          moltype = RNA  length = 25
FEATURE                 Location/Qualifiers
source                  1..25
                        mol_type = other RNA
                        organism = synthetic construct
SEQUENCE: 128
cagttcagaa tgatggatca agcta                                        25

SEQ ID NO: 129          moltype = RNA  length = 27
FEATURE                 Location/Qualifiers
source                  1..27
                        mol_type = other RNA
                        organism = synthetic construct
SEQUENCE: 129
tagcttgatc catcattctg aactgcc                                      27

SEQ ID NO: 130          moltype = DNA  length = 81
FEATURE                 Location/Qualifiers
source                  1..81
                        mol_type = other DNA
                        organism = synthetic construct
SEQUENCE: 130
ggagtcacac gcattagcgt aaagggggtg tttgtgcggt gtggagtgcg cgtgctaatg  60
ctggagtgtt tcccaggacc c                                            81

SEQ ID NO: 131          moltype = DNA  length = 88
FEATURE                 Location/Qualifiers
source                  1..88
                        mol_type = other DNA
                        organism = synthetic construct
SEQUENCE: 131
ccagagtgac gcagcaacag aggtgtagaa gtacacgtga acaagcttga aattgtctct  60
gacagaggtg gacacggtgg cttttagt                                     88

SEQ ID NO: 132          moltype = DNA  length = 21
FEATURE                 Location/Qualifiers
source                  1..21
                        mol_type = other DNA
                        organism = synthetic construct
SEQUENCE: 132
gggtcctggg aaacactcca g                                            21

SEQ ID NO: 133          moltype = DNA  length = 28
FEATURE                 Location/Qualifiers
source                  1..28
                        mol_type = other DNA
                        organism = synthetic construct
SEQUENCE: 133
gggtcctggg aaacactcca gcattagt                                     28

SEQ ID NO: 134          moltype = DNA  length = 33
FEATURE                 Location/Qualifiers
source                  1..33
                        mol_type = other DNA
                        organism = synthetic construct
SEQUENCE: 134
gggtcctggg aaacactcca gcattagcac gcg                               33

SEQ ID NO: 135          moltype = DNA  length = 51
FEATURE                 Location/Qualifiers
source                  1..51
                        mol_type = other DNA
                        organism = synthetic construct
SEQUENCE: 135
gggtcctggg aaacactcca gcattagcac gcgcactcca caccgcacaa a           51
```

```
SEQ ID NO: 136          moltype = DNA  length = 36
FEATURE                 Location/Qualifiers
source                  1..36
                        mol_type = other DNA
                        organism = synthetic construct
SEQUENCE: 136
actaaaagcc accgtgtcca cctctgtcag agacaa                          36

SEQ ID NO: 137          moltype = DNA  length = 51
FEATURE                 Location/Qualifiers
source                  1..51
                        mol_type = other DNA
                        organism = synthetic construct
SEQUENCE: 137
gcagcagcgt aaaaggggtg tttgtgcggt gtggagtgcg cgtgctgctg c         51

SEQ ID NO: 138          moltype = DNA  length = 51
FEATURE                 Location/Qualifiers
source                  1..51
                        mol_type = other DNA
                        organism = synthetic construct
SEQUENCE: 138
gcagcagcgt aaagagggtg tttgtgcggt gtggagtgcg cgtgctgctg c         51

SEQ ID NO: 139          moltype = DNA  length = 51
FEATURE                 Location/Qualifiers
source                  1..51
                        mol_type = other DNA
                        organism = synthetic construct
SEQUENCE: 139
gcagcagcgt aaagggggtg tttgtgcgat gtggagtgct ctgtctgctg c         51

SEQ ID NO: 140          moltype = DNA  length = 32
FEATURE                 Location/Qualifiers
source                  1..32
                        mol_type = other DNA
                        organism = synthetic construct
SEQUENCE: 140
gcagaagaag aagaagaaga agaagaagaa cg                              32

SEQ ID NO: 141          moltype = DNA  length = 85
FEATURE                 Location/Qualifiers
source                  1..85
                        mol_type = other DNA
                        organism = synthetic construct
SEQUENCE: 141
gcagcagcgt aaagggggtg tttgtgcggt gtggagtgcg cgcgcgctgc tgcgcagaag  60
aagaagaaga agaagaagaa gaacg                                      85

SEQ ID NO: 142          moltype = DNA  length = 83
FEATURE                 Location/Qualifiers
source                  1..83
                        mol_type = other DNA
                        organism = synthetic construct
SEQUENCE: 142
gcagcagcgt aaaggaagtg tttgtgcggt gtggagtgcg cgcgctgctg cgcagaagaa  60
gaagaagaag aagaagaaga acg                                        83

SEQ ID NO: 143          moltype = DNA  length = 32
FEATURE                 Location/Qualifiers
source                  1..32
                        mol_type = other DNA
                        organism = synthetic construct
SEQUENCE: 143
cgttcttctt cttcttcttc ttcttcttct gc                              32

SEQ ID NO: 144          moltype = AA  length = 760
FEATURE                 Location/Qualifiers
source                  1..760
                        mol_type = protein
                        organism = Homo sapiens
SEQUENCE: 144
MMDQARSAFS NLFGGEPLSY TRFSLARQVD GDNSHVEMKL AVDEEENADN NTKANVTKPK  60
RCSGSICYGT IAVIVFFLIG FMIGYLGYCK GVEPKTECER LAGTESPVRE EPGEDFPAAR  120
RLYWDDLKRK LSEKLDSTDF TGTIKLLNEN SYVPREAGSQ KDENLALYVE NQFREFKLSK  180
VWRDQHFVKI QVKDSAQNSV IIVDKNGRLV YLVENPGGYV AYSKAATVTG KLVHANFGTK  240
KDFEDLYTPV NGSIVIVRAG KITFAEKVAN AESLNAIGVL IYMDQTKFPI VNAELSFFGH  300
AHLGTGDPYT PGFPSFNHTQ FPPSRSSGLP NIPVQTISRA AAEKLFGNME GDCPSDWKTD  360
STCRMVTSES KNVKLTVSNV LKEIKILNIF GVIKGFVEPD HYVVVGAQRD AWGPGAAKSG  420
```

```
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QNVKHPVTGQ FLYQDSNWAS KVEKLTLDNA  540
AFPFLAYSGI PAVSFCFCED TDYPYLGTTM DTYKELIERI PELNKVARAA AEVAGQFVIK  600
LTHDVELNLD YERYNSQLLS FVRDLNQYRA DIKEMGLSLQ WLYSARGDFF RATSRLTTDF  660
GNAEKTDRFV MKKLNDRVMR VEYHFLSPYV SPKESPFRHV FWGSGSHTLP ALLENLKLRK  720
QNNGAFNETL FRNQLALATW TIQGAANALS GDVWDIDNEF                        760

SEQ ID NO: 145          moltype = AA  length = 801
FEATURE                 Location/Qualifiers
source                  1..801
                        mol_type = protein
                        organism = Homo sapiens
SEQUENCE: 145
MERLWGLFQR AQQLSPRSSQ TVYQRVEGPR KGHLEEEEED GEEGAETLAH FCPMELRGPE  60
PLGSRPRQPN LIPWAAAGRR AAPYLVLTAL LIFTGAFLLG YVAFRGSCQA CGDSVLVVSE  120
DVNYEPDLDF HQGRLYWSDL QAMFLQFLGE GRLEDTIRQT SLRERVAGSA GMAALTQDIR  180
AALSRQKLDH VWTDTHYVGL QFPDPAHPNT LHWVDEAGKV GEQLPLEDPD VYCPYSAIGN  240
VTGELVYAHY GRPEDLQDLR ARGVDPVGRL LLVRVGVISF AQKVTNAQDF GAQGVLIYPE  300
PADFSQDPPK PSLSSQQAVY GHVHLGTGDP YTPGFPSFNQ TQFPPVASSG LPSIPAQPIS  360
ADIASRLLRK LKGPVAPQEW QGSLLGSPYH LGPGPRLRLV VNNHRTSTPI NNIFGCIEGR  420
SEPDHYVVIG AQRDAWGPGA AKSAVGTAIL LELVRTFSSM VSNGFRPRRS LLFISWDGGD  480
FGSVGSTEWL EGYLSVLHLK AVVYVSLDNA VLGDDKFHAK TSPLLTSLIE SVLKQVDSPN  540
HSGQTLYEQV VFTNPSWDAE VIRPLPMDSS AYSFTAFVGV PAVEFSFMED DQAYPFLHTK  600
EDTYENLHKV LQGRLPAVAQ AVAQLAGQLL IRLSHDRLLP LDFGRYGDVV LRHIGNLNEF  660
SGDLKARGLT LQWVYSARGD YIRAAEKLRQ EIYSSEERDE RLTRMYNVRI MRVEFYFLSQ  720
YVSPADSPFR HIFMGRGDHT LGALLDHLRL LRSNSSGTPG ATSSTGFQES RFRRQLALLT  780
WTLQGAANAL SGDVWNIDNN F                                            801

SEQ ID NO: 146          moltype = AA  length = 763
FEATURE                 Location/Qualifiers
source                  1..763
                        mol_type = protein
                        organism = Mus musculus
SEQUENCE: 146
MMDQARSAFS NLFGGEPLSY TRFSLARQVD GDNSHVEMKL AADEEENADN NMKASVRKPK  60
RFNGRLCFAA IALVIFFLIG FMSGYLGYCK RVEQKEECVK LAETEETDKS ETMETEDVPT  120
SSRLYWADLK TLLSEKLNSI EFADTIKQLS QNTYTPREAG SQKDESLAYY IENQFHEFKF  180
SKVWRDEHYV KIQVKSSIGQ NMVTIVQSNG NLDPVESPEG YVAFSKPTEV SGKLVHANFG  240
TKKDFEELSY SVNGSLVIVR AGEITFAEKV ANAQSFNAIG VLIYMDKNKF PVVEADLALF  300
GHAHLGTGDP YTPGFPSFNH TQFPPSQSSG LPNIPVQTIS RAAAEKLFGK MEGSCPARWN  360
IDSSCKLELS QNQNVKLIVK NVLKERRILN IFGVIKGYEE PDRYVVVGAQ RDALGAGVAA  420
KSSVGTGLLL KLAQVFSDMI SKDGFRPSRS IIFASWTAGD FGAVGATEWL EGYLSSLHLK  480
AFTYINLDKV VLGTSNFKVS ASPLLYTLMG KIMQDVKHPV DGKSLYRDSN WISKVEKLSF  540
DNAAYPFLAY SGIPAVSFCF CEDADYPYLG TRLDTYEALT QKVPQLNQMV RTAAEVAGQL  600
IIKLTHDVEL NLDYEMYNSK LLSFMKDLNQ FKTDIRDMGL SLQWLYSARG DYFRATSRLT  660
TDFHNAEKTN RFVMREINDR IMKVEYHFLS PYVSPRESPF RHIFWGSGSH TLSALVENLK  720
LRQKNITAFN ETLFRNQLAL ATWTIQGVAN ALSGDIWNID NEF                    763

SEQ ID NO: 147          moltype = DNA  length = 82
FEATURE                 Location/Qualifiers
source                  1..82
                        mol_type = other DNA
                        organism = synthetic construct
SEQUENCE: 147
gtagaattcg agtgacgcag cagcgtaaag ggggtgtttg tgcgtgtgga gtgcgcgtgc  60
tgctgcgtca ctcgaattct ac                                           82

SEQ ID NO: 148          moltype = DNA  length = 61
FEATURE                 Location/Qualifiers
source                  1..61
                        mol_type = other DNA
                        organism = synthetic construct
SEQUENCE: 148
aaaacgtttt gcagcagcgt aaagggggtg tttgtgcggt gtggagtgcg cgtgctgctg  60
c                                                                  61
```